(12) United States Patent
Leiris et al.

(10) Patent No.: US 11,000,511 B2
(45) Date of Patent: May 11, 2021

(54) CHEMICAL COMPOUNDS AS ANTIBIOTICS

(71) Applicant: Antabio SAS, Labege (FR)

(72) Inventors: Simon Leiris, Labege (FR); David Thomas Davies, Labege (FR); Martin Everett, Labege (FR); Nicolas Sprynski, Labege (FR); Jonathan Mark Sutton, Margate Kent (GB); Michael Steven Bodnarchuk, Margate Kent (GB); Thomas David Pallin, Margate Kent (GB); Andrew Peter Cridland, Margate Kent (GB); Toby Jonathan Blench, Margate Kent (GB); David Edward Clark, Margate Kent (GB); Richard Leonard Elliott, Margate Kent (GB); Lilha Beyria, Labege (FR)

(73) Assignee: Antabio SAS, Labege (FR)

( * ) Notice: Subject to any disclaimer, the term of this patent is extended or adjusted under 35 U.S.C. 154(b) by 0 days.

(21) Appl. No.: 16/496,176

(22) PCT Filed: Mar. 21, 2018

(86) PCT No.: PCT/EP2018/057201
§ 371 (c)(1),
(2) Date: Sep. 20, 2019

(87) PCT Pub. No.: WO2018/172423
PCT Pub. Date: Sep. 27, 2018

(65) Prior Publication Data
US 2020/0155509 A1 May 21, 2020

(30) Foreign Application Priority Data
Mar. 21, 2017 (GB) .................................... 1704476

(51) Int. Cl.
*C07D 207/14* (2006.01)
*C07D 209/14* (2006.01)
(Continued)

(52) U.S. Cl.
CPC ........ *A61K 31/4184* (2013.01); *A61K 31/195* (2013.01); *A61K 31/343* (2013.01); *A61K 31/357* (2013.01); *A61K 31/381* (2013.01); *A61K 31/402* (2013.01); *A61K 31/404* (2013.01); *A61K 31/415* (2013.01); *A61K 31/423* (2013.01); *A61K 31/426* (2013.01); *A61K 31/437* (2013.01); *A61K 31/472* (2013.01); *A61K 31/496* (2013.01); *A61K 45/06* (2013.01); *C07D 207/14* (2013.01); *C07D 209/14* (2013.01); *C07D 213/56* (2013.01); *C07D 231/12* (2013.01); *C07D 235/14* (2013.01); *C07D 235/16* (2013.01);
(Continued)

(58) Field of Classification Search
CPC ............. C07C 2602/08; C07D 207/14; C07D 209/14; C07D 213/56; C07D 231/12; C07D 235/14; C07D 235/16; C07D 277/64; C07D 307/81; C07D 401/12; C07D 417/10; C07D 487/10; C07D 513/04
See application file for complete search history.

(56) References Cited

U.S. PATENT DOCUMENTS

| 5,457,196 A * | 10/1995 | Warshawsky ...... C07K 5/06139 540/521 |
| 2002/0128290 A1 | 9/2002 | Ohshima et al. |
| 2012/0122764 A1 | 5/2012 | Karki et al. |

FOREIGN PATENT DOCUMENTS

| DE | 4339198 A1 | 5/1995 |
| EP | 0117429 A1 | 9/1984 |

(Continued)

OTHER PUBLICATIONS

Cathcart et al., "Novel Inhibitors of the Pseudomonas aeruginosa Virulence Factor LasB: a Potential Therapeutic Approach for the Attenuation of Virulence Mechanisms in Pseudomonal Infection," Antimicrobial Agents and Chemotheraphy, vol. 55, No. 6, pp. 2670-2678 (2011).

(Continued)

*Primary Examiner* — Matthew P Coughlin
(74) *Attorney, Agent, or Firm* — Panitch Schwarze Belisario & Nadel LLP; Lars H. Genieser

(57) ABSTRACT

The invention relates to a compound which is an indane derivative according to Formula (I), or a pharmaceutically acceptable salt thereof, [FORMULA (I)] wherein $R^1$, $R^2$, $R^3$, n, $R^4$, p, q, L, X and m are as defined herein. The compounds are useful in the treatment of antibacterial infection either as stand alone antibiotics, or in combination with further antibiotics. The compounds can also be used in vitro, for example in cleaning compositions.

38 Claims, 2 Drawing Sheets

(51) Int. Cl.
| | |
|---|---|
| C07D 213/56 | (2006.01) |
| C07D 231/12 | (2006.01) |
| C07D 235/14 | (2006.01) |
| C07D 235/16 | (2006.01) |
| C07D 277/64 | (2006.01) |
| C07D 307/81 | (2006.01) |
| C07D 401/12 | (2006.01) |
| C07D 417/10 | (2006.01) |
| C07D 487/10 | (2006.01) |
| C07D 513/04 | (2006.01) |
| A61K 31/4184 | (2006.01) |
| A61K 31/195 | (2006.01) |
| A61K 31/343 | (2006.01) |
| A61K 31/357 | (2006.01) |
| A61K 31/381 | (2006.01) |
| A61K 31/402 | (2006.01) |
| A61K 31/404 | (2006.01) |
| A61K 31/415 | (2006.01) |
| A61K 31/423 | (2006.01) |
| A61K 31/426 | (2006.01) |
| A61K 31/437 | (2006.01) |
| A61K 31/472 | (2006.01) |
| A61K 31/496 | (2006.01) |
| A61K 45/06 | (2006.01) |

(52) U.S. Cl.
CPC ......... *C07D 277/64* (2013.01); *C07D 307/81* (2013.01); *C07D 401/12* (2013.01); *C07D 417/10* (2013.01); *C07D 487/10* (2013.01); *C07D 513/04* (2013.01)

(56) References Cited

FOREIGN PATENT DOCUMENTS

| | | |
|---|---|---|
| WO | 9803202 A1 | 1/1998 |
| WO | 2003094889 A1 | 11/2003 |
| WO | 2005016249 A2 | 2/2005 |
| WO | 2006029153 A2 | 3/2006 |
| WO | 2006122250 A2 | 11/2006 |
| WO | 2007073503 A2 | 6/2007 |
| WO | 2008036967 A2 | 3/2008 |
| WO | 2008151211 A1 | 12/2008 |
| WO | 2012065953 A1 | 5/2012 |
| WO | 212116415 A1 | 9/2012 |

OTHER PUBLICATIONS

Kany et al., "Binding Mode Characterization and Early in Vivo Evaluation of Fragment-Like Thiols as Inhibitors of the Virulence Factor LasB from Pseudomonas aeruginose," ACS Infectous Diseases, vol. 4, pp. 988-997 (2018).

Robinson et al., "Inhibitors of MMP-1: An Examination of P1'CaGEM-Disubtitution in the Succinamide Hydroxamate Series," Bioorganic & Medicinal Chemistry Letters, vol. 6, No. 14, pp. 1719-1724 (1996).

Yerdelen et al., "Synthesis of donepezil-based multifunctional agents for the treatment of Alzheimer's disease," Bioorganic & Medicinal Chemistry Letters, vol. 25, pp. 5576-5582 (2015).

\* cited by examiner

CHEMICAL COMPOUNDS AS ANTIBIOTICS

CROSS-REFERENCE TO RELATED APPLICATIONS

This application is a Section 371 of International Application No. PCT/EP2018/057201, filed Mar. 21, 2018, which was published in the English language on Sep. 27, 2018 as International Publication No. WO 2018/172423 A1, which claims priority under 35 U.S.C. § 119(b) to British Application No. 1704476.9, filed Mar. 21, 2017.

FIELD OF THE INVENTION

The present invention relates to compounds which are indane derivatives. The compounds of the invention find use in the prevention or treatment of bacterial infection. The invention also provides such compounds per se, pharmaceutical compositions comprising such compounds, and cleaning compositions comprising such compounds.

BACKGROUND

Antibiotics are a broad range of substances exhibiting anti-bacterial activity. A large number of antibiotic compounds are known and have been shown to exhibit antibacterial activity against a wide range of bacteria. However, currently available antibiotics are incapable of controlling some bacterial infections. In some cases, this is because the target bacteria have acquired antibiotic resistance, for example via horizontal gene transfer. In other cases, this is because the target bacteria are found in a state in which the efficacy of antibiotics which would otherwise be highly active is reduced. One such state is a bacterial biofilm.

Bacteria in biofilms are enclosed in a self-produced extracellular biopolymer matrix, which may include polysaccharides, proteins and DNA. Bacteria in biofilms typically exhibit different properties from free-living bacteria of the same species. Such properties typically include increased resistance to antibiotics and detergents and increased lateral gene transfer. For example, bacteria in biofilms typically display up to 1,000-fold higher tolerance to antibiotic challenge than their single cell, planktonic (free-living) counterparts.

Pathogenic bacteria are typically the target of antibacterial treatments, but biofilms formed by such bacteria are typically extremely difficult to eradicate using conventional therapeutic regimes. This limitation in the efficacy of antibacterial compounds is especially important for individuals who through immunodeficiency or other diseases or conditions cannot adequately combat bacterial infection. Such individuals include those suffering from cystic fibrosis.

Cystic fibrosis (CF) is a life-threatening disease affecting approximately 70,000 sufferers worldwide. CF is the most common lethal, hereditary disease in Caucasian populations, resulting from mutations in the cystic fibrosis transmembrane conductance regulator (CFTR) gene. The prevalence of CF in Europe is 1 in every 2,000-3,000 live births, and in North America is about 1 in every 3,500 births. In the UK there are approximately 9,800 people with CF.

The organs of individuals with CF typically have significantly thickened secretions. This in turn can lead to a range of pathological problems. For instance, individuals with CF typically have impaired ciliary clearance, and the lungs of such individuals are typically colonized and infected by bacteria from an early age. Such bacteria include *Staphylococcus aureus*, *Haemophilus influenza*, *Pseudomonas aeruginosa* and *Burkholderia cepacia*. *Pseudomonas aeruginosa* (PA) is the most common cause of chronic lung infection in individuals with CF, and chronic infection with PA is found in 9% of pre-school children, 32% of 10-15 year olds and the majority (between 59% and 80%) of adults with CF, leading to progressive lung damage and early death.

As the lung of the individual with CF is colonised by PA, the growth pattern of the bacteria changes and its capacity for survival improves. In chronic infection, PA bacteria on mucosal and epithelial surfaces, or in sputum, form biofilms as well as producing large quantities of alginate (the so-called mucoid phenotype) which reduce the effectiveness of phagocytosis and antibiotic therapy. This leads to chronic colonisation of the lung by PA that is not cleared by conventional antibiotic therapy.

Patients who are colonised with PA show a more rapid decline in lung function, faster decline in chest radiograph score, poor weight gain, increased hospitalisation rates and an increased need for antibiotic therapy. Median survival is reduced and mortality increased (2.6× risk of death). Most disease-related morbidity and mortality in CF is caused by progressive lung disease as a result of bacterial infection and airway inflammation, primarily associated with the effects of chronic PA lung infection and the persistence of PA biofilms. Despite intensive antibiotic treatment, adaptive mechanisms such as biofilm formation allow PA to resist both immune and antibiotic pressures, leading to recurrent exacerbations and respiratory failure.

Pathogenic bacteria such as PA are not only of importance in the context of CF. For example, the opportunistic pathogen PA can also cause septic shock, particularly in neutropenic patients, and can be responsible for infections of the urinary tract, the gastrointestinal network and skin and soft tissues. PA is also a frequent coloniser of medical devices such as catheters, nebulizers, and the like.

Accordingly, there is a clear need for new antibiotic compounds and compositions and adjuvant therapies for treating bacterial infection.

SUMMARY OF THE INVENTION

The inventors have surprisingly found that compounds of Formula (I) are potent inhibitors of the *Pseudomonas aeruginosa*-derived elastase enzyme LasB, which is important in biofilm formation.

LasB is also implicated in bacterial disease pathology, since secreted LasB degrades many host immune proteins and causes tissue damage. LasB, also known as pseudolysin, is secreted into the environment of the producer organism where it is able to proteolytically attack numerous host immune proteins (e.g. immunoglobulins, cytokines, SP-A) and tissue proteins (e.g. elastin). There are no mammalian homologues of LasB. The ability of LasB to attack host proteins contributes to immune evasion (e.g. avoidance of SP-A mediated phagocytosis, and degradation of immunoglobulin) whilst promoting tissue invasion and long term colonization. Inhibition of LasB therefore better equips the host to deal with immune attack.

LasB also has an important internal role within the bacterial cell cleaving nucleoside diphosphate kinase (NDK) to a smaller active form. Active form of NDK leads to increased GTP levels within the cell, increasing production of alginate. Alginate is a polysaccharide which is a major component of the extracellular biofilm matrix and which is required for swarming motility. Those two virulence phenotypes are associated with bacterial persistence in response to immune and antibiotic pressures. LasB activity has also been shown to upregulate rhamnolipid production, which is necessary for biofilm formation/maturation. Accordingly, inhibition of LasB assists impairment of biofilm formation and disruption of the established biofilm. This in turn is believed to better enable antibiotics currently in use to deal effectively with infection.

Accordingly, the invention provides a compound which is an indane derivative according to Formula (I), or a pharmaceutically acceptable salt thereof,

[FORMULA (I)]

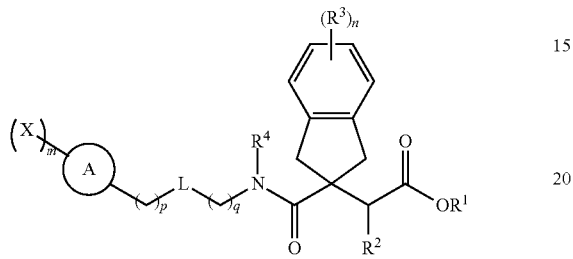

wherein
$R^1$ is selected from H, $R^{1a}$ and —$CH_2OC(O)R^{1a}$, wherein $R^{1a}$ is selected from an unsubstituted $C_1$ to $C_4$ alkyl group and phenyl;
$R^2$ is selected from H and unsubstituted $C_1$ to $C_3$ alkyl;
each $R^3$ group is independently selected from halogen; —OH; —$NH_2$, methyl and —$CF_3$;
n is an integer from 0 to 4;
$R^4$ is selected from H and unsubstituted $C_1$ to $C_3$ alkyl;
p is 0 or 1;
q is 0 or 1;
L is selected from the moieties:

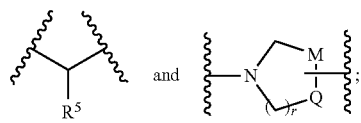

$R^5$ is selected from —$R^6$, —C(O)O$R^6$; —C(O)NR$^{10}R^6$; and —C(O)$R^6$;
$R^6$ is selected from
    H;
    a $C_1$ to $C_4$ alkyl group which is unsubstituted or is substituted with one, two or three groups independently selected from —OH; —NR$^{10}$R$^{11}$; —N$^+$R$^{10}$R$^{11}$R$^{12}$; and halogen; and
    a cyclic group selected from 3- to 10-membered carbocyclic and heterocyclic groups, 5- to 10-membered heteroaromatic groups and 6- to 10-membered aromatic groups; which cyclic group is unsubstituted or is substituted by one or two substituents independently selected from —OH; —NR$^{10}$R$^{11}$; —N$^+$R$^{10}$R$^{11}$R$^{12}$; halogen; and $C_1$ to $C_4$ alkyl groups which are themselves each independently unsubstituted or substituted with one, two or three groups independently selected from —OH; —NR$^{10}$R$^{11}$; —N$^+$R$^{10}$R$^{11}$R$^{12}$; and halogen;
    wherein when said cyclic group is a heterocyclic group comprising at least one nitrogen atom, said nitrogen atom(s) are independently selected from secondary, tertiary and quaternary nitrogen atom(s);
the moiety -M-Q- is selected from —$CH_2$—$CH_2$—; —$CH_2$—NH—; and —$CH_2$—O—;
    wherein a hydrogen atom from one of M and Q is replaced with the bond to the moiety

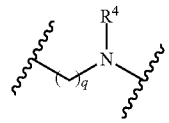

of Formula (I); with the proviso that when q is 0, the moiety -M-Q- is bonded to the —NR$^4$— moiety of Formula (I) via a ring carbon atom;
r is 1 or 2;
Ⓐ is a cyclic group selected from $C_6$ to $C_{10}$ aryl, 5- to 14-membered heteroaryl, and 4- to 14-membered carbocyclic and heterocyclic groups; wherein when Ⓐ is a heterocyclic or heteroaryl group comprising at least one nitrogen atom, said nitrogen atom(s) are independently selected from secondary, tertiary and quaternary nitrogen atom(s);
each X is independently selected from:
    a 4- to 10-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; halogen, —OH; and $C_1$ to $C_4$ alkoxy; $C_1$ to $C_4$ alkyl; $C_2$ to $C_4$ alkenyl; $C_2$ to $C_4$ alkynyl; and —NR$^X$—$C_1$ to $C_4$ alkyl; wherein each alkyl, alkenyl, alkoxy and alkynyl group is independently unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;
    wherein the nitrogen atom(s) in said heterocyclic group are independently selected from secondary, tertiary and quaternary nitrogen atom(s);
$C_2$ to $C_4$ alkoxy; $C_1$ to $C_4$ alkyl; $C_2$ to $C_4$ alkenyl; $C_2$ to $C_4$ alkynyl; and —NR$^X$—$C_1$ to $C_4$ alkyl each of which is unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; and methoxy which is substituted by one, two or three halogen substituents;
halogen, —OH and unsubstituted methoxy; and
$C_3$ to $C_6$ carbocyclyl; —O—$C_3$ to $C_6$ carbocyclyl; and —NR$^X$—$C_3$ to $C_6$ carbocyclyl; wherein each carbocyclyl group is unsubstituted or is substituted with one or two groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; $C_1$ to $C_4$ alkoxy; $C_1$ to $C_4$ alkyl; $C_2$ to $C_4$ alkenyl; $C_2$ to $C_4$ alkynyl; and —NR$^X$—$C_1$ to $C_4$ alkyl wherein each alkyl, alkenyl, alkoxy and alkynyl group is independently unsubstituted or is substituted with one, two or three groups independently selected from —OH, halogen; methoxy; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;

m is an integer from 0 to 3;

each R$^{10}$, R$^{11}$, R$^{12}$, R$^{13}$ and R$^{14}$ is independently H or methyl; and R$^X$ is H or unsubstituted C$_1$ to C$_3$ alkyl.

The invention also provides a compound which is an indane derivative according to Formula (I), or a pharmaceutically acceptable salt thereof, wherein R$^1$ is selected from H, R$^{1a}$ and —CH$_2$OC(O)R$^{1a}$, wherein R$^{1a}$ is selected from an unsubstituted C$_1$ to C$_4$ alkyl group and phenyl;

R$^2$ is selected from H and unsubstituted C$_1$ to C$_3$ alkyl;

each R$^3$ group is independently selected from halogen; —OH; —NH$_2$, methyl and —CF$_3$;

n is an integer from 0 to 4;

R$^4$ is selected from H and unsubstituted C$_1$ to C$_3$ alkyl;

p is 0 or 1;

q is 0 or 1;

L is selected from the moieties:

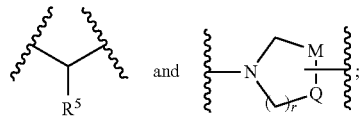

R$^5$ is selected from —R$^6$, —C(O)OR$^6$; —C(O)NR$^{10}$R$^6$; and —C(O)R$^6$;

R$^6$ is selected from
- —H;
- a C$_1$ to C$_4$ alkyl group which is unsubstituted or is substituted with one, two or three groups independently selected from —OH; —NR$^{10}$R$^{11}$; —N$^+$R$^{10}$R$^{11}$R$^{12}$; and halogen; and
- a cyclic group selected from 3- to 10-membered carbocyclic and heterocyclic groups; which cyclic group is unsubstituted or is substituted by one or two substituents independently selected from —OH; —NR$^{10}$R$^{11}$; —N$^+$R$^{10}$R$^{11}$R$^{12}$; halogen; and C$_1$ to C$_4$ alkyl groups which are themselves each independently unsubstituted or substituted with one, two or three groups independently selected from —OH; —NR$^{10}$R$^{11}$; —N$^+$R$^{10}$R$^{11}$R$^{12}$; and halogen;
  wherein when said cyclic group is a heterocyclic group comprising at least one nitrogen atom, said nitrogen atom(s) are independently selected from secondary, tertiary and quaternary nitrogen atom(s);

the moiety -M-Q- is selected from —CH$_2$—CH$_2$—; —CH$_2$—NH—; and —CH$_2$—O—;

wherein a hydrogen atom from one of M and Q is replaced with the bond to the moiety

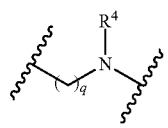

of Formula (I); with the proviso that when q is 0, the moiety -M-Q- is bonded to the —NR$^4$— moiety of Formula (I) via a ring carbon atom;

r is 1 or 2;

Ⓐ is a cyclic group selected from C$_6$ to C$_{10}$ aryl, 5- to 10-membered heteroaryl, and 4- to 10-membered carbocyclic and heterocyclic groups; wherein when Ⓐ is a heterocyclic or heteroaryl group comprising at least one nitrogen atom, said nitrogen atom(s) are independently selected from secondary, tertiary and quaternary nitrogen atom(s);

each X is independently selected from:
- a 4- to 6-membered nitrogen-containing heterocyclic group which is unsubstituted or is substituted by one or two substituents selected from unsubstituted C$_1$ to C$_2$ alkyl; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; NR$^{10}$C(NR$^{11}$)R$^{12}$; and —C(NR$^{11}$)R$^{12}$;
  wherein the nitrogen atom(s) in said heterocyclic group are independently selected from secondary, tertiary and quaternary nitrogen atom(s);
- C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; each of which is unsubstituted or is substituted with one or two groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; NR$^{10}$C(NR$^{11}$)R$^{12}$; and —C(NR$^{11}$)R$^{12}$; and
- halogen, —OH and methoxy;

m is an integer from 0 to 3;

each R$^{10}$, R$^{11}$, R$^{12}$, R$^{13}$ and R$^{14}$ is independently H or methyl; and R$^X$ is H or unsubstituted C$_1$ to C$_3$ alkyl.

The present invention also provides a compound as described herein for use in a method of treating or preventing bacterial infection in a subject in need thereof. Also provided is a method for treating or preventing bacterial infection in a subject, which method comprises administering to said subject an effective amount of a compound as described herein. Further provided is the use of a compound as described herein in the manufacture of a medicament for use in treating or preventing bacterial infection in a subject.

DETAILED DESCRIPTION OF THE INVENTION

Definitions

Figure 1:
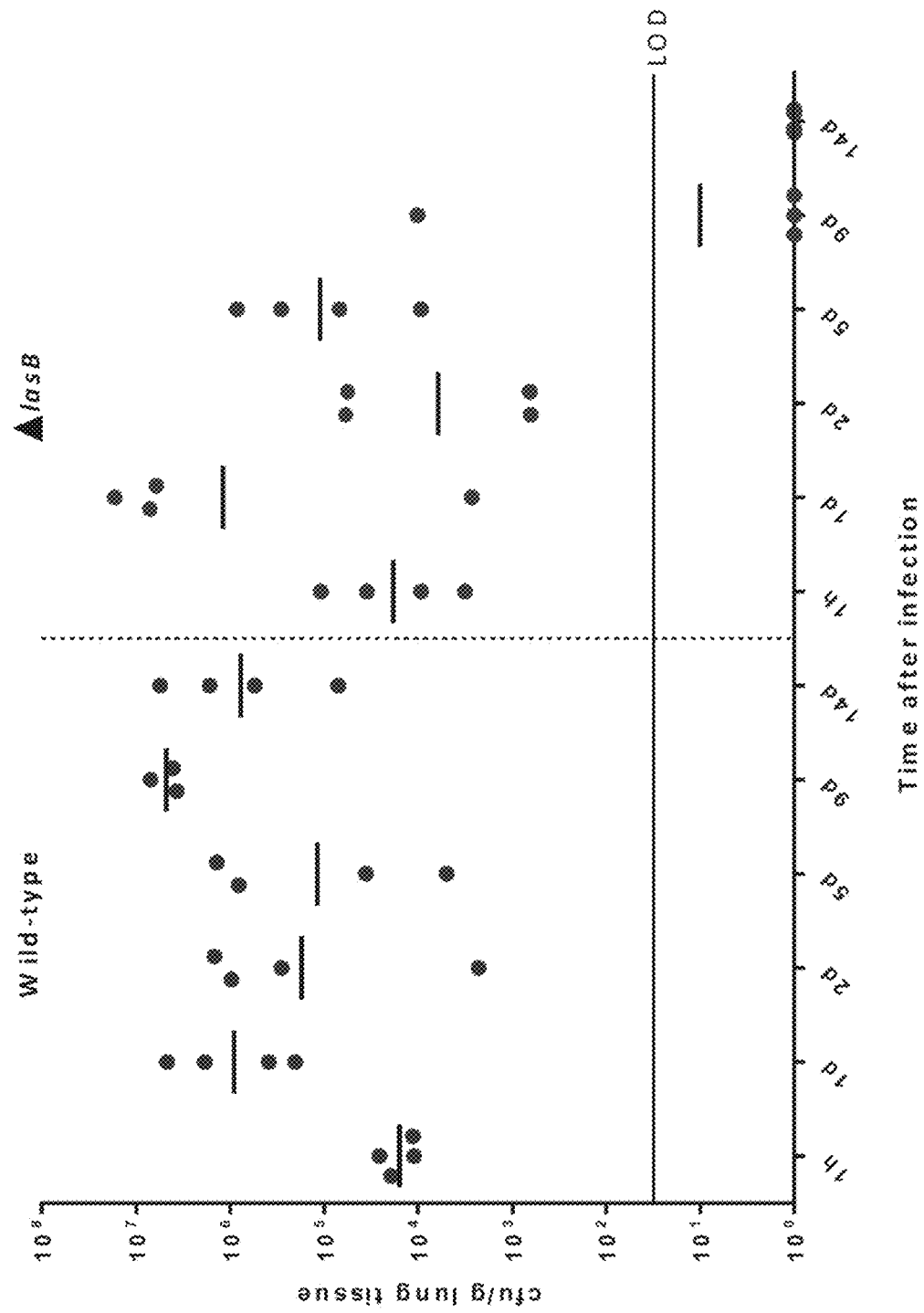
FIG. 1 shows the results of experiments described in Example 47: *P. aeruginosa* PA01 WT and PA01 ΔlasB burden recovered in lung tissue throughout infection time course in rat model (CFU/gram of lung tissue).

As used herein, a C$_1$ to C$_4$ alkyl group is a linear or branched alkyl group containing from 1 to 4 carbon atoms. A C$_1$ to C$_4$ alkyl group is often a C$_1$ to C$_3$ alkyl group. Examples of C$_1$ to C$_4$ alkyl groups include methyl, ethyl, n-propyl, iso-propyl, n-butyl, sec-butyl, and tert-butyl. A C$_1$ to C$_3$ alkyl group is typically a C$_1$ to C$_2$ alkyl group. A C$_1$ to C$_2$ alkyl group is methyl or ethyl, typically methyl. For the avoidance of doubt, where two alkyl groups are present, the alkyl groups may be the same or different.

As used herein, a $C_1$ to $C_4$ alkoxy group is typically a said $C_1$ to $C_4$ alkyl group attached to an oxygen atom. Typically, a $C_1$ to $C_4$ alkoxy group is a $C_1$ to $C_3$ alkoxy group. Examples of $C_1$ to $C_4$ alkoxy groups include methoxy, ethoxy, propoxy, and butoxy. Typically, a $C_1$ to $C_3$ alkoxy group is a $C_1$ to $C_2$ alkoxy group such as a methoxy or ethoxy group. For the avoidance of doubt, where two alkoxy groups are present, the alkoxy groups may be the same or different.

As used herein, a $C_2$-$C_4$ alkenyl group is a linear or branched alkenyl group containing from 2 to 4 carbon atoms and having one or more, e.g. one or two, typically one double bonds. Typically a $C_2$-$C_4$ alkenyl group is a $C_2$-$C_3$ alkenyl group. Examples of $C_2$-$C_4$ alkenyl groups include ethenyl, propenyl and butenyl. For the avoidance of doubt, where two alkenyl groups are present, the alkenyl groups may be the same or different.

As used herein, a $C_2$-$C_4$ alkynyl group is a linear or branched alkynyl group containing from 2 to 4 carbon atoms and having one or more, e.g. one or two, typically one triple bonds. Typically a $C_2$-$C_4$ alkynyl group is a $C_2$-$C_3$ alkynyl group. Examples of $C_2$ to $C_4$ alkynyl groups include ethynyl, propynyl and butynyl. For the avoidance of doubt, where two alkynyl groups are present, the alkynyl groups may be the same or different.

An alkyl, alkenyl, alkynyl or alkoxy group as used herein may be unsubstituted or substituted. Unless otherwise stated, substituted alkyl, alkenyl, alkynyl or alkoxy groups typically carry one or more, e.g. one, two or three e.g. one, or two, e.g. one substituent selected from halogen, OH, $-NR^{10}R^{11}$; $-N^+R^{10}R^{11}R^{12}$; $-NR^{10}C(NR^{11})NR^{12}R^{13}$; $-NR^{10}C(N^+R^{11}R^{12})NR^{13}R^{14}$; $NR^{10}C(NR^{11})R^{12}$; and $-C(NR^{11})R^{12}$ wherein $R^{10}$, $R^{11}$, $R^{12}$, $R^{13}$ and $R^{14}$ are as defined herein. Preferred substituents are $-NR^{10}R^{11}$ and $-N^+R^{10}R^{11}R^{12}$ unless otherwise stated. The substituents on a substituted alkyl, alkenyl, alkynyl or alkoxy group are typically themselves unsubstituted. Where more than one substituent is present, these may be the same or different.

As used herein, a halogen is typically chlorine, fluorine, bromine or iodine and is preferably chlorine, bromine or fluorine, especially chorine or fluorine.

A 3- to 14-membered carbocyclic group is a cyclic hydrocarbon containing from 3 to 14 carbon atoms. A 3- to 14-membered carbocyclic group is often a 4- to 14-membered carbocyclic group. Examples of such groups include 4- to 10-membered carbocylic groups and larger carbocyclic groups for example 12- or 13-membered carbocyclic groups. A 3- to 14-membered carbocyclic group is also often a 3- to 10-membered carbocyclic group. A 3- to 10-membered carbocyclic group is a cyclic hydrocarbon containing from 3 to 10 carbon atoms. A carbocyclic group may be saturated or partially unsaturated, but is typically saturated. A 3- to 10-membered partially unsaturated carbocyclic group is a cyclic hydrocarbon containing from 3 to 10 carbon atoms and containing 1 or 2, e.g. 1 double bond. A 3- to 10-membered carbocyclic group is typically a 4- to 10-membered carbocyclic group. A 3- to 10-membered carbocyclic group may be a fused bicyclic group, as defined herein. A 3- to 10-membered carbocyclic group may be a saturated 4- to 6-membered, preferably 5- or 6-membered carbocyclic group. Examples of 4- to 6-membered saturated carbocyclic groups include cyclobutyl, cyclopentyl and cyclohexyl groups.

A 3- to 14-membered heterocyclic group is a cyclic group containing from 3 to 14 atoms selected from C, O, N and S in the ring, including at least one heteroatom, and typically one or two heteroatoms. The heteroatom or heteroatoms are typically selected from O, N, and S, most typically from S and N, especially N. A 3- to 14-membered heterocyclic group is often a 4- to 14-membered heterocyclic group. Examples of such groups include 4- to 10-membered heterocyclic groups and larger carbocyclic groups for example 12- or 13-membered heterocyclic groups e.g. [1,3]dioxolo[4',5':4,5]benzo[1,2-d]thiazole. A 3- to 14-membered heterocyclic group may be a 9- or 10-membered heteroaromatic group fused to a 1,3-dioxolane or a 1-4-dioxane group. A 3- to 14-membered heterocyclic group is also often a 3- to 10-membered heterocyclic group. A 3- to 10-membered heterocyclic group is a cyclic group containing from 3 to 10 atoms selected from C, O, N and S in the ring, including at least one heteroatom, and typically one or two heteroatoms. The heteroatom or heteroatoms are typically selected from O, N, and S, most typically from S and N, especially N. For example, where the heterocyclic group is denoted a nitrogen-containing heterocyclic group, it contains one nitrogen atom and optionally a further heteroatom selected from O, N and S. A heterocyclic group may be saturated or partially unsaturated. A 3- to 10-membered partially unsaturated heterocyclic group is a cyclic group containing from 3 to 10 atoms selected from C, O, N and S in the ring and containing 1 or 2, e.g. 1 double bond.

A 3- to 10-membered heterocyclic group is typically a 4- to 10-membered heterocyclic group. A 4- to 10-membered heterocyclic group may be a monocyclic 5- or 6-membered heterocyclic group. Alternatively, a 4- to 10-membered heterocyclic group may be a 9- or 10-membered fused bicyclic heterocyclic group (i.e. a fused heterobicyclic group). In some compounds described herein, a 3- to 10-membered heterocyclic group is a 4- to 6-membered nitrogen-containing heterocyclic group which is unsubstituted or is substituted as described herein. Preferred 4- to 6-membered nitrogen-containing heterocyclic groups include azetidine, pyrrolidine, imidazolidine, piperidine, and piperazine, including quaternised derivatives thereof, as defined herein.

Examples of 5- and 6-membered saturated heterocyclic groups include piperazine, piperidine, morpholine, 1,3-oxazinane, pyrrolidine, imidazolidine, and oxazolidine, including quaternised derivatives thereof, as defined herein. Examples of 5- and 6-membered partially saturated heterocyclic groups include tetrahydropyrazine, tetrahydropyridine, dihydro-1,4-oxazine, tetrahydropyrimidine, dihydro-1,3-oxazine, dihydropyrrole, dihydroimidazole and dihydrooxazole, including quaternised derivatives thereof, as defined herein.

Examples of 9- and 10-membered fused heterobicyclic groups include 9-membered fused heterobicyclic groups such as indoline, 2,3-dihydrobenzofuran, 2,3-dihydrobenzo[b]thiophene, 2,3-dihydro-1H-benzo[d]imidazole, 2,3-dihydrobenzo[d]oxazole, 2,3-dihydrobenzo[d]thiazole, benzo[d][1,3]dioxole, 4,5,6,7-tetrahydrothiazolo[5,4-c]pyridine and 4,5,6,7-tetrahydrothiazolo[4,5-c]pyridine, including quaternised derivatives thereof, as defined herein; and 10-membered heterobicyclic groups such as 1,2,3,4-tetrahydroquinoline, 1,2,3,4-tetrahydroisoquinoline, chromane, isochromane, thiochromane, isothiochromane, 1,2,3,4-tetrahydroquinoxaline, 1,2,3,4-tetrahydroquinazoline, 1,4-dihydro-2H-benzo[d][1,3]oxazine, 3,4-dihydro-2H-benzo[b][1,4]oxazine, 3,4-dihydro-2H-benzo[b][1,4]thiazine, 1,4-dihydro-2H-benzo[d][1,3]thiazine, 4H-benzo[d][1,3]dioxine and 2,3-dihydrobenzo[b][1,4]dioxine, including quaternised derivatives thereof. Preferably, the fused heterobicyclic group comprises 1, 2 or 3, preferably 1 or 2 nitrogen atoms.

For the avoidance of doubt, references to a heterocyclic group also include fused polycyclic ring systems, including for instance fused bicyclic systems in which a heterocyclic group is fused to an aryl group. When the heterocyclic group is such a fused heterocyclic group, preferred examples are fused ring systems wherein a 5- to 6-membered heterocyclic group is fused to a phenyl group. References to a heterocyclic group also include spiro ring systems, for example 7-membered heterocyclic groups e.g. 2,6-diazaspiro[3.3]heptane.

As used herein, a $C_6$ to $C_{10}$ aryl group is a substituted or unsubstituted, monocyclic or fused polycyclic aromatic group containing from 6 to 10 carbon atoms in the ring portion. Examples include monocyclic groups such as phenyl and fused bicyclic groups such as naphthyl and indenyl. Phenyl (benzene) is preferred.

As used herein, a 5- to 14-membered heteroaryl group is a substituted or unsubstituted monocyclic or fused polycyclic aromatic group containing from 5 to 14 atoms in the ring portion, including at least one heteroatom, for example 1, 2 or 3 heteroatoms, typically selected from O, S and N. Examples of such groups include 5- to 10-membered heteroaryl groups and larger carbocyclic groups for example 12- or 13-membered heterocyclic groups e.g. [1,3]dioxolo[4',5':4,5]benzo[1,2-d]thiazole. As used herein, a 5- to 10-membered heteroaryl group is a substituted or unsubstituted monocyclic or fused polycyclic aromatic group containing from 5 to 10 atoms in the ring portion, including at least one heteroatom, for example 1, 2 or 3 heteroatoms, typically selected from O, S and N. A heteroaryl group is typically a 5- or 6-membered heteroaryl group or a 9- or 10-membered heteroaryl group. Preferably, the heteroaryl group comprises 1, 2 or 3, preferably 1 or 2 nitrogen atoms.

Examples of 5- and 6-membered heteroaryl groups include pyrrole, furan, thiophene, imidazole, oxazole, thiazole, pyridine, pyrimidine, and pyrazine. Examples of 9- and 10-membered heteroaryl groups include 9-membered heteroaryl groups such as indole, benzothiophene, benzofuran, benzoxazole, benzothiazole, benzimidazole, imidazo[1,2-a]pyridine, [1,2,4]triazolo[1,5-a]pyridine and imidazo[1,2-a]pyrazine, including quaternised derivatives thereof; and 10-membered heteroaryl groups such as quinoline, isoquinoline, quinazoline, and quinoxaline.

For the avoidance of doubt, references to a heteroaryl group also include fused polycyclic ring systems, including for instance fused bicyclic systems in which a heteroaryl group is fused to an aryl group. When the heteroaryl group is such a fused heteroaryl group, preferred examples are fused ring systems wherein a 5- to 6-membered heteroaryl group is fused to a phenyl group.

As used herein, a fused bicyclic group is a group comprising two cyclic moieties sharing a common bond between two atoms. A spiro bicyclic group is a group comprising two cyclic moieties sharing a common atom.

A carbocyclic, heterocyclic, aryl or heteroaryl group may be unsubstituted or substituted as described herein. For example, a carbocyclic, heterocyclic, aryl or heteroaryl group may be unsubstituted or substituted with 1, 2 or 3, typically 1 or 2 such as e.g. 1 substituent. Suitable substituents include halogen; OH; $-NR^{10}R^{11}$; $-N^+R^{10}R^{11}R^{12}$; $-NR^{10}C(NR^{11})NR^{12}R^{13}$; $-NR^{10}C(N^+R^{11}R^{12})NR^{13}R^{14}$; $NR^{10}C(NR^{11})R^{12}$; and $-C(NR^{11})R^{12}$ (wherein $R^{10}$, $R^{11}$, $R^{12}$, $R^{13}$ and $R^{14}$ are as defined herein); unsubstituted $C_1$ to $C_2$ alkyl; $C_1$ to $C_4$ alkyl groups which are themselves each independently unsubstituted or substituted with one, two or three groups independently selected from —OH, $-NR^{10}R^{11}$, $-N^+R^{10}R^{11}R^{12}$, and halogen; and X as depicted in Formula (I) and defined herein. The substituents on a substituted carbocyclic, heterocyclic, aryl or heteroaryl group are typically themselves unsubstituted, unless otherwise stated.

A number of the compounds described herein comprise heterocyclic or heteroaryl groups comprising at least one nitrogen atom. In such compounds, said nitrogen atom(s) are independently selected from secondary, tertiary and quaternary nitrogen atom(s). A quaternary nitrogen atom is present when the compound comprises a quaternised derivative of one or more monocyclic groups or fused bicyclic groups. As used herein, a quaternised derivative of a moiety such as a cyclic moiety is formed by bonding an additional alkyl group to a nitrogen atom in the moiety such that the valency of the said nitrogen atom increases from 3 to 4 and the nitrogen atom is positively charged.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as oxalic, citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) bases, for example hydroxides, carbonates, and bicarbonates, and organic bases such as alkyl amines, aralkyl (i.e. aryl-substituted alkyl; e.g. benzyl) amines and heterocyclic amines. Sodium salts, hydrochloride salts and acetate salts are preferred, in particular hydrochloride salts. For the avoidance of doubt, the term "A compound which is an indane derivative according to Formula (I), or a pharmaceutically acceptable salt thereof" includes those compounds of Formula (I) which can exist in zwitterionic form. Such compounds are "inner salts", and can be formed for example when $R^1$ is absent such that the moiety $-C(O)OR^1$ is $-COO^-$ and another moiety in the compound for example group X or $R^6$ as defined herein is positively charged.

In Formula (I), the stereochemistry is not limited. In particular, compounds of Formula (I) containing one or more stereocentre (e.g. one or more chiral centre) may be used in enantiomerically or diastereoisomerically pure form, or in the form of a mixture of isomers. Further, for the avoidance of doubt, the compounds of the invention may be used in any tautomeric form. Typically, the agent or substance described herein contains at least 50%, preferably at least 60, 75%, 90% or 95% of a compound according to Formula (I) which is enantiomerically or diasteriomerically pure. Thus, the compound is preferably substantially optically pure.

For the avoidance of doubt, the terms 'indanyl derivative' and 'indane derivative' may be used interchangeably and unless otherwise indicated refer to compounds of the invention, such as compounds of Formula (I).

Compounds of the Invention

Typically, in Formula (I), $R^1$ is selected from H and $R^{1a}$. More preferably, $R^1$ is H. $R^{1a}$ is typically an unsubstituted $C_1$ to $C_4$ alkyl group, such as an unsubstituted $C_1$ to $C_2$ alkyl group. More preferably, $R^{1a}$ is methyl or t-butyl.

Typically, in Formula (I), $R^2$ is selected from H and unsubstituted $C_1$ to $C_2$ alkyl. More preferably, $R^2$ is selected from H and methyl. Most preferably, $R^2$ is H.

In Formula (I), each $R^3$ group is typically independently selected from halogen; —OH; and —$NH_2$. More preferably, each $R^3$ group is independently selected from fluorine, chlorine and —OH, and most preferably each $R^3$ group is fluorine. Typically, n is an integer from 0 to 2; more preferably n is 0 or 1; most preferably n is 0.

In Formula (I), $R^4$ is typically H or methyl. Preferably, $R^4$ is H.

Preferably, in Formula (I), $R^1$ is selected from H and methyl; $R^2$ is selected from H and methyl; each $R^3$ group is independently selected from halogen; —OH; and —$NH_2$, n is 0 or 1, and $R^4$ is H. More preferably, in Formula (I), $R^1$ is H, $R^2$ is H, n is 0, and $R^4$ is H.

Typically, in Formula (I), q is 0. Often, p is 0. Preferably, q is 0 and p is 0 or 1. More preferably, q is 0 and p is 0.

In one embodiment, L is the moiety

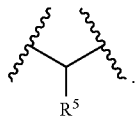

Typically, $R^5$ is selected from —$R^6$, —C(O)O$R^6$; and —C(O)$R^6$. Alternatively, $R^5$ can be selected from —$R^6$, —C(O)O$R^6$; and —C(O)N$R^{10}R^6$, where $R^{10}$ is H or methyl, typically H. Preferably, $R^5$ is selected from —$R^6$ and —C(O)O$R^6$. More preferably, $R^5$ is —$R^6$.

$R^6$ is selected from:
(i) H;
(ii) a $C_1$ to $C_4$ alkyl group which is unsubstituted or is substituted with one, two or three groups independently selected from —OH; —$NR^{10}R^{11}$; —$N^+R^{10}R^{11}R^{12}$; and halogen;
and
(iii) a cyclic group selected from 3- to 10-membered carbocyclic and heterocyclic groups, 5- to 10-membered heteroaromatic groups and 6- to 10-membered aromatic groups; which cyclic group is unsubstituted or is substituted by one or two substituents independently selected from —OH; —$NR^{10}R^{11}$; —$N^+R^{10}R^{11}R^{12}$; halogen; and $C_1$ to $C_4$ alkyl groups which are each independently unsubstituted or substituted with one, two or three groups independently selected from —OH; —$NR^{10}R^{11}$; —$N^+R^{10}R^{11}R^{12}$; and halogen.

$R^6$ is preferably selected from:
(i) H;
(ii) a $C_1$ to $C_4$ alkyl group which is unsubstituted or is substituted with one, two or three groups independently selected from —OH; —$NR^{10}R^{11}$; —$N^+R^{10}R^{11}R^{12}$; and halogen;
and
(iii) a cyclic group selected from 3- to 10-membered carbocyclic and heterocyclic groups; which cyclic group is unsubstituted or is substituted by one or two substituents independently selected from —OH; —$NR^{10}R^{11}$; —$N^+R^{10}R^{11}R^{12}$; halogen; and $C_1$ to $C_4$ alkyl groups which are each independently unsubstituted or substituted with one, two or three groups independently selected from —OH; —$NR^{10}R^{11}$; —$N^+R^{10}R^{11}R^{12}$; and halogen.

When $R^6$ is according to option (ii) above, $R^6$ is typically a $C_1$ to $C_4$ alkyl group which is unsubstituted or is substituted with one or two groups, preferably one group, independently selected from —OH; —$NR^{10}R^{11}$; and —$N^+R^{10}R^{11}R^{12}$; more preferably $R^6$ is a t-butyl group or is a $C_1$ to $C_2$ alkyl group which is unsubstituted or is substituted with one group selected from —OH; —$NR^{10}R^{11}$; and —$N^+R^{10}R^{11}R^{12}$; still more preferably $R^6$ is a $C_1$ to $C_2$ alkyl group which is unsubstituted or is substituted with one group selected from —$NR^{10}R^{11}$ and —$N^+R^{10}R^{11}R^{12}$, and most preferably $R^6$ is methyl or ethyl, preferably methyl.

When $R^6$ is according to option (iii) above, $R^6$ is a preferably a 3- to 10-membered carbocyclic or heterocyclic group or a 5- to 10-membered heteroaromatic group; more preferably a 3- to 10-membered heterocyclic group or a 5- to 10-membered heteroaromatic group; still more preferably a 5- to 6-membered heterocyclic group or a 5- to 6-membered heteroaromatic group. When $R^6$ is according to option (iii) above, $R^6$ is more typically a 3- to 10-membered heterocyclic group; preferably a 5- to 6-membered heterocyclic group. When $R^6$ is a heteroaromatic group, it is preferably a nitrogen-containing heteroaromatic group, more preferably an oxadiazole group e.g. 1,3,4-oxadiazole. When $R^6$ is a heterocyclic group, the heterocyclic group is preferably saturated. When $R^6$ is a heterocyclic group, it is preferably a nitrogen-containing heterocyclic group. More preferably, when $R^6$ is a heterocyclic group, $R^6$ is piperidine or piperazine, most preferably piperidine.

When $R^6$ is according to option (iii) above, $R^6$ is typically unsubstituted or is substituted by one or two substituents independently selected from $C_1$ to $C_4$ alkyl groups which are each independently unsubstituted or substituted with one, two or three groups independently selected from —OH; —$NR^{10}R^{11}$; —$N^+R^{10}R^{11}R^{12}$; and halogen; more preferably $R^6$ is unsubstituted or is substituted by one or two substituents independently selected from $C_1$ to $C_2$ alkyl groups which are each independently unsubstituted or substituted with one group selected from —OH; —$NR^{10}R^{11}$; —$N^+R^{10}R^{11}R^{12}$; and still more preferably $R^6$ is unsubstituted or is substituted by one or two methyl substituents.

Preferably, $R^6$ is according to option (i) above or option (ii) above. More preferably, $R^6$ is H (i.e., $R^6$ is according to option (i) above).

In another embodiment, L is the moiety

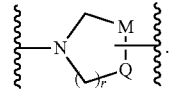

Preferably, r is 1.

The moiety -M-Q- is selected from —$CH_2$—$CH_2$—; —$CH_2$—NH—; and —$CH_2$—O—; wherein a hydrogen atom from one of M and Q is replaced with the bond to the moiety —$(CH_2)_q$—$NR^4$— of Formula (I). In other words, the moiety -M-Q- is selected from —CH($\sim\sim$)-$CH_2$—; —$CH_2$—CH($\sim\sim$)-; —CH($\sim\sim$)-NH—; —$CH_2$—N($\sim\sim$)-; and —CH($\sim\sim$)-O—; wherein $\sim\sim$ indicates the point of attachment to the moiety —$(CH_2)_q$—$NR^4$— of Formula (I).

When q is 0, the moiety —$(CH_2)_q$—$NR^4$— of Formula (I) is —$NR^4$—, and the moiety M-Q- is bonded to the —$NR^4$— moiety of Formula (I) via a ring carbon atom. In other words, when q is 0, -M-Q- is selected from —CH($\sim\sim$)-$CH_2$—; —$CH_2$—CH($\sim\sim$)-; —CH($\sim\sim$)-NH—; and —CH($\sim\sim$)-O—.

Preferably, -M-Q- is selected from —$CH_2$—$CH_2$— and —$CH_2$—NH—, more preferably —$CH_2$—$CH_2$—. Still more preferably, -M-Q- is selected from —CH$_2$—CH($\sim\sim$)- and —CH$_2$—N($\sim\sim$)-, more preferably —CH$_2$—CH($\sim\sim$)-.

Most preferably, the moiety

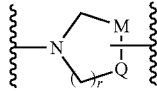

is piperidinylene or pyrrolidinylene, preferably pyrrolidinylene.

Preferably, in Formula (I), L is the moiety

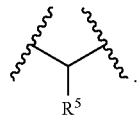

Preferably, therefore, in Formula (I):
q is 0;
p is 0 or 1;
L is selected from the moieties

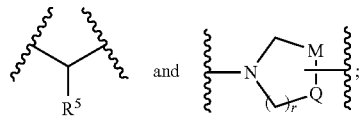

$R^5$ is selected from —$R^6$, —C(O)O$R^6$; —C(O)N$R^{10}R^6$; and —C(O)$R^6$, preferably from —$R^6$ and —C(O)O$R^6$;
$R^6$ is selected from:
(i) H;
(ii) a $C_1$ to $C_4$ alkyl group which is unsubstituted or is substituted with one or two groups, preferably one group, independently selected from —OH; —N$R^{10}R^{11}$; and —N$^+R^{10}R^{11}R^{12}$;
and
(iii) a 5- to 6-membered heterocyclic group or a 5- to 6-membered heteroaromatic group which is unsubstituted or is substituted by one or two substituents independently selected from $C_1$ to $C_2$ alkyl groups which are each independently unsubstituted or substituted with one group selected from —OH; —N$R^{10}R^{11}$; —N$^+R^{10}R^{11}R^{12}$; and the moiety

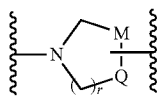

is selected from piperidinylene or pyrrolidinylene.

More preferably, therefore, in Formula (I):
q is 0;
p is 0 or 1;

L is selected from the moieties

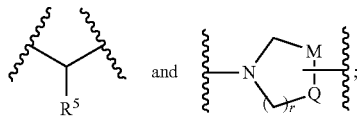

$R^5$ is selected from —$R^6$, —C(O)O$R^6$; —C(O)N$R^{10}R^6$; and —C(O)$R^6$, preferably from —$R^6$ and —C(O)O$R^6$;
$R^6$ is selected from:
(i) H;
(ii) a $C_1$ to $C_4$ alkyl group which is unsubstituted or is substituted with one or two groups, preferably one group, independently selected from —OH; —N$R^{10}R^{11}$; and —N$^+R^{10}R^{11}R^{12}$;
and
(iii) a 5- to 6-membered heterocyclic group which is unsubstituted or is substituted by one or two substituents independently selected from $C_1$ to $C_2$ alkyl groups which are each independently unsubstituted or substituted with one group selected from —OH; —N$R^{10}R^{11}$; —N$^+R^{10}R^{11}R^{12}$; and the moiety

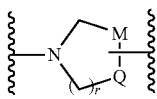

is selected from piperidinylene or pyrrolidinylene.
More preferably, in Formula (I):
q is 0;
p is 0;
L is the moiety

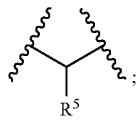

$R^5$ is —$R^6$; and
$R^6$ is selected from:
(i) H;
(ii) a $C_1$ to $C_2$ alkyl group which is unsubstituted or is substituted with one group selected from —N$R^{10}R^{11}$ and —N$^+R^{10}R^{11}R^{12}$;
and
(iii) piperidine and piperazine, each of which is unsubstituted or is substituted by one or two methyl substituents.

In a particularly preferred embodiment, p=q=0 and L represents a group —CH$_2$—.

In Formula (I), Ⓐ is preferably a cyclic group selected from $C_6$ to $C_{10}$ aryl, 5- to 10-membered heteroaryl, 4- to 10-membered carbocyclic and heterocyclic groups; and a 9- or 10-membered heteroaromatic group fused to a 1,3-dioxolane or a 1-4-dioxane group, more preferably Ⓐ is a cyclic group selected from $C_6$ to $C_{10}$ aryl, 5- to 10-membered heteroaryl, and 4- to 10-membered carbocyclic and heterocyclic groups. Ⓐ is more preferably a cyclic group selected from 5- to 10-membered heteroaryl, and 4- to 10-membered carbocyclic and heterocyclic groups. Ⓐ is more preferably a 5- to 10-membered heteroaryl group or a 4- to 10-membered heterocyclic group. Still more preferably, Ⓐ is a 5- to 10-membered heteroaryl group. When Ⓐ is a 5- to 10-membered heteroaryl group, it is preferably a 9- or 10-membered group. When Ⓐ is a heterocyclic or heteroaryl group, it preferably contains 1, 2 or 3, preferably 1 or 2 heteroatoms selected from O, N and S. When Ⓐ is a heterocyclic or heteroaryl group, it is preferably a nitrogen-containing group. When Ⓐ is a fused heteroaryl or heterocyclic group, Ⓐ is typically bonded to the moiety —(CH$_2$)$_p$-L- of Formula (I) via a heteroatom-containing ring. Ⓐ preferably comprises a benzene ring fused to a 5- or 6-membered heterocyclic or heteroaryl group as defined herein.

Preferably, Ⓐ is selected from pyrazole, benzene, benzothiazole, benzofuran, benzimidazole, benzothiophene, benzoxazole, indole, isoquinoline, 2,3-dihydrobenzofuran, 2,3-dihydrobenzo[b][1,4]dioxine, and 4,5,6,7-tetrahydrothiazolo[5,4-c]pyridine. More preferably, Ⓐ is selected from benzene, benzothiazole, benzofuran, 2,3-dihydrobenzofuran, benzimidazole, benzothiophene, indole, and 2,3-dihydrobenzo[b][1,4]dioxine. Still more preferably, Ⓐ is selected from benzene, benzothiazole, benzofuran, and indole. Sometimes, Ⓐ is not benzene. Even more preferably, Ⓐ is selected from benzothiazole, benzofuran and indole. Most preferably, Ⓐ is benzothiazole.

When Ⓐ is selected from benzothiazole, benzofuran, 2,3-dihydrobenzofuran, benzimidazole, benzothiophene, indole, benzoxazole and 2,3-dihydrobenzo[b][1,4]dioxine, Ⓐ is typically bonded to the moiety —(CH$_2$)$_p$-L- of Formula (I) as indicated below wherein ∼ indicates the point of attachment to the moiety —(CH$_2$)$_p$-L- in Formula (I).

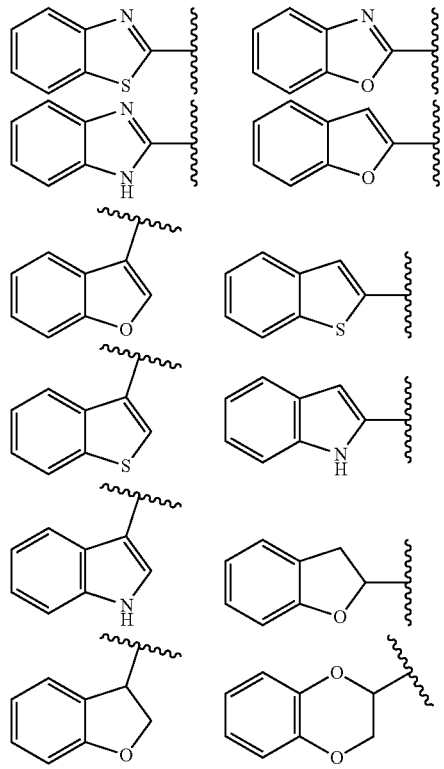

Ⓐ is substituted with none, one, two or three groups X. In Formula (I), each X is independently selected from:

(i) a 4- to 10-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; halogen, —OH; and C$_1$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; wherein each alkyl, alkenyl, alkoxy and alkynyl group is independently unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;

wherein the nitrogen atom(s) in said heterocyclic group are independently selected from secondary, tertiary and quaternary nitrogen atom(s);

(ii) C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; each of which is unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; and methoxy which is substituted with one, two or three halogen substituents (iii) halogen, —OH and unsubstituted methoxy; and (iv) C$_3$ to C$_6$ carbocyclyl; —O—C$_3$ to C$_6$ carbocyclyl; and —NR$^X$—C$_3$ to C$_6$ carbocyclyl; wherein each carbocyclyl group is unsubstituted or is substituted with one or two groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; C$_1$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; wherein each alkyl, alkenyl, alkoxy and alkynyl group is independently unsubstituted or is substituted with one, two or three groups independently selected from —OH, halogen; methoxy; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;

Preferably, each X is independently selected from:

(i) a 4- to 7-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; and unsubstituted or substituted C$_1$ to C$_2$ alkyl; wherein each substituted alkyl group is substituted with one, two or three groups independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;

wherein the nitrogen atom(s) in said heterocyclic group are independently selected from secondary, tertiary and quaternary nitrogen atom(s);

(ii) C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl each of which is unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; and methoxy which is substituted by one, two or three fluorine substituents;

(iii) halogen, —OH and unsubstituted methoxy; and (iv) C$_3$ to C$_6$ carbocyclyl; and —O—C$_3$ to C$_6$ carbocyclyl; wherein each carbocyclyl group is unsubstituted or is substituted with one or two groups independently selected from —NR$^{10}$R$^{11}$; —N$^+$R$^{10}$R$^{11}$R$^{12}$; and C$_1$ to C₄ alkyl which is unsubstituted or is substituted with one or two groups independently selected from —NR$^{10}$R$^{11}$; and —N$^+$R$^{10}$R$^{11}$R$^{12}$.

More preferably, in Formula (I), each X is independently selected from:
(i) a 4- to 6-membered nitrogen-containing heterocyclic group which is unsubstituted or is substituted by one or two substituents selected from C₁ to C₂ alkyl; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; NR$^{10}$C(NR$^{11}$)R$^{12}$; and —C(NR$^{11}$)R$^{12}$;
(ii) C₂ to C₄ alkoxy; C₁ to C₄ alkyl; C₂ to C₄ alkenyl; C₂ to C₄ alkynyl; and —NR$^X$—C₁ to C₄ alkyl; each of which is unsubstituted or is substituted with one or two groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; NR$^{10}$C(NR$^{11}$)R$^{12}$; and —C(NR$^{11}$)R$^{12}$;
and
(iii) halogen, —OH and methoxy;

X is preferably a basic group; i.e. a species having a lone pair of electrons that is capable of binding to a proton, or such a species in its protonated form. Alkylated analogues are also typically suitable.

When X is a 4- to 10-membered nitrogen-containing heterocyclic group according to option (i), X is preferably a 4- to 7-membered nitrogen-containing heterocyclic group. More preferably X is a 4- to 6-membered nitrogen-containing heterocyclic group or a spiro 7-membered nitrogen-containing heterocyclic group, for example a 4- to 6-membered nitrogen-containing heterocyclic group. Preferably, when X is a nitrogen-containing heterocyclic group according to option (i), X is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; and unsubstituted or substituted C₁ to C₂ alkyl; wherein each substituted alkyl group is substituted with one, two or three groups independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; preferably by one or two groups independently selected from —NR$^{10}$R$^{11}$ and —N$^+$R$^{10}$R$^{11}$R$^{12}$. More preferably, X is unsubstituted or is substituted by one or two substituents selected from C₁ to C₂ alkyl; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; NR$^{10}$C(NR$^{11}$)R$^{12}$; and —C(NR$^{11}$)R$^{12}$.

Accordingly, when X is according to option (i), X is preferably a 4- to 7-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; and unsubstituted or substituted C₁ to C₂ alkyl; wherein each substituted alkyl group is substituted with one, two or three groups independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; preferably by one or two groups independently selected from —NR$^{10}$R$^{11}$ and —N$^+$R$^{10}$R$^{11}$R$^{12}$. When X is a 4- to 7-membered nitrogen-containing heterocyclic group, X is preferably selected from piperazine, piperidine, pyrrolidine and azetidine and 2,6-diazaspiro[3.3]heptane. More preferably, when X is according to option (i), X is preferably a 4- to 7- or 4- to 6-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; and C₁ to C₂ alkyl which is unsubstituted or is substituted with one or two groups independently selected from —NR$^{10}$R$^{11}$ and —N$^+$R$^{10}$R$^{11}$R$^{12}$. More preferably, when X is according to option (i), X is a 4- to 6-membered nitrogen-containing heterocyclic group or a spiro 7-membered nitrogen-containing heterocyclic group, for example a 4- to 6-membered nitrogen-containing heterocyclic group which is unsubstituted or is substituted by one or two substituents selected from C₁ to C₂ alkyl; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; NR$^{10}$C(NR$^{11}$)R$^{12}$; and —C(NR$^{11}$)R$^{12}$, more preferably by —NR$^{10}$R$^{11}$ or —N$^+$R$^{10}$R$^{11}$R$^{12}$.

Still more preferably, when X is according to option (i), X is a 4- to 6-membered nitrogen-containing heterocyclic group which is unsubstituted or is substituted by one or two substituents selected from C₁ to C₂ alkyl; —NR$^{10}$R$^{11}$; and —N$^+$R$^{10}$R$^{11}$R$^{12}$. When X is according to option (i), X is most preferably substituted by one substituent. When X is a 4- to 6-membered nitrogen-containing heterocyclic group, X is preferably selected from piperazine, piperidine, pyrrolidine and azetidine; more preferably from piperazine, piperidine and pyrrolidine; most preferably piperazine; each of which is unsubstituted or is substituted by one or two substituents selected from C₁ to C₂ alkyl; —NR$^{10}$R$^{11}$; and —N$^+$R$^{10}$R$^{11}$R$^{12}$; more preferably by one substituent selected from methyl, —NH₂ and —N$^+$Me₃. For the avoidance of doubt, a substituted nitrogen-containing heterocyclic group X may be substituted at a ring nitrogen atom (for example a piperazine ring may be substituted by one or two methyl groups so that X is 1-methylpiperazine or 1,1-dimethylpiperazin-1-ium etc.) or at a ring carbon atom (for example a pyrrolidine ring may be substituted by an —NR$^{10}$R$^{11}$ or —N$^+$R$^{10}$R$^{11}$R$^{12}$ group so that X is pyrrolidin-3-amine, N,N-dimethylpyrrolidin-3-amine; or N,N,N-trimethylpyrrolidin-3-aminium etc.)

When X is according to option (ii), X is preferably selected from C₂ to C₄ alkoxy; C₁ to C₄ alkyl; C₂ to C₄ alkenyl; C₂ to C₄ alkynyl; and —NR$^X$—C₁ to C₄ alkyl each of which is unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; or X is methoxy which is substituted by one, two or three fluorine substituents; e.g. X may be —OCF₃. More preferably, when X is according to option (ii), X is selected from C₂ to C₄ alkoxy; C₁ to C₄ alkyl; C₂ to C₄ alkenyl; C₂ to C₄ alkynyl; and —NR$^X$—C₁ to C₄ alkyl; each of which is unsubstituted or is substituted with one or two groups independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; NR$^{10}$C(NR$^{11}$)R$^{12}$; and —C(NR$^{11}$)R$^{12}$.

More preferably, when X is according to option (ii), X is selected from C₂ to C₄ alkoxy; C₁ to C₄ alkyl; C₂ to C₄ alkenyl; C₂ to C₄ alkynyl; and —NR$^X$—C₁ to C₄ alkyl; each of which is unsubstituted or is substituted with one or two groups independently selected from —NR$^{10}$R$^{11}$ and —N$^+$R$^{10}$R$^{11}$R$^{12}$. Still more preferably, when X is according to option (ii), X is selected from C₂ to C₃ alkoxy; C₁ to C₃ alkyl; C₂ to C₃ alkenyl; C₂ to C₃ alkynyl; and —NR$^X$—C₁ to C₃ alkyl; each of which is unsubstituted or is substituted with one group selected from —NR$^{10}$R$^{11}$ and —N$^+$R$^{10}$R$^{11}$R$^{12}$. In one embodiment, X is not —OMe. Most preferably, when X is according to option (ii), X is selected from C₁ to C₃ alkyl; C₂ to C₄ alkenyl; and C₂ to C₃ alkynyl, each of which is substituted with one group selected from —NR$^{10}$R$^{11}$ and —N$^+$R$^{10}$R$^{11}$R$^{12}$.

R$^X$ is typically H or C$_1$ to C$_2$ alkyl; more preferably H or methyl, most preferably H.

When X is according to option (iii), X is preferably chlorine, bromine, —OH, or methoxy; preferably methoxy or —OH, more preferably —OH.

When X is according to option (iv), X is preferably selected from C$_3$ to C$_6$ carbocyclyl; and —O—C$_3$ to C$_6$ carbocyclyl; wherein each carbocyclyl group is unsubstituted or is substituted with one or two groups independently selected from —NR$^{10}$R$^{11}$; —N$^+$R$^{10}$R$^{11}$R$^{12}$; and C$_1$ to C$_4$ alkyl which is unsubstituted or is substituted with one or two groups independently selected from —NR$^{10}$R$^{11}$; and —N$^+$R$^{10}$R$^{11}$R$^{12}$. More preferably, when X is according to option (iv), X is selected from C$_3$ to C$_4$ carbocyclyl; and —O—C$_3$ to C$_4$ carbocyclyl; wherein each carbocyclyl group is unsubstituted or is substituted with one or two groups independently selected from —NR$^{10}$R$^{11}$; —N$^+$R$^{10}$R$^{11}$R$^{12}$; and C$_1$ to C$_2$ alkyl which is unsubstituted or is substituted with one or two groups independently selected from —NR$^{10}$R$^{11}$; and —N$^+$R$^{10}$R$^{11}$R$^{12}$. Most preferably, when X is according to option (iv), X is selected from C$_4$ carbocyclyl and —O— C$_4$ carbocyclyl and is unsubstituted or is substituted with one group selected from —NR$^{10}$R$^{11}$; —N$^+$R$^{10}$R$^{11}$R$^{12}$ and C$_1$ to C$_2$ alkyl which is unsubstituted or is substituted with one or two groups independently selected from —NR$^{10}$R$^{11}$; and —N$^+$R$^{10}$R$^{11}$R$^{12}$.

Preferably, X is according to option (i), (ii) or (iii) above. More preferably, X is according to option (i) or (ii) above, or X is methoxy. More preferably, X is according to option (ii) or is methoxy, most preferably X is according to option (ii).

Preferably, therefore, each X is independently selected from:
(i) a 4- to 6-membered nitrogen-containing heterocyclic group which is unsubstituted or is substituted by one or two substituents selected from C$_1$ to C$_2$ alkyl; —NR$^{10}$R$^{11}$; and N$^+$R$^{10}$R$^{11}$R$^{12}$;
(ii) C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; each of which is unsubstituted or is substituted with one or two groups independently selected from —NR$^{10}$R$^{11}$ and —N$^+$R$^{10}$R$^{11}$R$^{12}$;
and
(iii) chlorine, bromine, —OH or methoxy;

When X is bonded to a nitrogen atom, X can also usefully be a protecting group such as Boc [$^t$Bu-OC(O)—]. Such compounds are useful as intermediates in the preparation of the compounds of the invention.

In Formula (I), m is typically 0, 1 or 2. m is preferably 0 or 1. m is more preferably 1.

When at least one group X is present in the compound of Formula (I), at least one group X is typically bonded to group Ⓐ at a different atom than that from which group Ⓐ is bonded to the moiety —(CH$_2$)$_p$-L- of Formula (I). When Ⓐ is a fused heteroaryl or heterocyclic group formed from a benzene group fused to a heterocyclic or heteroaryl ring, at least one group X is preferably bonded to Ⓐ via the benzene ring. For example, when Ⓐ is selected from benzothiazole, benzofuran, 2,3-dihydrobenzofuran, benzimidazole, benzothiophene, indole, benzoxazole and 2,3-dihydrobenzo[b][1,4]dioxine, at least one group X is preferably bonded to Ⓐ at position 1 or position 2 as indicated below (wherein ~~ indicates the point of attachment of Ⓐ to the moiety —(CH$_2$)$_p$-L- in Formula (I)); more preferably a group X is bonded to Ⓐ at position 1.

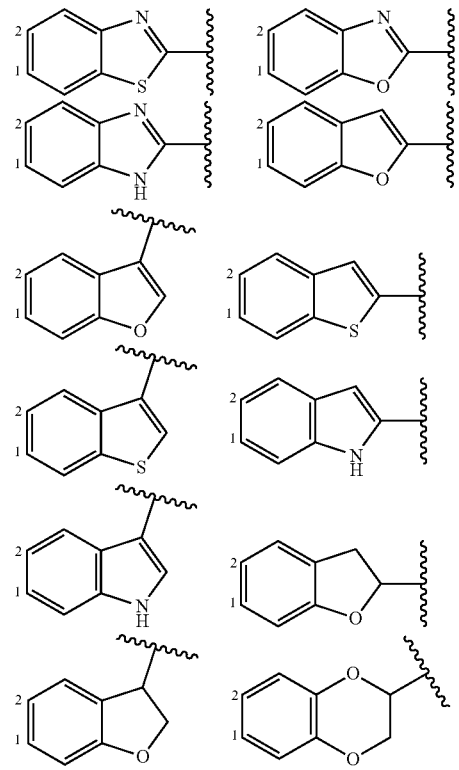

In Formula (I), each R$^{10}$, R$^{11}$, R$^{12}$, R$^{13}$ and R$^{14}$ is independently H or methyl. When comprised in a —NR$^{10}$R$^{11}$ group, R$^{10}$ and R$^{11}$ are each preferably H. When comprised in a —N$^+$R$^{10}$R$^{11}$R$^{12}$ group, R$^{10}$, R$^{11}$ and R$^{12}$ are each preferably methyl. When comprised in a —NR$^{10}$C (NR$^{11}$)NR$^{12}$R$^{13}$ group, R$^{10}$, R$^{11}$R$^{12}$ and R$^{13}$ are each preferably H. When comprised in a —NR$^{10}$C(N$^+$R$^{11}$R$^{12}$)NR$^{13}$R$^{14}$ group, R$^{10}$, R$^{13}$ and R$^{14}$ are each preferably H, and R$^{11}$ and R$^{12}$ are preferably methyl. When comprised in a NR$^{10}$C(NR$^{11}$)R$^{12}$ group, R$^{10}$ is preferably H and R$^{12}$ is preferably methyl. When comprised in a —C(NR$^{11}$)R$^{12}$ group, R$^{12}$ is preferably methyl.

Preferably, therefore, in Formula (I):
Ⓐ is a benzene or is a 5- to 10-membered heteroaryl group comprising at least one nitrogen atom selected from secondary, tertiary and quaternary nitrogen atom(s);
m is an integer from 0, 1 or 2; and
each X is independently selected from:
(i) a 4- to 7-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$) NR$^{12}$R$^{13}$; —NR$^{10}$C(N$^+$R$^{11}$R$^{12}$)NR$^{13}$R$^{14}$; —NR$^{10}$C (NR$^{11}$)R$^{12}$; —C(NR$^{11}$)R$^{12}$; and C$_1$ to C$_2$ alkyl which is unsubstituted or is substituted with one or two groups independently selected from —NR$^{10}$R$^{11}$ and —N$^+$R$^{10}$R$^{11}$R$^{12}$;
(ii) C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; each of which is unsubstituted or is substituted with one or two groups independently selected from —OH, halogen; —NR$^{10}$R$^{11}$; —N$^+$R$^{10}$R$^{11}$R$^{12}$; —NR$^{10}$C(NR$^{11}$) NR$^{12}$R$^{13}$; —NR$^{10}$C(N$^+$R$^{11}$R$^{12}$)NR$^{13}$R$^{14}$; —NR$^{10}$C $(NR^{11})R^{12}$; and —$C(NR^{11})R^{12}$; or X is methoxy which is substituted by one, two or three fluorine substituents;
(iii) halogen, —OH and unsubstituted methoxy; and
(iv) $C_3$ to $C_4$ carbocyclyl; and —O—$C_3$ to $C_4$ carbocyclyl; wherein each carbocyclyl group is unsubstituted or is substituted with one or two groups independently selected from —$NR^{10}R^{11}$; —$N^+R^{10}R^{11}R^{12}$; and $C_1$ to $C_2$ alkyl which is unsubstituted or is substituted with one or two groups independently selected from —$NR^{10}R^{11}$; and —$N^+R^{10}R^{11}R^{12}$.

More preferably, therefore, in Formula (I):
Ⓐ is selected from pyrazole, benzene, benzothiazole, benzofuran, benzimidazole, benzothiophene, benzoxazole, indole, isoquinoline, 2,3-dihydrobenzofuran, 2,3-dihydrobenzo[b][1,4]dioxine, and 4,5,6,7-tetrahydrothiazolo[5,4-c]pyridine;
m is 0, 1 or 2;
each X is independently selected from:
  (i) a 4- to 6-membered nitrogen-containing heterocyclic group which is unsubstituted or is substituted by one substituent selected from $C_1$ to $C_2$ alkyl; —$NR^{10}R^{11}$; and —$N^+R^{10}R^{11}R^{12}$;
  (ii) $C_2$ to $C_3$ alkoxy; $C_1$ to $C_3$ alkyl; $C_2$ to $C_3$ alkenyl; $C_2$ to $C_3$ alkynyl; and —$NR^X$—$C_1$ to $C_3$ alkyl; each of which is unsubstituted or is substituted with one group selected from —$NR^{10}R^{11}$ and —$N^+R^{10}R^{11}R^{12}$;
  and
  (iii) chlorine, bromine, —OH and methoxy.

Still more preferably, in Formula (I):
Ⓐ is selected from benzene, benzothiazole, benzofuran, and indole;
m is 1;
X is independently selected from:
  (i) piperazine, piperidine, pyrrolidine and azetidine each of which is unsubstituted or is substituted by one substituent selected from methyl, —$NH_2$ and —$N^+Me_3$;
  and
  (ii) $C_1$ to $C_3$ alkyl; $C_2$ to $C_3$ alkenyl and $C_2$ to $C_3$ alkynyl, each of which is substituted with one group selected from —$NR^{10}R^{11}$ and —$N^+R^{10}R^{11}R^{12}$;

In some particularly preferred compounds of Formula (I):
$R^1$ is selected from H and methyl;
$R^2$ is selected from H and methyl;
each $R^3$ group is independently selected from halogen; —OH; and —$NH_2$;
n is 0 or 1;
$R^4$ is H;
q is 0;
p is 0 or 1;
L is selected from the moieties

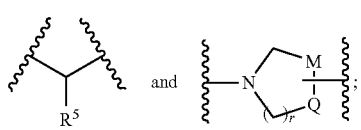

$R^5$ is selected from —$R^6$, —$C(O)OR^6$; —$C(O)NR^{10}R^6$; and —$C(O)R^6$, preferably from —$R^6$ and —$C(O)OR^6$;

$R^6$ is selected from:
  (i) H;
  (ii) a $C_1$ to $C_4$ alkyl group which is unsubstituted or is substituted with one or two groups, preferably one group, independently selected from —OH; —$NR^{10}R^{11}$; and —$N^+R^{10}R^{11}R^{12}$;
  and
  (iii) a 5- to 6-membered heterocyclic group which is unsubstituted or is substituted by one or two substituents independently selected from $C_1$ to $C_2$ alkyl groups which are each independently unsubstituted or substituted with one group selected from —OH: —$NR^{10}R^{11}$; —$N^+R^{10}R^{11}R^{12}$;
the moiety

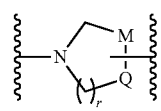

is selected from piperidinylene or pyrrolidinylene; and
A, m X are as defined herein.

Preferably, in these particularly preferred compounds:
Ⓐ is selected from pyrazole, benzene, benzothiazole, benzofuran, benzimidazole, benzothiophene, benzoxazole, indole, isoquinoline, 2,3-dihydrobenzofuran, 2,3-dihydrobenzo[b][1,4]dioxine, and 4,5,6,7-tetrahydrothiazolo[5,4-c]pyridine;
m is 0, 1 or 2; and
each X is independently selected from:
  (i) a 4- to 6-membered nitrogen-containing heterocyclic group which is unsubstituted or is substituted by one or two substituents selected from $C_1$ to $C_2$ alkyl; —$NR^{10}R^{11}$; and —$N^+R^{10}R^{11}R^{12}$;
  (ii) $C_2$ to $C_4$ alkoxy; $C_1$ to $C_4$ alkyl; $C_2$ to $C_4$ alkenyl; $C_2$ to $C_4$ alkynyl; and —$NR^X$—$C_1$ to $C_4$ alkyl; each of which is unsubstituted or is substituted with one or two groups independently selected from —$NR^{10}R^{11}$ and —$N^+R^{10}R^{11}R^{12}$;
  and
  (iii) chlorine, bromine, —OH and methoxy.

In some most preferred compounds of Formula (I):
$R^1$ is H;
$R^2$ is H;
n is 0;
$R^4$ is H;
q is 0;
p is 0;
L is the moiety

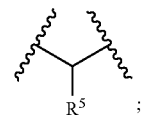

$R^5$ is —$R^6$; and
$R^6$ is selected from:
  (i) H;
  (ii) a $C_1$ to $C_2$ alkyl group which is unsubstituted or is substituted with one group selected from —$NR^{10}R^{11}$ and —$N^+R^{10}R^{11}R^{12}$;
  and
  (iii) piperidine and piperazine, each of which is unsubstituted or is substituted by one or two methyl substituents;

A is selected from benzene, benzothiazole, benzofuran, and indole;

m is 1; and

X is independently selected from:
(i) piperazine, piperidine, pyrrolidine and azetidine each of which is unsubstituted or is substituted by one substituent selected from methyl, —NH$_2$ and —N$^+$Me$_3$;
and
(ii) C$_1$ to C$_3$ alkyl, C$_2$ to C$_3$ alkenyl and C$_2$ to C$_3$ alkynyl, each of which is substituted with one group selected from —NR$^{10}$R$^{11}$ and —N$^+$R$^{10}$R$^{11}$R$^{12}$.

In this embodiment, it is particularly preferred that L represents —CH$_2$—.

Particularly preferred compounds of the invention are:

2-(2-{[(5-chloro-1H-1,3-benzodiazol-2-yl)methyl]carbamoyl}-2,3-dihydro-1H-inden-2-yl)acetic acid;
2-[2-(3-isoquinolylmethylcarbamoyl)indan-2-yl]acetic acid;
2-[2-[(1-methylpyrazol-4-yl)methylcarbamoyl]indan-2-yl]acetic acid;
2-[2-[(5-methoxy-1H-benzimidazol-2-yl)methylcarbamoyl]indan-2-yl]acetic acid;
2-(2-{[(1-benzofuran-2-yl)methyl]carbamoyl}-2,3-dihydro-1H-inden-2-yl)acetic acid;
2-(2-{[(5-methyl-1-benzofuran-2-yl)methyl]carbamoyl}-2,3-dihydro-1H-inden-2-yl)acetic acid;
2-[2-[(5-methyl-2,3-dihydrobenzofuran-2-yl)methylcarbamoyl]indan-2-yl]acetic acid;
2-[2-[[1-(3-chlorophenyl)pyrrolidin-3-yl]carbamoyl]indan-2-yl]acetic acid;
2-[2-[(1-methylindol-2-yl)methylcarbamoyl]indan-2-yl]acetic acid;
2-(2-{[(1,3-benzothiazol-2-yl)methyl]carbamoyl}-2,3-dihydro-1H-inden-2-yl)acetic acid;
2-(2-{[2-(3-methyl-1-benzofuran-2-yl)methyl]carbamoyl}-2,3-dihydro-1H-inden-2-yl)acetic acid;
2-[2-[2-(1H-benzimidazol-2-yl)ethylcarbamoyl]indan-2-yl]acetic acid;
2-[2-[2-(4-hydroxyphenyl)ethylcarbamoyl]indan-2-yl]acetic acid;
2-[2-[2-(1H-indol-3-yl)ethylcarbamoyl]indan-2-yl]acetic acid;
2-[2-[(4-hydroxyphenyl)methylcarbamoyl]indan-2-yl]acetic acid;
2-[2-(benzylcarbamoyl)indan-2-yl]acetic acid;
2-[2-(2,3-dihydro-1,4-benzodioxin-3-ylmethylcarbamoyl)indan-2-yl]acetic acid;
2-[2-[(5-bromobenzofuran-2-yl)methylcarbamoyl]indan-2-yl]acetic acid;
2-[2-[2-(benzofuran-2-yl)ethylcarbamoyl]indan-2-yl]acetic acid;
2-[2-[(2-methylbenzofuran-3-yl)methylcarbamoyl]indan-2-yl]acetic acid;
2-[2-[(1-methylimidazol-4-yl)methylcarbamoyl]indan-2-yl]acetic acid;
2-[2-[2-(1,3-benzothiazol-2-yl)ethylcarbamoyl]indan-2-yl]acetic acid;
2-[2-(benzothiophen-2-ylmethylcarbamoyl)indan-2-yl]acetic acid;
2-[2-[(5-methoxy-1,3-benzothiazol-2-yl)methylcarbamoyl]indan-2-yl]acetic acid;
2-[2-[(5-chloro-1,3-benzothiazol-2-yl)methylcarbamoyl]indan-2-yl]acetic acid;
2-[2-(1H-indol-3-ylmethylcarbamoyl)indan-2-yl]acetic acid;
2-[2-[2-(1H-indol-2-yl)ethylcarbamoyl]indan-2-yl]acetic acid;
2-[2-(benzofuran-3-ylmethylcarbamoyl)indan-2-yl]acetic acid;
2-[2-(1H-indol-2-ylmethylcarbamoyl)indan-2-yl]acetic acid;
2-[2-[2-(benzothiophen-2-yl)ethylcarbamoyl]indan-2-yl]acetic acid;
2-[2-[2-(1,3-benzoxazol-2-yl)ethylcarbamoyl]indan-2-yl]acetic acid;
2-[2-[[6-(3-aminopropyl)-1,3-benzothiazol-2-yl]methylcarbamoyl]indan-2-yl]acetic acid;
2-[2-[(6-methoxy-1,3-benzothiazol-2-yl)methylcarbamoyl]indan-2-yl]acetic acid;
2-[2-(4,5,6,7-tetrahydrothiazolo[5,4-c]pyridin-2-ylmethylcarbamoyl)indan-2-yl]acetic acid;
(2-{[(2S)-1-hydroxy-3-(1H-indol-3-yl)propan-2-yl]carbamoyl}-1,3-dihydroinden-2-yl)acetic acid;
(2-{[(1S)-1-{[2-(dimethylamino)ethyl]carbamoyl}-2-(1H-indol-3-yl)ethyl]carbamoyl}-1,3-dihydroinden-2-yl)acetic acid;
2-(2-{[(2S)-3-(1H-indol-3-yl)-1-[(1-methylpiperidin-4-yl)oxy]-1-oxopropan-2-yl]carbamoyl}-2,3-dihydro-1H-inden-2-yl)acetic acid;
(2-{[(1 S)-2-(1H-indol-3-yl)-1-{[2-(trimethylammonio)ethyl]carbamoyl}ethyl]carbamoyl}-1,3-dihydroinden-2-yl)acetate
2-[2-[[6-[3-(dimethylamino)prop-1-ynyl]-1,3-benzothiazol-2-yl]methylcarbamoyl]indan-2-yl]acetic acid;
2-[2-[[6-[3-(dimethylamino)propyl]-1,3-benzothiazol-2-yl]methylcarbamoyl]indan-2-yl]acetic acid;
3-[2-[[[2-(carboxymethyl)indane-2-carbonyl]amino]methyl]-1,3-benzothiazol-6-yl]propyl-trimethyl-ammonium;
2-[2-[[6-[(E)-3-aminoprop-1-enyl]-1,3-benzothiazol-2-yl]methylcarbamoyl]indan-2-yl]acetic acid;
2-[2-[[5-(3-aminopropyl)-1,3-benzothiazol-2-yl]methylcarbamoyl]indan-2-yl]acetic acid;
2-[2-[(6-piperazin-1-yl-1,3-benzothiazol-2-yl)methylcarbamoyl]indan-2-yl]acetic acid;
2-[2-[[6-(4-methylpiperazin-1-yl)-1,3-benzothiazol-2-yl]methylcarbamoyl]indan-2-yl]acetic acid;
2-[2-[[6-(4,4-dimethylpiperazin-4-ium-1-yl)-1,3-benzothiazol-2-yl]methylcarbamoyl]indan-2-yl]acetic acid;
(S)-2-(2-((1-(tert-butoxy)-3-(1H-indol-3-yl)-1-oxopropan-2-yl)carbamoyl)-2,3-dihydro-1H-inden-2-yl)acetic acid;
(S)-2-(2-((1-amino-3-(4-hydroxyphenyl)-1-oxopropan-2-yl)carbamoyl)-2,3-dihydro-1H-inden-2-yl)acetic acid;
(2-(carboxymethyl)-2,3-dihydro-1H-indene-2-carbonyl)-L-tyrosine;
(2-(carboxymethyl)-2,3-dihydro-1H-indene-2-carbonyl)-L-tryptophan;
2-(2-(((1H-benzo[d]imidazol-2-yl)methyl)carbamoyl)-2,3-dihydro-1H-inden-2-yl)acetic acid;
(S)-2-(2-((1-amino-3-(1H-indol-3-yl)-1-oxopropan-2-yl)carbamoyl)-2,3-dihydro-1H-inden-2-yl)acetic acid;
(S)-2-(2-((3-(1H-indol-3-yl)-1-methoxy-1-oxopropan-2-yl)carbamoyl)-2,3-dihydro-1H-inden-2-yl)acetic acid;
2-(2-((thiazol-2-ylmethyl)carbamoyl)-2,3-dihydro-1H-inden-2-yl)acetic acid;
2-(2-((quinolin-2-ylmethyl)carbamoyl)-2,3-dihydro-1H-inden-2-yl)acetic acid;
2-(2-(((1-methyl-1H-benzo[d]imidazol-2-yl)methyl)carbamoyl)-2,3-dihydro-1H-inden-2-yl)acetic acid;
2-[2-(benzofuran-3-ylmethylcarbamoyl)indan-2-yl]acetic acid;
2-[2-[[(1R*)-1-(benzofuran-2-yl)ethyl]carbamoyl]indan-2-yl]acetic acid;

2-[2-[[(1S*)-1-(benzofuran-2-yl)ethyl]carbamoyl]indan-2-yl]acetic acid;
2-(2-(((4-fluorobenzo[d]thiazol-2-yl)methyl)carbamoyl)-2,3-dihydro-1H-inden-2-yl)acetic acid;
2-(2-(((4-bromobenzo[d]thiazol-2-yl)methyl)carbamoyl)-2,3-dihydro-1H-inden-2-yl)acetic acid;
2-(2-(((4-methoxybenzo[d]thiazol-2-yl)methyl)carbamoyl)-2,3-dihydro-1H-inden-2-yl)acetic acid;
2-(2-(((4-iodobenzo[d]thiazol-2-yl)methyl)carbamoyl)-2,3-dihydro-1H-inden-2-yl)acetic acid;
2-(2-(((4-ethoxybenzo[d]thiazol-2-yl)methyl)carbamoyl)-2,3-dihydro-1H-inden-2-yl)acetic acid;
2-(2-(((4-methylbenzo[d]thiazol-2-yl)methyl)carbamoyl)-2,3-dihydro-1H-inden-2-yl)acetic acid;
2-(2-(((4-morpholinobenzo[d]thiazol-2-yl)methyl)carbamoyl)-2,3-dihydro-1H-inden-2-yl)acetic acid;
2-(2-(((6-(3-(dimethylamino)azetidin-1-yl)benzo[d]thiazol-2-yl)methyl)carbamoyl)-2,3-dihydro-1H-inden-2-yl)acetic acid;
2-[2-[[6-[3-(trimethylammonio)azetidin-1-yl]-1,3-benzothiazol-2-yl]methylcarbamoyl]indan-2-yl]acetate;
2-[2-[[6-(2-aminoethylamino)-1,3-benzothiazol-2-yl]methylcarbamoyl]indan-2-yl]acetic acid;
2-[2-[[6-[3-(2-aminoethyl)azetidin-1-yl]-1,3-benzothiazol-2-yl]methylcarbamoyl]indan-2-yl]acetic acid;
2-[2-[[6-(6-methyl-2,6-diazaspiro[3.3]heptan-2-yl)-1,3-benzothiazol-2-yl]methylcarbamoyl]indan-2-yl]acetic acid;
2-[2-[[5-(2-aminoethylamino)-1,3-benzothiazol-2-yl]methylcarbamoyl]indan-2-yl]acetic acid;
2-[2-[[5-(3-aminoazetidin-1-yl)-1,3-benzothiazol-2-yl]methylcarbamoyl]indan-2-yl]acetic acid;
2-[2-[[5-[3-(dimethylamino)azetidin-1-yl]-1,3-benzothiazol-2-yl]methylcarbamoyl]indan-2-yl]acetic acid;
2-[2-[[5-[3-(trimethylammonio)azetidin-1-yl]-1,3-benzothiazol-2-yl]methylcarbamoyl]indan-2-yl]acetate;
2-[2-[[5-[2-(dimethylamino)ethylamino]-1,3-benzothiazol-2-yl]methylcarbamoyl]indan-2-yl]acetic acid;
2-[2-[[5-[2-(trimethylammonio)ethylamino]-1,3-benzothiazol-2-yl]methylcarbamoyl]indan-2-yl]acetate;
2-[2-[[6-(3-aminocyclobutoxy)-1,3-benzothiazol-2-yl]methylcarbamoyl]indan-2-yl]acetic acid;
2-[2-[[6-[3-(dimethylamino)cyclobutoxy]-1,3-benzothiazol-2-yl]methylcarbamoyl]indan-2-yl]acetic acid;
2-[2-[[6-(2-aminoethyl)-1,3-benzothiazol-2-yl]methylcarbamoyl]indan-2-yl]acetic acid;
2-[2-[[6-[(dimethylamino)methyl]-1,3-benzothiazol-2-yl]methylcarbamoyl]indan-2-yl]acetic acid;
2-[2-[[6-[(trimethylammonio)methyl]-1,3-benzothiazol-2-yl]methylcarbamoyl]indan-2-yl]acetate;
2-[2-[[5-(2-aminoethyl)-1,3-benzothiazol-2-yl]methylcarbamoyl]indan-2-yl]acetic acid;
2-[2-[[5-[(dimethylamino)methyl]-1,3-benzothiazol-2-yl]methylcarbamoyl]indan-2-yl]acetic acid;
2-[2-[[5-[(trimethylammonio)methyl]-1,3-benzothiazol-2-yl]methylcarbamoyl]indan-2-yl]acetate;
2-[2-[[6-[3-(trimethylammonio)prop-1-ynyl]-1,3-benzothiazol-2-yl]methylcarbamoyl]indan-2-yl]acetate;
2-[2-[[5-[(E)-3-aminoprop-1-enyl]-1,3-benzothiazol-2-yl]methylcarbamoyl]indan-2-yl]acetic acid;
2-[2-[[5-[3-(dimethylamino)prop-1-ynyl]-1,3-benzothiazol-2-yl]methylcarbamoyl]indan-2-yl]acetic acid;
2-[2-[[5-[3-(dimethylamino)propyl]-1,3-benzothiazol-2-yl]methylcarbamoyl]indan-2-yl]acetic acid;
2-[2-[[5-[3-(trimethylammonio)propyl]-1,3-benzothiazol-2-yl]methylcarbamoyl]indan-2-yl]acetate;
2-(2-(((6-((1 r,3r)-3-((dimethylamino)methyl)cyclobutyl)benzo[d]thiazol-2-yl)methyl)carbamoyl)-2,3-dihydro-1H-inden-2-yl)acetic acid;
2-[2-[[6-[(1r,3r)-3-[(trimethylammonio)methyl]cyclobutyl]-1,3-benzothiazol-2-yl]methylcarbamoyl]indan-2-yl]acetate;
2-(2-(((6-((1s,3 s)-3-((dimethylamino)methyl)cyclobutyl)benzo[d]thiazol-2-yl)methyl)carbamoyl)-2,3-dihydro-1H-inden-2-yl)acetic acid;
2-[2-[[6-[(1 s,3s)-3-[(trimethylammonio)methyl]cyclobutyl]-1,3-benzothiazol-2-yl]methylcarbamoyl]indan-2-yl]acetate;
2-[2-[[6-[2-(dimethylamino)ethyl]-1,3-benzothiazol-2-yl]methylcarbamoyl]indan-2-yl]acetic acid;
2-[2-[[6-[2-(trimethylammonio)ethyl]-1,3-benzothiazol-2-yl]methylcarbamoyl]indan-2-yl]acetate;
2-[2-[[5-[2-(dimethylamino)ethyl]-1,3-benzothiazol-2-yl]methylcarbamoyl]indan-2-yl]acetic acid;
2-[2-[[5-[2-(trimethylammonio)ethyl]-1,3-benzothiazol-2-yl]methylcarbamoyl]indan-2-yl]acetate;
2-[2-[[6-[3-(aminomethyl)azetidin-1-yl]-1,3-benzothiazol-2-yl]methylcarbamoyl]indan-2-yl]acetic acid;
2-[2-[[6-(3-aminoazetidin-1-yl)-1,3-benzothiazol-2-yl]methylcarbamoyl]indan-2-yl]acetic acid;
2-[2-[[6-[(3 S)-3-aminopyrrolidin-1-yl]-1,3-benzothiazol-2-yl]methylcarbamoyl]indan-2-yl]acetic acid;
2-[2-[[6-[(3R)-3-aminopyrrolidin-1-yl]-1,3-benzothiazol-2-yl]methylcarbamoyl]indan-2-yl]acetic acid;
2-[2-[[5-[(3 S)-3-aminopyrrolidin-1-yl]-1,3-benzothiazol-2-yl]methylcarbamoyl]indan-2-yl]acetic acid;
2-[2-[[5-[(3R)-3-aminopyrrolidin-1-yl]-1,3-benzothiazol-2-yl]methylcarbamoyl]indan-2-yl]acetic acid;
2-[2-[[6-[2-(dimethylamino)ethylamino]-1,3-benzothiazol-2-yl]methylcarbamoyl]indan-2-yl]acetic acid;
2-[2-[[5-(4-methylpiperazin-1-yl)-1,3-benzothiazol-2-yl]methylcarbamoyl]indan-2-yl]acetic acid;
2-[2-[(6-hydroxy-1,3-benzothiazol-2-yl)methylcarbamoyl]indan-2-yl]acetic acid;
2-[2-[(6-ethoxy-1,3-benzothiazol-2-yl)methylcarbamoyl]indan-2-yl]acetic acid;
2-[2-[[6-(2-hydroxyethoxy)-1,3-benzothiazol-2-yl]methylcarbamoyl]indan-2-yl]acetic acid;
2-[2-[[6-[2-(dimethylamino)ethoxy]-1,3-benzothiazol-2-yl]methylcarbamoyl]indan-2-yl]acetic acid;
2-[2-[[6-[2-(trimethylammonio)ethoxy]-1,3-benzothiazol-2-yl]methylcarbamoyl]indan-2-yl]acetate;
2-[2-[[5-[2-(dimethylamino)ethoxy]-1,3-benzothiazol-2-yl]methylcarbamoyl]indan-2-yl]acetic acid;
2-[2-[[5-[2-(trimethylammonio)ethoxy]-1,3-benzothiazol-2-yl]methylcarbamoyl]indan-2-yl]acetate;
2-[2-[(5,6-dimethoxy-1,3-benzothiazol-2-yl)methylcarbamoyl]indan-2-yl]acetic acid;
2-[2-([1,3]dioxolo[4,5-f][1,3]benzothiazol-6-ylmethylcarbamoyl)indan-2-yl]acetic acid;
(S)-2-(2-((1-((1,1-dimethylpiperidin-1-ium-4-yl)oxy)-3-(1H-indol-3-yl)-1-oxopropan-2-yl)carbamoyl)-2,3-dihydro-1H-inden-2-yl)acetate;
(S)-2-(2-((2-(1H-indol-3-yl)-1-(5-methyl-1,3,4-oxadiazol-2-yl)ethyl)carbamoyl)-2,3-dihydro-1H-inden-2-yl)acetic acid;
(S)-2-(2-((1-(5-(aminomethyl)-1,3,4-oxadiazol-2-yl)-2-(1H-indol-3-yl)ethyl)carbamoyl)-2,3-dihydro-1H-inden-2-yl)acetic acid;
(S)-2-(2-((1-(5-(2-aminopropan-2-yl)-1,3,4-oxadiazol-2-yl)-2-(1H-indol-3-yl)ethyl)carbamoyl)-2,3-dihydro-1H-inden-2-yl)acetic acid;

2-(2-((benzo[d]thiazol-2-ylmethyl)carbamoyl)-5,6-difluoro-2,3-dihydro-1H-inden-2-yl)acetic acid;
2-(2-((benzo[d]thiazol-2-ylmethyl)carbamoyl)-5,6-dichloro-2,3-dihydro-1H-inden-2-yl)acetic acid;
2-(2-(((5-(3-(dimethylamino)azetidin-1-yl)-6-methoxybenzo[d]thiazol-2-yl)methyl)carbamoyl)-2,3-dihydro-1H-inden-2-yl)acetic acid;
2-(2-(((6-methoxy-5-(3-(trimethylammonio)azetidin-1-yl)benzo[d]thiazol-2-yl)methyl)carbamoyl)-2,3-dihydro-1H-inden-2-yl)acetate;
2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetic acid;
2-(5,6-difluoro-2-((((6-methoxy-5-(3-(trimethylammonio)propoxy)benzo[d]thiazol-2-yl)methyl)carbamoyl)-2,3-dihydro-1H-inden-2-yl)acetate;
2-(2-(((5-(2-(dimethylamino)ethoxy)-6-methoxybenzo[d]thiazol-2-yl)methyl)carbamoyl)-2,3-dihydro-1H-inden-2-yl)acetic acid;
2-[2-(thiazolo[4,5-c]pyridin-2-ylmethylcarbamoyl)indan-2-yl]acetic acid;
2-[2-[[6-(trifluoromethoxy)-1,3-benzothiazol-2-yl]methylcarbamoyl]indan-2-yl]acetic acid;
2-[2-[(5-methyl-6,7-dihydro-4H-thiazolo[5,4-c]pyridin-2-yl)methylcarbamoyl]indan-2-yl]acetic acid; and
2-[2-[(5-hydroxy-1,3-benzothiazol-2-yl)methylcarbamoyl]indan-2-yl]acetic acid;
and pharmaceutically acceptable salts thereof.

More particularly preferred compounds of the invention are:
2-(2-{[(5-chloro-1H-1,3-benzodiazol-2-yl)methyl]carbamoyl}-2,3-dihydro-1H-inden-2-yl)acetic acid;
2-[2-(3-isoquinolylmethylcarbamoyl)indan-2-yl]acetic acid;
2-[2-[(1-methylpyrazol-4-yl)methylcarbamoyl]indan-2-yl]acetic acid;
2-[2-[(5-methoxy-1H-benzimidazol-2-yl)methylcarbamoyl]indan-2-yl]acetic acid;
2-(2-{[(1-benzofuran-2-yl)methyl]carbamoyl}-2,3-dihydro-1H-inden-2-yl)acetic acid;
2-(2-{[(5-methyl-1-benzofuran-2-yl)methyl]carbamoyl}-2,3-dihydro-1H-inden-2-yl)acetic acid;
2-[2-[(5-methyl-2,3-dihydrobenzofuran-2-yl)methylcarbamoyl]indan-2-yl]acetic acid;
2-[2-[[1-(3-chlorophenyl)pyrrolidin-3-yl]carbamoyl]indan-2-yl]acetic acid;
2-[2-[(1-methylindol-2-yl)methylcarbamoyl]indan-2-yl]acetic acid;
2-(2-{[(1,3-benzothiazol-2-yl)methyl]carbamoyl}-2,3-dihydro-1H-inden-2-yl)acetic acid;
2-(2-{[2-(3-methyl-1-benzofuran-2-yl)methyl]carbamoyl}-2,3-dihydro-1H-inden-2-yl)acetic acid;
2-[2-[2-(1H-benzimidazol-2-yl)ethylcarbamoyl]indan-2-yl]acetic acid;
2-[2-[2-(4-hydroxyphenyl)ethylcarbamoyl]indan-2-yl]acetic acid;
2-[2-[2-(1H-indol-3-yl)ethylcarbamoyl]indan-2-yl]acetic acid;
2-[2-[(4-hydroxyphenyl)methylcarbamoyl]indan-2-yl]acetic acid;
2-[2-(benzylcarbamoyl)indan-2-yl]acetic acid;
2-[2-(2,3-dihydro-1,4-benzodioxin-3-ylmethylcarbamoyl)indan-2-yl]acetic acid;
2-[2-[(5-bromobenzofuran-2-yl)methylcarbamoyl]indan-2-yl]acetic acid;
2-[2-[2-(benzofuran-2-yl)ethylcarbamoyl]indan-2-yl]acetic acid;
2-[2-[(2-methylbenzofuran-3-yl)methylcarbamoyl]indan-2-yl]acetic acid;
2-[2-[(1-methylimidazol-4-yl)methylcarbamoyl]indan-2-yl]acetic acid;
2-[2-[2-(1,3-benzothiazol-2-yl)ethylcarbamoyl]indan-2-yl]acetic acid;
2-[2-(benzothiophen-2-ylmethylcarbamoyl)indan-2-yl]acetic acid;
2-[2-[(5-methoxy-1,3-benzothiazol-2-yl)methylcarbamoyl]indan-2-yl]acetic acid;
2-[2-[(5-chloro-1,3-benzothiazol-2-yl)methylcarbamoyl]indan-2-yl]acetic acid;
2-[2-(1H-indol-3-ylmethylcarbamoyl)indan-2-yl]acetic acid;
2-[2-[2-(1H-indol-2-yl)ethylcarbamoyl]indan-2-yl]acetic acid;
2-[2-(benzofuran-3-ylmethylcarbamoyl)indan-2-yl]acetic acid;
2-[2-(1H-indol-2-ylmethylcarbamoyl)indan-2-yl]acetic acid;
2-[2-[2-(benzothiophen-2-yl)ethylcarbamoyl]indan-2-yl]acetic acid;
2-[2-[2-(1,3-benzoxazol-2-yl)ethylcarbamoyl]indan-2-yl]acetic acid;
2-[2-[[6-(3-aminopropyl)-1,3-benzothiazol-2-yl]methylcarbamoyl]indan-2-yl]acetic acid;
2-[2-[(6-methoxy-1,3-benzothiazol-2-yl)methylcarbamoyl]indan-2-yl]acetic acid;
2-[2-(4,5,6,7-tetrahydrothiazolo[5,4-c]pyridin-2-ylmethylcarbamoyl)indan-2-yl]acetic acid;
(2-{[(2S)-1-hydroxy-3-(1H-indol-3-yl)propan-2-yl]carbamoyl}-1,3-dihydroinden-2-yl)acetic acid;
(2-{[(1S)-1-{[2-(dimethylamino)ethylcarbamoyl}-2-(1H-indol-3-yl)ethyl]carbamoyl}-1,3-dihydroinden-2-yl)acetic acid;
2-(2-{[(2S)-3-(1H-indol-3-yl)-1-[(1-methylpiperidin-4-yl)oxy]-1-oxopropan-2-yl]carbamoyl}-2,3-dihydro-1H-inden-2-yl)acetic acid;
(2-{[(1S)-2-(1H-indol-3-yl)-1-{[2-(trimethylammonio)ethyl]carbamoyl}ethyl]carbamoyl}-1,3-dihydroinden-2-yl)acetate
2-[2-[[6-[3-(dimethylamino)prop-1-ynyl]-1,3-benzothiazol-2-yl]methylcarbamoyl]indan-2-yl]acetic acid;
2-[2-[[6-[3-(dimethylamino)propyl]-1,3-benzothiazol-2-yl]methylcarbamoyl]indan-2-yl]acetic acid;
3-[2-[[[2-(carboxymethyl)indane-2-carbonyl]amino]methyl]-1,3-benzothiazol-6-yl]propyl-trimethyl-ammonium;
2-[2-[[6-[(E)-3-aminoprop-1-enyl]-1,3-benzothiazol-2-yl]methylcarbamoyl]indan-2-yl]acetic acid;
2-[2-[[5-(3-aminopropyl)-1,3-benzothiazol-2-yl]methylcarbamoyl]indan-2-yl]acetic acid;
2-[2-[(6-piperazin-1-yl-1,3-benzothiazol-2-yl)methylcarbamoyl]indan-2-yl]acetic acid;
2-[2-[[6-(4-methylpiperazin-1-yl)-1,3-benzothiazol-2-yl]methylcarbamoyl]indan-2-yl]acetic acid; and
2-[2-[[6-(4,4-dimethylpiperazin-4-ium-1-yl)-1,3-benzothiazol-2-yl]methylcarbamoyl]indan-2-yl]acetic acid;
and pharmaceutically acceptable salts thereof.

Further preferred compounds according to the invention and which can be synthesized in accordance with the methods described herein include:
2-[2-[2-(1-methyl-4-piperidyl)ethylcarbamoyl]indan-2-yl]acetic acid;
2-[2-[2-(1,1-dimethylpiperidin-1-ium-4-yl)ethylcarbamoyl]indan-2-yl]acetate;

2-[2-[(1-benzylpyrrolidin-3-yl)carbamoyl]indan-2-yl]acetic acid;
2-[2-[(1,3-dimethylbenzimidazol-3-ium-2-yl)methylcarbamoyl]indan-2-yl]acetate;
2-[2-[(2-methylisoquinolin-2-ium-3-yl)methylcarbamoyl]indan-2-yl]acetate;
2-[2-[(1-methyl-4-piperidyl)methylcarbamoyl]indan-2-yl]acetic acid;
2-[2-[(1,1-dimethylpiperidin-1-ium-4-yl)methylcarbamoyl]indan-2-yl]acetate;
2-[2-[2-(1-methylimidazol-4-yl)ethylcarbamoyl]indan-2-yl]acetic acid;
2-[2-[(5,5-dimethyl-6,7-dihydro-4H-thiazolo[5,4-c]pyridin-5-ium-2-yl)methylcarbamoyl]indan-2-yl]acetate;
2-[2-[[(3R)-1-phenylpyrrolidin-3-yl]carbamoyl]indan-2-yl]acetic acid;
2-[2-[[(3S)-1-phenylpyrrolidin-3-yl]carbamoyl]indan-2-yl]acetic acid;
2-[2-(imidazo[1,2-a]pyridin-2-ylmethylcarbamoyl)indan-2-yl]acetic acid;
2-[2-(1,3-benzoxazol-2-ylmethylcarbamoyl)indan-2-yl]acetic acid;
2-[2-[(3-hydroxyphenyl)methylcarbamoyl]indan-2-yl]acetic acid;
2-[2-[(5-methylthiazolo[4,5-c]pyridin-5-ium-2-yl)methylcarbamoyl]indan-2-yl]acetate;
2-[2-[(5-hydroxy-2-pyridyl)methylcarbamoyl]indan-2-yl]acetic acid; and
2-[2-[1,3-benzothiazol-2-ylmethyl(methyl)carbamoyl]indan-2-yl]acetic acid.

Synthesis

The compounds of the invention can be prepared by any suitable method. For example, as described in more detail below, lactone (2) is typically commercially available or can be prepared using techniques familiar to those skilled in the art, for example using methods described in WO 2006/29153. Reaction of (2) with amine (A) ([(X)$_m$-Ⓐ—(CH$_2$)$_p$-L-(CH$_2$)$_q$—NHR$^4$]) yields products (3) and (1) which can be separated using conventional techniques such as column chromatography. Esters and other derivatives of the carboxylic acid group in 1 can be made by well known techniques in the art.

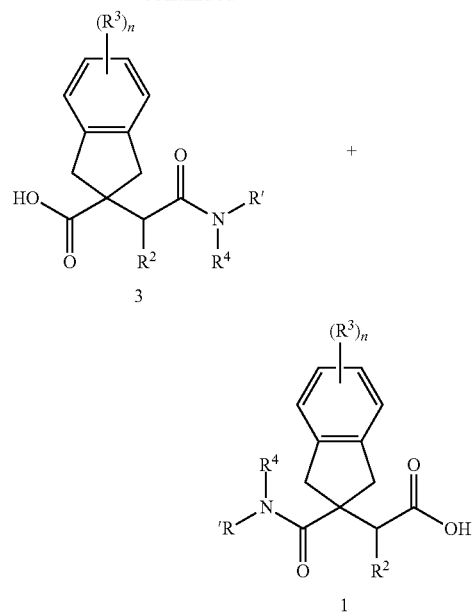

Alternatively, lactone (2) can be reacted with an alcohol (B) to yield products (4) and (5) as shown in Scheme B. This reaction yields a regioisomeric mixture of major isomer (4) and minor isomer (5) which are separable by standard column chromatography or recrystallization. Suitable alcohols are benzyl alcohol or 3,4-dimethoxybenzyl alcohol. Reaction of pure acid (4) with amine (C) by standard amide coupling methods known to those skilled in the art yields compound (6), as shown in Scheme C. Subsequent ester removal, for example by hydrogenation (for benzyl ester) or trifluoroacetic acid treatment for (3,4-dimethoxybenzyl ester) yields amide (1).

Scheme A

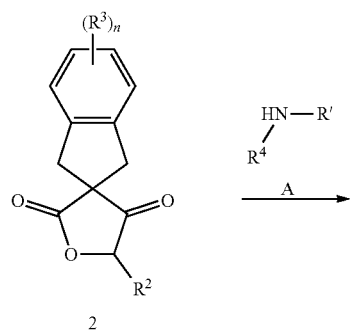

Scheme B

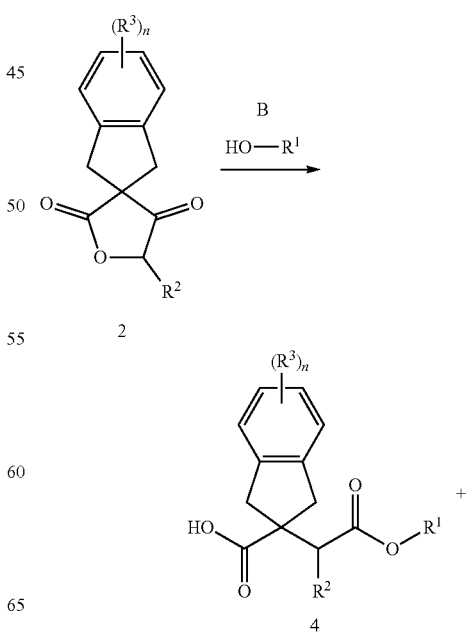

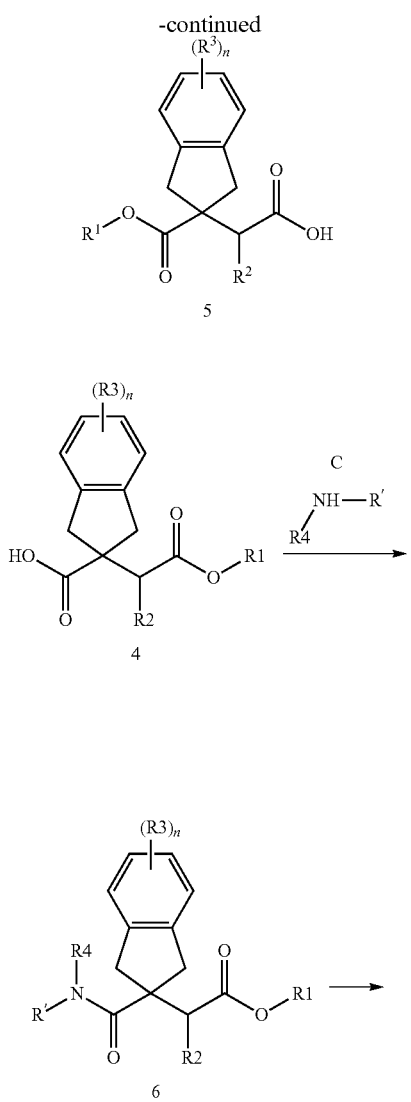

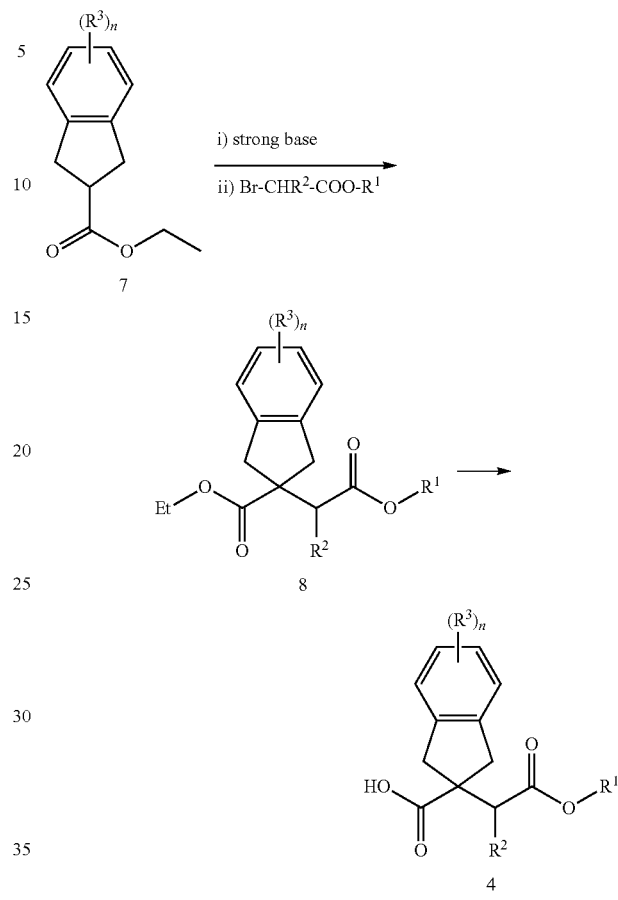

As described below, intermediate (4) can also be made via regiospecific synthesis from commercially available components by reaction of an indanyl derivative (7) with base, followed by alkylation (Bell, I. M. and Stump, C. A., WO2006/29153; Robinson, R. P. et al, Bioorganic and Medicinal Chemistry Letters, 1996, 1719); Scheme C. Basic hydrolysis of (8) yields intermediate (4). Amide formation and optional treatment with e.g. TFA to remove the ester then affords the desired acid (1).

Amidation of intermediate (4) with compound (10) [$(X)_m$-Ⓐ—$(CH_2)_p$-L-$(CH_2)_q$-$NHR^4$] yields the desired amide. Compound (10) can be made by routine methods available to those skilled in the art, or can be obtained commercially.

Some preferred compounds of the invention are benzothiazole compounds. Substituted benzothiazoles can be synthesized as shown in Scheme D. This method is particularly suitable for 4-substituted benzothiazoles.

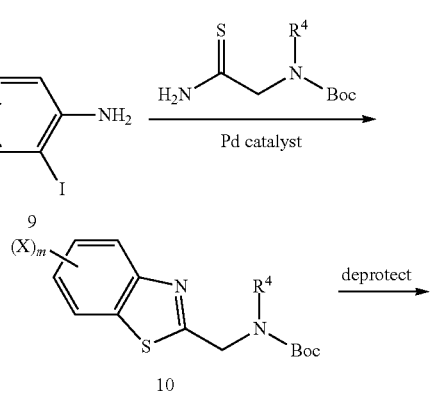

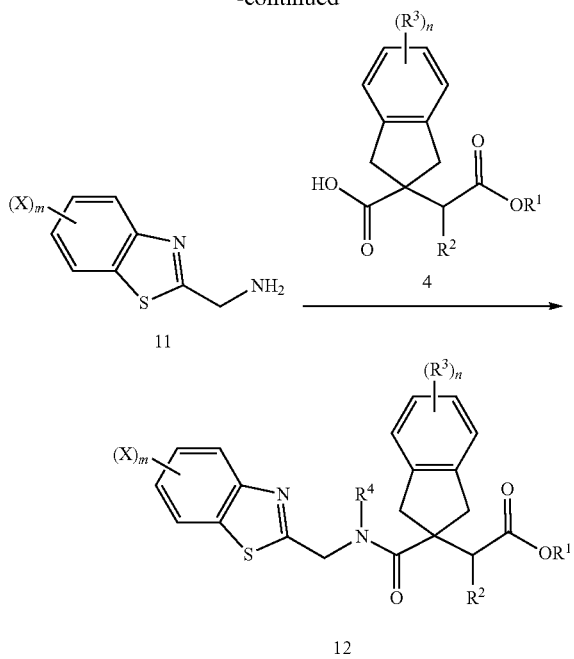

Palladium catalysed cyclisation of aniline (9) with Boc-protected thioamide glycine derivative followed by Boc deprotection affords primary amine (11) Amide formation and optional treatment with e.g. TFA to remove the $R^1$ ester then affords the corresponding carboxylic acid. Compound (9) can be made by routine methods available to those skilled in the art, or can be obtained commercially e.g. as aniline. For compounds of Formula (I) wherein the moiety $—(CH_2)_p$-L-$(CH_2)_q—$ is not $—CH_2—$, the reagent used in the aniline cyclisation reaction is $H_2N—C(S)—(CH_2)_p$-L-$(CH_2)_q—NR^4$-Boc. Such reagents can be made by routine methods available to those skilled in the art, or can be obtained commercially.

Substituted benzothiazoles can also be synthesized as shown in Scheme E. This method is particularly suitable for 5- or 6-substituted benzothiazoles.

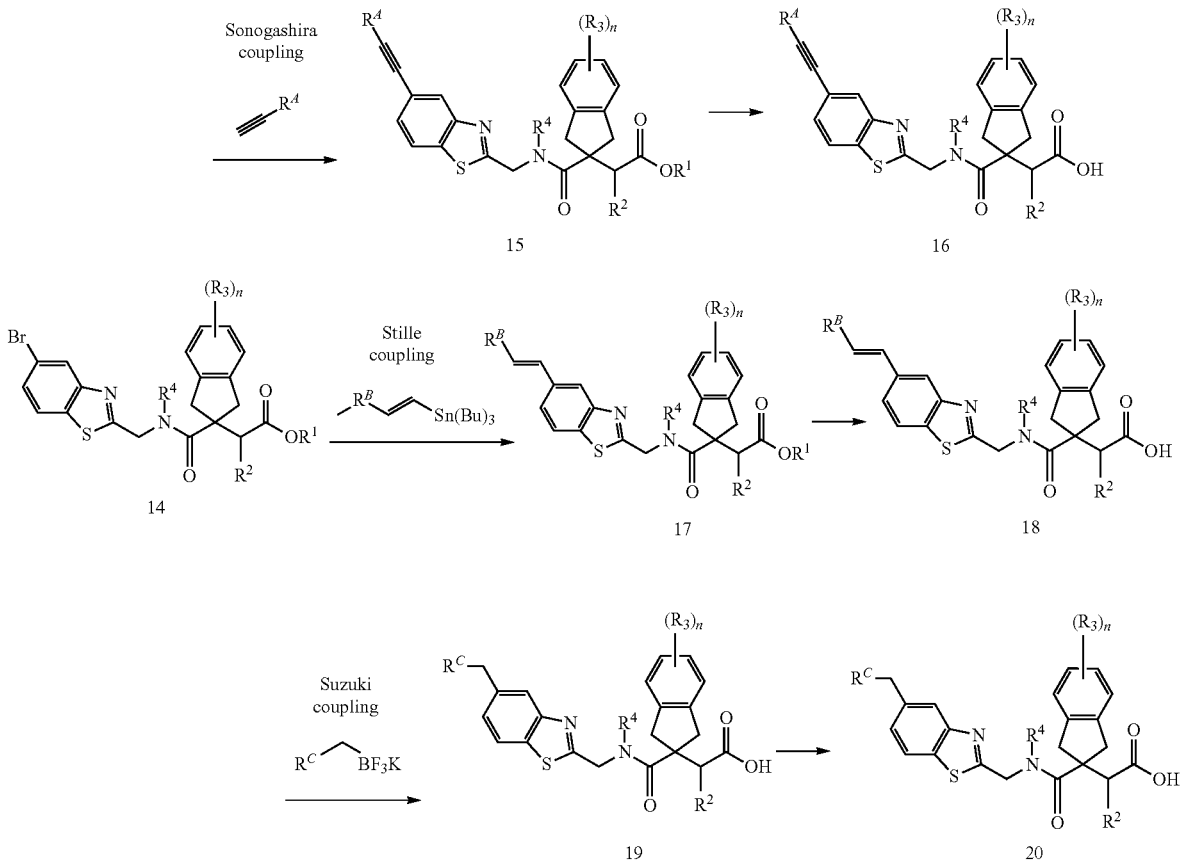

Intermediate (14) can be obtained in accordance with the method shown in Scheme D, e.g. starting with 5-bromo-2-iodo-aniline (or 4-bromo-2-iodo-aniline for 6-substituted benzothiazole). Sonogashira, Stille or Suzuki coupling reactions routine to those skilled in the art afford (15), (17) and (19) which after optional treatment with TFA to remove the $R^1$ ester give the corresponding carboxylic acids (16), (18) and (20). In Scheme E, $R^A$, $R^B$ and $R^C$ together with the alkyl, alkenyl or alkynyl moieties to which they are attached (e.g. in (15)-(20)) correspond to group X in Formula (I). The alkyl, alkenyl or alkynyl moieties used in the Sonogashira, Stille or Suzuki coupling reactions can be made by routine methods available to those skilled in the art, or can be obtained commercially.

Substituted benzothiazoles can also be made using the methods shown in Scheme F. These Chan-Lam coupling reactions are particularly suitable to synthesis of 5- or 6-substituted benzothiazole derivatives.

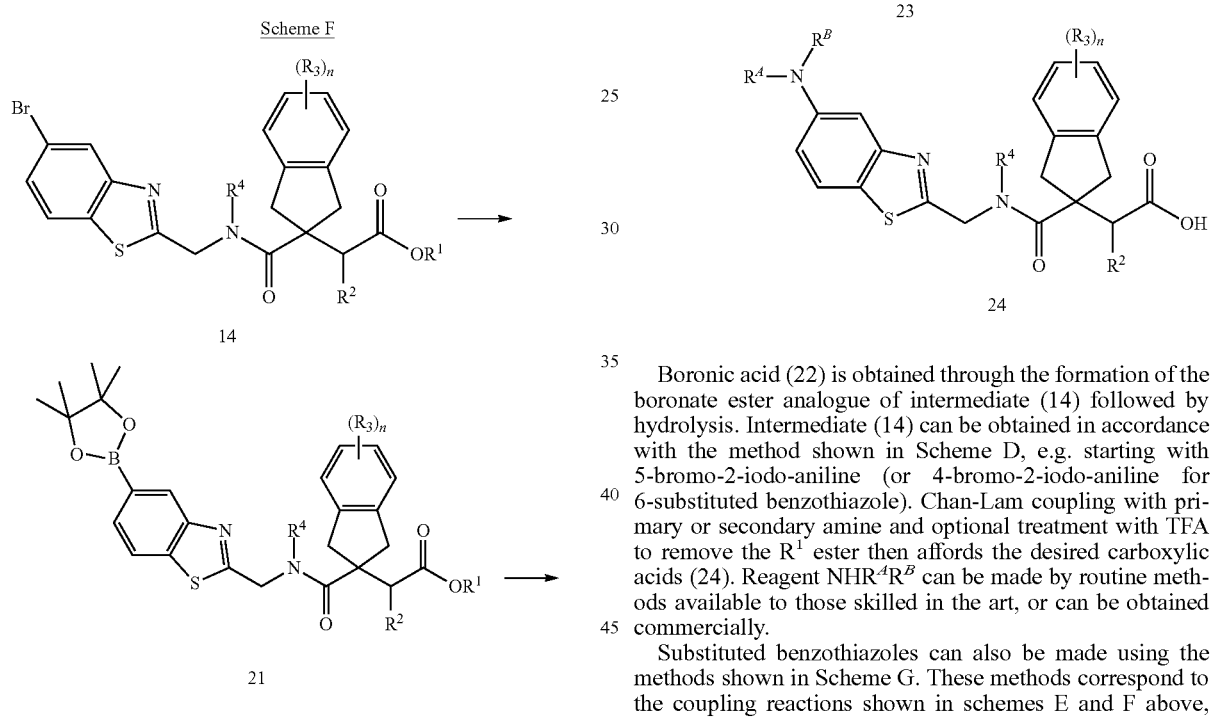

Boronic acid (22) is obtained through the formation of the boronate ester analogue of intermediate (14) followed by hydrolysis. Intermediate (14) can be obtained in accordance with the method shown in Scheme D, e.g. starting with 5-bromo-2-iodo-aniline (or 4-bromo-2-iodo-aniline for 6-substituted benzothiazole). Chan-Lam coupling with primary or secondary amine and optional treatment with TFA to remove the $R^1$ ester then affords the desired carboxylic acids (24). Reagent $NHR^A R^B$ can be made by routine methods available to those skilled in the art, or can be obtained commercially.

Substituted benzothiazoles can also be made using the methods shown in Scheme G. These methods correspond to the coupling reactions shown in schemes E and F above, conducted before the peptide coupling step.

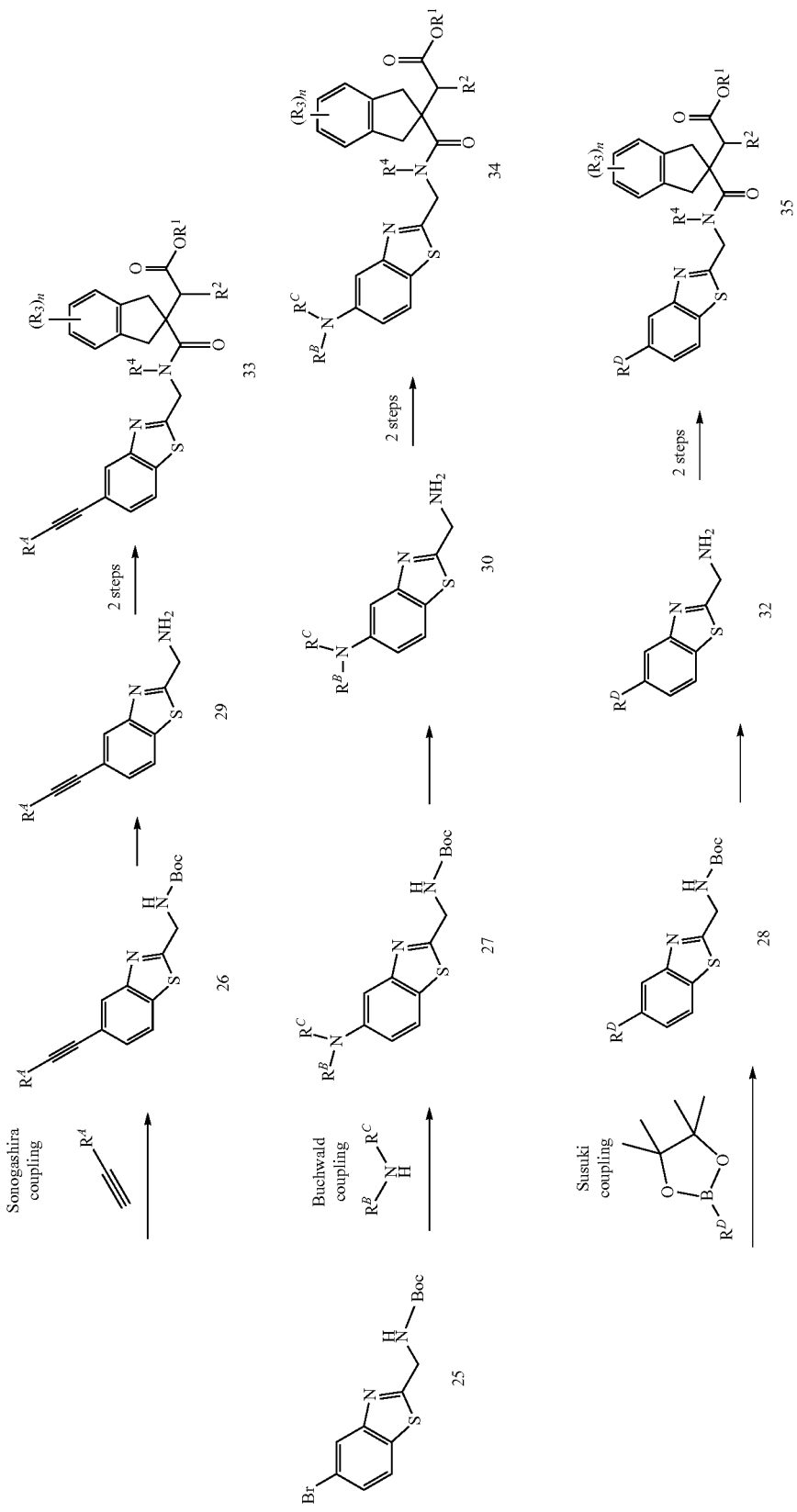

Note that this method has been used to prepare 5- and 6-substituted benzothiazole compounds. This method is based on the introduction of substituents in 5- or 6-position of the benzothiazole before the peptide coupling step. Intermediate (25) is obtained following method D above starting with 5-bromo-2-iodo-aniline (or 4-bromo-2-iodo-aniline for 6-substituted benzothiazole). Sonogashira, Buchwald or Suzuki coupling reactions afford (26), (27) and (28) respectively. Removal of the Boc protection with TFA affords the primary amines (29), (30) and (31) which lead to carboxylic acids (when $R^1$ is H) (33), (34) and (35) following method D.

Substituted benzothiazoles can also be made using the methods shown in Scheme H. These methods correspond to a Buchwald coupling reaction on a carboxylic acid scaffold. This method is suitable for compounds of Formula (I) wherein $R^1$ is H.

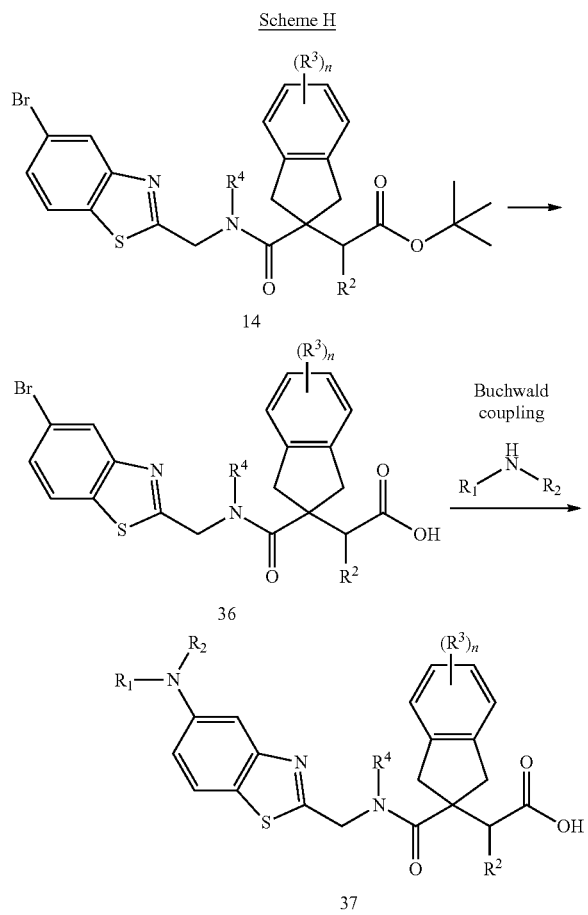

Scheme H

Note that this method has been used to prepare 5- and 6-substituted benzothiazole compounds. 5-substituted benzothiazoles (37) are obtained after Buchwald coupling on 5-bromo benzothiazole carboxylic acid intermediate (36) which is obtained after treatment with TFA and removal of the tert-butyl ester of (14).

Therapeutic Efficacy

The compounds of the present invention are therapeutically useful. The present invention therefore provides compounds as described herein, for use in medicine. The present invention provides compounds as described herein, for use in treating the human or animal body. For the avoidance of doubt, the agent may comprise a compound of the invention in the form of a solvate. Also provided is a pharmaceutical composition comprising a compound of the invention together with a pharmaceutically acceptable carrier or diluent. Typically, the composition contains up to 85 wt % of a compound of the invention. More typically, it contains up to 50 wt % of a compound of the invention. Preferred pharmaceutical compositions are sterile and pyrogen free. Further, when the pharmaceutical compositions provided by the invention contain a compound of the invention which is optically active, the compound of the invention is typically a substantially pure optical isomer.

The composition of the invention may be provided as a kit comprising instructions to enable the kit to be used in the methods described herein or details regarding which subjects the method may be used for.

As explained above, the compounds of the invention are useful in treating or preventing bacterial infection. In particular, they are useful as inhibitors of LasB, in particular LasB of *Pseudomonas aeruginosa* (PA). The inhibition of LasB in the bacteria prevents LasB secreted by bacteria from hydrolysing host tissue and host immune-response proteins, thereby supporting the subject in its natural response to bacterial infection and inflammation. They are therefore useful as standalone adjuncts in antibacterial therapy, for example in chemotherapy regimes. Further, the compounds are useful in inhibiting biofilm formation, and/or in disrupting a biofilm. This activity in preventing biofilm formation or disrupting established biofilms facilitates antibiotic agents in eradication of bacterial infection. It also facilitates the host's own immune system in attacking the bacterial infection. The compounds may therefore be used as stand alone antibacterial agents, or they may be used in combination with antibiotic agents to enhance the action of the antibiotic agent.

The present invention therefore also provides a combination comprising (i) a compound of the invention as described herein and (ii) an antibiotic agent. The compound of the invention and the antibiotic agent may be provided in a single formulation, or they may be separately formulated. Where separately formulated, the two agents may be administered simultaneously or separately. They may be provided in the form of a kit, optionally together with instructions for their administration.

Where formulated together, the two active agents may be provided as a pharmaceutical composition comprising (i) a compound of the invention as described herein and (ii) a further antibacterial compound; and (iii) a pharmaceutically acceptable carrier or diluent.

Preferably, the antibiotic agent is efficacious against *Pseudomonas* infection. Most preferably, the antibiotic is tobramycin, neomycin, streptomycin, gentamycin, ceftazidime, ticarcillin, piperacillin, tazobactam, imipenem, meropenem, rifampicin, ciprofloxacin, amikacin, colistin, aztreonam or levofloxacin.

The combinations of the invention are also useful in treating or preventing bacterial infection. The present invention therefore provides a combination as described herein for use in treating or preventing bacterial infection. Also provided is a method for preventing or treating bacterial infection in a subject, which method comprises administering to said subject an effective amount of a combination as described herein. Further provided is a compound of the invention as described herein for the manufacture of a medicament for use in treating or preventing bacterial infection in combination with an antibiotic agent. Also provided is a combination as described herein for the manufacture of a medicament for use in preventing or treating bacterial infection.

In one aspect, the subject is a mammal, in particular a human. However, it may be non-human. Preferred non-human animals include, but are not limited to, primates, such as marmosets or monkeys, commercially farmed animals, such as horses, cows, sheep or pigs, and pets, such as dogs, cats, mice, rats, guinea pigs, ferrets, gerbils or hamsters. The subject can be any animal that is capable of being infected by a bacterium.

The compounds and combinations described herein are useful in the treatment of bacterial infection which occurs after a relapse following an antibiotic treatment. The compounds and combinations can therefore be used in the treatment of a patient who has previously received antibiotic treatment for the (same episode of) bacterial infection.

The bacterium causing the infection may be any bacterium expressing LasB or an analogue thereof. Typically the bacterium causing the infection expresses LasB. The bacterium may, for instance, be any bacterium that can form a biofilm. The bacterium may be Gram-positive or Gram-negative. In a preferred instance the bacterium is Gram-negative. The bacterium may in particular be a pathogenic bacterium.

The bacterial infection may be caused by *Bacillus, Pseudomonas, Staphylococcus, Streptococcus, Listeria, Escherichia* or *Burkholderia*. For example, the bacterium may be one selected from *Staphylococcus aureus, Haemophilus influenza, Pseudomonas aeruginosa* and *Burkholderia cepacia*.

In one preferred instance, the bacterium may be one selected from a bacterium of the family Pseudomonadaceae. For example, the bacterium may be selected from one of the following genera: *Pseudomonas, Azomonas, Azomonotrichon, Azorhizophilus, Azotobacter, Cellvibrio, Mesophilobacter, Rhizobacter, Rugamonas* and *Serpens*. Preferably the bacterium is a *Pseudomonas*, particularly where the condition to be treated is pneumonia. The bacterium may be an opportunistic pathogen. The bacterium may be selected from *Pseudomonas aeruginosa, Pseudomonas oryzihabitans*, and *Pseudomonas plecoglossicida*, and most preferably, the bacterium is *Pseudomonas aeruginosa* (PA).

The compound or combination of the invention may be used to treat or prevent infections and conditions caused by any one or a combination of the above-mentioned bacteria. In particular, the compound or combination of the invention may be used in the treatment or prevention of pneumonia. The compound or combination may also be used in the treatment of septic shock, urinary tract infection, and infections of the gastrointestinal tract, skin or soft tissue.

The compounds and combinations are particularly useful in the treatment of patients suffering from cystic fibrosis. Preferably, the compound or combination of the invention may be used in the treatment or prevention of pneumonia in a subject suffering from cystic fibrosis. For example, the subject may have any of the six CFTR mutation classes, and/or may be infected by or chronically colonised by PA. The compounds and combinations of the invention may also be used in the treatment of neutropenic patients.

A compound or combination of the invention can be administered to the subject in order to prevent the onset or reoccurrence of one or more symptoms of the bacterial infection. This is prophylaxis. In this embodiment, the subject can be asymptomatic. The subject is typically one that has been exposed to the bacterium. A prophylactically effective amount of the agent or formulation is administered to such a subject. A prophylactically effective amount is an amount which prevents the onset of one or more symptoms of the bacterial infection.

A compound or combination of the invention can be administered to the subject in order to treat one or more symptoms of the bacterial infection. In this embodiment, the subject is typically symptomatic. A therapeutically effective amount of the agent or formulation is administered to such a subject. A therapeutically effective amount is an amount effective to ameliorate one or more symptoms of the disorder.

The compound or combination of the invention may be administered in a variety of dosage forms. Thus, it can be administered orally, for example as tablets, troches, lozenges, aqueous or oily suspensions, dispersible powders or granules. Formulation composition of the invention may also be administered parenterally, whether subcutaneously, intravenously, intramuscularly, intrasternally, transdermally or by infusion techniques. The compound or combination may also be administered as a suppository. Preferably, compound or combination may be administered via inhaled (aerosolised) or intravenous administration, most preferably by inhaled (aerosolised) administration.

The compound or combination of the invention is typically formulated for administration with a pharmaceutically acceptable carrier or diluent. For example, solid oral forms may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

The compound or combination of the invention may be formulated for inhaled (aerosolised) administration as a solution or suspension. The compound or combination of the invention may be administered by a metered dose inhaler (MDI) or a nebulizer such as an electronic or jet nebulizer. Alternatively, the compound or combination of the invention may be formulated for inhaled administration as a powdered drug, such formulations may be administered from a dry powder inhaler (DPI). When formulated for inhaled administration, the compound or combination of the invention may be delivered in the form of particles which have a mass median aerodynamic diameter (MMAD) of from 1 to 100 μm, preferably from 1 to 50 μm, more preferably from 1 to 20 μm such as from 3 to 10 μm, e.g. from 4 to 6 μm. When the compound or combination of the invention is delivered as a nebulized aerosol, the reference to particle diameters defines the MMAD of the droplets of the aerosol. The MMAD can be measured by any suitable technique such as laser diffraction.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol.

The suspension or solutions for intramuscular injections or inhalation may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for inhalation, injection or infusion may contain as carrier, for example, sterile water or preferably they may be in the form of sterile, aqueous, isotonic saline solutions. Pharmaceutical compositions suitable for delivery by needleless injection, for example, transdermally, may also be used.

A therapeutically or prophylactically effective amount of the compound of the invention is administered to a subject. The dose may be determined according to various parameters, especially according to the compound used; the age, weight and condition of the subject to be treated; the route of administration; and the required regimen. Again, a physician will be able to determine the required route of administration and dosage for any particular subject. A typical daily dose is from about 0.01 to 100 mg per kg, preferably from about 0.1 mg/kg to 50 mg/kg, e.g. from about 1 to 10 mg/kg of body weight, according to the activity of the specific inhibitor, the age, weight and conditions of the subject to be treated, the type and severity of the disease and the frequency and route of administration. Preferably, daily dosage levels are from 5 mg to 2 g.

The antibacterial properties of the compounds described herein mean that they are also useful in the treatment of bacterial infection in vitro, i.e. other than by the treatment of human or animal subjects. Thus, the invention also provides a cleaning composition comprising a indane derivative of Formula (I) or a salt thereof. The cleaning composition may further comprise, for example, a detergent, a surfactant (including ionic and non-ionic surfactants), a diluent, a bleach (including a hypochlorite such as sodium hypochlorite or calcium hypochlorite, chlorine, chlorine dioxide, hydrogen peroxide or an adduct thereof, sodium perborate, and sodium percarbonate), an alcohol (such as ethanol or isopropanol), or a disinfectant. Typically, the disinfectant may be selected from benzyl-4-chlorophenol, amylphenol, phenylphenol, glutaraldehyde, alkyl dimethyl benzyl ammonium chloride, alkyl dimethyl ethylbenzyl ammonium chloride, iodine, peracetic acid and chlorine dioxide. Typically, the detergent may be an alkaline detergent such as sodium hydroxide, sodium metasilicate, or sodium carbonate, or an acid detergent such as hydrochloric acid, nitric acid, sulfuric acid, phosphoric acid, citric acid, or tartaric acid.

The invention further provides the use of the indane derivative of Formula (I) as described herein for the prevention or treatment of bacterial contamination in vitro. Such use may be an in vitro method for the prevention or treatment of bacterial infection which comprises a step of treatment of an object with a compound or combination of the invention. Such use is a non-therapeutic use and may involve, for example, prevention or treatment of bacterial contamination on a surface, such as a surface of an indwelling medical device, or an object used in a clinical setting. The surface may be the surface of a catheter, a nebulizer, a ventilator, or a face mask. Typically, the bacterial contamination is caused by any bacteria described herein. Preferably, the bacteria is *Pseudomonas aeruginosa*.

The following Examples illustrate the invention. They do not however, limit the invention in any way. In this regard, it is important to understand that the particular assay used in the Examples section is designed only to provide an indication of biological activity. There are many assays available to determine biological activity, and a negative result in any one particular assay is therefore not determinative.

Experimental Details

General Synthetic Methodology

As described below, there are eight main synthetic methods to the compounds of the invention.

Method A. Non-Regioselective Ring Opening of Lactone (2)

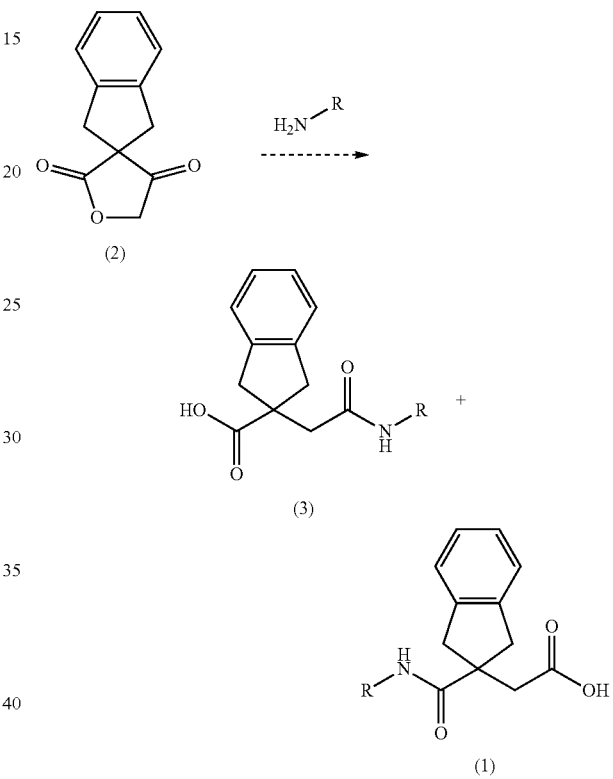

Lactone (2) is commercially available from suppliers such as Enamine and is also readily prepared from cyclisation of the corresponding commercially-available diacid with acetyl chloride (Bell, I. M. and Stump, C. A., WO 2006/29153).

Reaction of (2) with amines gives a regioisomeric mixture of major isomer (3) and minor isomer (1) which are separable by standard column chromatography.

Method B. Regioselective Synthesis of Key Intermediate (4)

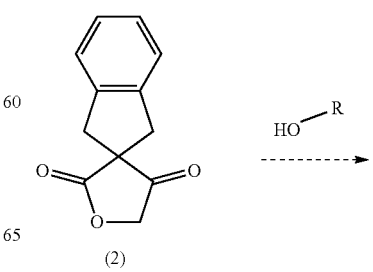

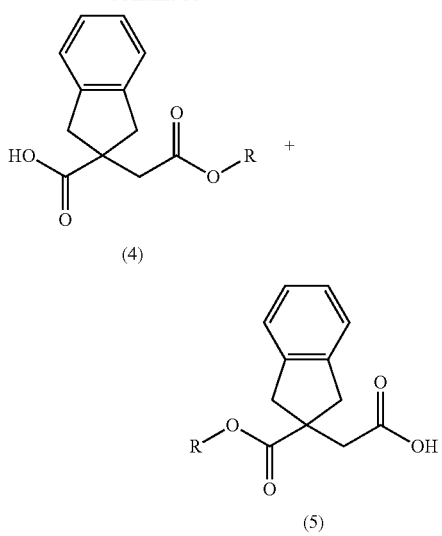

Lactone (2) can be reacted with alcohols ROH to give a regioisomeric mixture of major isomer (4) and minor isomer (5) which are separable by standard column chromatography or recrystallization. Suitable alcohols are benzyl alcohol or 3,4-dimethoxybenzyl alcohol.

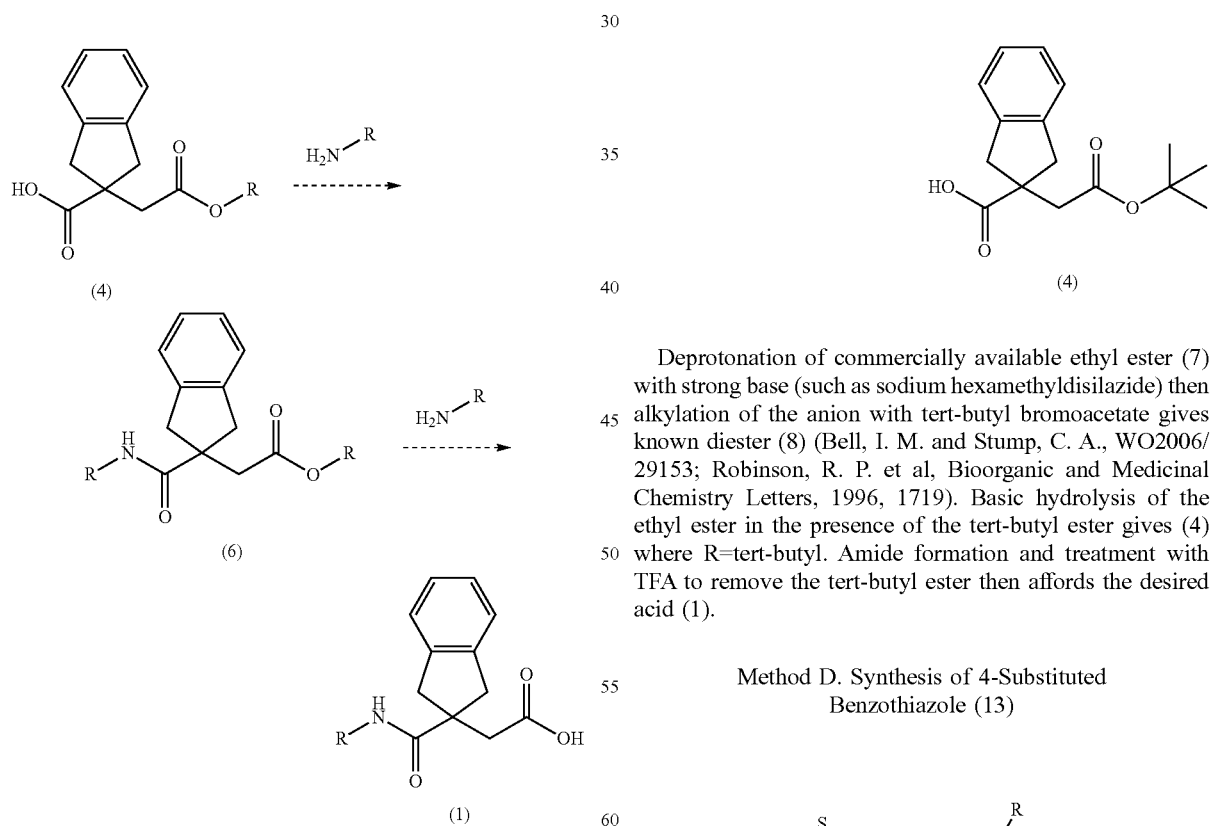

Amide formation can be performed on pure acid (4) by standard amide coupling methods to give (6) followed by ester removal for example by hydrogenation (for benzyl ester) or trifluoroacetic acid treatment (for 3,4-dimethoxybenzyl ester) then gives amide (1).

Method C. Regiospecific Synthesis of Key Intermediate (4)

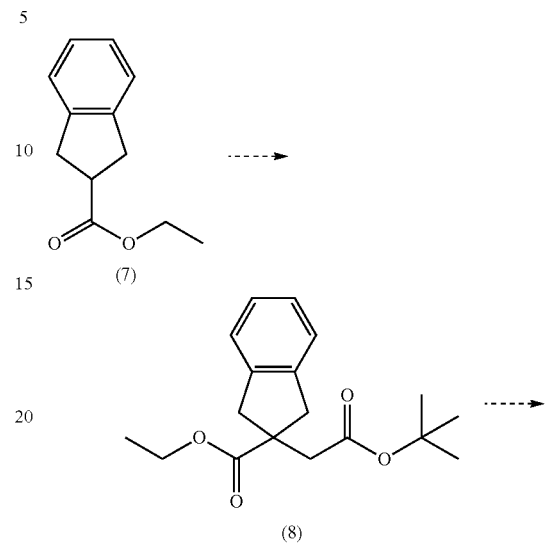

Deprotonation of commercially available ethyl ester (7) with strong base (such as sodium hexamethyldisilazide) then alkylation of the anion with tert-butyl bromoacetate gives known diester (8) (Bell, I. M. and Stump, C. A., WO2006/29153; Robinson, R. P. et al, Bioorganic and Medicinal Chemistry Letters, 1996, 1719). Basic hydrolysis of the ethyl ester in the presence of the tert-butyl ester gives (4) where R=tert-butyl. Amide formation and treatment with TFA to remove the tert-butyl ester then affords the desired acid (1).

Method D. Synthesis of 4-Substituted Benzothiazole (13)

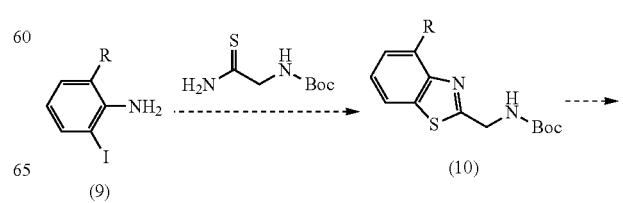

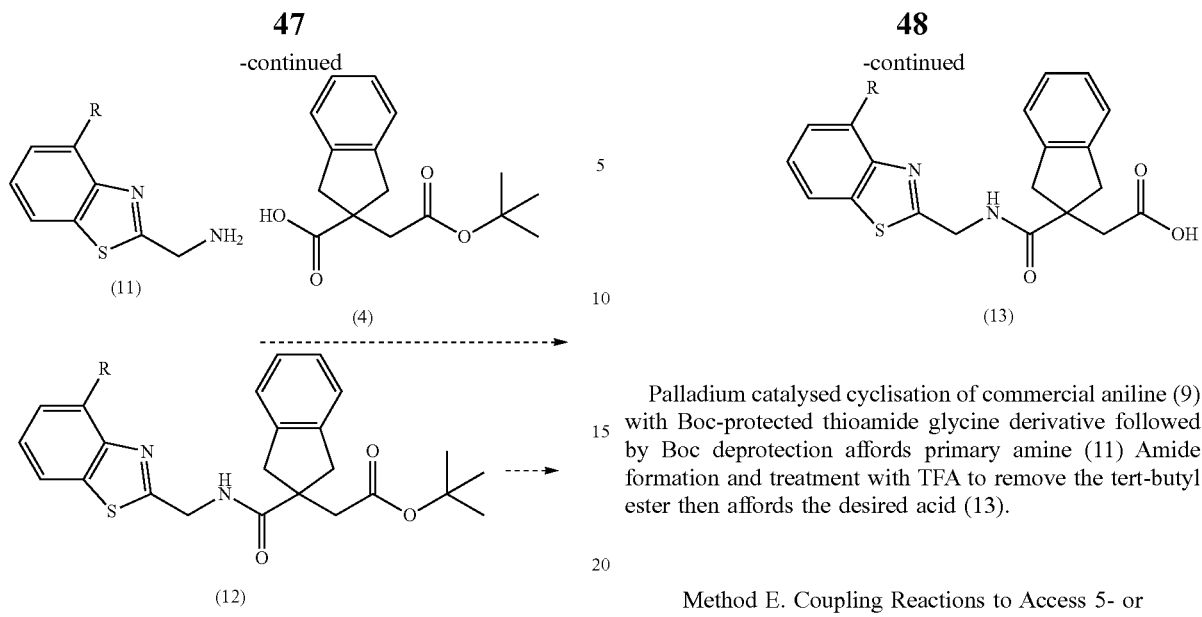
Palladium catalysed cyclisation of commercial aniline (9) with Boc-protected thioamide glycine derivative followed by Boc deprotection affords primary amine (11) Amide formation and treatment with TFA to remove the tert-butyl ester then affords the desired acid (13).
Method E. Coupling Reactions to Access 5- or 6-Substituted Benzothiazole Derivatives

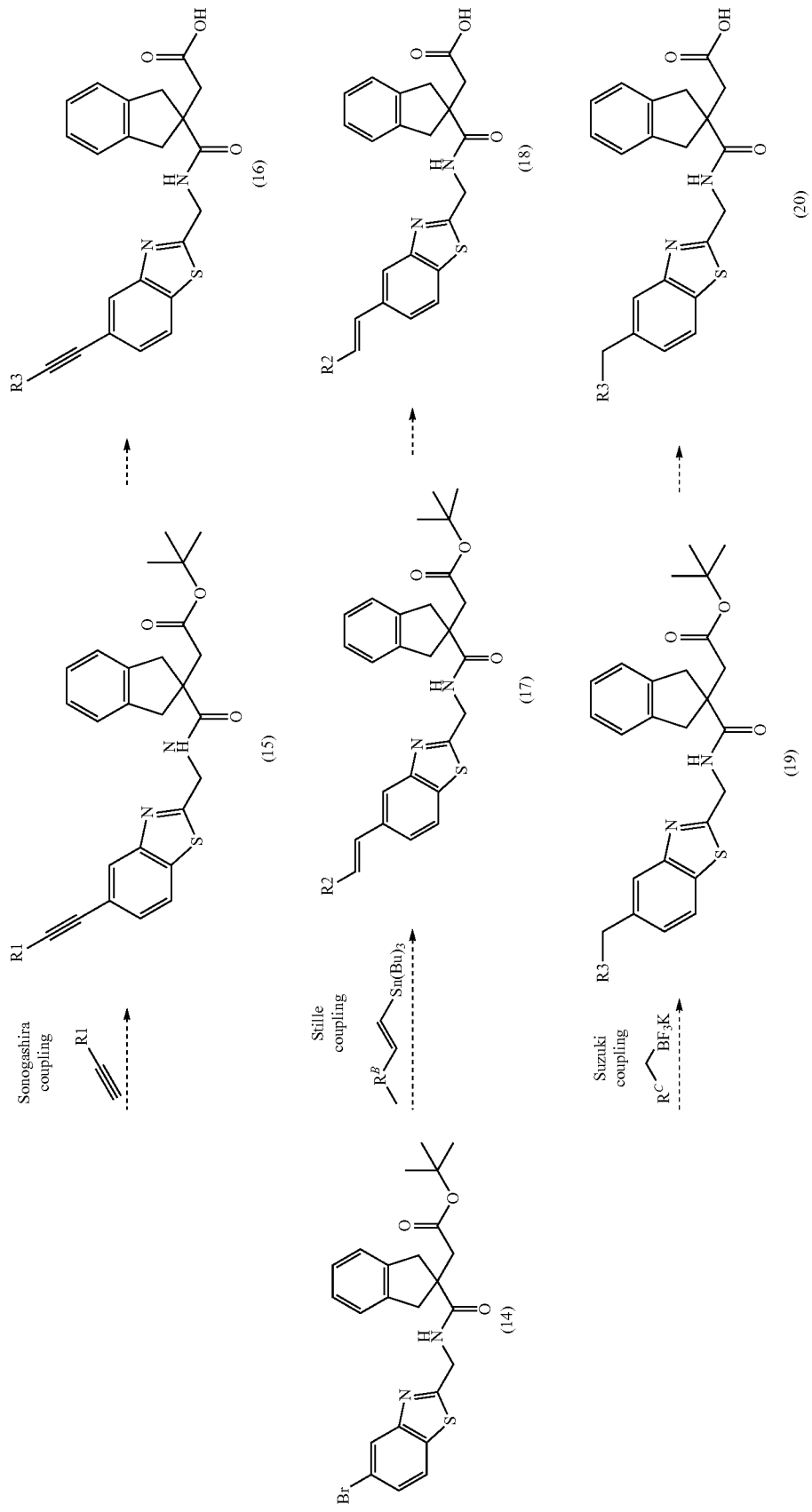

Note that this Method has been used to prepare 5- and 6-substituted benzothiazole compounds. Intermediate (14) is obtained following Method D starting with 5-bromo-2-iodo-aniline (or 4-bromo-2-iodo-aniline for 6-substituted benzothiazole). Sonogashira, Stille or Suzuki coupling reactions afford (15), (17) and (18) which after treatment with TFA and removal of the tert-butyl ester give the corresponding carboxylic acids (16), (18) and (20).

Method F. Chan-Lam Coupling Reactions to Access 5- or 6-Substituted Benzothiazole Derivative (24)

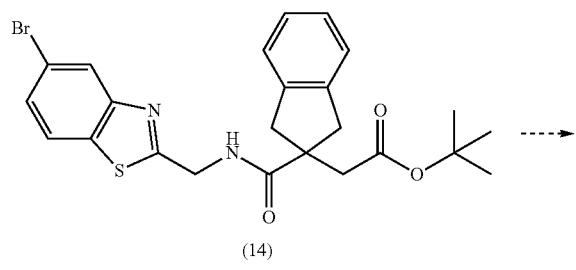

(14)

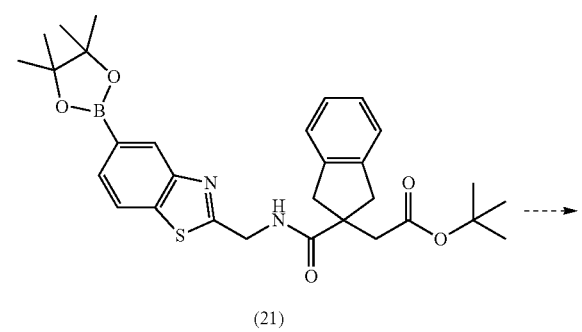

(21)

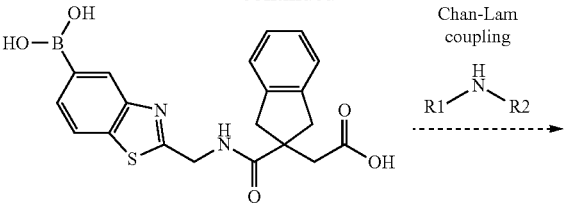

(22)

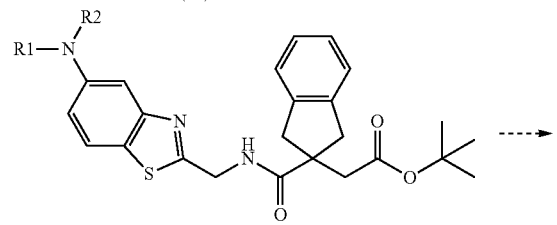

(23)

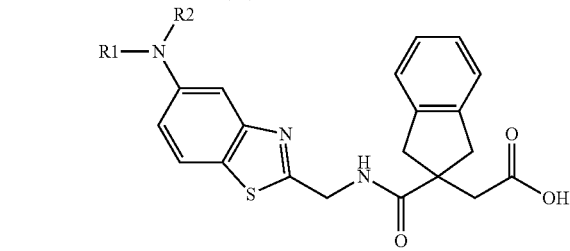

(24)

Note that this Method has been used to prepare 5- and 6-substituted benzothiazole compounds. Boronic acid (22) is obtained through the formation of the boronate ester analogue of intermediate (14) followed by hydrolysis. Chan-Lam coupling with primary or secondary amine and treatment with TFA then affords the desired carboxylic acids (24).

Method G. Coupling Reactions Described in Method E and F Before Peptide Coupling

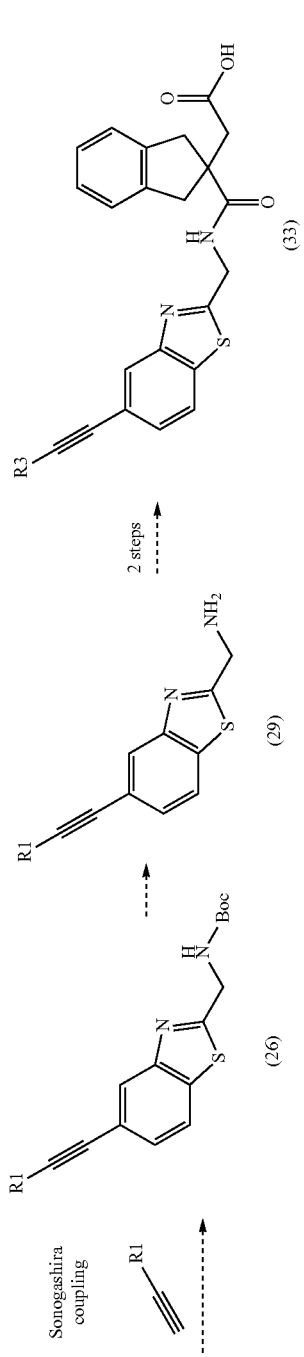
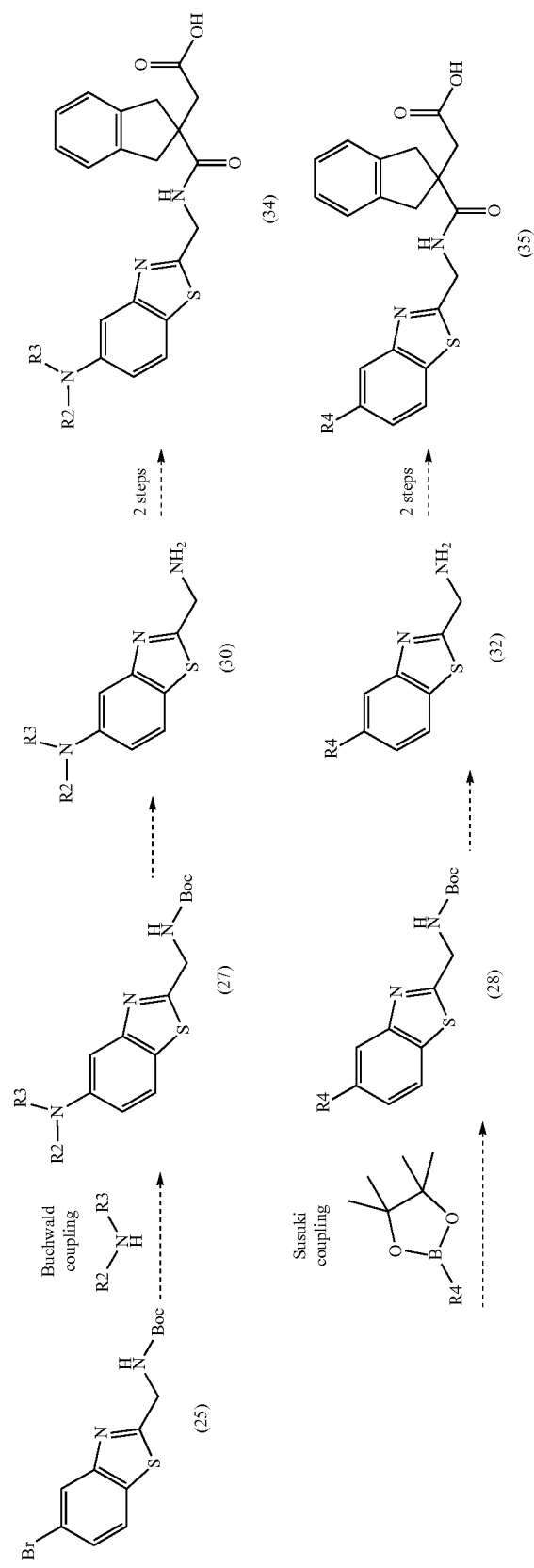

Note that this method has been used to prepare 5- and 6-substituted benzothiazole compounds. This alternative method is based on the introduction of substituents in 5- or 6-position of the benzothiazole before the peptide coupling step. Intermediate (25) is obtained following method D above starting with 5-bromo-2-iodo-aniline (or 4-bromo-2-iodo-aniline for 6-substituted benzothiazole). Sonogashira, Buchwald or Suzuki coupling reactions afford (26), (27) and (28) respectively. Removal of the Boc protection with TFA affords the primary amines (29), (30) and (31) which lead to carboxylic acids (33), (34) and (35) following method D.

Method H. Buchwald Coupling on Carboxylic Acid Scaffold

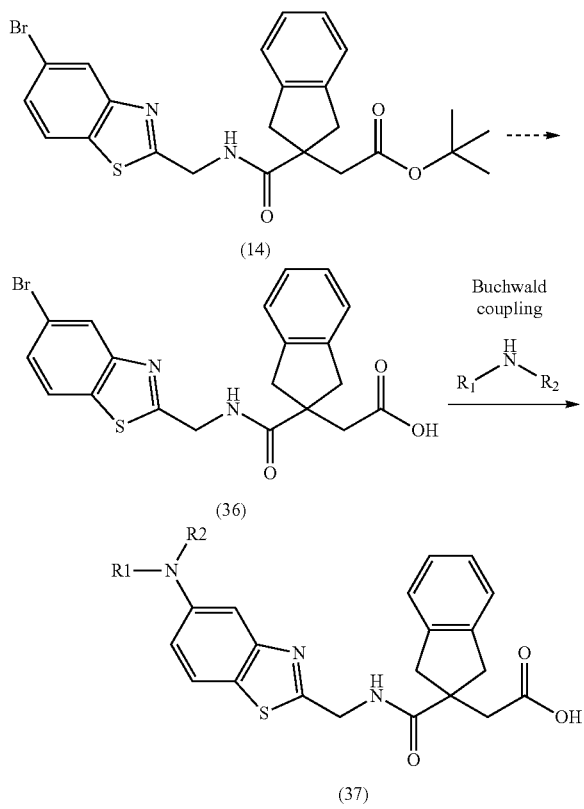

Note that this method has been used to prepare 5- and 6-substituted benzothiazole compounds. 5-substituted benzothiazoles (37) are obtained after Buchwald coupling on 5-bromo benzothiazole carboxylic acid intermediate (36) which is obtained after treatment with TFA and removal of the tert-butyl ester of (14).

EXAMPLES

1H NMR spectra are reported at 300, 400 or 500 MHz in DMSO-d6 solutions (δ in ppm), using DMSO-$d_5$ as reference standard (2.50 ppm), or $CDCl_3$ solutions using chloroform as the reference standard (7.25 ppm). When peak multiplicities are reported, the following abbreviations are used: s (singlet), d (doublet), t (triplet), m (multiplet), bs (broadened singlet), bd (broadened doublet), dd (doublet of doublets), dt (doublet of triplets), q (quartet). Coupling constants, when given, are reported in hertz (Hz).

The term "purified by prep hplc (MDAP)" refers compound purification using a mass-directed auto purification system on an Agilent 1260 infinity machine with an XSelect CHS Prep C18 column, eluting with 0.1% FA in water/ACN and detection with a Quadruploe LC/MS.

Abbreviations

ACN Acetonitrile
AcOH Acetic acid
AIBN Azobisisobutyronitrile
aq. Aqueous
Bpin Bis(pinacolato)diboron
$CaCl_2$ Calcium chloride
$Cs_2CO_3$ Cesium carbonate
cfu Colony forming unit
COMU (1-Cyano-2-ethoxy-2-oxoethylidenaminooxy)dimethylamino-morpholino-carbenium hexafluorophosphate
$Cu(OAc)_2$ Copper(II) acetate
CuO Copper oxide
DCM Dichloromethane
DEA Diethylamine
DIPEA N,N-Diisopropylethylamine
DMAP 4-Dimethylaminopyridine
DMF N,N-Dimethylformamide
DMSO Dimethyl sulfoxide
dppf 1,1'-Bis(diphenylphosphino)ferrocene
EDC.HCl N-(3-Dimethylaminopropyl)-N'-ethylcarbodiimide hydrochloride
$Et_2O$ Diethyl ether
EtOAc Ethyl acetate
EtOH Ethanol
$Et_3N$ Triethylamine
Ex Excitation
FA Formic acid
FCC Flash column chromatography purification on silica
h Hour(s)
$H_2$ Hydrogen
HATU 1-[Bis(dimethylamino)methylene]-1H-1,2,3-triazolo[4,5-b]pyridinium 3-oxid hexafluorophosphate
HCl Hydrochloric acid/hydrochloride salt
HOBt Hydroxybenzotriazole
$H_2SO_4$ Sulfuric Acid
IPA Iso-propyl alcohol
Km Michaelis constant
KOH Potassium hydroxide
MeI Methyl iodide
MeOH Methanol
min Minute(s)
$MgSO_4$ Magnesium sulfate
$N_2$ Nitrogen
NBS N-bromo succinimide
$Na_2CO_3$ Sodium carbonate
$NaHCO_3$ Sodium bicarbonate
$Na_2SO_4$ Sodium sulfate
$Pd_2(dba)_3$ Tris(dibenzylideneacetone)dipalladium(0)
$PdCl_2(PPh_3)_2$ Bis(triphenylphosphine)palladium(II) dichloride
$PdCl_2$(dppf) [1,1'-Bis(diphenylphosphino)ferrocene]dichloropalladium(II)
RT Room temperature
SCX-2 Strong cation exchange resin (silica-propyl sulfonic acid)
T % B Time, % solvent B
TES Triethylsilane
TMSOTf Trimethylsilyl trifluoromethanesulfonate
TFA Trifluoroacetic acid
THF Tetrahydrofuran
$T_3P$ Propylphosphinic anhydride The chemical formula below depicts the structure of (RuPhos) Palladium (II) phenethylamine chloride (1:1 MTBE adduct) used for Buchwald coupling steps (RuPhos Pd G1 complex).

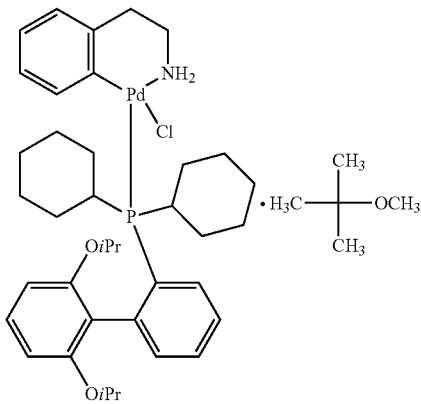

Example 1

2-(2-{[(5-Chloro-1H-1,3-benzodiazol-2-yl)methyl]carbamoyl}-2,3-dihydro-1H-inden-2-yl)acetic acid

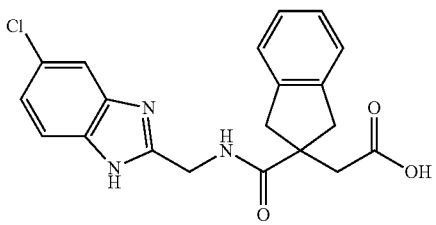 [SMILES: O=C(O)CC1(C(=O)NCc2nc3cc(Cl)ccc3[nH]2)Cc2ccccc2C1]

Method A was used as described above.

A solution of 1,3-dihydrospiro[indene-2,3'-oxolane]-2',5'-dione (100 mg, 0.5 mmol) in THF (1 mL) was treated with DIPEA (255 mg, 2 mmol) and (5-chloro-1H-1,3-benzodiazol-2-yl)methanamine dihydrochloride salt (135 mg, 0.55 mmol). The mixture was stirred overnight then filtered and evaporated. The residue (approximately a 1:1 mixture of regioisomers) was chromatographed on silica eluting with 0-20% (2M $NH_3$/MeOH) in DCM affording fraction 1 (desired regioisomer) then fraction 2 (undesired regioisomer). Fraction 1 was evaporated to give a yellow oil which was triturated with ether, filtered and dried, affording the title compound as a white solid (30 mg, 16%). M/z 384.1 $(M+H)^+$ and 386.1 $(M+H)^+$. $^1$H NMR (d6-DMSO) δ 8.52 (1H, t), 7.55 (1H, s), 7.45 (1H, m), 7.25-7.20 (2H, m), 7.10-7.20 (3H, m), 4.50 (2H, d), 3.42 (2H, d, J=16 Hz), 2.95 (2H, d, J=16 Hz), 2.65 (2H, s).

Example 2

2-[2-(3-isoquinolylmethylcarbamoyl)indan-2-yl]acetic acid

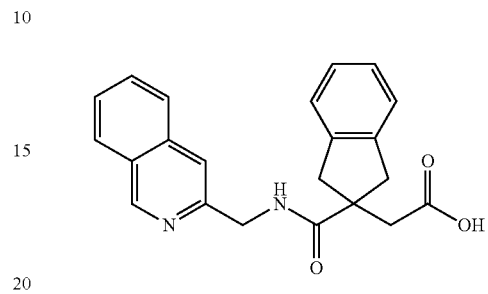

Method A was used as described above.

A solution of 1,3-dihydrospiro[indene-2,3'-oxolane]-2',5'-dione (100 mg, 0.5 mmol) in THF (5 mL) was treated with $Et_3N$ (0.2 mL, 1.5 mmol) and (isoquinolin-3-yl)methanamine (102 mg, 0.64 mmol). The mixture was stirred overnight then filtered and evaporated. The residue (approximately a 1:1 mixture of regioisomers) was purified by preparative HPLC (X Select C18 column, eluting with ammonium bicarbonate/ACN/water) giving a partial separation of isomers. The impure desired regioisomer was further purified by preparative SFC (Chiralpak-AD-H column, eluting with $CO_2$/MeOH) affording the pure title compound as a white solid (65 mg, 36%). M/z 361.3 $(M+H)^+$. $^1$H NMR (d6-DMSO) δ 9.58 (1H, bs), 9.24 (1H, s), 8.11 (1H, m), 7.82 (1H, m), 7.78 (1H, m), 7.63 (1H, m), 7.59 (1H, m), 7.19 (4H, m), 4.52 (2H, s), 3.42 (2H, d, J=16 Hz), 2.99 (2H, d, J=16 Hz), 2.64 (2H, m).

Other compounds prepared by Method A and purified in a similar manner by preparative HPLC are shown in the Table below, wherein R is the moiety:

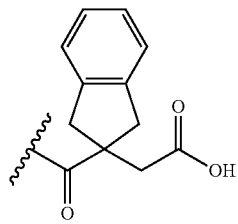 [SMILES: *C(=O)C1(CC(=O)O)Cc2ccccc2C1]

| Example | Structure | Name, MS and NMR data |
|---|---|---|
| 3 | 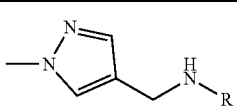 | 2-[2-[(1-methylpyrazol-4-yl)methylcarbamoyl]-indan-2-yl]acetic acid<br>M/z 314.3 $(M + H)^+$<br>$^1$H NMR (d6-DMSO) δ 11.5 (1H, bs), 8.45 (1H, bs), 7.40 (1H, s), 7.22 (1H, s), 7.18 (2H, m), 7.10 (2H, m), 4.09 (2H, d, J = 5.6 Hz), 3.75 (3H, s), 3.34 (2H, m), 2.91 (2H, d, J = 16 Hz), 2.61 (2H, s). |

| Example | Structure | Name, MS and NMR data |
|---|---|---|
| 4 | 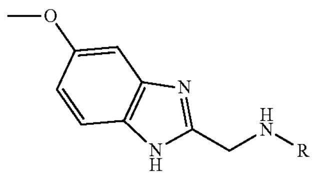 | 2-[2-[(5-methoxy-1H-benzimidazol-2-yl)-methylcarbamoyl]indan-2-yl]acetic acid<br>M/z 380.4 (M + H)+<br>1H NMR (d6-DMSO) δ 8.47 (1H, t), 7.35 (1H, d), 7.20 (2H, m), 7.12 (2H, m), 6.97 (1H, d), 6.75 (1H, dd), 4.47 (2H, d), 3.75 (3H, s), 3.42 2H, d, J = 16 Hz), 2.95 (2H, d, J = 16 Hz), 2.70 (2H, s). |

Example 5

2-(2-{[(1-Benzofuran-2-yl)methyl]carbamoyl}-2,3-dihydro-1H-inden-2-yl)acetic acid Method B was used as described above.

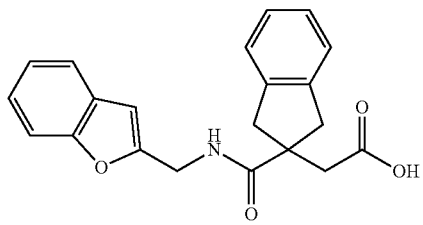 [SMILES: O=C(O)CC1(C(=O)NCc2cc3ccccc3o2)Cc2ccccc2C1]

a. 2-[2-(Benzyloxy)-2-oxoethyl]-2,3-dihydro-1H-indene-2-carboxylic acid

A mixture of 1,3-dihydrospiro[indene-2,3'-oxolane]-2',5'-dione (500 mg, 2.5 mmol) and benzyl alcohol (400 mg, 3.7 mmol) in toluene (2 mL) was heated at 100° C. under argon overnight. The cooled solution was diluted slowly with cyclohexane (5 mL) and filtered, washing with cyclohexane to afford a white solid (0.54 g, 70%). M/z 311.3 (M+H)+ b. Benzyl 2-(2-{[(1-benzofuran-2-yl)methyl]carbamoyl}-2,3-dihydro-1H-inden-2-yl)acetate A solution of 2-[2-(benzyloxy)-2-oxoethyl]-2,3-dihydro-1H-indene-2-carboxylic acid (50 mg, 0.16 mmol) and DIPEA (62 mg, 0.48 mmol) in DMF was treated with HATU (73 mg, 0.19 mmol). After 15 min (1-benzofuran-2-yl)methanamine HCl (44 mg, 0.24 mmol) was added. After 1.25 h the mixture was diluted with water (5 mL) and extracted with EtOAc (2×5 mL). The combined extracts were dried and evaporated affording a brown oil (100 mg). M/z 440.5 (M+H)+.

c. 2-(2-{[(1-Benzofuran-2-yl)methyl]carbamoyl}-2,3-dihydro-1H-inden-2-yl)acetic acid A solution of benzyl 2-(2-{[(1-benzofuran-2-yl)methyl]carbamoyl}-2,3-dihydro-1H-inden-2-yl)acetate (100 mg) in EtOAc (5 mL) was hydrogenated overnight over 10% palladium on charcoal (20 mg). The mixture was heated to 50° C. and hydrogenated for a further 8 h. The mixture was filtered and evaporated affording a yellow oil (100 mg) which was purified by chromatography on silica eluting with 0-40% EtOAc in cyclohexane affording the title compound as a colourless oil (32 mg, 57% yield over 2 steps). M/z 350.4 (M+H)+. 1H NMR (d6-DMSO) δ 8.45-8.35 (1H, bs), 7.50 (2H, t), 7.25-7.15 (4H, m), 7.15-7.00 (2H, m), 6.55 (1H, s), 4.43 (2H, d), 3.42 (2H, d, J=16 Hz), 2.97 (2H, d, J=16 Hz), 2.72 (2H, s).

Example 6

2-(2-{[(5-methyl-1-benzofuran-2-yl)methyl]carbamoyl}-2,3-dihydro-1H-inden-2-yl)acetic acid Method B was used as described above.

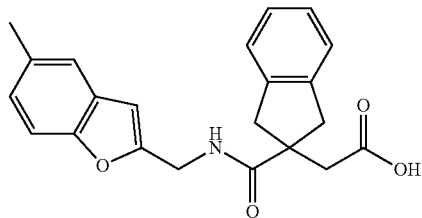 [SMILES: Cc1ccc2oc(CNC(=O)C3(CC(=O)O)Cc4ccccc4C3)cc2c1]

a. 2-{2-[(3,4-dimethoxyphenyl)methoxy]-2-oxoethyl}-2,3-dihydro-1H-indene-2-carboxylic acid A mixture of 1,3-dihydrospiro[indene-2,3'-oxolane]-2',5'-dione (5.0 g, 24.7 mmol) and 3,4-dimethoxybenzyl alcohol (4.3 ml, 24.7 mmol) in toluene (40 mL) was heated at 100° C. under argon overnight. The cooled solution was evaporated and the residue chromatographed on silica eluting with 0-100% EtOAc in hexane giving a yellow viscous oil (9.1 g, 100%).

M/z 369.1 (negative ionisation) (M−H)−.

b. 3,4-dimethoxyphenyl)methyl 2-(2-{[(5-methyl-1-benzofuran-2-yl)methyl]carbamoyl}-2,3-dihydro-1H-inden-2-yl)acetate A solution of 2-{2-[(3,4-dimethoxyphenyl)methoxy]-2-oxoethyl}-2,3-dihydro-1H-indene-2-carboxylic acid (250 mg, 0.7 mmol) in DMF (5 mL) was treated with DIPEA (0.4 mL, 2.4 mmol) and HATU (360 mg, 0.95 mmol). After 0.25 h, a solution of (5-methyl-1-benzofuran-2-yl)methanamine (196 mg, 1.2 mmol) in DMF (2 mL) was added and the mixture stirred overnight. The reaction mixture was diluted with aq. NaHCO3 solution and extracted with EtOAc. The combined extracts were dried and evaporated affording a brown oil (0.64 g) which was purified by chromatography on silica eluting with 0-100% EtOAc in cyclohexane affording a yellow oil (216 mg, 62% yield over 2 steps). M/z 514.6 (M+H)+.

c. 2-(2-{[(5-methyl-1-benzofuran-2-yl)methyl]carbamoyl}-2,3-dihydro-1H-inden-2-yl)acetic acid A solution of 3,4-dimethoxyphenyl)methyl 2-(2-{[(5-methyl-1-benzofuran-2-yl)methyl]carbamoyl}-2,3-dihydro-1H-inden-2-yl)acetate (212 mg, 0.41 mmol) in MeOH (4 ml) was hydrogenated over 10% Pd/C (53 mg) for 7 h. The mixture was filtered through celite and evaporated. The residue was purified by preparative hplc (MDAP) affording the title compound as a white solid (35 mg, 24%). M/z 364.4 (M+H)$^+$. $^1$H NMR (d6-DMSO) δ 12.0 (1H, bs), 8.61 (1H, bs), 7.39 (1H, s), 7.31 (1H, m), 7.19 (4H, m), 7.03 (1H, m), 6.44 (1H, s), 4.43 (2H, m), 3.41 (2H, d, J=16 Hz), 2.98 (2H, d, J=16 Hz), 2.69 (2H, s), 2.39 (3H, s).

Example 7

2-[2-[(5-methyl-2,3-dihydrobenzofuran-2-yl)methylcarbamoyl]indan-2-yl]acetic acid A solution of 3,4-dimethoxyphenyl)methyl 2-(2-{[(5-methyl-1-benzofuran-2-yl)methyl]carbamoyl}-2,3-dihydro-1H-inden-2-yl)acetate (109 mg, 0.21 mmol) in MeOH (2 ml) was hydrogenated over 10% Pd/C (40 mg) for 3 days. The mixture was filtered through celite and evaporated. The residue was purified by preparative hplc (MDAP) affording the title compound as a white solid (42 mg, 55%). M/z 366.4 (M+H)$^+$. $^1$H NMR (d6-DMSO) δ 8.00-7.95 (1H, bs), 7.20-7.15 (2H, m), 7.15-7.05 (2H, m), 6.95 (1H, s), 6.88 (1H, d), 6.60 (1H, d), 4.75 (1H, m), 3.40-3.25 (3H, m), 3.15-3.05 (2H, m), 2.95 (3H, m), 2.65 (2H, s), 2.20 (3H, s).

Further compounds prepared by Method B are shown in the Table below, wherein R is the moiety:

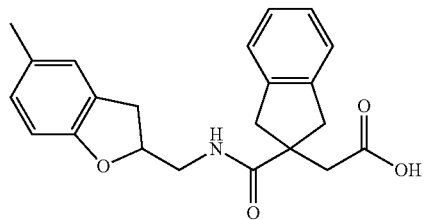 [SMILES: Cc1ccc2c(c1)CC(CNC(=O)C1(CC(=O)O)Cc3ccccc3C1)O2]

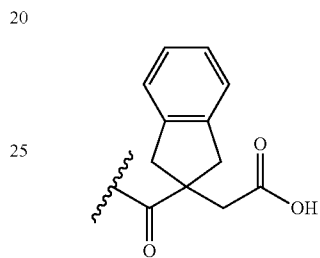

| Example | Structure | Name; MS and MNR data |
|---|---|---|
| 8 | Cl-phenyl-pyrrolidin-NH-R | 2-[2-[[1-(3-chlorophenyl)pyrrolidin-3-yl]carbamoyl]indan-2-yl]acetic acid<br>M/z 399.2 (M + H)$^+$ and M/z 401.2 (M + H)$^+$<br>$^1$H NMR (d6-DMSO) δ 8.79 (1H, bs), 8.33 (1H, s), 7.18 (5H, m), 6.59 (1H, m), 6.45 (2H, m), 4.39 (1H, m), 3.42 (1H, m), 3.39 (3H, m), 3.25 (1H, m), 3.06 (1H, m), 2.91 (2H, d, J = 16 Hz), 2.58 (2H, s), 2.12 (1H, m), 1.95 (1H, m).<br>The amine required was prepared by standard Buchwald reaction of 3-chlorobromobenzene with tert-butyl N-(pyrrolidin-3-yl)carbamate (both compounds commercially available from standard suppliers) followed by BOC removal using HCl in dioxane, following the 2-step procedure as described in WO2009/158426. |
| 9 | indole-CH2-NH-R | 2-[2-[(1-methylindol-2-yl)methylcarbamoyl]indan-2-yl]acetic acid<br>M/z 363.3 (M + H)$^+$<br>$^1$H NMR (d6-DMSO) δ 10.02 (1H, bs), 7.45 (1H, d), 7.37 (1H, d), 7.11 (5H, m), 6.98 (1H, m), 6.31 (1H, s), 4.49 (2H, d), 3.65 (3H, s), 3.40 (2H, d, J = 16 Hz), 2.94 (2H, d, J = 16 Hz), 2.44 (2H, s). |

Example 10

2-(2-{[(1,3-Benzothiazol-2-yl)methyl]carbamoyl}-2,3-dihydro-1H-inden-2-yl)acetic acid Method C was used as described above.

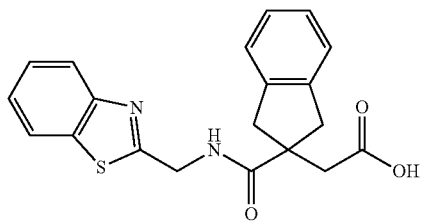

a. Methyl 2-[2-(tert-butoxy)-2-oxoethyl]-2,3-dihydro-1H-indene-2-carboxylate A solution of commercially available methyl 2,3-dihydro-1H-indene-2-carboxylate (4.53 g, 25.7 mmol) in THF (100 mL) was treated with a solution of sodium hexamethylsilazide in THF (1M, 38.6 ml, 38.8 mmol) dropwise at −70° C. under $N_2$. After 0.25 h, tert-butyl bromoacetate (5.7 mL, 38.6 mmol) was added dropwise, ensuring the internal temperature did not rise above −60° C. After the addition was complete the mixture was allowed to warm to RT over 0.5 h then quenched with saturated aq. ammonium chloride solution (150 mL). The mixture was extracted three times with EtOAc and the combined organic extracts were washed with brine, dried ($MgSO_4$) and evaporated (11.2 g). This was chromatographed on silica eluting with 0-40% EtOAc in hexane affording methyl 2-[2-(tert-butoxy)-2-oxoethyl]-2,3-dihydro-1H-indene-2-carboxylate as a yellow oil (5.7 g, 77%). M/z 291.4 (M+H)$^+$ and M/z 235.3 (M+H)$^+$ (loss of isobutene)

b. 2-[2-(tert-Butoxy)-2-oxoethyl]-2,3-dihydro-1H-indene-2-carboxylic acid

A solution of methyl 2-[2-(tert-butoxy)-2-oxoethyl]-2,3-dihydro-1H-indene-2-carboxylate (4.0 g, 13.8 mmol) in EtOH/$H_2O$ (80 mL/40 mL) was treated with KOH (4.3 g, 75.8 mmol). After 3.5 h the mixture was diluted with water and washed with ether. The aqueous phase was acidified to pH 3 with solid citric acid monohydrate and extracted with EtOAc. The combined organic extracts were washed with brine, dried ($Na_2SO_4$) and evaporated affording the crude product as a solid (3.7 g). This was dissolved in chloroform, filtered and evaporated to give 2-[2-(tert-butoxy)-2-oxoethyl]-2,3-dihydro-1H-indene-2-carboxylic acid as a white solid (1.76 g, 47%). M/z 277.3 (M+H)$^+$.

c. tert-Butyl 2-(2-{[(1,3-benzothiazol-2-yl)methyl]carbamoyl}-2,3-dihydro-1H-inden-2-yl)acetate A solution of 2-[2-(tert-butoxy)-2-oxoethyl]-2,3-dihydro-1H-indene-2-carboxylic acid (530 mg, 1.92 mmol), HATU (876 mg, 2.3 mmol) and DIPEA (1.34 mL, 7.7 mmol) in DMF (10 mL) was stirred for 0.25 h then 1,3-benzothiazol-2-ylmethanamine (350 mg, 1.74 mmol) was added. The mixture was stirred for 2.5 days then evaporated. The residue was dissolved in EtOAc and washed with saturated aq. $NaHCO_3$ solution, water and brine, then the organic extract was dried ($Na_2SO_4$) and evaporated affording the crude product (628 mg). This was chromatographed on silica eluting with 0-100% EtOAc in hexane affording tert-butyl 2-(2-{[(1,3-benzothiazol-2-yl)methyl]carbamoyl}-2,3-dihydro-1H-inden-2-yl)acetate as a white solid (520 mg, 64%). M/z 423.2 (M+H)$^+$.

d. 2-(2-{[(1,3-Benzothiazol-2-yl)methyl]carbamoyl}-2,3-dihydro-1H-inden-2-yl)acetic acid A solution of tert-butyl 2-(2-{[(1,3-benzothiazol-2-yl)methyl]carbamoyl}-2,3-dihydro-1H-inden-2-yl)acetate (520 mg, 1.23 mmol) in DCM (20 mL) was treated with TFA (2 mL). After 0.75 h a further portion of TFA (1 mL) was added. The mixture was stirred overnight then evaporated, azeotroping twice with toluene. The residue was chromatographed on silica eluting with 0-100% EtOAc in hexane affording an oil which was dissolved in ACN/water and freeze dried affording the title compound as a white solid (327 mg, 72%). M/z 367.4 (M+H)$^+$. $^1$H NMR (d6-DMSO) δ 8.80-8.70 (1H, t), 8.05 (1H, d), 7.92 (1H, d), 7.50 (1H, t), 7.40 (1H, t), 7.20 (2H, m), 7.15 (2H, m), 4.67 (2H, d), 3.45 (2H, d, J=16 Hz), 3.00 (2H, d, J=16 Hz), 2.75 (2H, s).

Further compounds prepared by Method C are shown in the Table below, wherein R is the moiety:

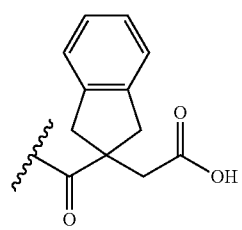 [SMILES: *C(=O)C1(CC(=O)O)Cc2ccccc2C1]

| Example | Structure | Name, MS and NMR data |
|---|---|---|
| 11 | 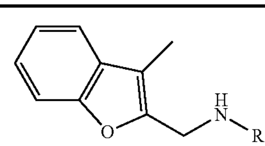 | 2-(2-{[2-(3-methyl-1-benzofuran-2-yl)methyl]carbamoyl}-2,3-dihydro-1H-inden-2-yl)acetic acid<br>M/z 364.4 (M + H)$^+$<br>$^1$H NMR (d6-DMSO) δ 8.31 (1H, s), 7.51 (1H, d), 7.45 (1H, d), 7.25 (2H, m), 7.14 (2H, m), 7.09 (2H, m), 4.40 (2H, d), 3.36 (2H, d, J = 16 Hz), 2.90 (2H, d, J = 16 Hz), 2.58 (2H, s), 2.17 (3H, s). |

-continued

| Example | Structure | Name, MS and NMR data |
|---|---|---|
| 12 | 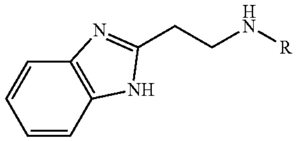 | 2-[2-[2-(1H-benzimidazol-2-yl)ethylcarbamoyl]indan-2-yl]acetic acid<br>M/z 364.4 (M + H)⁺<br>$^1$H NMR (d6-DMSO) δ 12.1 (1H, bs), 7.90 (1H, m), 7.45 (2H, m), 7.19-7.08 (6H, m), 3.48 (2H, m), 3.34 (2H, m), 2.92 (4H, m), 2.65 (2H, s). |
| 13 | 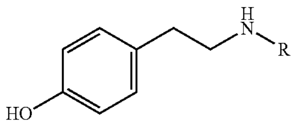 | 2-[2-[2-(4-hydroxyphenyl)ethylcarbamoyl]indan-2-yl]acetic acid<br>M/z 340.4 (M + H)⁺<br>$^1$H NMR (d6-DMSO) δ 12.00 (1H, bs), 9.20 (1H, bs), 7.64 (1H, bs), 7.14 (4H, m), 6.92 (2H, d, J = 7.2 Hz), 6.64 (2H, d, J = 7.6 Hz), 3.32 (2H, d, J = 16.3 Hz), 3.18 (2H, m), 2.91 (2H, d, J = 16.3 Hz), 2.63 (2H, s). |
| 14 | 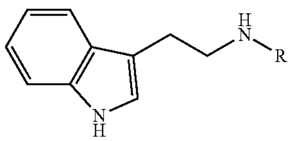 | 2-[2-[2-(1H-indol-3-yl)ethylcarbamoyl]indan-2-yl]acetic acid<br>M/z 362.4 (M + H)⁺<br>$^1$H NMR (d6-DMSO) δ 8.60 (1H, bs), 8.39 (1H, s), 7.54 (1H, d), 7.32 (1H, d), 7.18-6.94 (7H, m), 3.49 (4H, m), 2.91 (2H, d, J = 16.5 Hz), 2.78 (2H, m), 2.57 (2H, s). |
| 15 | 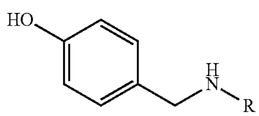 | 2-[2-[(4-hydroxyphenyl)methylcarbamoyl]indan-2-yl]acetic acid<br>M/z 336.6 (M + H)⁺<br>$^1$H NMR (d6-DMSO) δ 9.20 (1H, bs), 8.10 (1H, bs), 7.15 (4H, m), 6.97 (2H, d), 6.64 (2H, d), 4.16 (2H, d), 3.39 (2H, m), 2.94 (2H, d, J = 16.5 Hz), 2.68 (2H, s). |
| 16 | 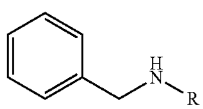 | 2-[2-(benzylcarbamoyl)indan-2-yl]acetic acid<br>M/z 310.4 (M + H)⁺<br>$^1$H NMR (d6-DMSO) δ 12.05 (1H, bs), 8.20 (1H, m), 7.28-7.10 (9H, m), 4.28 (2H, d, J = 5.4 Hz), 3.40 (2H, d, J = 16.3 Hz), 2.94 (2H, d, J = 16.3 Hz), 2.72 (2H, s). |
| 17 | 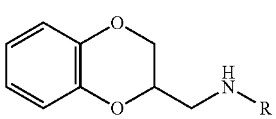 | 2-[2-(2,3-dihydro-1,4-benzodioxin-3-ylmethylcarbamoyl)indan-2-yl]acetic acid<br>M/z 375.2 (M + H)⁺<br>$^1$H NMR (d6-DMSO) δ 8.00 (1H, bs), 7.15 (4H, m), 6.85 (4H, m), 4.23 (1H, m), 4.14 (1H, m), 3.85 (1H, m), 3.41 (4H, m), 2.92 (2H, d, J = 16.4 Hz), 2.70 (2H, s). |
| 18 | 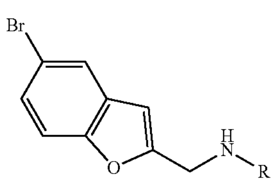 | 2-[2-[(5-bromobenzofuran-2-yl)methylcarbamoyl]indan-2-yl]acetic acid<br>M/z 428.3 (M + H)⁺ and M/z 430.4 (M + H)⁺<br>$^1$H NMR (d6-DMSO) δ 8.45-8.35 (1H, bs), 7.50 (1H, d), 7.38 (1H, d), 7.22 (2H, m), 7.12 (2H, m), 6.55 (1H, s), 4.45 (2H, d), 3.42 (2H, d, J = 16 Hz), 2.95 (2H, d, J = 16 Hz), 2.75 (2H, s). |
| 19 | 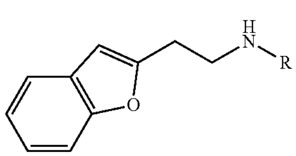 | 2-[2-[2-(benzofuran-2-yl)ethylcarbamoyl]indan-2-yl]acetic acid<br>M/z 364.4 (M + H)⁺<br>$^1$H NMR (d6-DMSO) δ 12.00 (1H, bs), 7.87 (1H, m), 7.53-7.46 (2H, m), 7.23-7.09 (6H, m), 6.53 (1H, s), 3.43-3.29 (4H, m), 2.93-2.87 (4H, m), 2.64 (2H, s). |
| 20 | 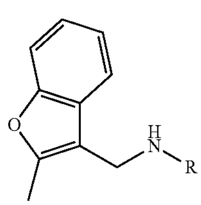 | 2-[2-[(2-methylbenzofuran-3-yl)methylcarbamoyl]indan-2-yl]acetic acid<br>M/z 364.4 (M + H)⁺<br>$^1$H NMR (d6-DMSO) δ 12.00 (1H, bs), 8.04 (1H, m), 7.49 (1H, d, J = 7.6 Hz), 7.41 (1H, d, J = 7.2 Hz), 7.20-7.08 (6H, m), 4.33 (2H, d, J = 5.2 Hz), 3.30 (2H, m), 2.91 (2H, d, J = 16.2 Hz), 2.65 (2H, s), 2.40 (3H, s). |

-continued

| Example | Structure | Name, MS and NMR data |
|---|---|---|
| 21 | (1-methylimidazol-4-yl)methyl-NHR | 2-[2-[(1-methylimidazol-4-yl)methylcarbamoyl]indan-2-yl]acetic acid<br>M/z 314.05 (M + H)+<br>1H NMR (d6-DMSO) δ 13.1 (1H, bs), 8.79 (1H, bs), 8.30 (1H, bs), 7.28-7.11 (5H, m), 4.26 (2H, d, J = 5.2 Hz), 3.78 (3H, s), 3.38 (2H, m), 2.94 (2H, d, J = 16.2 Hz), 2.68 (2H, s). |
| 22 | 2-(1,3-benzothiazol-2-yl)ethyl-NHR | 2-[2-[2-(1,3-benzothiazol-2-yl)ethylcarbamoyl]indan-2-yl]acetic acid<br>M/z 381.4 (M + H)+<br>1H NMR (d6-DMSO) δ 12.00 (1H, bs), 8.03 (1H, m), 7.91 (2H, m), 7.48 (1H, m), 7.40 (1H, m), 7.15 (2H, m), 7.10 (2H, m), 3.51 (2H, m), 3.36 (2H, d, J = 16.2 Hz), 3.21 (2H, m), 2.92 (2H, d, J = 16.2 Hz), 2.65 (2H, s). |
| 23 | benzothiophen-2-ylmethyl-NHR | 2-[2-(benzothiophen-2-ylmethylcarbamoyl)indan-2-yl]acetic acid<br>M/z 366.5 (M + H)+<br>1H NMR (d6-DMSO) δ 8.50 (1H, bs), 7.86 (1H, d), 7.71 (1H, d), 7.31 (2H, m), 7.19 (2H, m), 7.14 (3H, m), 4.53 (2H, d), 3.42 (2H, d, J = 16 Hz), 2.97 (2H, d, J = 16 Hz), 2.71 (2H, s). |
| 24 | (5-methoxy-1,3-benzothiazol-2-yl)methyl-NHR | 2-[2-[(5-methoxy-1,3-benzothiazol-2-yl)methylcarbamoyl]indan-2-yl]acetic acid<br>M/z 397.5 (M + H)+<br>1H NMR (d6-DMSO) δ 8.85-8.75 (1H, bs), 7.90 (1H, d), 7.45 (1H, s), 7.25 (2H, m), 7.15 (2H, m), 7.05 (1H, d), 4.65 (2H, d), 3.85 (3H, s), 3.45 (2H, d, J = 16 Hz), 3.00 (2H, d, J = 16 Hz), 2.72 (2H, s). |
| 25 | (5-chloro-1,3-benzothiazol-2-yl)methyl-NHR | 2-[2-[(5-chloro-1,3-benzothiazol-2-yl)methylcarbamoyl]indan-2-yl]acetic acid<br>M/z 401.8 (M + H)+ and M/z 403.7 (M + H)+<br>1H NMR (d6-DMSO) δ 8.90-8.80 (1H, bs), 8.10 (1H, d), 8.00 (1H, s), 7.45 (1H, d), 7.25 (2H, m), 7.15 (2H, m), 4.68 (2H, d), 3.45 (2H, d, J = 16 Hz), 3.00 (2H, d, J = 16 Hz), 2.74 (2H, s). |
| 26 | 1H-indol-3-ylmethyl-NHR | 2-[2-(1H-indol-3-ylmethylcarbamoyl)indan-2-yl]acetic acid<br>M/z 349.5 (M + H)+<br>1H NMR (d6-DMSO) δ 8.81 (1H, bs), 7.49 (1H, d), 7.32 (1H, d), 7.14 (6H, m), 6.94 (1H, m), 4.42 (2H, d), 3.38 (2H, d, J = 16 Hz), 2.92 (2H, d, J = 16 Hz), 2.56 (2H, s). |
| 27 | 2-(1H-indol-2-yl)ethyl-NHR | 2-[2-[2-(1H-indol-2-yl)ethylcarbamoyl]indan-2-yl]acetic acid<br>M/z 363.5 (M + H)+<br>1H NMR (d6-DMSO) δ 10.95 (1H, s), 8.15 (1H, bs), 7.39 (1H, d, J = 7.2 Hz), 7.26 (1H, d, J = 7.2 Hz), 7.14-7.09 (4H, m), 6.97 (1H, m), 6.92 (1H, m), 6.10 (1H, s), 3.40-3.31 (4H, m), 2.91 (2H, d, J = 16.2 Hz), 2.84 (2H, m), 2.61 (2H, s). |
| 28 | benzofuran-3-ylmethyl-NHR | 2-[2-(benzofuran-3-ylmethylcarbamoyl)indan-2-yl]acetic acid<br>M/z 350.3 (M + H)+<br>1H NMR (d6-DMSO) δ 8.38 (1H, bs), 7.50 (2H, m), 7.25-7.12 (6H, m), 6.55 (1H, s), 4.42 (2H, d), 3.42 (2H, d, J = 16 Hz), 2.97 (2H, d, J = 16 Hz), 2.73 (2H, s). |
| 29 | 1H-indol-2-ylmethyl-NHR | 2-[2-(1H-indol-2-ylmethylcarbamoyl)indan-2-yl]acetic acid<br>M/z 349.3 (M + H)+<br>1H NMR (d6-DMSO) δ 8.61 (1H, bs), 8.22 (1H, bs), 7.39 (1H, d, J = 8 Hz), 7.30 (1H, d, J = 7.6 Hz), 7.19 (2H, m), 7.12 (2H, m), 6.96 (1H, m), 6.92 (1H, m), 6.15 (1H, s), 4.44 (2H, d), 3.42 (2H, d, J = 16 Hz), 2.95 (2H, d, J = 16 Hz), 2.65 (2H, s). |

-continued

| Example | Structure | Name, MS and NMR data |
|---|---|---|
| 30 | 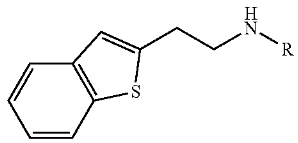 | 2-[2-[2-(benzothiophen-2-yl)ethylcarbamoyl]indan-2-yl]acetic acid<br>M/z 380.4 (M + H)+<br>1H NMR (d6-DMSO) δ 12.02 (1H, bs), 7.85 (2H, m), 7.72 (1H, m), 7.30 (2H, m), 7.20-7.08 (5H, m), 3.35 (4H, m), 2.99 (2H, m), 2.92 (2H, d, J = 16 Hz), 2.62 (2H, s). |
| 31 | 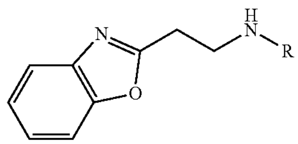 | 2-[2-[2-(1,3-benzoxazol-2-yl)ethylcarbamoyl]indan-2-yl]acetic acid<br>M/z 365.4 (M + H)+<br>1H NMR (d6-DMSO) δ 12.01 (1H, bs), 8.00 (1H, bs), 7.65 (2H, m), 7.33 (2H, m), 7.15 (2H, m), 7.08 (2H, m), 3.53 (2H, m), 3.32 (2H, d, J = 16.2 Hz), 3.04 (2H, m), 2.90 (2H, d, J = 16.2 Hz), 2.61 (2H, s). |
| 32 | 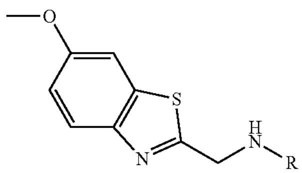 | 2-[2-[(6-methoxy-1,3-benzothiazol-2-yl)methylcarbamoyl]indan-2-yl]acetic acid<br>M/z 392.2 (M + H)+<br>1H NMR (d6-DMSO) δ 12.2 (1H, s), 8.69 (1H, m), 7.79 (1H, d, J = 8.8 Hz), 7.58 (1H, d, J = 2.8 Hz), 7.21 (2H, m), 7.14 (2H, m), 7.06 (1H, m), 4.61 (2H, d, J = 5.6 Hz), 3.81 (3H, s), 3.46 (2H, d, J = 16.2 Hz), 2.98 (2H, d, J = 16 Hz), 2.73 (2H, s). |
| 33 | 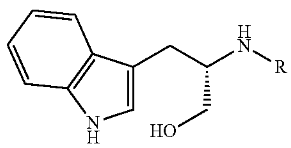 | (2-{[(2S)-1-hydroxy-3-(1H-indol-3-yl)propan-2-yl]carbamoyl}-1,3-dihydroinden-2-yl)acetic acid<br>M/z 393.5 (M + H)+<br>1H NMR (d6-DMSO) δ 10.70 (1H, bs), 7.60 (1H, d), 7.45 (1H, bs), 7.40 (1H, d), 7.20-7.10 (4H, m), 7.05-7.00 (2H, m), 6.95 (1H, t), 4.00 (1H, m), 3.45-3.25 (4H, m), 2.95-2.85 (3H, m), 2.75 (1H, m), 2.65 (2H, m). |
| 34 | 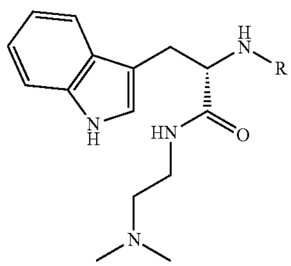 | (2-{[(1S)-1-{[2-(dimethylamino)ethyl]carbamoyl}-2-(1H-indol-3-yl)ethyl]carbamoyl}-1,3-dihydroinden-2-yl)acetic acid<br>M/z 482.2 (M + H)+<br>1H NMR (d6-DMSO) δ 10.70 (1H, bs), 8.40 (1H, bs), 7.72 (1H, d), 7.50 (1H, d), 7.32 (1H, d), 7.20-7.10 (3H, m), 7.05 (1H, t), 6.95-6.90 (2H, m), 4.45 (1H, m), 3.40 (3H, m), 3.30 (1H, d), 3.05-2.95 (2H, m), 2.95-2.85 (2H, m), 2.80 (1H, d), 2.70 (1H, d), 2.62 (1H, d), 2.55 (6H, s), 2.40 (1H, d).<br>The amine was prepared following the procedure of Tammler, U. et al, European J. Med. Chem., 2003, 38, 481. |

Example 35 (Method G)

2-[2-[[6-[3-(dimethylamino)prop-1-ynyl]-1,3-benzothiazol-2-yl]methylcarbamoyl]indan-2-yl]acetic acid

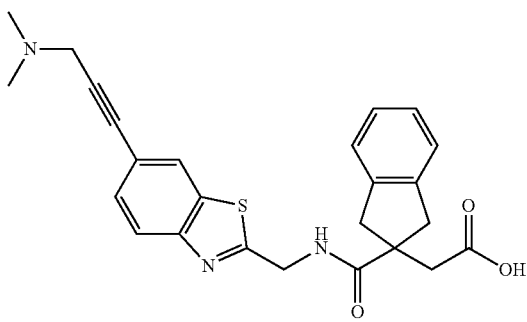 [SMILES: CN(C)CC#Cc1ccc2nc(CNC(=O)C3(CC(=O)O)Cc4ccccc4C3)sc2c1]

a. tert-butyl N-[(6-bromo-1,3-benzothiazol-2-yl)methyl]carbamate

CuO (0.8 g, 10.13 mmol) was added to a stirred solution of 4-bromo-2-iodo-aniline (3 g, 10.13 mmol) and tert-butyl N-(2-amino-2-thioxo-ethyl)carbamate (1.92 g, 10.13 mmol) in DMF (30 mL) at RT and the reaction mixture was degassed with argon for 15 min. Then dppf (280 mg, 0.50 mmol) and Pd$_2$(dba)$_3$ (185.4 mg, 0.20) were added to the reaction mixture and degassed with argon for further 5 min. The reaction mixture was stirred in sealed tube at 60° C. for 3 h and filtered through celite pad which was washed with EtOAc (50 mL). The filtrate was washed with water (2×30 mL) and concentrated under reduced pressure. The crude compound was purified by flash chromatography eluting with 22% EtOAc in petroleum ether affording a yellow solid (5 g, 72%). M/z 343.0 (M+H)+.

b. (6-bromo-1,3-benzothiazol-2-yl)methanamine

4N HCl in dioxane (10 mL) was added to a solution of tert-butyl N-[(6-bromo-1,3-benzothiazol-2-yl)methyl]carbamate (5 g, 14.61 mmol) in dioxane (10 mL) at 0° C. The reaction mixture was stirred at RT for 16 h and concentrated under reduced pressure. The crude compound was triturated with n-pentane (20 mL) and Et₂O (20 mL) affording a white solid (3.5 g, 86%). M/z 243.1 (M)⁺.

c. tert-butyl 2-[2-[(6-bromo-1,3-benzothiazol-2-yl)methylcarbamoyl]indan-2-yl]acetate Et₃N (6 mL, 43.01 mmol), 2-(2-tert-butoxy-2-oxo-ethyl)indane-2-carboxylic acid (2.17 g, 7.88 mmol) and T₃P (8 mL, 10.75 mmol) were added to a stirred solution of (6-bromo-1,3-benzothiazol-2-yl)methanamine (2 g, 7.16 mmol) in DMF (20 mL) at RT. The reaction mixture was stirred for 16 h and diluted with ice cold water (120 mL). The resulting precipitate was filtered, washed with water and dried under high vacuum affording a white solid (1.9 g, 56%). M/z 501.3 (M+H)⁺.

d. tert-butyl 2-[2-[[6-[3-(dimethylamino)prop-1-ynyl]-1,3-benzothiazol-2-yl]methylcarbamoyl]indan-2-yl]acetate N,N-dimethylprop-2-yn-1-amine (331 mg, 3.98 mmol), CuI (75.7 mg, 0.39 mmol) and Et₃N (0.56 mL, 3.98 mmol) were added to a stirred solution of tert-butyl 2-[2-[(6-bromo-1,3-benzothiazol-2-yl)methylcarbamoyl]indan-2-yl]acetate (400 mg, 0.79 mmol) in THF (10 mL) at RT and the reaction mixture was degassed with argon for 15 min. After that PdCl₂(PPh₃)₂ (111 mg, 0.15 mmol) was added and the reaction mixture was degassed with argon for further 5 min. The reaction mixture was stirred in sealed tube at 80° C. for 18 h, filtered through celite pad which was washed with EtOAc (50 mL). The filtrate was concentrated under reduced pressure. The crude compound was purified by Combi-flash chromatography eluting with 5% MeOH in DCM affording a pale brown solid (240 mg, 59%). M/z 504.5 (M+H)⁺.

e. tert-butyl 2-[2-[[6-[3-(dimethylamino)prop-1-ynyl]-1,3-benzothiazol-2-yl]methylcarbamoyl]indan-2-yl]acetate TFA:TES (5:1, 6 mL) were added to a solution of tert-butyl 2-[2-[[6-[3-(dimethylamino)prop-1-ynyl]-1,3-benzothiazol-2-yl]methylcarbamoyl]indan-2-yl]acetate (140 mg, 0.27 mmol) in DCM (5 mL) at RT. The reaction mixture was stirred at RT for 5 h and concentrated under reduced pressure. The residue was washed with n-pentane (10 mL) and Et₂O (10 mL). The crude compound was purified by preparative HPLC (X-BRIDGE-C18 (150*30); 5 u, Flow rate: 25 mL/min; mobile phase: 0.05% FA in H₂O:ACNACN) affording the title compound as a white solid (32 mg, 26%). M/z 448.2 (M+H)⁺. ¹H NMR (d6-DMSO) δ 8.83 (1H, bs), 8.14 (1H, d, J=1.0 Hz), 7.89 (1H, d, J=8.5 Hz), 7.51 (1H, dd, J=8.5 Hz, J=1.5 Hz), 7.22-7.20 (2H, m), 7.15-7.13 (2H, m), 4.66 (2H, d, J=6.0 Hz), 3.47 (2H, s), 3.45 (2H, d, J=16.5 Hz), 2.99 (2H, d, J=16.5 Hz), 2.73 (2H, s), 2.26 (6H, s).

Example 36

2-[2-[[6-[3-(dimethylamino)propyl]-1,3-benzothiazol-2-yl]methylcarbamoyl]indan-2-yl]acetic acid

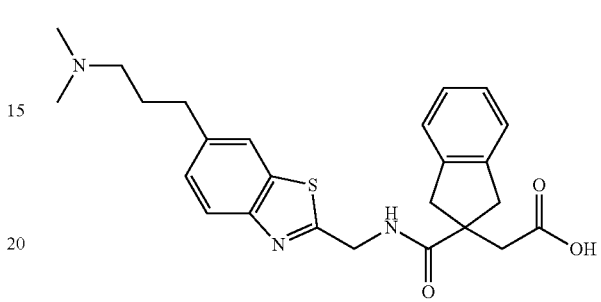

a. tert-butyl 2-[2-[[6-[3-(dimethylamino)propyl]-1,3-benzothiazol-2-yl]methylcarbamoyl]indan-2-yl]acetate 10% Pd/C (120 mg) was added to a stirred solution of tert-butyl 2-[2-[[6-[3-(dimethylamino)prop-1-ynyl]-1,3-benzothiazol-2-yl]methylcarbamoyl]indan-2-yl]acetate (180 mg, 0.35 mmol) in EtOH (8 mL) at RT under N₂. The reaction mixture was stirred under H₂ (balloon) for 20 h, then filtered through a celite pad which was washed with MeOH (20 mL). The filtrate was concentrated under reduced pressure. The obtained brown solid was used as such in the next step (155 mg, 85%). M/z 508.3 (M+H)⁺.

b. 2-[2-[[6-[3-(dimethylamino)propyl]-1,3-benzothiazol-2-yl]methylcarbamoyl]indan-2-yl]acetic acid TFA:TES (5:1, 5 mL) was added to a solution of tert-butyl 2-[2-[[6-[3-(dimethylamino)propyl]-1,3-benzothiazol-2-yl]methylcarbamoyl]indan-2-yl]acetate (110 mg, 0.216 mmol) in DCM (5 mL) at RT. The reaction mixture was stirred at RT for 6 h and concentrated under reduced pressure. The crude compound was purified by preparative HPLC (KROMOSIL-C18 (25*150 MM); 10 u; Flow rate: 25 mL/min; mobile phase: 0.05% FA in H₂O:ACNACN) affording the title product as an off-white solid (65 mg, 67%). M/z 452.2 (M+H)⁺. ¹H NMR (d6-DMSO) δ 9.08 (1H, bs), 7.81 (2H, m), 7.32 (1H, dd, J=8.4 Hz, J=1.6 Hz), 7.22-7.19 (2H, m), 7.15-7.12 (2H, m), 4.61 (2H, d, J=5.6 Hz), 3.45 (2H, d, J=16 Hz), 2.98 (2H, d, J=16.4 Hz), 2.72-2.68 (4H, m), 2.25 (2H, dd, J=7.6 Hz, J=6.8 Hz), 2.16 (6H, s), 1.76-1.72 (2H, m).

Example 37

3-[2-[[[2-(carboxymethyl)indane-2-carbonyl]amino]methyl]-1,3-benzothiazol-6-yl]propyl-trimethyl-ammonium

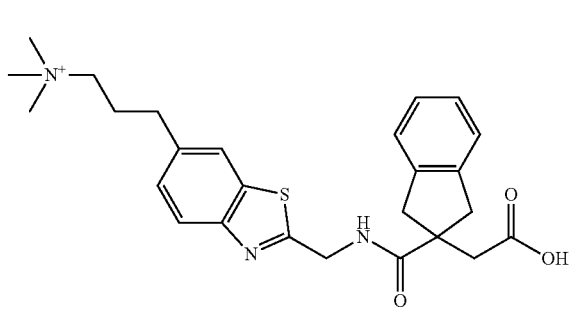 [SMILES: C[N+](C)(C)CCCc1ccc2nc(CNC(=O)C3(CC(=O)O)Cc4ccccc4C3)sc2c1]

a. 3-[2-[[[2-(2-tert-butoxy-2-oxo-ethyl)indane-2-carbonyl]amino]methyl]-1,3-benzothiazol-6-yl]propyl-trimethyl-ammonium MeI (109 mg, 0.76 mmol) was added to a solution of tert-butyl 2-[2-[[6-[3-(dimethylamino)propyl]-1,3-benzothiazol-2-yl]methylcarbamoyl]indan-2-yl]acetate (130 mg, 0.25 mmol) in THF (3 mL) at 0° C. The reaction mixture was stirred at RT for 5 h and concentrated under reduced pressure. The crude residue was triturated with Et$_2$O (2×10 mL) affording an off-white solid which was used as such in the next step (180 mg). M/z 522.3 (M)$^+$.

b. 3-[2-[[[2-(carboxymethyl)indane-2-carbonyl]amino]methyl]-1,3-benzothiazol-6-yl]propyl-trimethyl-ammonium TFA:TES (5:1, 3 mL) was added to a stirred solution of 3-[2-[[[2-(2-tert-butoxy-2-oxo-ethyl)indane-2-carbonyl]amino]methyl]-1,3-benzothiazol-6-yl]propyl-trimethyl-ammonium (180 mg, 0.34 mmol) in DCM (5 mL) at RT. The reaction mixture was stirred at RT for 4 h then concentrated under reduced pressure. The residue was washed with n-pentane (10 mL) and Et$_2$O (10 mL). The crude compound was purified by preparative HPLC (X-BRIDGE-C18 (150*30); 5 u; Flow rate: 25 mL/min; mobile phase: 0.05% FA in H$_2$O:ACN) affording the title product as a pale yellow solid (58 mg, 48% over 2 steps). M/z 466.2 (M)$^+$. $^1$H NMR (d6-DMSO) δ 6 8.49 (1H, bs), 7.92 (1H, s), 7.86 (1H, d, J=8.5 Hz), 7.37 (1H, dd, J=8.5 Hz, J=1.5 Hz), 7.19-7.15 (2H, m), 7.12-7.09 (2H, m), 4.66 (2H, d, J=5.0 Hz), 3.39 (2H, d, J=16 Hz), 3.29-3.26 (2H, m), 3.02 (9H, s), 2.89 (2H, d, J=16 Hz), 2.75 (2H, t, J=7.5 Hz), 2.39 (2H, s), 2.10-2.06 (2H, m).

Example 38 (Method E)

2-[2-[[6-(3-aminopropyl)-1,3-benzothiazol-2-yl]methylcarbamoyl]indan-2-yl]acetic acid

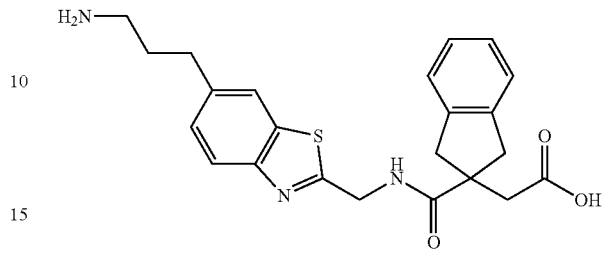

a. tert-butyl N-[(E)-3-tributylstannylallyl]carbamate

Tributyltin hydride (10.3 g, 35.4 mmol) and AIBN (264.4 mg, 1.61 mmol) were added to a solution of tert-butyl N-prop-2-ynylcarbamate (5 g, 32.2 mmol) in toluene (60 mL) at RT. The reaction mixture was stirred at 120° C. for 2 h and concentrated under reduced pressure. The crude compound was purified by flash chromatography eluting with 3% EtOAc in petroleum ether affording a colourless liquid (12 g, 83%). M/z 348.1 (M-Boc+H)$^+$.

b. tert-butyl 2-[2-[[6-[(E)-3-(tert-butoxycarbonylamino)prop-1-enyl]-1,3-benzothiazol-2-yl]methylcarbamoyl]indan-2-yl]acetate tert-Butyl N-[(E)-3-tributylstannylallyl]carbamate (900 mg, 1.99 mmol) was added to a stirred solution of tert-butyl 2-[2-[(6-bromo-1,3-benzothiazol-2-yl)methylcarbamoyl]indan-2-yl]acetate (500 mg, 0.99 mmol) in DMF (10 mL) at RT and the reaction mixture was purged with argon for 15 min. PdCl$_2$(PPh$_3$)$_2$(140 mg, 0.19 mmol) was added and the reaction mixture was purged with argon for further 5 min and then heated in sealed tube at 80° C. for 2 h. The reaction mixture was diluted with EtOAc (20 mL) and cold water (20 mL). The organic layer was separated, washed with water (2×10 mL), dried over anhydrous Na$_2$SO$_4$, filtered and concentrated under reduced pressure. The crude compound was purified by flash chromatography eluting with 5% MeOH in DCM affording a pale brown solid (280 mg, 49%). M/z 578.3 (M+H)$^+$.

c. tert-butyl 2-[2-[[6-[3-(tert-butoxycarbonylamino)propyl]-1,3-benzothiazol-2-yl]methylcarbamoyl]indan-2-yl]acetate 10% Pd/C (120 mg) was added to a stirred solution of tert-butyl 2-[2-[[6-[(E)-3-(tert-butoxycarbonylamino)prop-1-enyl]-1,3-benzothiazol-2-yl]methylcarbamoyl]indan-2-yl]acetate (180 mg, 0.31 mmol) in EtOH (8 mL) at RT under N$_2$. The reaction mixture was stirred under H$_2$ (balloon) for 16 h and filtered through a celite pad which was washed with MeOH (20 mL). The filtrate was concentrated under reduced pressure. The crude compound was used as such in the next step (135 mg, 75%). M/z 580.3 (M+H)$^+$.

d. 2-[2-[[6-(3-aminopropyl)-1,3-benzothiazol-2-yl]methylcarbamoyl]indan-2-yl]acetic acid TFA:TES (5:1, 5 mL) was added to a solution of tert-butyl 2-[2-[[6-[3-(tert-butoxycarbonylamino)propyl]-1,3-benzothiazol-2-yl]methylcarbamoyl]indan-2-yl]acetate (130 mg, 0.22 mmol) in DCM (5 mL) at RT. The reaction mixture was stirred at RT for 6 h and concentrated under reduced pressure. The crude compound was purified by preparative HPLC (X-BRIDGE-C18 (150*30); 5 u; Flow rate: 25 mL/min; mobile phase: 0.05% FA in H$_2$O:ACN) affording the title product as a white sold (38 mg, 41%). M/z 424.2 (M+H)$^+$. $^1$H NMR (d6-DMSO) δ 11.40 (1H, bs), 7.82 (1H, t, J=8.5 Hz), 7.78 (1H, s), 7.32 (1H, dd, J=8.5 Hz, J=1.5 Hz), 7.19-7.09 (4H, m), 4.64 (2H, d, J=5.0 Hz), 3.42 (2H, d, J=16.0 Hz), 2.93 (2H, d, J=16.0 Hz), 2.73-2.68 (4H, m), 2.50-2.48 (2H, bs), 1.82-1.79 (2H, m).

Example 39

2-[2-[[6-[(E)-3-aminoprop-1-enyl]-1,3-benzothiazol-2-yl]methylcarbamoyl]indan-2-yl]acetic acid

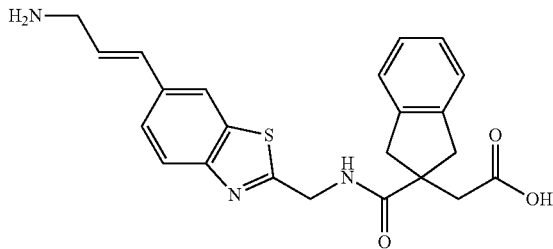 [SMILES: NC/C=C/c1ccc2nc(CNC(=O)C3(CC(=O)O)Cc4ccccc4C3)sc2c1]

TFA:TES (5:1, 5 mL) was added to a solution of tert-butyl 2-[2-[[6-[(E)-3-(tert-butoxycarbonylamino)prop-1-enyl]-1,3-benzothiazol-2-yl]methylcarbamoyl]indan-2-yl]acetate (550 mg, 0.95 mmol) in DCM (10 mL) at RT. The reaction mixture was stirred at RT for 3 h and concentrated under reduced pressure. The crude compound was triturated with Et$_2$O (20 mL) affording an off-white solid (300 mg, 74.8%). M/z 422.1 (M+H)$^+$. $^1$H NMR (d6-DMSO) δ 12.10 (1H, s), 8.75 (1H, t, J=6.0 Hz), 8.09 (1H, d, J=1.5 Hz), 7.95 (3H, bs), 7.90 (1H, d, J=8.5 Hz), 7.59 (1H, dd, J=8.5 Hz, J=1.5 Hz), 7.23-7.20 (2H, m), 7.16-7.13 (2H, m), 6.84 (1H, d, J=16 Hz), 6.35-6.29 (1H, m), 4.64 (2H, d, J=6.0 Hz), 3.65 (2H, bs), 3.46 (2H, d, J=16.5 Hz), 3.00 (2H, d, J=16.5 Hz), 2.74 (2H, s).

Example 40

2-[2-[[5-(3-aminopropyl)-1,3-benzothiazol-2-yl]methylcarbamoyl]indan-2-yl]acetic acid

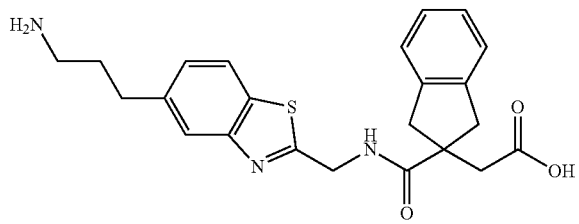 [SMILES: NCCCc1ccc2sc(CNC(=O)C3(CC(=O)O)Cc4ccccc4C3)nc2c1]

a. tert-butyl N-[(5-bromo-1,3-benzothiazol-2-yl)methyl]carbamate

CuO (1 g, 12.6 mmol) was added to a stirred solution of 5-bromo-2-iodo-aniline (2.5 g, 8.30 mmol) and tert-butyl N-(2-amino-2-thioxo-ethyl)carbamate (2 g, 10.9 mmol) in DMF (15 mL) at RT and the reaction mixture was purged with argon for 15 min. Then dppf (929 mg, 1.60 mmol) and Pd$_2$(dba)$_3$ (768 mg, 0.8 mmol) were added to the reaction mixture and degassed with argon for further 5 min. The reaction mixture was stirred in a sealed tube at 70° C. for 4 h and filtered through celite pad which was washed with EtOAc (50 mL). The filtrate was washed with water (2×30 mL) and concentrated under reduced pressure. The crude compound was purified by flash chromatography eluting with 20% EtOAc in petroleum ether affording an off white solid (2 g, 71%). M/z 343.0 (M+H)$^+$.

b. (5-bromo-1,3-benzothiazol-2-yl)methanamine hydrochloride

4N HCl in dioxane (30 mL) was added to a solution of tert-butyl N-[(5-bromo-1,3-benzothiazol-2-yl)methyl]carbamate (3 g, 8.7 mmol) in dioxane (50 mL) at 0° C. The reaction mixture was stirred at RT for 4 h and concentrated under reduced pressure. The crude compound was triturated with n-pentane (20 mL) and Et$_2$O (20 mL) affording a pale yellow solid (2.2 g, 90%). M/z 243.0 (M)$^+$.

c. tert-butyl 2-[2-[(5-bromo-1,3-benzothiazol-2-yl)methylcarbamoyl]indan-2-yl]acetate Et$_3$N (1.5 mL, 10.8 mmol) was added to a stirred solution of (5-bromo-1,3-benzothiazol-2-yl)methanamine hydrochloride (800 mg, 2.8 mmol) in DMF (10 mL) at RT and stirred for 15 min. Then 2-(2-tert-butoxy-2-oxo-ethyl)indane-2-carboxylic acid (1 g, 3.6 mmol), EDC.HCl (833 mg, 4.3 mmol) and HOBt (684 mg, 5.0 mmol) were added. The reaction mixture was stirred at RT for 16 h, diluted with ice cold water (100 mL) and extracted with EtOAc (2×50 mL). The organic layer was washed with brine solution, dried over Na$_2$SO$_4$ and concentrated under reduced pressure. The crude compound was purified by flash chromatography eluting with 25% EtOAc in petroleum ether affording an off white solid (1 g, 56%). M/z 501.1 (M+H)$^+$.

d. tert-butyl 2-[2-[[5-[(E)-3-(tert-butoxycarbonylamino)prop-1-enyl]-1,3-benzothiazol-2-yl]methylcarbamoyl]indan-2-yl]acetate Tert-butyl N-[(E)-3-tributylstannylallyl]carbamate (713 mg, 1.6 mmol) was added to a stirred solution of tert-butyl 2-[2-[(5-bromo-1,3-benzothiazol-2-yl)methylcarbamoyl]indan-2-yl]acetate (400 mg, 0.8 mmol) in DMF (5 mL) at RT and the reaction mixture was purged with argon for 15 min. Then PdCl$_2$(PPh$_3$)$_2$(112 mg, 0.16 mmol) was added. The reaction mixture was purged with argon for further 2 min, stirred in a sealed tube at 75° C. for 2 h, diluted with ice cold water (50 mL) and extracted with EtOAc (2×50 mL). The organic layer was washed with brine solution, dried over Na$_2$SO$_4$, filtered and concentrated under reduced pressure. The crude compound was purified by flash chromatography eluting with 25% EtOAc in petroleum ether affording an off white solid (240 mg, 52%). M/z 578.3 (M+H)$^+$.

e. tert-butyl 2-[2-[[5-[3-(tert-butoxycarbonylamino)propyl]-1,3-benzothiazol-2-yl]methylcarbamoyl]indan-2-yl]acetate 10% Pd/C (150 mg) was added to a stirred solution of tert-butyl 2-[2-[[5-[(E)-3-(tert-butoxycarbonylamino)prop-1-enyl]-1,3-benzothiazol-2-yl]methylcarbamoyl]indan-2- yl]acetate (200 mg, 0.34 mmol) in EtOH (8 mL) at RT under N₂. The reaction mixture was stirred under H₂ (balloon) for 16 h and filtered through celite pad which was washed with MeOH (20 mL). The filtrate was concentrated under reduced pressure. The brown solid was used as such in the next step (194 mg, 97%). M/z 580.3 (M+H)⁺.

f. 2-[2-[[5-(3-aminopropyl)-1,3-benzothiazol-2-yl]methylcarbamoyl]indan-2-yl]acetic acid TFA:TES (5:1, 2 mL) was added to a solution of tert-butyl 2-[2-[[5-[3-(tert-butoxycarbonylamino)propyl]-1,3-benzothiazol-2-yl]methylcarbamoyl]indan-2-yl]acetate (194 mg, 0.33 mmol) in DCM (5 mL) at RT. The reaction mixture was stirred at RT for 4 h and concentrated under reduced pressure. The crude compound was purified by preparative HPLC (KROMOSIL-C18 (25*150 MM); 10 u; Flow rate: 25 mL/min; mobile phase: 0.05% FA in H₂O:ACN) affording the title product as an off-white solid (41 mg, 30%). M/z 424.1 (M+H)⁺. ¹H NMR (d6-DMSO) δ 11.30 (1H, bs), 7.86 (1H, d, J=8.5 Hz), 7.74 (1H, s), 7.22 (1H, d, J=8.5 Hz), 7.18-7.10 (4H, m), 4.64 (2H, d, J=5.5 Hz), 3.46 (2H, d, J=16.0 Hz), 2.94 (2H, d, J=16 Hz), 2.78-2.72 (4H, m), 2.52-2.50 (2H, bs), 1.88-1.86 (2H, m).

Example 41

2-[2-[(6-piperazin-1-yl-1,3-benzothiazol-2-yl)methylcarbamoyl]indan-2-yl]acetic acid

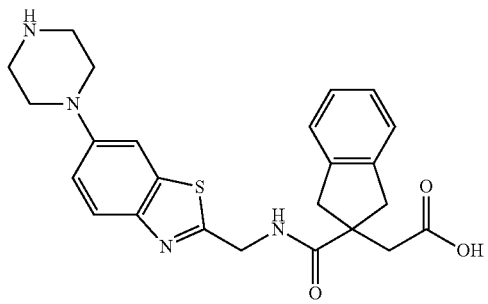 [SMILES: O=C(O)CC1(C(=O)NCc2nc3ccc(N4CCNCC4)cc3s2)Cc2ccccc2C1]

a. 2-[2-[(6-bromo-1,3-benzothiazol-2-yl)methylcarbamoyl]indan-2-yl]acetic acid TFA:TES (5:1, 5 mL) was added to a solution of tert-butyl 2-[2-[(6-bromo-1,3-benzothiazol-2-yl)methylcarbamoyl]indan-2-yl]acetate (400 mg, 0.79 mmol) in DCM (5 mL) at RT. The reaction mixture was stirred at RT for 5 h and concentrated under reduced pressure. The residue was washed with n-pentane (2×10 mL). Then water (12 mL) was added and stirred for 15 min. The resulting precipitate was filtered, washed with water (5 mL) and dried under vacuum affording an off white solid (300 mg, 85.7%). M/z 445.1 (M+H)⁺.

b. 2-[2-[[6-(4-tert-butoxycarbonylpiperazin-1-yl)-1,3-benzothiazol-2-yl]methylcarbamoyl]indan-2-yl]acetic acid Tert-butyl piperazine-1-carboxylate (94 mg, 0.50 mmol) and K₃PO₄ (215 mg, 1.01 mmol) were added to a stirred solution of 2-[2-[(6-bromo-1,3-benzothiazol-2-yl)methylcarbamoyl]indan-2-yl]acetic acid (150 mg, 0.33 mmol) in THF (5 mL) at RT and the reaction mixture was purged with argon for 15 min. Ruphos Pd G1 (50 mg, 0.06 mmol) was then added. The reaction mixture was purged with argon for further 5 min, then stirred in a sealed tube at 75° C. for 20 h and filtered through celite pad which was washed with EtOAc (50 mL). The filtrate was concentrated under reduced pressure. The crude compound was purified by preparative HPLC (KROMOSIL-C18 (25*150 MM); 10 u; Flow rate: 25 mL/min; mobile phase: 0.05% FA in H₂O:ACN) affording an off-white solid (56 mg, 30%). M/z 551.2 (M+H)⁺.

c. 2-[2-[(6-piperazin-1-yl-1,3-benzothiazol-2-yl)methylcarbamoyl]indan-2-yl]acetic acid TFA:TES (5:1, 1 mL) was added to a solution of 2-[2-[[6-(4-tert-butoxycarbonylpiperazin-1-yl)-1,3-benzothiazol-2-yl]methylcarbamoyl]indan-2-yl]acetic acid (32 mg, 0.05 mmol) in DCM (1 mL) at RT. The reaction mixture was stirred at RT for 3 h and concentrated under reduced pressure. The crude compound was purified by preparative HPLC (INERTSIL-ODS (250*20 MM); 5 u; Flow rate: 18 mL/min; mobile phase: 0.05% FA in H₂O:ACN) affording the title product as a pale yellow solid (14 mg, 53.8%). M/z 451.2 (M+H)⁺. ¹H NMR (d6-DMSO) δ 9.99 (1H, bs), 8.37 (1H, bs), 7.71 (1H, d, J=9.0 Hz), 7.44 (1H, d, J=2.0 Hz), 7.20-7.11 (5H, m), 4.59 (2H, d, J=5.0 Hz), 3.43 (2H, d, J=16.5 Hz), 3.10 (4H, bs), 2.96 (2H, d, J=16.5 Hz), 2.88 (4H, bs), 2.60 (2H, s).

Example 42

2-[2-[[6-(4-methylpiperazin-1-yl)-1,3-benzothiazol-2-yl]methylcarbamoyl]indan-2-yl]acetic acid

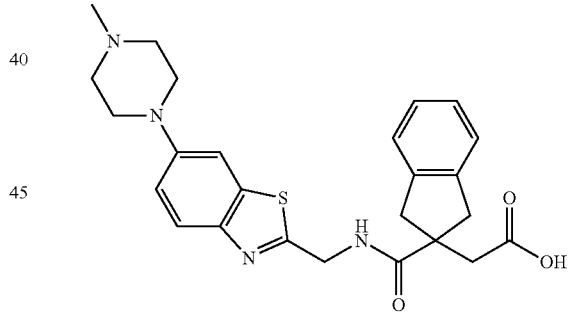

N-methylpiperazine (40.5 mg, 0.40 mmol) and K₃PO₄ (171.6 mg, 1.01 mmol) were added to a stirred solution of 2-[2-[(6-bromo-1,3-benzothiazol-2-yl)methylcarbamoyl]indan-2-yl]acetic acid (120 mg, 0.26 mmol) in THF (5 mL) at RT and the reaction mixture was purged with argon for 15 min. Ruphos Pd G1 (39.2 mg, 0.05 mmol) was added. The reaction mixture was purged with argon for further 5 min, stirred in a sealed tube at 80° C. for 20 h and filtered through celite pad which was washed with EtOAc (50 mL). The filtrate was concentrated under reduced pressure. The crude compound was purified by preparative HPLC (YMC-TRI-ART-C18 (150*30); 10 u; Flow rate: 25 mL/min; mobile phase: 0.05% FA in H₂O:ACN) affording the title product as a yellow solid (23 mg, 18.4%). M/z 465.2 (M+H)⁺. ¹H NMR (d6-DMSO) δ 10.27 (1H, bs), 8.39 (1H, bs), 7.71 (1H, d, J=9.0 Hz), 7.46 (1H, d, J=2.0 Hz), 7.19-7.11 (5H, m), 4.59

(2H, d, J=4.5 Hz), 3.43 (2H, d, J=16.0 Hz), 3.18-3.16 (4H, m), 2.95 (2H, d, J=16.5 Hz), 2.57 (2H, bs), 2.47-2.45 (4H, m), 2.22 (3H, s).

Example 43

2-[2-[[6-(4,4-dimethylpiperazin-4-ium-1-yl)-1,3-benzothiazol-2-yl]methylcarbamoyl]indan-2-yl]acetic acid

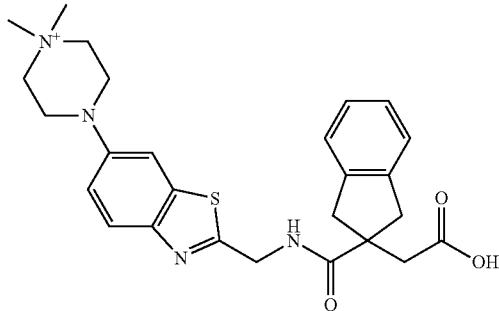 [SMILES: C[N+]1(C)CCN(c2ccc3nc(CNC(=O)C4(CC(=O)O)Cc5ccccc5C4)sc3c2)CC1]

a. tert-butyl N-[[6-(4-methylpiperazin-1-yl)-1,3-benzothiazol-2-yl]methyl]carbamate N-methyl piperazine (657.8 mg, 6.57 mmol) and $K_3PO_4$ (2.8 g, 13.1 mmol) were added to a stirred solution of tert-butyl N-[(6-bromo-1,3-benzothiazol-2-yl)methyl]carbamate (1.5 g, 4.38 mmol) in THF (20 mL) at RT and the reaction mixture was purged with argon for 15 min. Ruphos Pd G1 (639.1 mg, 0.87 mmol) was added. The reaction mixture was then purged with argon for further 5 min, stirred in a sealed tube at 80° C. for 16 h and filtered through celite pad which washed with EtOAc (50 mL). The filtrate was concentrated under reduced pressure. The crude compound was purified by flash chromatography eluting with 4% MeOH in DCM affording a yellow solid (550 mg, crude). M/z 363.2 (M+H)$^+$.

b. [6-(4-methylpiperazin-1-yl)-1,3-benzothiazol-2-yl]methanamine hydrochloride 4N HCl in dioxane (4 mL) was added to a solution of tert-butyl N-[[6-(4-methylpiperazin-1-yl)-1,3-benzothiazol-2-yl]methyl]carbamate (550 mg, 1.51 mmol) in dioxane (5 mL) at 0° C. The reaction mixture was stirred at RT for 4 h and concentrated under reduced pressure. The crude compound was triturated with n-pentane (5 mL) and $Et_2O$ (5 mL) affording a white solid (450 mg, crude). M/z 263.1 (M+H)$^+$.

c. tert-butyl 2-[2-[[6-(4-methylpiperazin-1-yl)-1,3-benzothiazol-2-yl]methylcarbamoyl]indan-2-yl]acetate $Et_3N$ (1.1 mL, 8.05 mmol) was added to a stirred solution of [6-(4-methylpiperazin-1-yl)-1,3-benzothiazol-2-yl]methanamine hydrochloride (400 mg, 1.34 mmol) in DMF (5 mL) at RT and stirred for 15 min. 2-(2-tert-butoxy-2-oxoethyl)indane-2-carboxylic acid (407 mg, 1.47 mmol) and $T_3P$ (1.18 mL, 2.01 mmol) were then added. The reaction mixture was stirred at RT for 16 h, diluted with water (30 mL) and extracted with EtOAc (2×50 mL). The combined organic layer was washed with brine, dried over $Na_2SO_4$, filtered and concentrated under reduced pressure. The crude compound was purified by flash chromatography eluting with 4% MeOH in DCM affording a yellow solid (160 mg, 23% over 3 steps). M/z 521.3 (M+H)$^+$.

d. tert-butyl 2-[2-[[6-(4,4-dimethylpiperazin-4-ium-1-yl)-1,3-benzothiazol-2-yl]methylcarbamoyl]indan-2-yl]acetate MeI (130 mg, 0.92 mmol) was added to a solution of tert-butyl 2-[2-[[6-(4-methylpiperazin-1-yl)-1,3-benzothiazol-2-yl]methylcarbamoyl]indan-2-yl]acetate (160 mg, 0.30 mmol) in THF (3 mL) at 0° C. The reaction mixture was stirred at RT for 4 h and concentrated under reduced pressure. The crude residue was triturated with $Et_2O$ (2×10 mL) affording a yellow solid which was used as such in the next step (160 mg, crude). M/z 535.2 (M)$^+$.

e. 2-[2-[[6-(4,4-dimethylpiperazin-4-ium-1-yl)-1,3-benzothiazol-2-yl]methylcarbamoyl]indan-2-yl]acetic acid TFA:TES (5:1, 2 mL) was added to a stirred solution of tert-butyl 2-[2-[[6-(4,4-dimethylpiperazin-4-ium-1-yl)-1,3-benzothiazol-2-yl]methylcarbamoyl]indan-2-yl]acetate (120 mg, 0.22 mmol) in DCM (5 mL) at RT. The reaction mixture was stirred at RT for 2 h and concentrated under reduced pressure. The residue was washed with n-pentane (10 mL) and $Et_2O$ (10 mL). The crude compound was purified by preparative HPLC (X-BRIDGE-C18 (150*30); 5 u; Flow rate: 25 mL/min; mobile phase: 0.05% FA in $H_2O$: ACN) affording the title product as a pale pink solid (52 mg, 48.5%). M/z 479.3 (M)$^+$. $^1$H NMR (d6-DMSO) δ 12.50 (1H, bs), 7.80 (1H, d, J=9.0 Hz), 7.62 (1H, d, J=2.5 Hz), 7.23 (1H, dd, J=9.0 Hz, J=2.5 Hz), 7.19-7.14 (2H, m), 7.12-7.09 (2H, m), 4.61 (2H, d, J=5.5 Hz), 3.57-3.55 (8H, m), 3.39 (2H, d, J=16 Hz), 3.18 (6H, s), 2.89 (2H, d, J=16 Hz), 2.38 (2H, s).

Example 44

2-[2-(4,5,6,7-tetrahydrothiazolo[5,4-c]pyridin-2-ylmethylcarbamoyl)indan-2-yl]acetic acid

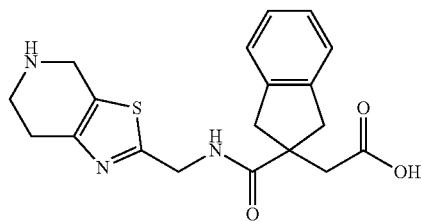 [SMILES: O=C(O)CC1(C(=O)NCc2nc3c(s2)CNCC3)Cc2ccccc2C1]

a. benzyl 3-bromo-4-oxo-piperidine-1-carboxylate

DIPEA (4.64 mL, 26.81 mmol) and TMSOTf (4.29 mL, 25.73 mmol) were added to a stirred solution of benzyl 4-oxopiperidine-1-carboxylate (5 g, 21.44 mmol) in DCM (50 mL) at 0° C. The reaction mixture was stirred for 30 min at 0° C. and NBS (3.81 g, 21.44 mmol) was added at 0° C. The reaction mixture was stirred at RT for 16 h, diluted with water (50 mL) and extracted with DCM (2×100 mL). The combined organic layer was washed with brine, dried over $Na_2SO_4$, filtered and concentrated under reduced pressure.

The crude compound was purified by column chromatography eluting with 10-15% EtOAc in petroleum ether affording a pale yellow liquid (4.5 g, 67.4%). M/z 312.2 (M+H)⁺.

b. benzyl 2-(aminomethyl)-6,7-dihydro-4H-thiazolo [5,4-c]pyridine-5-carboxylate

Tert-butyl N-(2-amino-2-thioxo-ethyl)carbamate (489.4 mg, 2.57 mmol) was added to a stirred solution of benzyl 3-bromo-4-oxo-piperidine-1-carboxylate (800 mg, 2.57 mmol) in IPA (10 mL) at RT. The reaction mixture was stirred at 90° C. for 16 h and concentrated under reduced pressure. The residue was diluted with water (5 mL), acidified (pH~2) with 1N HCl and extracted with Et₂O (2×20 mL). The aqueous phase was basified (pH~8) with saturated NaHCO₃ solution and extracted with DCM (2×50 mL). The combined organic layer was washed with brine, dried over Na₂SO₄ and concentrated under reduced pressure affording a pale brown solid (220 mg, 28.5%). M/z 304.3 (M+H)⁺.

c. benzyl 2-[[[2-(2-tert-butoxy-2-oxo-ethyl)indane-2-carbonyl]amino]methyl]-6,7-dihydro-4H-thiazolo [5,4-c]pyridine-5-carboxylate Et₃N (1.5 mL, 10.86 mmol), EDC.HCl (1.25 g, 6.51 mmol) and HOBt (1.02 g, 7.60 mmol) were added to a stirred solution of 2-(2-tert-butoxy-2-oxo-ethyl)indane-2-carboxylic acid (1.5 g, 5.43 mmol) in DMF (15 mL) at RT and stirred for 15 min at RT. Then benzyl 2-(aminomethyl)-6,7-dihydro-4H-thiazolo[5,4-c]pyridine-5-carboxylate (1.64 g, 5.43 mmol) was added. The reaction mixture was stirred at RT overnight, diluted with ice cold water (50 mL) and extracted with EtOAc (2×100 mL). The combined organic layer was washed with brine, dried over Na₂SO₄, filtered and evaporated under reduced pressure. The crude compound was purified by flash chromatography eluting with 3-5% MeOH in DCM affording a pale brown solid (1.9 g, 68.5%). M/z 562.2 (M+H)⁺.

d. tert-butyl 2-[2-(4,5,6,7-tetrahydrothiazolo[5,4-c] pyridin-2-ylmethylcarbamoyl)indan-2-yl]acetate 10% Pd/C (800 mg) was added to a stirred solution of benzyl 2-[[[2-(2-tert-butoxy-2-oxo-ethyl)indane-2-carbonyl]amino]methyl]-6,7-dihydro-4H-thiazolo[5,4-c]pyridine-5-carboxylate (800 mg, 1.42 mmol) in MeOH (15 mL) at RT. The reaction mixture was stirred at RT under H₂ (balloon) for 1 day and filtered through celite pad which was washed with MeOH (50 mL). The filtrate was evaporated under reduced pressure. The crude compound was purified by column chromatography eluting with 10-20% MeOH in DCM affording a pale yellow solid (290 mg, 47.6%). M/z 428.2 (M+H)⁺.

e. 2-[2-(4,5,6,7-tetrahydrothiazolo[5,4-c]pyridin-2-ylmethylcarbamoyl)indan-2-yl]acetic acid TFA (0.21 mL, 2.81 mmol) and TES (0.021 mL, 0.14 mmol) were added to a stirred solution of tert-butyl 2-[2-(4,5,6,7-tetrahydrothiazolo[5,4-c]pyridin-2-ylmethylcarbamoyl)indan-2-yl]acetate (60 mg, 0.14 mmol) in DCM (3 mL) at RT. The reaction mixture was stirred at RT for 4 h and concentrated under reduced pressure. The crude compound was purified by preparative HPLC (X-BRIDGE-C18 (150*30); 5 u; Flow rate: 25 mL/min; mobile phase: 0.05% FA in H₂O:ACN) affording the title product as an off white solid 15 mg, 29%). M/z 372.1 (M+H)⁺. ¹H NMR (d6-DMSO) δ 8.71 (1H, m), 7.20-7.17 (2H, m), 7.14-7.11 (2H, m), 4.45 (2H, d, J=6 Hz), 3.93 (2H, s), 3.41 (2H, d, J=16.4 Hz), 3.09-3.06 (2H, m), 2.96 (2H, d, J=16.4 Hz), 2.69 (2H, bs), 2.69-2.65 (2H, m).

Example 45

2-(2-{[(2S)-3-(1H-indol-3-yl)-1-[(1-methylpiperidin-4-yl)oxy]-1-oxopropan-2-yl]carbamoyl}-2,3-dihydro-1H-inden-2-yl)acetic acid

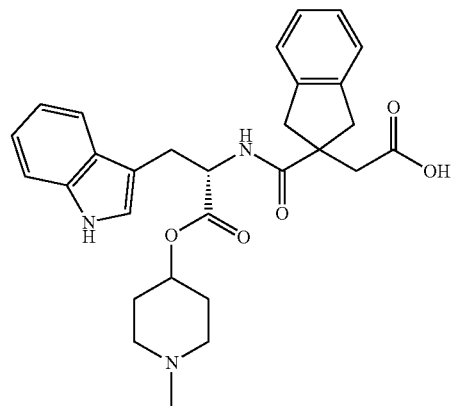 [SMILES: CN1CCC(OC(=O)[C@H](Cc2c[nH]c3ccccc23)NC(=O)C2(CC(=O)O)Cc3ccccc3C2)CC1]

a. 1-methylpiperidin-4-yl (2S)-2-{[(benzyloxy)carbonyl]amino}-3-(1H-indol-3-yl)propanoate A solution of L-N-carbobenzyloxytryptophan (1 g, 3 mmol) in DCM (20 mL) was treated with EDC.HCl (850 mg, 4.4 mmol), DMAP (37 mg, 0.3 mmol) and 1-methylpiperidine-4-ol (510 mg, 4.4 mmol). After 2.5 h the mixture was washed with aq. NaHCO₃ solution, dried and evaporated. The residue was chromatographed on silica eluting with 0-50% IPA in DCM affording a clear oil (1.05 g, 82%). M/z 436.4 (M+H)⁺.

b. 1-methylpiperidin-4-yl (2S)-2-amino-3-(1H-indol-3-yl)propanoate

A solution of 1-methylpiperidin-4-yl (2S)-2-{[(benzyloxy)carbonyl]amino}-3-(1H-indol-3-yl)propanoate (1.05 g, 2.4 mmol) in IPA (25 ml) was hydrogenated over 10% palladium on charcoal for 1 h. Filtration and evaporation gave a clear oil (350 mg, 48%). M/z 302.4 (M+H)⁺.

c. 1-methylpiperidin-4-yl (2S)-2-({2-[2-(tert-butoxy)-2-oxoethyl]-2,3-dihydro-1H-inden-2-yl}formamido)-3-(1H-indol-3-yl)propanoate (Method C)

A solution of 2-[2-(tert-butoxy)-2-oxoethyl]-2,3-dihydro-1H-indene-2-carboxylic acid (320 mg, 1.1 mmol), HATU (536 mg, 1.4 mmol) and DIPEA (0.5 mL, 2.9 mmol) in DMF (10 mL) was stirred for 0.5 h then 1-methylpiperidin-4-yl (2S)-2-amino-3-(1H-indol-3-yl)propanoate (192 mg, 0.34 mmol) was added. After 45 min the mixture was diluted with EtOAc and with aq. NaHCO₃ solution, water, dried and evaporated. The residue was chromatographed on silica eluting with 0-80% IPA in DCM affording a clear oil (192 mg, 30%). M/z 560.7 (M+H)⁺.

d. 2-(2-{[(2S)-3-(1H-indol-3-yl)-1-[(1-methylpiperidin-4-yl)oxy]-1-oxopropan-2-yl]carbamoyl}-2,3-dihydro-1H-inden-2-yl)acetic acid A solution of 1-methylpiperidin-4-yl (2S)-2-({2-[2-(tert-butoxy)-2-oxoethyl]-2,3-dihydro-1H-inden-2-yl}formamido)-3-(1H-indol-3-yl)propanoate (90 mg, 0.16 mmol) in DCM (3 mL) was treated with TFA (1 mL). After 0.5 h the mixture was diluted with toluene and evaporated. The residue was dissolved in toluene and re-evaporated. The residue was purified by preparative hplc (MDAP) affording the title compound as a white solid (28 mg, 35%). M/z 504.6 (M+H)⁺. ¹H NMR (d6-DMSO) δ 10.80 (1H, bs), 8.00 (1H, d), 7.52 (1H, d), 7.35 (1H, d), 7.20-7.10 (3H, m), 7.05-7.10 (2H, m), 6.97 (1H, t), 4.60 (1H, m), 4.45 (1H, m), 3.40-3.30 (2H, m), 3.18-3.08 (4H, m), 3.00 (1H, d), 2.95 (1H, d), 2.70 (2H, s), 2.30 (1H, m), 2.20 (3H, s), 1.75 (1H, m), 1.60 (1H, m), 1.50 (1H, m), 1.38 (1H, m).

Example 46

(2-{[(1S)-2-(1H-indol-3-yl)-1-{[2-(trimethylammonio)ethyl]carbamoyl}ethyl]carbamoyl}-1,3-dihydroinden-2-yl)acetate

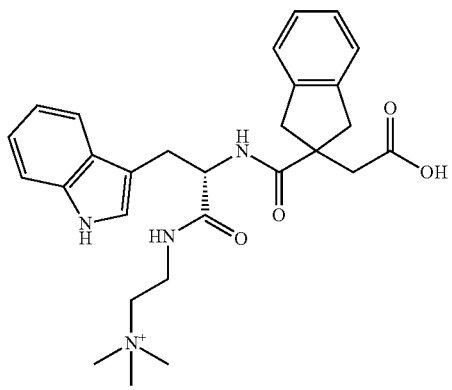 [SMILES: C[N+](C)(C)CCNC(=O)[C@H](Cc1c[nH]c2ccccc12)NC(=O)C1(CC(=O)O)Cc2ccccc2C1]

a. tert-Butyl 2-(2-{[(1S)-1-{[2-(dimethylamino)ethyl]carbamoyl}-2-(1H-indol-3-yl)ethyl]carbamoyl}-1,3-dihydroinden-2-yl)acetate A solution of 2-[2-(tert-butoxy)-2-oxoethyl]-2,3-dihydro-1H-indene-2-carboxylic acid (300 mg, 1.09 mmol), HATU (456 mg, 1.2 mmol) and DIPEA (0.3 mL, 1.7 mmol) in DCM (6 mL) was stirred for 0.25 h then a solution of (2S)-2-amino-N-[2-(dimethylamino)ethyl]-3-(1H-indol-3-yl)propanamide (328 mg, 1.2 mmol) (prepared as in Tammler, U., et al, European J. Med. Chem., 2003, 38, 481) in DCM (4 mL) was added. After 22 h, the mixture was diluted with DCM and washed with saturated aq. NaHCO₃ solution, then the organic extract was dried (Na₂SO₄) and evaporated affording the crude product. This was chromatographed on silica eluting with 0-10% (2M ammonia in MeOH) in DCM affording a yellow foam (317 mg, 55%). M/z 533.7 (M+H)⁺.

b. (2-{[(1S)-2-(1H-indol-3-yl)-1-{[2 (trimethylammonio)ethyl]carbamoyl}ethyl]carbamoyl}-1,3-dihydroinden-2-yl)acetate A solution of tert-butyl 2-(2-{[(1S)-1-{[2-(dimethylamino)ethyl]carbamoyl}-2-(1H-indol-3-yl)ethyl]carbamoyl}-1,3-dihydroinden-2-yl)acetate (140 mg, 0.26 mmol) in THF (2.5 mL) was treated with MeI (0.025 mL, 0.4 mmol). After 2.5 h more MeI (0.025 mL, 0.4 mmol) was added. After 0.5 h the mixture was evaporated to give a yellow foam. This was redissolved in DCM (2 mL) and treated with TFA (0.5 mL). After 2.5 h the mixture was diluted with toluene and evaporated to give a yellow oil. This was purified by preparative hplc (MDAP) affording the title compound as a white solid (70 mg, 55%). M/z 491.2 (M)⁺. ¹H NMR (d6-DMSO) δ 10.80 (1H, bs), 9.60 (1H, bs), 7.85 (1H, d), 7.50 (1H, d), 7.30 (1H, d), 7.18-7.10 (3H, m), 7.10 (1H, m), 7.05 (1H, m), 7.00 (1H, t), 4.35 (1H, m), 3.55-3.35 (8H, m), 3.30 (1H, dd), 3.25 (1H, d), 3.10 (9H, s), 2.95 (1H, d), 2.75 (1H, d), 2.70 (1H, d), 2.60 (1H, d), 2.30 (1H, d).

Example 47

(S)-2-(2-((1-(tert-butoxy)-3-(1H-indol-3-yl)-1-oxopropan-2-yl)carbamoyl)-2,3-dihydro-1H-inden-2-yl)acetic acid

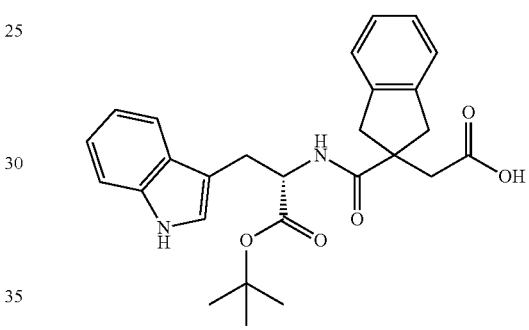

Method B was used as described above (example 5), using (S)-amino-3-(1H-indol-3-yl)-propionic acid tert-butyl ester hydrochloride as amine. M/z 463.2 (M+H)⁺. ¹H NMR (d6-DMSO) δ 12.98 (1H, bs), 10.78 (1H, s), 7.90 (1H, bd), 7.50 (1H, d), 7.32 (1H, d), 7.17-7.10 (5H, m), 7.06 (1H, t), 6.97 (1H, t), 4.38 (1H, q), 3.07 (2H, dd), 2.94 (2H, t), 2.67 (2H, s), 1.28 (9H, s). 2H under water peak.

Example 48

(S)-2-(2-((1-amino-3-(4-hydroxyphenyl)-1-oxopropan-2-yl)carbamoyl)-2,3-dihydro-1H-inden-2-yl) acetic acid

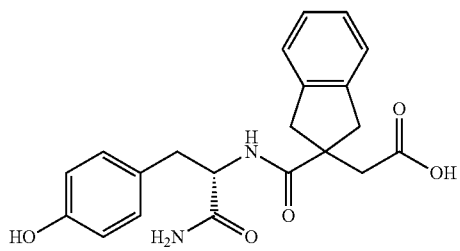 [SMILES: NC(=O)[C@H](Cc1ccc(O)cc1)NC(=O)C1(CC(=O)O)Cc2ccccc2C1]

Method B was used as described above (example 5), using L-tyrosinamide as amine. M/z 383.2 (M+H)⁺. ¹H NMR (d6-DMSO) δ 12.37 (1H, bs), 9.11 (1H, s), 7.65 (1H, d), 7.17-7.10 (6H, m), 6.90 (2H, d), 6.57 (2H, d), 4.31 (1H, m), 3.28 (1H, d), 3.08 (1H, d), 2.99 (1H, dd), 2.85-2.76 (3H, m), 2.69 (1H, dd), 2.62 (1H, d).

Example 49

(2-(carboxymethyl)-2,3-dihydro-1H-indene-2-carbonyl)-L-tyrosine

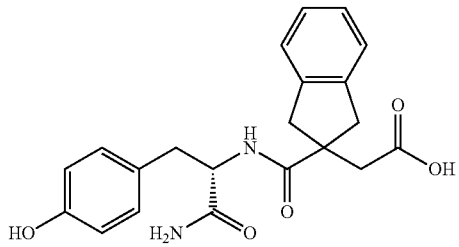 [SMILES: NC(=O)[C@H](Cc1ccc(O)cc1)NC(=O)C1(CC(=O)O)Cc2ccccc2C1]

Method B was used as described above (example 5), using (S)-2-amino-3-(4-hydroxyl-phenyl)-propionic acid tert-butyl ester as amine. M/z 384.2 (M+H)+. 1H NMR (d6-DMSO) δ 12.32 (2H, bs), 9.15 (1H, bs), 7.69 (1H, d), 7.18-7.10 (4H, m), 6.95 (2H, d), 6.61 (2H, d), 4.31 (1H, m), 3.21 (1H, d), 2.97-2.88 (3H, m), 2.81 (1H, dd), 2.66 (2H, s). 1H under water peak.

Example 50

(2-(carboxymethyl)-2,3-dihydro-1H-indene-2-carbonyl)-L-tryptophan

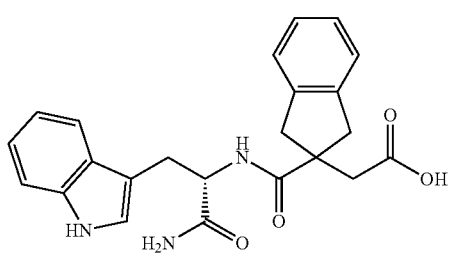 [SMILES: NC(=O)[C@H](Cc1c[nH]c2ccccc12)NC(=O)C1(CC(=O)O)Cc2ccccc2C1]

Method B was used as described above (example 5), using L-tryptophan as amine. M/z 407.0 (M+H)+. 1H NMR (d6-DMSO) δ 12.28 (2H, bs), 10.77 (1H, s), 7.73 (1H, d), 7.52 (1H, d), 7.32 (1H, d), 7.17-7.10 (4H, m), 7.07-7.03 (2H, m), 6.97 (1H, t), 4.45 (1H, q), 3.14 (1H, dd), 3.07 (1H, dd), 2.94 (2H, dd), 2.67 (2H, s). 2H under water peak.

Example 51

2-(2-(((1H-benzo[d]imidazol-2-yl)methyl)carbamoyl)-2,3-dihydro-1H-inden-2-yl)acetic

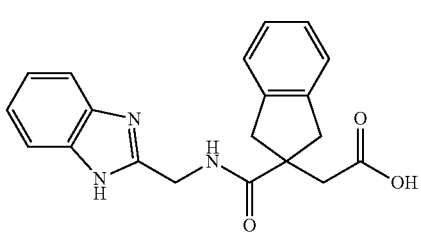 [SMILES: O=C(O)CC1(C(=O)NCc2nc3ccccc3[nH]2)Cc2ccccc2C1]

Method C was used as described above (example 10), using 2-(aminomethyl)indole hydrochloride as the amine. M/z 350 (M+H)+. 1H NMR (d6-DMSO) δ 12.46 (2H, bs), 8.48 (1H, t), 7.55-7.50 (2H, m), 7.23-7.17 (4H, m), 7.16-7.12 (2H, m), 4.52 (2H, d), 3.48 (2H, d), 2.97 (2H, d), 2.72 (2H, s).

Example 52

(S)-2-(2-((1-amino-3-(1H-indol-3-yl)-1-oxopropan-2-yl)carbamoyl)-2,3-dihydro-1H-inden-2-yl)acetic acid

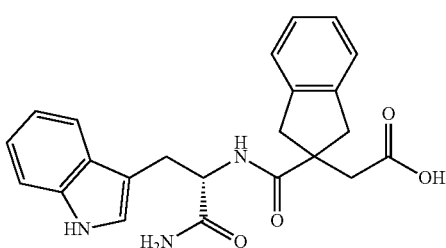

Method C was used as described above (example 10) using L-tryptophanamide hydrochloride as amine. M/z 406 (M+H)+. 1H NMR (d6-DMSO) δ 12.37 (1H, bs), 10.71 (1H, s), 7.68 (1H, d), 7.55 (1H, d), 7.31 (1H, d), 7.18 (1H, s), 7.16-7.10 (5H, m), 7.04 (1H, t), 6.97-6.93 (2H, m), 4.44 (1H, m), 3.28 (1H, d), 3.22 (1H, d), 3.10 (1H, d), 2.98 (1H, dd), 2.85-2.75 (3H, m), 2.63 (1H, d).

Example 53

(S)-2-(2-((3-(1H-indol-3-yl)-1-methoxy-1-oxopropan-2-yl)carbamoyl)-2,3-dihydro-1H-inden-2-yl)acetic acid

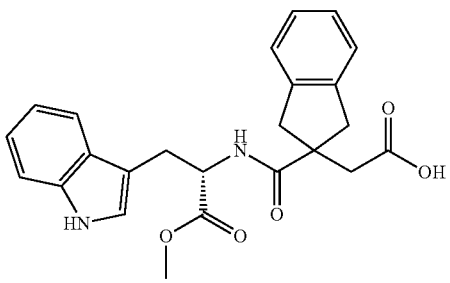 [SMILES: COC(=O)[C@H](Cc1c[nH]c2ccccc12)NC(=O)C1(CC(=O)O)Cc2ccccc2C1]

Method C was used as described above (example 10) using L-tryptophan methyl ester hydrochloride as amine. M/z 421.4 (M+H)⁺. ¹H NMR (d6-DMSO) δ 11.90 (1H, bs), 10.81 (1H, bs), 8.01 (1H, bs), 7.47 (1H, d), 7.32 (1H, d), 7.18-7.03 (6H, m), 6.99-6.93 (1H, m), 4.48 (1H, q), 3.54 (3H, s), 3.16 (2H, s), 3.16-3.04 (2H, m), 2.93 (2H, dd), 2.66 (2H, dd).

Example 54

2-(2-((thiazol-2-ylmethyl)carbamoyl)-2,3-dihydro-1H-inden-2-yl)acetic acid

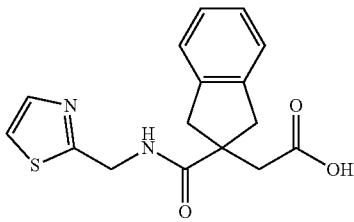 [SMILES: O=C(O)CC1(C(=O)NCc2nccs2)Cc2ccccc2C1]

Method C was used as described above (example 10), using 2-(aminomethyl)thiazole as amine. M/z 317.3 (M+H)⁺. ¹H NMR (d6-DMSO) δ 12.06 (1H, bs), 8.69 (1H, bs), 7.68 (1H, d), 7.58 (1H, d), 7.22-7.18 (2H, m), 7.15-7.10 (2H, m), 4.54 (2H, d), 3.43 (2H, d), 2.98 (2H, d), 2.72 (2H, s).

Example 55

2-(2-((quinolin-2-ylmethyl)carbamoyl)-2,3-dihydro-1H-inden-2-yl)acetic acid

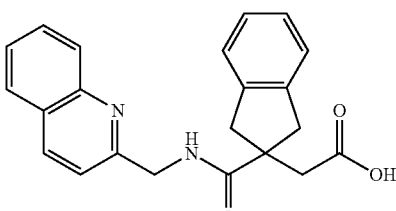

Method C was used as described above (example 10), using quinol-2-ylmethanamine as amine. M/z 361.4 (M+H)⁺. ¹H NMR (d6-DMSO) δ 12.11 (1H, bs), 8.50 (1H, bs), 8.25 (1H, d), 7.95-7.92 (2H, m), 7.74 (1H, m), 7.57 (1H, m), 7.38 (1H, d), 7.24-7.21 (2H, m), 7.17-7.13 (2H, m), 4.54 (2H, d), 3.50 (2H, d), 3.01 (2H, d), 2.77 (2H, s).

Example 56

2-(2-(((1-methyl-1H-benzo[d]imidazol-2-yl)methyl)carbamoyl)-2,3-dihydro-1H-inden-2-yl)acetic acid

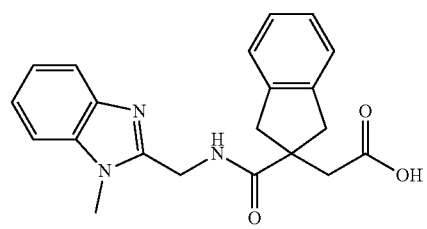 [SMILES: Cn1c(CNC(=O)C2(CC(=O)O)Cc3ccccc3C2)nc2ccccc21]

a. tert-butyl (2-((2-(methylamino)phenyl)amino)-2-oxoethyl)carbamate

To a solution of Boc-Gly-OH (3.26 g, 18.6 mmol) in DCM (150 mL) were added COMU (8.78 g, 20.5 mmol), DIPEA (7.14 mL, 41.0 mmol) and N-methylbezene-1,2,-diamine (2.50 g, 20.5 mmol) sequentially and the mixture stirred at RT for 2 h. The reaction mixture was washed with water, dried (Na₂SO₄), filtered and concentrated in vacuo to leave a residue. FCC (0-100% EtOAc in isohexane) gave a cream foam (4.29 g, 82%). M/z 280 (M+H)⁺.

b. tert-butyl ((1-methyl-1H-benzo[d]imidazol-2-yl)methyl)carbamate

A mixture of tert-butyl (2-((2-(methylamino)phenyl)amino)-2-oxoethyl)carbamate (4.29 g, 15.4 mmol) in AcOH (100 mL) was stirred at 70° C. for 1 h, then cooled to RT and concentrated in vacuo. The residue was redissolved in EtOAc, washed with saturated aq NaHCO₃ solution, dried (Na₂SO₄), filtered and concentrated in vacuo. The resulting solid was triturated with Et₂O/isohexane (1:5) and isohexane, then dried in vacuo to leave a cream solid (2.53 g, 63%). M/z 262 (M+H)⁺.

c. (1-methyl-1H-benzo[d]imidazol-2-yl)methanamine

A mixture of tert-butyl ((1-methyl-1H-benzo[d]imidazol-2-yl)methyl)carbamate (2.53 g, 9.68 mmol) in TFA (20 mL) and DCM (80 mL) was stirred at RT for 2 h. The solution was applied to an SCX-2 cartridge (75 g, prewashed with DCM). The cartridge was washed with MeOH then the product eluted with 2M NH₃ in MeOH; concentration in vacuo left a brown solid (1.63 g, quant.). M/z 162 (M+H)⁺.

d. 2-(2-(((1-methyl-1H-benzo[d]imidazol-2-yl)methyl)carbamoyl)-2,3-dihydro-1H-inden-2-yl)acetic acid Method C was used as described above (example 10), using (1-methyl-1H-benzo[d]imidazol-2-yl)methanamine as amine. M/z 364.1 (M+H)+. 1H NMR (d6-DMSO) δ 12.28 (1H, bs), 8.35 (1H, t), 7.58 (1H, d), 7.53 (1H, d), 7.25 (1H, t), 7.22-7.17 (3H, m), 7.14-7.11 (2H, m), 4.58 (2H, d), 3.71 (3H, s), 3.44 (2H, d), 2.94 (2H, d), 2.72 (2H, s).

Example 57

2-[2-(benzofuran-3-ylmethylcarbamoyl)indan-2-yl]acetic acid

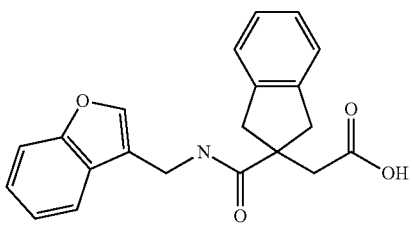 [SMILES: O=C(O)CC1(C(=O)NCc2coc3ccccc23)Cc2ccccc2C1]

a. Benzofuran-3-carbaldehyde oxime

To a solution of benzofuran-3-carbaldehyde (100 mg, 0.68 mmol) in EtOH:H2O (4 mL, 1:1) was added hydroxylamine hydrochloride (71 mg, 1.02 mmol) and sodium hydroxide (137 mg, 3.42 mmol) at RT and stirred at RT for 2.5 h. The reaction mixture was cooled to 0° C. and acidified with 1N HCl to pH~2. The resulting precipitate was filtered and washed with water and then dried in vacuum to obtain the product (80 mg, 73%) as an off white solid. M/z 162.3 (M+H)+.

b. Benzofuran-3-ylmethanamine

To a stirred solution of benzofuran-3-carbaldehyde oxime (80 mg, 0.49 mmol) in AcOH (2 mL) was added zinc (49 mg, 0.74 mmol) at RT and stirred at RT for 6 h. The reaction mixture was diluted with cold water (5 mL) and basified with ammonium hydroxide to pH~9 and then extracted with EtOAc (2×30 mL). The combined organic layer was dried with Na2SO4, filtered and the solvent removed to give the product (60 mg, 82%) as a pale brown liquid. M/z 148.3 (M+H)+.

c. 2-[2-(benzofuran-3-ylmethylcarbamoyl)indan-2-yl]acetic acid

Method C was used as described above (example 10), using benzofuran-3-ylmethanamine as amine. M/z 350.46 (M+H)+. 1H NMR (400 MHz, DMSO-d6): δ 12.18 (1H, bs), 8.37 (1H, bs), 7.49 (1H, dd, J=10.8 Hz, J=8.4 Hz), 7.25-7.12 (6H, m), 6.55 (1H, s), 4.42 (2H, d, J=5.6 Hz), 3.42 (2H, d, J=16.5 Hz), 2.97 (2H, d, J=16.5 Hz), 2.73 (2H, s).

Example 58

2-[2-[[(1R*)-1-(benzofuran-2-yl)ethyl]carbamoyl]indan-2-yl]acetic acid

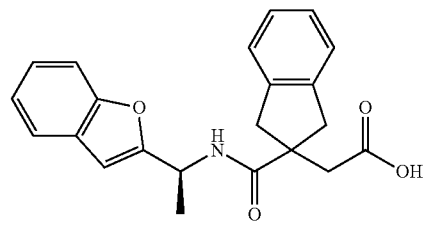 [SMILES: C[C@H](NC(=O)C1(CC(=O)O)Cc2ccccc2C1)c1cc2ccccc2o1]

The title product was synthesised from 1-(benzofuran-2-yl)ethan-1-one following the same procedure described for the synthesis of example 57.

The crude compound was purified by preparative HPLC [ATLANTIS T3 (250*19 mm), 5 u, Mobile phase: A: 0.1% FA in H2O, B: ACN], 70% yield, off-white solid.

The 180 mg of enantiomer mixture was purified by SFC [Chiralcel OX—H (4.6*250 mm), 5 u, Mobile phase: 80% CO2 gas, 20% (0.5% DEA in MeOH)]. M/z 364.5 (M+H)+. 1H NMR (300 MHz, DMSO-d6): δ 12.18 (1H, bs), 8.14 (1H, d, J=8.1 Hz), 7.55-7.49 (2H, m), 7.27-7.11 (6H, m), 6.60 (1H, s), 5.20-5.12 (1H, m), 3.43 (2H, d, J=16 Hz), 2.95 (2H, dd, J=16 Hz, J=3 Hz), 2.73 (2H, s), 1.46 (3H, d, J=6.9 Hz).

Example 59

2-[2-[[(1S*)-1-(benzofuran-2-yl)ethyl]carbamoyl]indan-2-yl]acetic acid

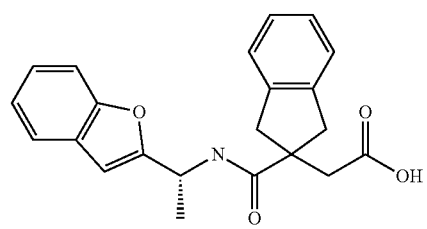 [SMILES: C[C@@H](NC(=O)C1(CC(=O)O)Cc2ccccc2C1)c1cc2ccccc2o1]

M/z 364.5 (M+H)+. 1H NMR (400 MHz, DMSO-d6): δ 12.20 (1H, bs), 8.46 (1H, bs), 7.55 (1H, dd, J=8.4 Hz, J=1.2 Hz), 7.49 (1H, d, J=8 Hz), 7.27-7.11 (6H, m), 6.61 (1H, s), 5.20-5.13 (1H, m), 3.43 (2H, d, J=16.4 Hz), 2.96 (2H, dd, J=16.4 Hz, J=4.8 Hz), 2.69 (2H, s), 1.46 (3H, d, J=6.8 Hz).

Example 60

2-(2-(((4-fluorobenzo[d]thiazol-2-yl)methyl)carbamoyl)-2,3-dihydro-1H-inden-2-yl)acetic acid

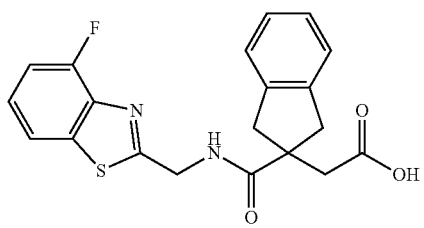 [SMILES: O=C(O)CC1(C(=O)NCc2nc3c(F)cccc3s2)Cc2ccccc2C1]

a. tert-Butyl ((4-fluorobenzo[d]thiazol-2-yl)methyl)carbamate

A solution of 2-fluoro-6-iodoaniline (200 mg, 0.844 mmol) in DMF (0.5 mL) was added to a mixture of tert-butyl (2-amino-2-thioxoethyl)carbamate (209 mg, 1.10 mmol), CuO (101 mg, 1.27 mmol), $Pd_2(dba)_3$ (77 mg, 0.084 mmol), and dppf (94 mg, 0.169 mmol) in DMF (1 mL). The sealed vial was stirred at 90° C. for 1 h and cooled to RT. FCC (10-30% EtOAc in isohexane) afforded the title compound as a yellow solid (217 mg, 91%). M/z 305 $(M+Na)^+$.

b. (4-Fluorobenzo[d]thiazol-2-yl)methanamine

To an ice-cooled solution of tert-butyl ((4-fluorobenzo[d]thiazol-2-yl)methyl)carbamate (284 mg, 1.01 mmol) in DCM (4 mL) was added TFA (1 mL). The mixture was stirred at RT for 2 h, then evaporated, azeotroping twice with toluene. The residue was dissolved in a mixture of DCM and MeOH and loaded on to a 2 g SCX-2 cartridge. The cartridge was washed with DCM/MeOH (1:1) mixture, then eluted with 1M $NH_3$ in MeOH; concentration in vacuo left a residue. FCC (1-5% [2M $NH_3$ in MeOH] in DCM) afforded the title compound as a light red solid (71.2 mg, 39%). M/z 183 $(M+H)^+$.

c. tert-Butyl 2-(2-(((4-fluorobenzo[d]thiazol-2-yl)methyl)carbamoyl)-2,3-dihydro-1H-inden-2-yl)acetate To a solution of 2-[2-(tert-butoxy)-2-oxoethyl]-2,3-dihydro-1H-indene-2-carboxylic acid (118 mg, 0.43 mmol), (4-fluorobenzo[d]thiazol-2-yl)methanamine (71 mg, 0.39 mmol) and DIPEA (0.20 mL, 1.17 mmol) in DMF (1.5 mL) was added HATU (222 mg, 0.58 mmol) portionwise over 3 min. The mixture was stirred at RT for 1 h then partitioned between EtOAc and dilute HCl. The aq. phase was extracted with more EtOAc, and the combined organic extracts were washed with water, then brine, dried ($Na_2SO_4$) and concentrated in vacuo to leave a residue. FCC (20-40% EtOAc in isohexane) afforded the title compound as a colourless gum (187 mg, quant.). M/z 463 $(M+Na)^+$.

d. 2-(2-(((4-Fluorobenzo[d]thiazol-2-yl)methyl)carbamoyl)-2,3-dihydro-1H-inden-2-yl)acetic acid To an ice-cooled solution of tert-butyl 2-(2-(((4-fluorobenzo[d]thiazol-2-yl)methyl)carbamoyl)-2,3-dihydro-1H-inden-2-yl)acetate (0.39 mmol) in DCM (4 mL) was added TFA (1.5 mL). The mixture was stirred at RT for 3 h, then evaporated, azeotroping twice with toluene to leave a residue. FCC (2-8% MeOH in DCM) afforded the title compound a colourless foam (123 mg, 82%, 2 steps). M/z 385.0 $(M+H)^+$. $^1H$ NMR (d6-DMSO) δ 12.19 (1H, bs), 8.79 (1H, t), 7.84 (1H, d), 7.42 (1H, m), 7.36-7.31 (1H, m), 7.24-7.20 (2H, m), 7.18-7.12 (2H, m), 4.68 (2H, d), 3.47 (2H, d), 3.00 (2H, d), 2.74 (2H, s).

Example 61

2-(2-(((4-bromobenzo[d]thiazol-2-yl)methyl)carbamoyl)-2,3-dihydro-1H-inden-2-yl)acetic acid

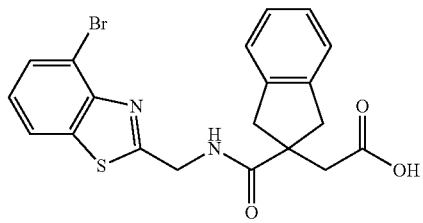 [SMILES: O=C(O)CC1(C(=O)NCc2nc3c(Br)cccc3s2)Cc2ccccc2C1]

Using Method D (example 60), but using 2-bromo-6-iodoaniline, the title compound was made as a white solid. M/z 444.8 $(M+H)^+$. $^1H$ NMR (d6-DMSO) δ 12.17 (1H, bs), 8.82 (1H, bs), 8.04 (1H, d), 7.73 (1H, d), 7.32 (1H, t), 7.24-7.19 (2H, m), 7.17-7.12 (2H, m), 4.68 (2H, d), 3.49 (2H, d), 3.00 (2H, d), 2.74 (2H, s).

Example 62

2-(2-(((4-methoxybenzo[d]thiazol-2-yl)methyl)carbamoyl)-2,3-dihydro-1H-inden-2-yl)acetic acid

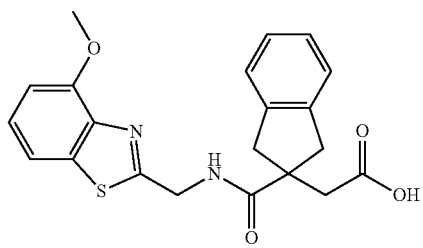 [SMILES: COc1cccc2sc(CNC(=O)C3(CC(=O)O)Cc4ccccc4C3)nc12]

Using Method D (example 60), but using 2-iodo-6-methoxyaniline, the title compound was made as a white solid. M/z 396.9 $(M+H)^+$. $^1H$ NMR (d6-DMSO) δ 12.16 (1H, bs), 8.72 (1H, t), 7.54 (1H, d), 7.33 (1H, t), 7.23-7.19 (2H, m), 7.16-7.12 (2H, m), 7.02 (1H, d), 4.63 (2H, d), 3.93 (3H, s), 3.47 (2H, d), 2.99 (2H, d), 2.74 (2H, s).

Example 63

2-(2-(((4-iodobenzo[d]thiazol-2-yl)methyl)carbamoyl)-2,3-dihydro-1H-inden-2-yl)acetic acid

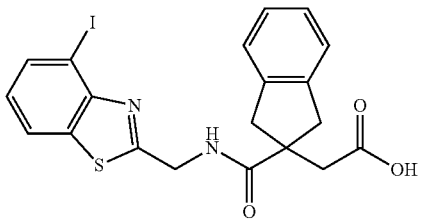 [SMILES: O=C(O)CC1(C(=O)NCc2nc3c(I)cccc3s2)Cc2ccccc2C1]

a. 2,6-Diiodoaniline

AcOH (0.12 mL, 2.1 mmol) was added to a solution of 2-iodoaniline (438 mg, 2.0 mmol) in toluene (40 mL). After stirring for 5 min at RT, N-iodosuccinimide (450 mg, 2.0 mmol) was added. The mixture was stirred for 24 h, then washed with a mixture of NaHCO$_3$ and sodium metabisulfite in water, followed by water, dried (Na$_2$SO$_4$) and concentrated in vacuo to leave a residue. FCC (5-20% EtOAc in isohexane) afforded the title compound as a pale red solid (163 mg, 24%). M/z 346 (M+H)$^+$.

b. tert-Butyl ((4-iodobenzo[d]thiazol-2-yl)methyl)carbamate

A solution of 2,6-diiodoaniline (100 mg, 0.29 mmol) in ACN (1.5 mL) was added to a mixture of tert-butyl (2-amino-2-thioxoethyl)carbamate (66 mg, 0.348 mmol), calcium oxide (24 mg, 0.44 mmol), Pd$_2$(dba)$_3$ (53 mg, 0.058 mmol), and dppf (129 mg, 0.232 mmol) in ACN (0.5 mL). The sealed vial was stirred at 60° C. for 5 h and cooled to RT. FCC (0-15% EtOAc in toluene, then 10-30% EtOAc in isohexane) afforded the title compound as a yellow gum (46 mg, 41%). M/z 413 (M+Na)$^+$.

c. 2-(2-(((4-Iodobenzo[d]thiazol-2-yl)methyl)carbamoyl)-2,3-dihydro-1H-inden-2-yl)acetic acid Using Method D (example 60), but using tert-butyl ((4-iodobenzo[d]thiazol-2-yl)methyl)carbamate, the title compound was made as a light brown solid. M/z 493.3 (M+H)$^+$. $^1$H NMR (d6-DMSO) δ 12.17 (1H, bs), 8.82 (1H, bs), 8.04 (1H, d), 7.92 (1H, d), 7.25-7.20 (2H, m), 7.18-7.12 (3H, m), 4.67 (2H, d), 3.49 (2H, d), 3.00 (2H, d), 2.75 (2H, s).

Example 64

2-(2-(((4-ethoxybenzo[d]thiazol-2-yl)methyl)carbamoyl)-2,3-dihydro-1H-inden-2-yl)acetic acid

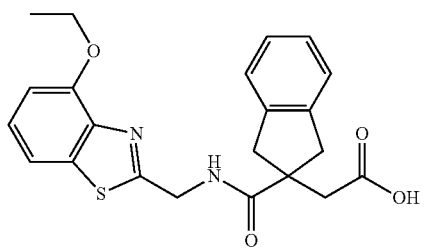 [SMILES: CCOc1cccc2sc(CNC(=O)C3(CC(=O)O)Cc4ccccc4C3)nc12]

a. 1-Ethoxy-3-iodo-2-nitrobenzene

Potassium tert-butoxide (92 mg, 0.824 mmol) was added portionwise over 5 min to a solution of 1-fluoro-3-iodo-2-nitrobenzene (200 mg, 0.749 mmol) and EtOH (0.052 mL, 0.90 mmol) in toluene (3 mL), then the mixture was stirred at RT for 2 h. FCC (toluene) afforded the title compound as a colourless solid (247 mg, assume quantitative). $^1$H NMR (CDCl$_3$) δ 7.41 (1H, d), 7.10 (1H, t), 7.00 (1H, d), 4.13 (2H, q), 1.40 (3H, t).

b. 2-Ethoxy-6-iodoaniline

To a solution of 1-ethoxy-3-iodo-2-nitrobenzene (0.749 mmol) in EtOH (3 mL) was added iron powder (210 mg, 3.75 mmol). AcOH (0.80 mL, 14.0 mmol) was added and the mixture stirred at RT for 5 min, then heated at 85° C. for 1 h. The cooled reaction mixture was diluted with EtOH and filtered through celite. The filtrate was concentrated in vacuo to leave a residue. FCC (50-100% toluene in isohexane) afforded the title compound as a colourless oil (171 mg, 87%, 2 steps). M/z 264 (M+H)$^+$.

c. 2-(2-(((4-Ethoxybenzo[d]thiazol-2-yl)methyl)carbamoyl)-2,3-dihydro-1H-inden-2-yl)acetic acid Using Method D (example 60), but using 2-ethoxy-6-iodoaniline, the title compound was made as a white solid. M/z 411.4 (M+H)$^+$. $^1$H NMR (d6-DMSO) δ 12.16 (1H, bs), 8.73 (1H, t), 7.53 (1H, d), 7.31 (1H, t), 7.24-7.19 (2H, m), 7.17-7.12 (2H, m), 7.00 (1H, d), 4.64 (2H, d), 4.21 (2H, q), 3.47 (2H, d), 2.99 (2H, d), 2.74 (2H, s), 1.41 (3H, t).

Example 65

2-(2-(((4-methylbenzo[d]thiazol-2-yl)methyl)carbamoyl)-2,3-dihydro-1H-inden-2-yl)acetic acid

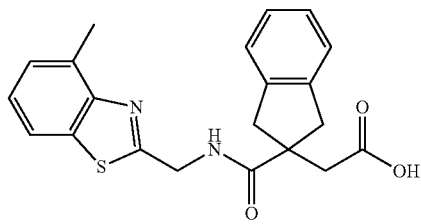 [SMILES: Cc1cccc2sc(CNC(=O)C3(CC(=O)O)Cc4ccccc4C3)nc12]

Using Method D (example 60), but using o-toluidine, the title compound was made as a light brown solid. M/z 381.3 (M+H)$^+$. $^1$H NMR (d6-DMSO) δ 12.16 (1H, bs), 8.73 (1H, t), 7.81 (1H, m), 7.31-7.27 (2H, m), 7.24-7.19 (2H, m), 7.17-7.11 (2H, m), 4.67 (2H, d), 3.48 (2H, d), 3.00 (2H, d), 2.75 (2H, s), 2.63 (3H, s).

Example 66

2-(2-(((4-morpholinobenzo[d]thiazol-2-yl)methyl)carbamoyl)-2,3-dihydro-1H-inden-2-yl)acetic acid

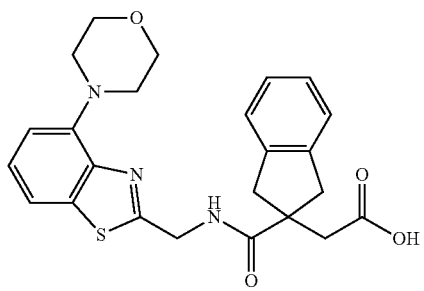 [SMILES: O=C(O)CC1(C(=O)NCc2nc3c(N4CCOCC4)cccc3s2)Cc2ccccc2C1]

a. 4-(3-Iodo-2-nitrophenyl)morpholine

To a solution of 1-fluoro-3-iodo-2-nitrobenzene (228 mg, 0.854 mmol) in toluene (3 mL) was added potassium carbonate (177 mg, 1.28 mmol) and morpholine (1 mL). The mixture was heated at 85° C. for 3 h. The cooled reaction mixture was evaporated and the residue partitioned between EtOAc and water. The aq. phase was extracted with more EtOAc, and the combined organic extracts were washed with water, then brine, dried ($Na_2SO_4$) and concentrated in vacuo to leave a residue. FCC (20-50% EtOAc in isohexane) gave the title compound as a light yellow solid (168 mg, 59%). M/z 335 $(M+H)^+$.

b. 2-(2-(((4-Morpholinobenzo[d]thiazol-2-yl)methyl)carbamoyl)-2,3-dihydro-1H-inden-2-yl)acetic acid Using Method D (example 60), but using 4-(3-iodo-2-nitrophenyl)morpholine, the title compound was made as a white solid. M/z 452.4 $(M+H)^+$. $^1H$ NMR (d6-DMSO) δ 12.15 (1H, bs), 8.72 (1H, t), 7.54 (1H, d), 7.28 (1H, t), 7.24-7.19 (2H, m), 7.17-7.12 (2H, m), 6.88 (1H, d), 4.65 (2H, d), 3.84-3.77 (4H, m), 3.47 (2H, d), 3.40-3.34 (4H, m), 3.00 (2H, d), 2.73 (2H, s).

Example 67

2-(2-(((6-(3-(dimethylamino)azetidin-1-yl)benzo[d]thiazol-2-yl)methyl)carbamoyl)-2,3-dihydro-1H-inden-2-yl)acetic acid

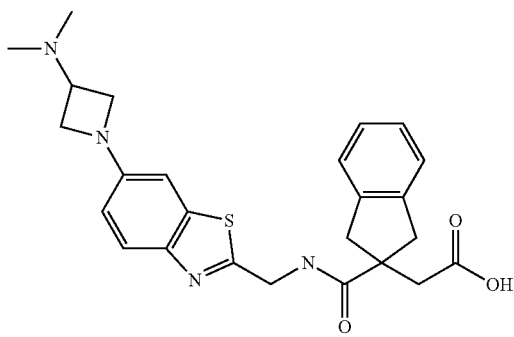 [SMILES: CN(C)C1CN(c2ccc3nc(CNC(=O)C4(CC(=O)O)Cc5ccccc5C4)sc3c2)C1]

a. tert-butyl 2-(2-(((6-(4,4,5,5-tetramethyl-1,3,2-dioxaborolan-2-yl)benzo[d]thiazol-2-yl)methyl)carbamoyl)-2,3-dihydro-1H-inden-2-yl)acetate To a solution of tert-butyl 2-(2-(((6-bromobenzo[d]thiazol-2-yl)methyl)carbamoyl)-2,3-dihydro-1H-inden-2-yl)acetate (1.5 g, 3.0 mmol) in dioxane (20 mL) was added potassium acetate (588 mg, 6.0 mmol) and Bpin (838 mg, 3.3 mmol) at RT and the reaction mixture was purged with argon for 15 min. Then $PdCl_2$(dppf).DCM (171 mg, 0.21 mmol) was added to the reaction mixture and purged with argon for further 5 min. The reaction mixture was stirred in sealed tube at 90° C. for 4 h. The reaction mixture was filtered through celite pad and washed the pad with EtOAc (50 mL). The organic extracts were washed with water (2×50 mL) and brine, then dried over sodium sulphate, filtered and the solvent removed to give crude product (1.6 g, crude) as a brown semi solid. Mixture of boronic acid M/z 467.2 $(M+H)^+$ and boronate ester M/z 549.2 $(M+H)^+$.

b. (2-((2-(2-(tert-butoxy)-2-oxoethyl)-2,3-dihydro-1H-indene-2-carboxamido)methyl)benzo[d]thiazol-6-yl)boronic acid To a solution of tert-butyl 2-(2-(((6-(4,4,5,5-tetramethyl-1,3,2-dioxaborolan-2-yl)benzo[d]thiazol-2-yl)methyl)carbamoyl)-2,3-dihydro-1H-inden-2-yl)acetate (1.6 g, 2.9 mmol) in $THF:H_2O$ (4:1, 20 mL) was added sodium periodate (1.9 g, 8.7 mmol) at RT and stirred for 30 min. Then 1N HCl (2 mL, 2.0 mmol) was added to the reaction mixture at RT and stirred at RT for 16 h. The reaction mixture was diluted with water and extracted with EtOAc. The organic extracts were washed with water and brine, then dried over sodium sulphate, filtered and the solvent removed. The crude compound was purified by column chromatography (100-200 silica gel, gradient 10% MeOH/DCM) to yield the product (900 mg, 66%) as a yellow solid. M/z 467.2 $(M+H)^+$.

c. tert-butyl 2-(2-(((6-(3-(dimethylamino)azetidin-1-yl)benzo[d]thiazol-2-yl)methyl)carbamoyl)-2,3-dihydro-1H-inden-2-yl)acetate To a solution of (2-((2-(2-(tert-butoxy)-2-oxoethyl)-2,3-dihydro-1H-indene-2-carboxamido)methyl)benzo[d]thiazol-6-yl)boronic acid (320 mg, 0.68 mmol) in DCM (10 mL) was added $Et_3N$ (0.58 mL, 4.11 mmol) and molecular sieves (1 g) at RT. Then the reaction mixture was purged with oxygen for 10 min. After that N,N-dimethylazetidin-3-amine dihydrochloride (237 mg, 1.37 mmol) and $Cu(OAc)_2$ (373 mg, 2.05 mmol) added at RT and the reaction mixture was purged with oxygen for 10 min. The reaction mixture was stirred at RT under oxygen atmosphere for 16 h. The reaction mixture was filtered through celite pad and washed the pad with DCM. The filtrate concentrated under reduced pressure. The crude compound was purified by column chromatography (12 g silica cartridge, gradient 5%-10% MeOH/DCM) to yield the product (120 mg, 33.6%) as pale brown thick mass. M/z 521.2 $(M+H)^+$.

d. 2-(2-(((6-(3-(dimethylamino)azetidin-1-yl)benzo[d]thiazol-2-yl)methyl)carbamoyl)-2,3-dihydro-1H-inden-2-yl)acetic acid To a solution of tert-butyl 2-(2-(((6-(3-(dimethylamino)azetidin-1-yl)benzo[d]thiazol-2-yl)methyl)carbamoyl)-2,3-dihydro-1H-inden-2-yl)acetate (110 mg, 0.21 mmol) in DCM (5 mL) was added TFA:TES (5:1, 1 mL) at RT. The reaction mixture was stirred vigorously at RT for 2 h and the solvent was removed to the residue. The above residue was triturated with n-pentane and Et₂O to get the crude compound. The crude compound was purified by preparative HPLC [INERTSIL-ODS (250×20 mm), 5 u, Mobile phase: A: 0.05% FA in H₂O, B: ACN, Gradient: (A:B):-0/10, 8/60, 8.1/98, 10/98, 10.1/10, 13/10; Flow rate: 20 mL/min] to give the product (26 mg, 26.8%) as a pale yellow solid. M/z 465.1 (M+H)⁺. ¹H NMR (500 MHz, DMSO-d₆): δ 12.21 (1H, bs), 8.66 (1H, bs), 7.68 (1H, d, J=8.5 Hz), 7.21-7.19 (2H, m), 7.15-7.12 (2H, m), 6.92 (1H, d, J=2 Hz), 6.59 (1H, dd, J=8.5 Hz, J=2 Hz), 4.56 (2H, d, J=6 Hz), 3.94 (2H, t, J=7 Hz), 3.58 (2H, dd, J=7 Hz, J=5 Hz), 3.45 (2H, d, J=16.5 Hz), 3.20-3.18 (1H, m), 2.98 (2H, d, J=16.5 Hz), 2.72 (2H, s), 2.11 (6H, s).

Example 68

2-[2-[[6-[3-(trimethylammonio)azetidin-1-yl]-1,3-benzothiazol-2-yl]methylcarbamoyl]indan-2-yl]acetate

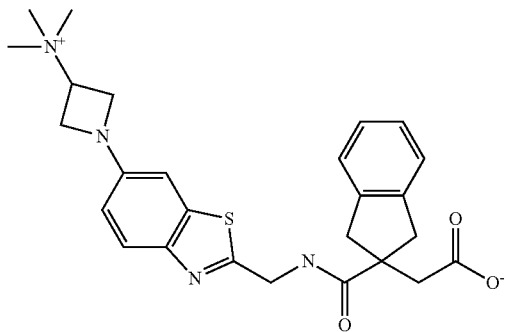 [SMILES: C[N+](C)(C)C1CN(c2ccc3nc(CNC(=O)C4(CC(=O)[O-])Cc5ccccc5C4)sc3c2)C1]

a. 1-(2-((2-(2-(tert-butoxy)-2-oxoethyl)-2,3-dihydro-1H-indene-2-carboxamido)-methyl)benzo[d]thiazol-6-yl)-N,N,N-trimethylazetidin-3-aminium iodide To a solution of tert-butyl 2-(2-(((6-(3-(dimethylamino)azetidin-1-yl)benzo[d]thiazol-2-yl)methyl)carbamoyl)-2,3-dihydro-1H-inden-2-yl)acetate (120 mg, 0.23 mmol) in THF (5 mL) was added MeI (0.04 mL, 0.69 mmol) at 0° C. The mixture was stirred at RT for 3 h. The reaction mixture was concentrated under reduced pressure to give the residue. The resulting residue was triturated with n-pentane and Et₂O to give the product (120 mg, crude) as a yellow solid. M/z 535.2 (M)⁺.

b. 2-[2-[[6-[3-(trimethylammonio)azetidin-1-yl]-1,3-benzothiazol-2-yl]methylcarbamoyl]indan-2-yl]acetate To a solution of 1-(2-((2-(2-(tert-butoxy)-2-oxoethyl)-2,3-dihydro-1H-indene-2-carboxamido)methyl)benzo[d]thiazol-6-yl)-N,N,N-trimethylazetidin-3-aminium iodide (110 mg, 0.20 mmol) in DCM (5 mL) was added TFA:TES (5:1, 1 mL) at room temperature. The reaction mixture was stirred vigorously at room temperature for 2 h and the solvent was removed to the residue. The above residue was triturated with n-pentane and Et₂O. The crude compound was purified by preparative HPLC [YMC-TRIART-C18 (150×25 mm), 10 u, Mobile phase: A: 0.05% FA in H₂O, B: ACN, Gradient: (A:B):-0/10, 7/50, 7.1/98, 9/98, 9.1/10, 11/10; Flow rate: 25 mL/min] to yield the product (48 mg, 48.9%) as an off white solid. M/z 479.2 (M)⁺. ¹H NMR (500 MHz, DMSO-d₆): δ 7.77 (1H, d, J=9 Hz), 7.17-7.15 (2H, m), 7.12-7.10 (2H, m), 7.06 (1H, d, J=2.5 Hz), 6.64 (1H, dd, J=9 Hz, J=2.5 Hz), 4.59 (2H, d, J=6 Hz), 4.48-4.45 (1H, m), 4.32-4.30 (2H, dd, J=10 Hz, J=3.5 Hz), 4.09 (2H, dd, J=10 Hz, J=8.0 Hz), 3.40 (2H, d, J=16 Hz), 3.15 (9H, s), 2.90 (2H, d, J=16 Hz), 2.43 (2H, s).

Example 69

2-[2-[[6-(2-aminoethylamino)-1,3-benzothiazol-2-yl]methylcarbamoyl]indan-2-yl]acetic acid

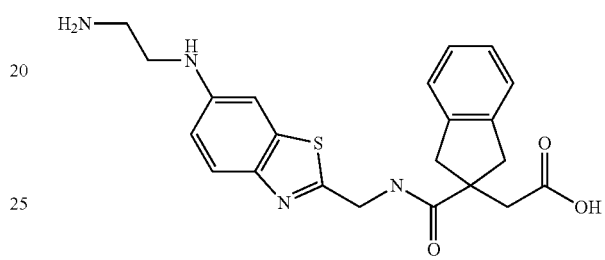

a. tert-butyl 2-(2-(((6-((2-((tert-butoxycarbonyl)amino)ethyl)amino)benzo[d]thiazol-2-yl)methyl)carbamoyl)-2,3-dihydro-1H-inden-2-yl)acetate To a stirred solution of (2-((2-(2-(tert-butoxy)-2-oxoethyl)-2,3-dihydro-1H-indene-2-carboxamido)methyl)benzo[d]thiazol-6-yl)boronic acid (400 mg, 0.85 mmol) in DCM (15 mL) was added Et₃N (0.6 mL, 4.29 mmol) and molecular sieves (500 mg) at RT and purged with oxygen for 10 min. Then tert-butyl (2-aminoethyl)carbamate (164 mg, 1.03 mmol) and Cu(OAc)₂ (466 mg, 2.57 mmol) was added and the reaction mixture was purged with oxygen for 10 min. The reaction mixture was stirred at RT under oxygen atmosphere for 16 h, filtered through celite pad and washed the pad with DCM. The filtrate was evaporated. The crude compound was purified by column chromatography (12 g silica cartridge, gradient 5%-10% MeOH/DCM) to yield the product (130 mg, 26%) as a green solid. M/z 581.2 (M+H)⁺.

b. 2-[2-[[6-[3-(trimethylammonio)azetidin-1-yl]-1,3-benzothiazol-2-yl]methylcarbamoyl]indan-2-yl]acetate To a solution of tert-butyl 2-(2-(((6-((2-((tert-butoxycarbonyl)amino)ethyl)amino)benzo[d]thiazol-2-yl)methyl)carbamoyl)-2,3-dihydro-1H-inden-2-yl)acetate (120 mg, 0.2 mmol) in DCM (5 mL) was added TFA:TES (1.2 mL, 5:1) at RT. The reaction mixture was stirred vigorously at RT for 4 h and the solvent was removed. The above residue was triturated with n-pentane and Et₂O. The crude compound was purified by preparative HPLC [KROMASIL-C18-(150*25 mm), 10 u, Mobile phase: A: 0.05% FA in H₂O: B: ACN, Gradient: (T % B):-0/5, 7/40, 7.1/98, 9/98, 9.1/5, 11/5; Flow rate: 25 mL/min] to give the title product (45 mg, 52%) as an off white solid. M/Z 425.1 (M+H)⁺. ¹H NMR (500 MHz, DMSO-d₆): 7.61 (1H, d, J=9 Hz), 7.20-7.18 (2H, m), 7.14-7.12 (2H, m), 7.05 (1H, d, J=2.5 Hz), 6.78 (1H, dd, J=9 Hz, J=2.5 Hz), 5.97 (1H, t, J=4.5 Hz), 4.55 (2H, d, J=5.5

Hz), 3.45 (2H, d, J=16 Hz), 3.22 (2H, obs), 2.96 (2H, d, J=16 Hz), 2.96-2.86 (2H, m), 2.63 (2H, s).

Example 70

2-[2-[[6-[3-(2-aminoethyl)azetidin-1-yl]-1,3-benzothiazol-2-yl]methylcarbamoyl]indan-2-yl]acetic acid

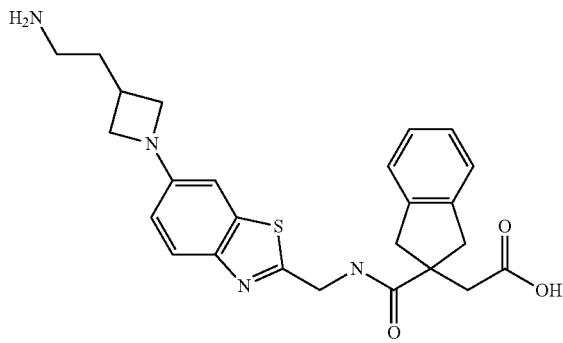 [SMILES: NCCC1CN(c2ccc3nc(CNC(=O)C4(CC(=O)O)Cc5ccccc5C4)sc3c2)C1]

a. tert-butyl 2-(2-(((6-(3-(2-((tert-butoxycarbonyl)amino)ethyl)azetidin-1-yl)benzo[d]thiazol-2-yl)methyl)carbamoyl)-2,3-dihydro-1H-inden-2-yl)acetate To a stirred solution of (2-((2-(2-(tert-butoxy)-2-oxoethyl)-2,3-dihydro-1H-indene-2-carboxamido)methyl)benzo[d]thiazol-6-yl)boronic acid (400 mg, 0.85 mmol) in DCM (10 mL) was added Et$_3$N (0.36 mL, 2.57 mmol) and molecular sieves (500 mg) at RT under air purging. After 10 min., tert-butyl (2-(azetidin-3-yl)ethyl)carbamate hydrochloride (110 mg, 0.42 mmol) and Cu(OAc)$_2$ (156 mg, 0.85 mmol) was added to the reaction mixture. The greenish coloured mixture was stirred at RT under air for 16 h, filtered through celite pad and washed the pad with DCM. The filtrate was evaporated. The crude compound was purified by preparative HPLC [KROMOSIL-C18 (150*25), 10 u, Mobile phase: A: 0.05% FA in H$_2$O, B: ACN, Gradient: (T % B):-0/50, 8/80, 10/80, 10.1/98, 12/98, 12.1/50, 14/50; Flow rate: 25 mL/min] to yield the product (105 mg, 20%) as an off white solid. M/z 621.3 (M+H)$^+$.

b. 2-[2-[[6-[3-(2-aminoethyl)azetidin-1-yl]-1,3-benzothiazol-2-yl]methylcarbamoyl]indan-2-yl]acetic acid To a stirred solution of tert-butyl 2-(2-(((6-(3-(2-((tert-butoxycarbonyl)amino)ethyl)azetidin-1-yl)benzo[d]thiazol-2-yl)methyl)carbamoyl)-2,3-dihydro-1H-inden-2-yl)acetate (90 mg, 0.14 mmol) in DCM (5 mL) was added TFA (2 mL) at RT. The reaction mixture was stirred vigorously at RT for 4 h and the solvent was removed. The above residue was triturated with n-pentane and Et$_2$O. The crude compound was purified by preparative HPLC [YMC-TRIART-C18 (150*25), 10 u; Mobile phase: A: 0.05% FA in H$_2$O, B: ACN, Gradient: (T % B):-0/10, 7/53, 7.1/98, 9/98, 9.1/10, 11/10; Flow rate: 25 mL/min] to yield the title product (40 mg, 60%) as an off white solid. M/z 465.2 (M+H)$^+$. $^1$H NMR (500 MHz, DMSO-d$_6$): 11.05 (1H, bs), 7.68 (1H, d, J=9 Hz), 7.17-7.15 (2H, m), 7.12-7.09 (2H, m), 6.88 (1H, d, J=2.5 Hz), 6.54 (1H, dd, J=9 Hz, J=2.5 Hz), 4.60 (2H, d, J=5 Hz), 3.88 (2H, t, J=7.5 Hz), 3.43-3.46 (6H, obs), 2.94 (2H, d, J=16 Hz), 2.72-2.60 (3H, m), 1.85-1.79 (2H, m).

Example 71

2-[2-[[6-(6-methyl-2,6-diazaspiro[3.3]heptan-2-yl)-1,3-benzothiazol-2-yl]methylcarbamoyl]indan-2-yl] acetic acid

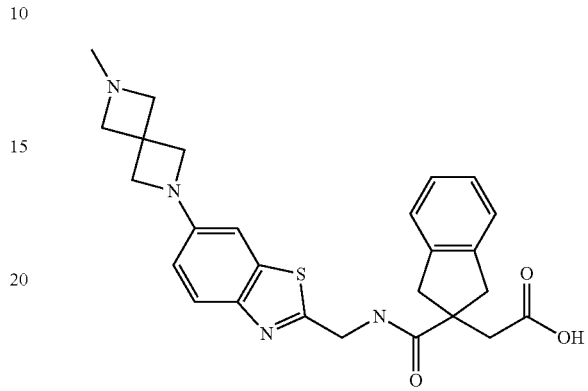

a. tert-butyl 2-(2-(((6-(6-methyl-2,6-diazaspiro[3.3]heptan-2-yl)benzo[d]thiazol-2-yl)methyl)carbamoyl)-2,3-dihydro-1H-inden-2-yl)acetate To a stirred solution of (2-((2-(2-(tert-butoxy)-2-oxoethyl)-2,3-dihydro-1H-indene-2-carboxamido)methyl)benzo[d]thiazol-6-yl)boronic acid (350 mg, 0.75 mmol) in DCM (40 mL) was added Et$_3$N (0.31 mL, 2.25 mmol) and molecular sieves (500 mg) at RT under air purging. After 10 min., 2-methyl-2,6-diazaspiro[3.3]heptane (168 mg, 1.5 mmol) and Cu(OAc)$_2$ (273 mg, 1.52 mmol) was added to the reaction mixture. The greenish colour mixture was stirred at RT under air for 16 h, filtered through celite pad and washed the pad with DCM. The filtrate was evaporated. The crude compound was purified by preparative HPLC [X-BRIDGE-C18 (150×30 mm); 5 u, Mobile phase: A: 0.05% FA in H$_2$O, B: ACN, Gradient: (T % B):-0/20, 8/70, 8.1/98, 10/98, 10.1/20, 13/20; Flow rate: 25 mL/min] to yield the product (110 mg, 27%) as a pale brown solid. M/z 533.3 (M+H)$^+$.

b. 2-[2-[[6-(6-methyl-2,6-diazaspiro[3.3]heptan-2-yl)-1,3-benzothiazol-2-yl]methylcarbamoyl]indan-2-yl]acetic acid To a stirred solution of tert-butyl 2-(2-(((6-(6-methyl-2,6-diazaspiro[3.3]heptan-2-yl)benzo[d]thiazol-2-yl)methyl)carbamoyl)-2,3-dihydro-1H-inden-2-yl)acetate (100 mg, 0.18 mmol) in DCM (5 mL) was added TFA (1 mL) at RT. The reaction mixture was stirred vigorously at RT for 4 h and the solvent was removed. The residue was triturated with n-pentane and Et$_2$O. The crude compound was purified by preparative HPLC [SUNFIRE-C18 (150×25 mm); 5 u, Mobile phase: A: 0.05% FA in H$_2$O, B: ACN, Gradient: (T % B):-0/10, 1/10, 7/40, 8/40, 8.1/98, 10.1/98, 10.1/10, 13/10; Flow rate: 25 mL/min] to yield the title product (29 mg, 33%) as an off white solid. M/z 477.2 (M+H)$^+$. $^1$H NMR (500 MHz, DMSO-d$_6$): 8.71 (1H, t, J=5.5 Hz), 7.68 (1H, d, J=9 Hz), 7.21-7.19 (2H, m), 7.15-7.12 (2H, m), 6.93 (1H, d, J=2 Hz), 6.57 (1H, dd, J=9.0 Hz, J=2 Hz), 4.55 (2H, d, J=6 Hz), 3.92 (4H, s), 3.55 (4H, obs), 3.44 (2H, d, J=16.5 Hz), 2.98 (2H, d, J=16.5 Hz), 2.71 (2H, s), 2.34 (3H, s).

Example 72

2-[2-[[5-(2-aminoethylamino)-1,3-benzothiazol-2-yl]methylcarbamoyl]indan-2-yl]acetic acid

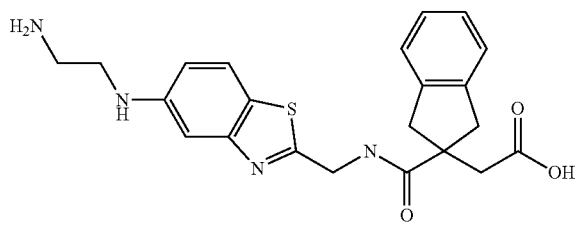 [SMILES: NCCNc1ccc2sc(CNC(=O)C3(CC(=O)O)Cc4ccccc4C3)nc2c1]

Method F was used as described above (example 67 and 69), using tert-butyl 2-(2-(((5-bromobenzo[d]thiazol-2-yl)methyl)carbamoyl)-2,3-dihydro-1H-inden-2-yl)acetate. The crude compound was purified by preparative HPLC [YMC-TRIART-C18 (150×25 mm), 10 u, Mobile phase: A: 0.05% Formic Acid in H$_2$O, B: MeCN, Gradient: (T % B):-0/10, 8/55, 8.1/98, 10/98, 10.1/10, 12/10; Flow rate: 25 mL/min], 24.6% yield, off-white solid. M/z 425 (M+H)$^+$.

$^1$H NMR (500 MHz, DMSO-d$_6$): δ 10.46 (1H, brs), 7.58 (1H, d, J=9.0 Hz), 7.19-7.17 (2H, m), 7.13-7.11 (2H, m), 7.03 (1H, d, J=2.0 Hz), 6.73 (1H, dd, J=8.5 Hz, J=2.0 Hz), 5.98 (1H, bs), 4.61 (2H, d, J=6 Hz), 3.43 (2H, d, J=16 Hz), 3.21 (2H, obs), 2.95 (2H, d, J=16 Hz), 2.90-2.88 (2H, m), 2.50 (2H, s).

Example 73

2-[2-[[5-(3-aminoazetidin-1-yl)-1,3-benzothiazol-2-yl]methylcarbamoyl]indan-2-yl]acetic acid

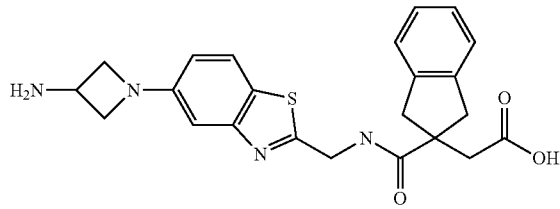 [SMILES: NC1CN(c2ccc3sc(CNC(=O)C4(CC(=O)O)Cc5ccccc5C4)nc3c2)C1]

Method F was used as described above (example 67 and 70), using tert-butyl 2-(2-(((5-bromobenzo[d]thiazol-2-yl)methyl)carbamoyl)-2,3-dihydro-1H-inden-2-yl)acetate and tert-butyl N-(azetidin-3-yl)carbamate. The crude compound was purified by preparative HPLC [X-BRIDGE-C18 (150*30 mm), 5 u, Mobile phase: A: 0.05% TFA in H$_2$O, B: MeCN, Gradient: (% B): 0/10, 8/50, 9/50, 9.1/98, 11/98, 11.1/10, 14/10, 20 Flow Rate: 25 mL/min], 20% yield, pale yellow solid. M/z 437.1 (M+H)$^+$. $^1$H NMR (500 MHz, DMSO-d$_6$): δ 9.57 (1H, bs), 7.73 (1H, d, J=8.5 Hz), 7.20-7.19 (2H, m), 7.14-7.11 (2H, m), 6.85 (1H, d, J=2 Hz), 6.56 (1H, dd, J=8.5 Hz, J=2 Hz), 4.60 (2H, d, J=5.5 Hz), 4.08 (2H, bs), 3.84-3.80 (1H, m), 3.46-3.42 (4H, obs), 2.98 (2H, d, J=16 Hz), 2.65 (2H, s).

Example 74

2-[2-[[5-[3-(dimethylamino)azetidin-1-yl]-1,3-benzothiazol-2-yl]methylcarbamoyl]indan-2-yl]acetic acid

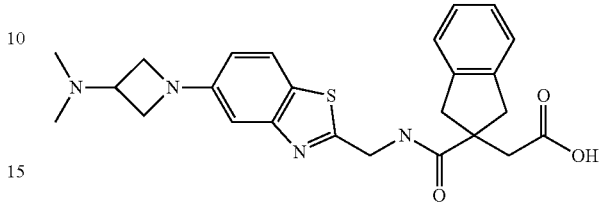

Method F was used as described above (example 67), using tert-butyl 2-(2-(((5-bromobenzo[d]thiazol-2-yl)methyl)carbamoyl)-2,3-dihydro-1H-inden-2-yl)acetate. The crude compound was purified by preparative HPLC [X-BRIDGE-C18 (150×30 mm), 5 u, Mobile phase: A: 0.05% Formic Acid in H$_2$O, B: MeCN, Gradient: (% B):-0/10, 8/50, 9/50, 9.1/98, 11/98, 11.1/10, 14/10; Flow rate: 18 mL/min], 18% yield, off-white solid. M/z 465.0 (M+H)$^+$. $^1$H NMR (500 MHz, DMSO-d$_6$): δ 12.14 (1H, bs), 8.69 (1H, t, J=5.5 Hz), 7.74 (1H, d, J=8.5 Hz), 7.22-7.19 (2H, m), 7.15-7.12 (2H, m), 6.87 (1H, d, J=2.0 Hz), 6.58 (1H, dd, J=8.5 Hz, J=2 Hz), 4.59 (2H, d, J=6 Hz), 3.95 (2H, t, J=7 Hz), 3.56 (2H, dd, J=7 Hz, J=6 Hz), 3.46 (2H, d, J=16.5 Hz), 3.22-3.18 (1H, m), 2.99 (2H, d, J=16.5 Hz), 2.73 (2H, s), 2.12 (6H, s).

Example 75

2-[2-[[5-[3-(trimethylammonio)azetidin-1-yl]-1,3-benzothiazol-2-yl]methylcarbamoyl]indan-2-yl]acetate

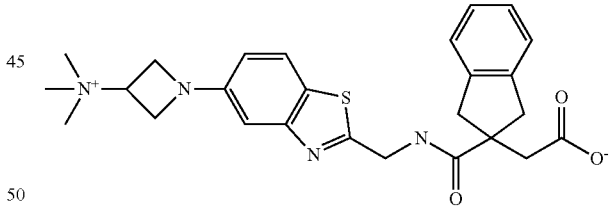

Method F was used as described above (example 67 and 68), using tert-butyl 2-(2-(((5-bromobenzo[d]thiazol-2-yl)methyl)carbamoyl)-2,3-dihydro-1H-inden-2-yl)acetate. The crude compound was purified by preparative HPLC [KROMOSIL-C18 (150×25 mm), 10 u, Mobile phase: A: 0.05% Formic Acid in H$_2$O, B: MeCN, Gradient: (% B):−0/10, 7.5/41, 7.6/98, 10/98, 10.1/10, 12/10; Flow rate: 25 mL/min], 36% yield, off-white solid. M/z 479 (M)$^+$. $^1$H NMR (500 MHz, DMSO-d$_6$): δ 12.62 (1H, bs), 7.86 (1H, d, J=8.5 Hz), 7.16-7.15 (2H, m), 7.11-7.09 (2H, m), 6.96 (1H, d, J=2.5 Hz), 6.62 (1H, dd, J=2.5 Hz, J=8.5 Hz), 4.63 (2H, d, J=5.5 Hz), 4.48-4.46 (1H, m), 4.34 (2H, dd, J=10.0 Hz, J=3.5 Hz), 4.09 (2H, dd, J=10.0 Hz, J=8 Hz), 3.39 (2H, d, J=16.0 Hz), 3.16 (9H, s), 2.89 (2H, d, J=16.0 Hz), 2.39 (2H, s).

Example 76

2-[2-[[5-[2-(dimethylamino)ethylamino]-1,3-benzo-thiazol-2-yl]methylcarbamoyl]indan-2-yl]acetic acid

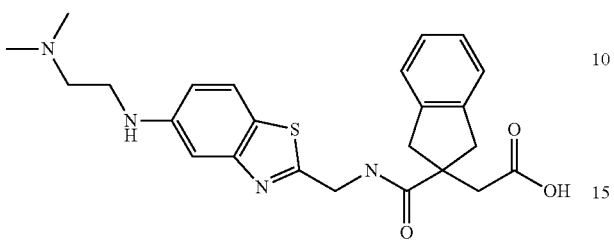

Method F was used as described above (example 67), using tert-butyl 2-(2-(((5-bromobenzo[d]thiazol-2-yl)methyl)carbamoyl)-2,3-dihydro-1H-inden-2-yl)acetate and N',N'-dimethylethane-1,2-diamine. The crude compound was purified by preparative HPLC [YMC TRIART C18 (150×25 mm); 10 u, mobile phase: A: 0.05% Formic Acid in H$_2$O, B: MeCN, Gradient (% B): 0/5, 8/50, 8.1/98, 10.5/98, 10.5/5, 13/5, Flow rate: 25 mL/min], 21% yield, off white solid. M/z 453.2 (M+H)$^+$. $^1$H NMR (500 MHz, DMSO-d$_6$): δ 8.71 (1H, t, d=6 Hz), 7.61 (1H, d, J=8.5 Hz), 7.22-7.20 (2H, m), 7.15-7.12 (2H, m), 7.01 (1H, d, J=2 Hz), 6.78 (1H, dd, J=8.5 Hz, J=2 Hz), 5.61 (1H, bs), 4.59 (2H, d, J=6 Hz), 3.45 (2H, d, J=16.5 Hz), 3.164-3.12 (2H, bt), 2.99 (2H, d, J=16.5 Hz), 2.72 (2H, s), 2.56-2.54 (2H, bt), 2.26 (6H, s).

Example 77

2-[2-[[5-[2-(trimethylammonio)ethylamino]-1,3-benzothiazol-2-yl]methylcarbamoyl]indan-2-yl]acetate

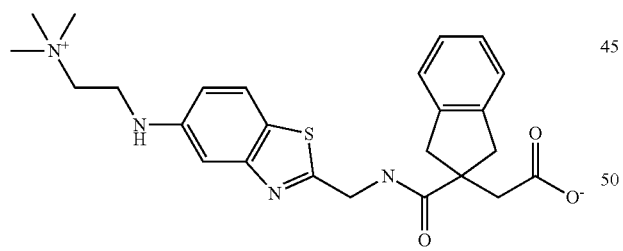

Method F was used as described above (example 67 and 68), using tert-butyl 2-(2-(((5-bromobenzo[d]thiazol-2-yl)methyl)carbamoyl)-2,3-dihydro-1H-inden-2-yl)acetate and N',N'-dimethylethane-1,2-diamine. The crude compound was purified by preparative HPLC [X-BRIDGE-C18 (150*30 mm), 5 u, mobile phase: A: 0.05% Formic Acid in H$_2$O, B: MeCN, Gradient (% B): 0/15, 8/58, 8.1/98, 10/98, 10.1/15, 13/15, Flow rate: 25 mL/min], 36.6% yield, pale yellow solid. M/z 467.1 (M)$^+$. $^1$H NMR (500 MHz, DMSO-d$_6$): δ 12.48 (1H, bs), 7.70 (1H, d, J=9 Hz), 7.16-7.09 (5H, m), 6.79 (1H, dd, J=9 Hz, J=2.5 Hz), 6.05 (1H, bt), 4.61 (2H, d, J=5 Hz), 3.65-3.56 (2H, m), 3.52-3.48 (2H, m), 3.42-3.38 (2H, obs), 3.15 (9H, s), 2.90 (2H, d, J=16 Hz), 2.39 (2H, s).

Example 78

2-[2-[[6-(3-aminocyclobutoxy)-1,3-benzothiazol-2-yl]methylcarbamoyl]indan-2-yl]acetic acid

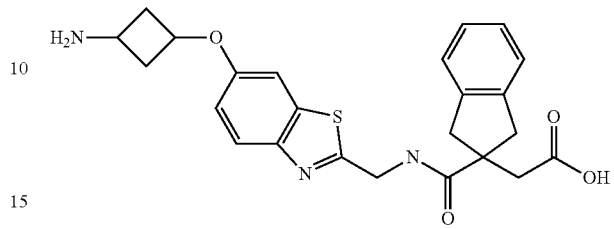

Method F was used as described above (example 67 and 69), using tert-butyl N-(3-hydroxycyclobutyl)carbamate. The crude compound was purified by preparative HPLC [YMC-TRIART-C18 (150×25 mm), 10 u, Mobile phase: A: 0.1% Formic Acid in H$_2$O, B: MeCN, Gradient: (% B):-0/5, 8/40, 9/40, 9.1/98, 11/98, 11.1/5, 13/5; Flow rate: 20 mL/min], 23.8% yield, white solid. M/z 452.1 (M+H)$^+$. Chiral HPLC shown 13% % 86% of cis/trans isomers. $^1$H NMR (500 MHz, DMSO-d$_6$): δ 9.80 (1H, bs, 1H), 7.79-7.77 (1H, m), 7.45-7.39 (1H, d, J=2.5 Hz), 7.20-7.18 (2H, m), 7.14-7.11 (2H, m), 6.99-6.97 (1H, m), 4.59 (2H, d, J=5.5 Hz), 3.40-3.37 (1H, m), 3.43 (2H, d, J=16.5 Hz), 3.16-3.11 (1H, m), 2.96 (2H, d, J=16.5 Hz), 2.84-2.81 (2H, m), 2.62 (2H, s), 1.90-1.88 (2H, m).

Example 79

2-[2-[[6-[3-(dimethylamino)cyclobutoxy]-1,3-benzo-thiazol-2-yl]methylcarbamoyl]indan-2-yl]acetic acid

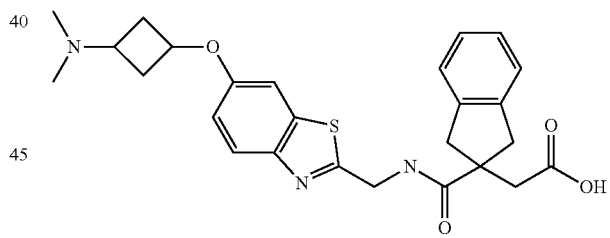

a. 3-aminocyclobutanol

To a stirred solution of tert-butyl (3-hydroxycyclobutyl)carbamate (500 mg, 2.67 mmol) in DCM (5 mL), was added TFA (1.0 mL) at 0° C. The reaction mixture was stirred at room temperature for 1 h. The reaction mixture was evaporated. The crude compound was triturated with pentane (20 mL) to obtain pure 3-aminocyclobutanol (310 mg, crude) as a pale yellow sticky material. M/Z 88.2 (M+H)$^+$.

b. 3-(dimethylamino)cyclobutanol

HCHO (3 mL) and HCOOH (3 mL) was to 3-aminocyclobutanol (300 mg, 3.44 mmol) at room temperature and heated to reflux for 3 h. The reaction mixture was evaporated to get the crude compound. The crude compound was dissolved in MeOH (20 mL) and treated with Dowex 50WX4 (H+ form) resin for 30 minutes. Then the resin was filtered and washed with MeOH (2×10 mL). After that, the resin was eluted with 7.0 M NH₃ in MeOH (100 mL) and the eluant was evaporated to get 3-(dimethylamino)cyclobutanol (92 mg, 30% yield for 2 steps) as a pale yellow sticky material. M/z 116.0 (M+H)+.

c. 2-[2-[[6-[3-(dimethylamino)cyclobutoxy]-1,3-benzothiazol-2-yl]methylcarbamoyl]indan-2-yl]acetic acid Method F was used as described above (example 67), using 3-(dimethylamino)cyclobutanol.

The crude compound was purified by preparative HPLC [(YMC-TRIART-C18 (150*25 mm), 10 u, Mobile phase: A: 0.1% Formic acid in H₂O: B: MeCN, Gradient: (% B):-0/10, 8/45, 9/45, 9.1/98, 11/98, 11.1/10, 13/10, Flow Rate: 25 mL/min], 19% yield, off white solid. M/z 480.2 (M+H)+. ¹H NMR (500 MHz, DMSO-d₆): δ 9.82 (1H, bs), 7.78 (1H, d, J=8.5 Hz), 7.47 (1H, d, J=2.5 Hz), 7.20-7.18 (2H, m), 7.14-7.11 (2H, m), 7.00 (1H, dd, J=8.5 Hz, J=2.5 Hz), 4.59 (2H, d, J=6 Hz), 4.47-4.44 (1H, m), 3.43 (2H, d, J=16 Hz), 2.98 (2H, d, J=16 Hz), 2.69-2.63 (2H, m), 2.62 (2H, s), 2.36-2.32 (1H, m), 2.04 (6H, s), 1.84-1.78 (2H, m).

Example 80

2-[2-[[6-(2-aminoethyl)-1,3-benzothiazol-2-yl]methylcarbamoyl]indan-2-yl]acetic acid

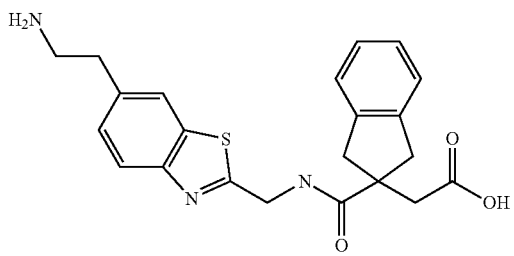 [SMILES: NCCc1ccc2nc(CNC(=O)C3(CC(=O)O)Cc4ccccc4C3)sc2c1]

a. tert-butyl 2-(2-(((6-(2-((tert-butoxycarbonyl)amino)ethyl)benzo[d]thiazol-2-yl)methyl)carbamoyl)-2,3-dihydro-1H-inden-2-yl)acetate To a solution of tert-butyl 2-(2-(((6-bromobenzo[d]thiazol-2-yl)methyl)carbamoyl)-2,3-dihydro-1H-inden-2-yl)acetate (250 mg, 0.5 mmol) in toluene:H₂O (3:1, 12 mL) was added Cs₂CO₃ (324 mg, 1.0 mmol) and potassium (2-((tert-butoxycarbonyl)amino)ethyl)trifluoroborate (150 mg, 0.6 mmol) at RT and the reaction mixture was purged with argon for 15 min. Then PdCl₂(dppf).DCM (20 mg, 0.02 mmol) was added to the reaction mixture and purged with argon for further 5 min. The reaction mixture was stirred in sealed tube at 90° C. for 16 h. The reaction mixture was diluted with EtOAc, washed with water and brine. The organic extracts were then dried over sodium sulphate, filtered and the solvent removed. The crude compound was purified by column chromatography (100-200 silica gel, gradient 35%-40% EtOAc/pet ether) to yield the product (100 mg, 35.5%) as a brown semi solid. M/z 566.3 (M+H)+.

b. 2-[2-[[6-(2-aminoethyl)-1,3-benzothiazol-2-yl]methylcarbamoyl]indan-2-yl]acetic acid To a solution of tert-butyl 2-(2-(((6-(2-((tert-butoxycarbonyl)amino)ethyl)benzo[d]thiazol-2-yl)methyl)carbamoyl)-2,3-dihydro-1H-inden-2-yl)acetate (110 mg, 0.2 mmol) in DCM (5 mL) was added TFA (2 mL) at RT. The reaction mixture was stirred vigorously at RT for 4 h and the solvent was removed. The residue was triturated with n-pentane and Et₂O. The crude compound was purified by preparative HPLC [X-SELECT-CN (250×20 mm), 5 u, Mobile phase: A: 0.05% FA in H₂O, B: ACN, Gradient: (T % B):-0/5, 8/50, 9/50, 9.1/98, 11/98, 11.1/5, 14/5; Flow rate: 20 mL/min] to obtain the title product (23.6 mg, 29.6%) as a white solid. M/Z 409.9 (M+H)+. ¹H NMR (500 MHz, DMSO-d₆): δ 10.48 (1H, bs), 7.86 (1H, s), 7.84 (1H, d, J=8.5 Hz), 7.33 (1H, d, J=8.5 Hz), 7.19-7.18 (2H, m), 7.13-7.11 (2H, m), 4.64 (2H, d, J=5 Hz), 3.43 (2H, d, J=16 Hz), 3.05-2.85 (6H, m), 2.58 (2H, s).

Example 81

2-[2-[[6-[(dimethylamino)methyl]-1,3-benzothiazol-2-yl]methylcarbamoyl]indan-2-yl]acetic acid

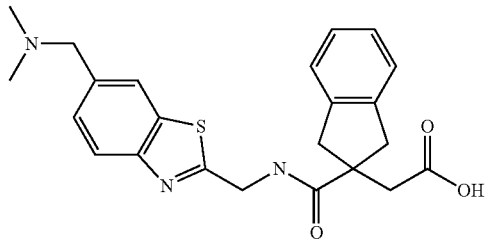 [SMILES: CN(C)Cc1ccc2nc(CNC(=O)C3(CC(=O)O)Cc4ccccc4C3)sc2c1]

a. tert-butyl 2-(2-(((6-((dimethylamino)methyl)benzo[d]thiazol-2-yl)methyl)carbamoyl)-2,3-dihydro-1H-inden-2-yl)acetate To a solution of tert-butyl 2-(2-(((6-bromobenzo[d]thiazol-2-yl)methyl)carbamoyl)-2,3-dihydro-1H-inden-2-yl)acetate (1 g, 2.0 mmol) in THF:H₂O (10:1, 20 mL) was added Cs₂CO₃ (1.9 g, 6.0 mmol) and potassium ((dimethylamino)methyl)trifluoroborate (396 mg, 2.4 mmol) at RT and the reaction mixture was purged with argon for 15 min. Then 2-dicyclohexylphosphino-2',4',6'-triisopropylbiphenyl (95.3 mg, 0.2 mmol) and palladium acetate (67.3 mg, 0.1 mmol) was added to the reaction mixture and purged with argon for further 5 min. The reaction mixture was stirred in sealed tube at 80° C. for 8 h. The reaction mixture was filtered through celite pad and washed the pad with DCM. The filtrate concentrated under reduced pressure. The crude compound was purified by column chromatography (100-200 silica gel, gradient 10% MeOH/DCM and further purified by reverse phase column chromatography 40 g C18 cartridge, gradient 35%-40% of ACN/0.05% FA in H₂O) to yield the product (160 mg, 16.7%) as a yellow semi solid. M/z 480.1 (M+H)+.

b. 2-[2-[[6-[(dimethylamino)methyl]-1,3-benzothiazol-2-yl]methylcarbamoyl]indan-2-yl]acetic acid To a solution of tert-butyl 2-(2-(((6-((dimethylamino)methyl)benzo[d]thiazol-2-yl)methyl)carbamoyl)-2,3-dihydro-1H-inden-2-yl)acetate (50 mg, 0.1 mmol) in DCM (2 mL) was added TFA (0.7 mL) at 0° C. The reaction mixture was stirred vigorously at RT for 2 h and the solvent was removed. The residue was triturated with n-pentane and Et₂O. The crude compound was purified by preparative HPLC [SYMMETRY-C8 (19×300 mm), 7 u, Mobile phase: A: 0.05% FA in H₂O, B: ACN, Gradient: (T % B):-0/10, 7/45, 7.1/98, 10/98, 10.1/10, 14/10; Flow rate: 20 mL/min] to yield the title product (28.7 mg, 36%) as an off white solid. M/z 424.1 (M+H)⁺. ¹H NMR (500 MHz, DMSO-d₆): δ 8.74 (1H, t, J=5.5 Hz), 7.99 (1H, s), 7.92 (1H, d, J=8.5 Hz), 7.48 (1H, d, J=8.5 Hz), 7.22-7.20 (2H, m), 7.15-7.12 (2H, m), 4.65 (2H, d, J=6 Hz), 3.87 (2H, bs), 3.46 (2H, d, J=16.5 Hz), 3.00 (2H, d, J=16.5 Hz), 2.74 (2H, s), 2.40 (6H, s).

Example 82

2-[2-[[6-[(trimethylammonio)methyl]-1,3-benzothiazol-2-yl]methylcarbamoyl]indan-2-yl]acetate

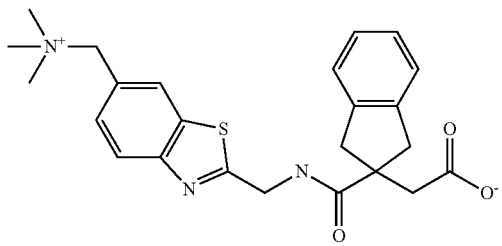 [SMILES: C[N+](C)(C)Cc1ccc2nc(CNC(=O)C3(CC(=O)[O-])Cc4ccccc4C3)sc2c1]

a. 1-(2-((2-(2-(tert-butoxy)-2-oxoethyl)-2,3-dihydro-1H-indene-2-carboxamido)methyl)benzo[d]thiazol-6-yl)-N,N,N-trimethylmethanaminium iodide To a solution of tert-butyl 2-(2-(((6-((dimethylamino)methyl)benzo[d]thiazol-2-yl)methyl)carbamoyl)-2,3-dihydro-1H-inden-2-yl)acetate (90 mg, 0.18 mmol) in THF (5 mL) was added MeI (0.03 mL, 0.56 mmol) at 0° C. The mixture was stirred at RT for 16 h. The reaction mixture was concentrated under reduced pressure. The crude compound was purified by preparative TLC (eluent 5% MeOH/DCM) to obtain the product (75 mg, 81%) as a yellow solid. M/z 494.1 (M)⁺.

b. 2-[2-[[6-[(trimethylammonio)methyl]-1,3-benzothiazol-2-yl]methylcarbamoyl]indan-2-yl]acetate To a solution of 1-(2-((2-(2-(tert-butoxy)-2-oxoethyl)-2,3-dihydro-1H-indene-2-carboxamido)methyl)benzo[d]thiazol-6-yl)-N,N,N-trimethylmethanaminium iodide (70 mg, 0.14 mmol) in DCM (5 mL) was added TFA (1 mL) at 0° C. The reaction mixture was stirred vigorously at RT for 2 h and the solvent was removed. The residue was triturated with n-pentane and Et₂O. The crude compound was purified by preparative HPLC [SUNFIRE-C18 (150×30 mm), 5 u, Mobile phase: A: 0.05% FA in H₂O, B: ACN, Gradient: (A:B):-0/5, 1/5, 8/50, 8.1/98, 10/98, 10.1/5, 13/5; Flow rate: 25 mL/min] to yield the title product (31 mg, 50%) as a white solid. M/z 438.1 (M)⁺. ¹H NMR (500 MHz, DMSO-d₆): δ 8.22 (1H, t, J=2 Hz), 8.04 (1H, d, J=8.5 Hz), 7.61 (1H, dd, J=8.5 Hz, J=2 Hz), 7.20-7.19 (2H, m), 7.13-7.12 (2H, m), 4.68 (2H, d, J=5.5 Hz), 4.62 (2H, s), 3.44 (2H, d, J=16.5 Hz), 3.04 (9H, s), 2.96 (2H, d, J=16.5 Hz), 2.61 (2H, s).

Example 83

2-[2-[[5-(2-aminoethyl)-1,3-benzothiazol-2-yl]methylcarbamoyl]indan-2-yl]acetic acid

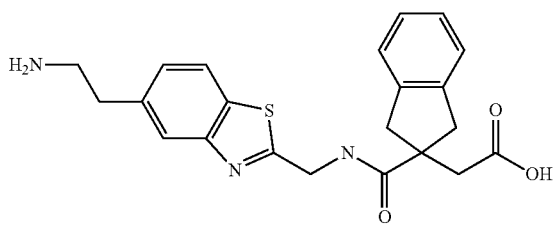 [SMILES: NCCc1ccc2sc(CNC(=O)C3(CC(=O)O)Cc4ccccc4C3)nc2c1]

Method E (Suzuki coupling) was used as described above (example 80), using tert-butyl 2-(2-(((5-bromobenzo[d]thiazol-2-yl)methyl)carbamoyl)-2,3-dihydro-1H-inden-2-yl) acetate. M/z 410.2 (M+H)⁺. ¹H NMR (500 MHz, DMSO-d₆): δ 11.0 (1H, bs), 7.88-7.80 (1H, m), 7.76 (1H, s), 7.25-7.17 (3H, m), 7.12-7.10 (2H, m), 4.66 (2H, d, J=5.0 Hz), 3.43 (2H, d, J=16.0 Hz), 3.01-2.85 (6H, m), 2.56 (2H, s).

Example 84

2-[2-[[5-[(dimethylamino)methyl]-1,3-benzothiazol-2-yl]methylcarbamoyl]indan-2-yl]acetic acid

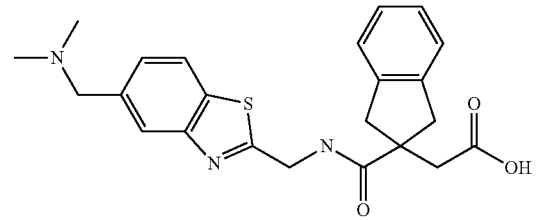 [SMILES: CN(C)Cc1ccc2sc(CNC(=O)C3(CC(=O)O)Cc4ccccc4C3)nc2c1]

Method E (Suzuki coupling) was used as described above (example 81), using tert-butyl 2-(2-(((5-bromobenzo[d]thiazol-2-yl)methyl)carbamoyl)-2,3-dihydro-1H-inden-2-yl) acetate. M/z 424.1 (M+H)⁺. ¹H NMR (500 MHz, DMSO-d₆) δ 8.93 (1H, bs), 7.94 (1H, d, J=8 Hz), 7.79 (1H, s), 7.34 (1H, dd, J=8 Hz, J=1.5 Hz), 7.22-7.20 (2H, m), 7.15-7.12 (2H, m), 4.65 (2H, d, J=6 Hz), 3.52 (2H, s), 3.47 (2H, d, J=16.5 Hz), 3.01 (2H, d, J=16.5 Hz), 2.72 (2H, s), 2.16 (6H, s).

Example 85

2-[2-[[5-[(trimethylammonio)methyl]-1,3-benzothiazol-2-yl]methylcarbamoyl]indan-2-yl]acetate

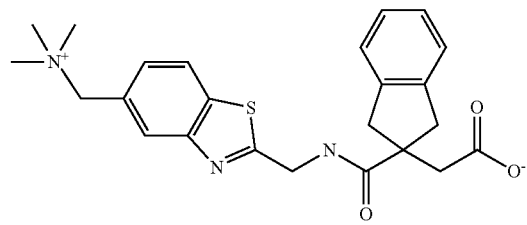 [SMILES: C[N+](C)(C)Cc1ccc2sc(CNC(=O)C3(CC(=O)[O-])Cc4ccccc4C3)nc2c1]

Method E (Suzuki coupling) was used as described above (example 82), using tert-butyl 2-(2-(((5-bromobenzo[d]thiazol-2-yl)methyl)carbamoyl)-2,3-dihydro-1H-inden-2-yl)acetate. M/z 438.2 (M)+. 1H NMR (500 MHz, DMSO-d6) δ 10.39 (1H, bs), 8.19 (1H, d, J=8.5 Hz), 8.12 (1H, d, J=1.5 Hz), 7.53 (1H, dd, J=8.5 Hz, J=1.5 Hz), 7.20-7.18 (2H, m), 7.13-7.11 (2H, m), 4.68 (2H, d, J=5 Hz), 4.65 (2H, s), 3.43 (2H, d, J=16.5 Hz), 3.05 (9H, s), 2.95 (2H, d, J=16.5 Hz), 2.60 (2H, s).

Example 86

2-[2-[[6-[3-(trimethylammonio)prop-1-ynyl]-1,3-benzothiazol-2-yl]methylcarbamoyl]indan-2-yl]acetate

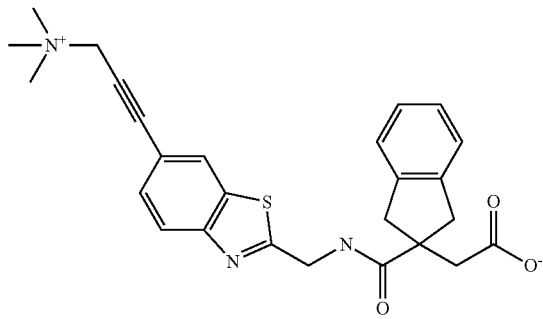 [SMILES: C[N+](C)(C)CC#Cc1ccc2nc(CNC(=O)C3(CC(=O)[O-])Cc4ccccc4C3)sc2c1]

Prepared using tert-butyl 2-[2-[[6-[3-(dimethylamino)prop-1-ynyl]-1,3-benzothiazol-2-yl]methylcarbamoyl]indan-2-yl]acetate (example 35), using the conditions described in example 82 (Method E—Sonogashira coupling). M/z 462.2 (M)+. 1H NMR (500 MHz, DMSO-d6): δ 12.25 (1H, bs), 8.37 (1H, d, J=1.5 Hz), 7.97 (1H, d, J=8.5 Hz), 7.67 (1H, dd, J=8.5 Hz, J=1.5 Hz), 7.17-7.16 (2H, m), 7.11-7.10 (2H, m), 4.69 (2H, d, J=5.5 Hz), 4.63 (2H, s), 3.40 (2H, d, J=16 Hz), 3.20 (9H, s), 2.91 (2H, d, J=16 Hz), 2.44 (2H, s).

Example 87

2-[2-[[5-[(E)-3-aminoprop-1-enyl]-1,3-benzothiazol-2-yl]methylcarbamoyl]indan-2-yl]acetic acid

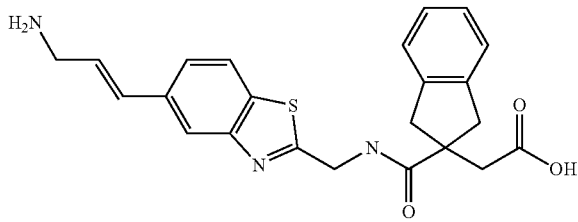

Prepared following Method E (Stille coupling) as described in example 38 (step a and b) using tert-butyl 2-[2-[(5-bromo-1,3-benzothiazol-2-yl)methylcarbamoyl]indan-2-yl]acetate and example 39. The crude compound was purified by preparative HPLC [SYMMETRY-C8 (300*19 mm), 7 u, Mobile phase: 0.1% FA in H2O, ACN, Gradient: (T % B):-0/35, 8/80, 8.1/98, 10/98, 10.1/35, 13/35; Flow rate: 20 mL/min] to obtain (E)-2-(2-(((5-(3-aminoprop-1-en-1-yl)benzo[d]thiazol-2-yl)methyl)carbamoyl)-2,3-dihydro-1H-inden-2-yl)acetic acid (46 mg, 63%), off-white solid. M/z 422.1 (M+H)+. 1H NMR (500 MHz, DMSO-d6): δ 10.7 (1H, bs), 8.39 (1H, bs), 7.95 (1H, d, J=8.5 Hz), 7.91 (1H, s), 7.48 (1H, dd, J=8.5 Hz, J=1.5 Hz), 7.19-7.17 (2H, m), 7.13-7.11 (2H, m), 6.73 (1H, d, J=16.0 Hz), 6.47-6.42 (1H, m), 4.65 (2H, d, J=5.0 Hz), 3.52-3.46 (2H, obs), 3.43 (2H, d, J=16.0 Hz), 2.95 (2H, d, J=16.0 Hz), 2.50 (2H, s).

Example 88

2-[2-[[5-[3-(dimethylamino)prop-1-ynyl]-1,3-benzothiazol-2-yl]methylcarbamoyl]indan-2-yl]acetic acid

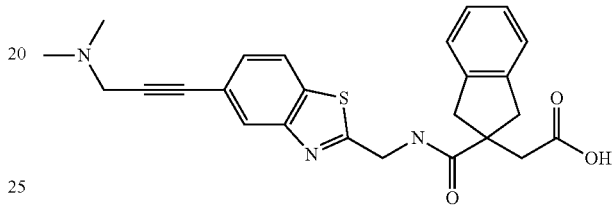

Prepared following Method G (Sonogashira coupling) as described in example 35 using tert-butyl 2-[2-[(5-bromo-1,3-benzothiazol-2-yl)methylcarbamoyl]indan-2-yl]acetate. M/z 448.1 (M+H)+. 1H NMR (500 MHz, DMSO-d6): δ 12.13 (1H, bs), 8.76 (1H, t, J=6.0 Hz), 8.03 (1H, d, J=8.0 Hz), 7.97 (1H, s), 7.45 (1H, d, J=8.0 Hz), 7.22-7.21 (2H, m), 7.15-7.13 (2H, m), 4.66 (2H, d, J=5.5 Hz), 3.59 (2H, s), 3.46 (2H, d, J=16.0 Hz), 3.01 (2H, d, J=16 Hz), 2.74 (2H, s), 2.34 (6H, s).

Example 89

2-[2-[[5-[3-(dimethylamino)propyl]-1,3-benzothiazol-2-yl]methylcarbamoyl]indan-2-yl]acetic acid

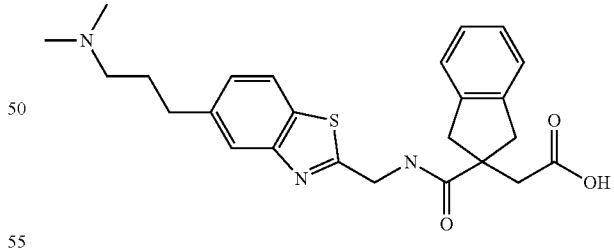

Prepared following Method G (Sonogashira coupling) as described in example 36 using tert-butyl 2-[2-[[6-[3-(dimethylamino)prop-1-ynyl]-1,3-benzothiazol-2-yl]methylcarbamoyl]indan-2-yl]acetate obtained in the synthesis of example 88. M/z 452.2 (M+H)+. 1H NMR (500 MHz, DMSO-d6): δ 9.57 (1H, bs), 7.89 (1H, d, J=8.5 Hz), 7.73 (1H, d, J=1.5 Hz), 7.25 (1H, dd, J=8.5 Hz, J=1.5 Hz), 7.21-7.19 (2H, m), 7.14-7.09 (2H, m), 4.64 (2H, d, J=5.5 Hz), 3.45 (2H, d, J=16.5 Hz), 2.97 (2H, d, J=16.5 Hz), 2.71 (2H, t, J=7.5 Hz), 2.64 (2H, s), 2.21 (2H, t, J=7.0 Hz), 2.14 (6H, s), 1.77-1.71 (2H, m).

Example 90

2-[2-[[5-[3-(trimethylammonio)propyl]-1,3-benzo-
thiazol-2-yl]methylcarbamoyl]indan-2-yl]acetate

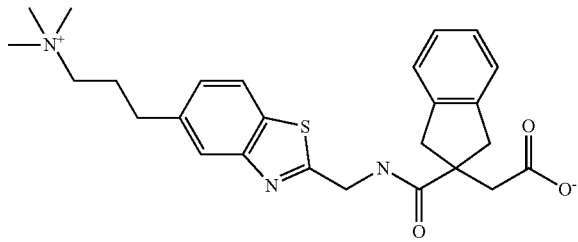 [SMILES: C[N+](C)(C)CCCc1ccc2sc(CNC(=O)C3(CC(=O)[O-])Cc4ccccc4C3)nc2c1]

Prepared following Method G (Sonogashira coupling) as described in example 37 using tert-butyl 2-[2-[[5-[3-(dimethylamino)propyl]-1,3-benzothiazol-2-yl]methylcarbamoyl]indan-2-yl]acetate obtained in the synthesis of example 89. M/z 466.2 (M)+. $^1$H NMR (500 MHz, DMSO-$d_6$): δ 12.8 (1H, bs), 7.99 (1H, d, J=8 Hz), 7.83 (1H, d, J=1.5 Hz), 7.30 (1H, dd, J=8.0 Hz, J=1.5 Hz), 7.16-7.14 (2H, m), 7.11-7.09 (2H, m), 4.66 (2H, d, J=5.5 Hz), 3.40 (2H, d, J=16 Hz), 3.30-3.20 (2H, m), 3.03 (9H, s), 2.8 (2H, d, J=16 Hz), 2.77 (2H, t, J=7.5 Hz), 2.37 (2H, s), 2.10-2.07 (2H, m).

Example 91

2-(2-(((6-((1 r,3r)-3-((dimethylamino)methyl)cy-
clobutyl)benzo[d]thiazol-2-yl)methyl)carbamoyl)-2,
3-dihydro-1H-inden-2-yl)acetic acid

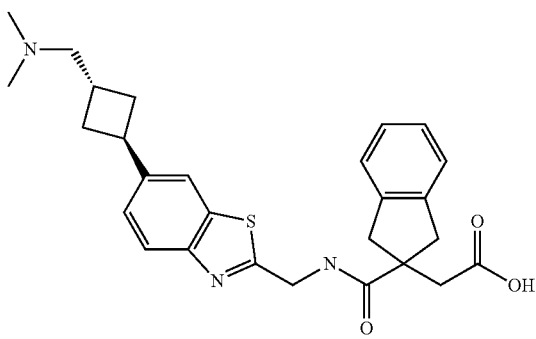 [SMILES: CN(C)C[C@H]1C[C@H](c2ccc3nc(CNC(=O)C4(CC(=O)O)Cc5ccccc5C4)sc3c2)C1]

a. 4-methylbenzenesulfonohydrazide

To a solution of 4-methylbenzenesulfonyl chloride (7.5 g, 39.3 mmol) in THF (80 mL) was added hydrazine hydrate (6 mL, 118 mmol) dropwise at 0° C. for 10 min. The reaction mixture was stirred at 0° C. for 2 h. The reaction mixture was partitioned between EtOAc (80 mL) and water (80 mL). The organic layer was separated and washed with water (2×50 mL). The organic extracts were then dried with Na$_2$SO$_4$, filtered and the solvent removed to yield the product (6.1 g, 83%) as a white solid. M/z 187.1 (M+H)+.

b. methyl 3-(2-(((tert-butoxycarbonyl)amino)methyl)benzo[d]thiazol-6-yl)cyclobutane-1-carboxylate To a solution of methyl 3-oxocyclobutane-1-carboxylate (2.1 g, 16.4 mmol) in dioxane (30 mL) was added 4-methylbenzenesulfonohydrazide (3 g, 16.4 mmol) at RT. The mixture was stirred at 90° C. for 2 h. The reaction mixture was cooled to RT and (2-(((tert-butoxycarbonyl)amino)methyl)benzo[d]thiazol-6-yl)boronic acid (2.5 g, 8.2 mmol) added and stirred for 10 min. Then potassium carbonate (3.3 g, 24.6 mmol) was added and the reaction mixture was stirred at 110° C. for 16 h. The reaction mixture was partitioned between EtOAc (70 mL) and water (70 mL). The organic layer was separated and washed with water (2×50 mL) and brine. The organic extracts were then dried with Na$_2$SO$_4$, filtered and the solvent removed. The crude compound was purified by column chromatography (40 g silica cartridge, gradient 20%-30% EtOAc/pet ether) to yield the product (1.1 g, 18%) as a pale brown liquid. M/z 377.2 (M+H)+.

c. tert-butyl((6-((1r,3r)-3-(hydroxymethyl)cyclobutyl)benzo[d]thiazol-2-yl)methyl)carbamate To a solution of methyl 3-(2-(((tert-butoxycarbonyl)amino)methyl)benzo[d]thiazol-6-yl)cyclobutane-1-carboxylate (2.2 g, 5.8 mmol) in THF (40 mL) was added DIBAL (23.4 mL, 23.4 mmol, 1M in toluene) dropwise at 0° C. for 15 min. The reaction mixture was stirred at 0° C. for 2 h. The reaction mixture was quenched with MeOH (15 mL) followed by water (30 mL) at 0° C. and then extracted the product with EtOAc (2×70 mL). The combined organic layer was dried with Na$_2$SO$_4$, filtered and the solvent removed. The crude compound was purified by column chromatography (40 g silica cartridge, gradient 35%-40% EtOAc/pet ether) to yield the product (1.1 g, 55%) as a yellow solid. LCMS (66% & 28.8% of cis and trans isomers, M/z 349.1 (M+H)+.

Both the cis and trans isomers (1.1 g) were purified by SFC.

Trans isomer (Peak-2): 550 mg, M/z 349.2 (M+H)+.

Cis isomer (Peak-1): 240 mg, M/z 349.1 (M+H)+.

d. ((1r,3r)-3-(2-(((tert-butoxycarbonyl)amino)methyl)benzo[d]thiazol-6-yl)cyclobutyl)methyl methanesulfonate To a solution of tert-butyl ((6-((1r,3r)-3-(hydroxymethyl)cyclobutyl)benzo[d]thiazol-2-yl)methyl)carbamate (530 mg, 1.5 mmol, trans isomer) in DCM (20 mL) was added Et$_3$N (0.32 mL, 2.2 mmol) and methanesulfonyl chloride (0.12 mL, 1.6 mmol) at 0° C. under N$_2$. The reaction mixture was stirred at 0° C. for 2 h. The reaction mixture was partitioned between DCM (60 mL) and water (30 mL). The organic layer was separated and washed with water (2×10 mL) and brine. The organic extracts were then dried with Na$_2$SO$_4$, filtered and solvent removed to give the product (620 mg, 95%) as a pale brown liquid. M/z 427.2 (M+H)+.

e. tert-butyl ((6-((1 r,3r)-3-((dimethylamino)methyl)cyclobutyl)benzo[d]thiazol-2-yl)methyl)carbamate To a stirred solution of ((1r,3r)-3-(2-(((tert-butoxycarbonyl)amino)methyl)benzo[d]thiazol-6-yl)cyclobutyl)methyl methanesulfonate (620 mg, 1.4 mmol) in ACN (5 mL) was added dimethylamine (10 mL, 1M in THF) at RT and refluxed in a sealed tube for 16 h. The reaction mixture was concentrated under reduced pressure. The crude compound was purified by column chromatography (12 g silica cartridge, gradient 5%-10% MeOH/DCM) to yield the product (510 mg, 93%) as a pale brown thick mass. M/z 376.2 (M+H)+.

f. 1-((1r,3r)-3-(2-(aminomethyl)benzo[d]thiazol-6-yl)cyclobutyl)-N,N-dimethylmethanamine hydrochloride To a solution of tert-butyl ((6-((1r,3r)-3-((dimethylamino) methyl)cyclobutyl)benzo[d]thiazol-2-yl)methyl)carbamate (500 mg, 1.33 mmol) in 1,4-dioxane (2.5 mL) was added 4M HCl in dioxane (2.5 mL) at RT. The reaction mixture was stirred at RT for 4 h. The reaction mixture was concentrated under reduced pressure. The resulting residue was triturated with n-pentane and Et$_2$O to yield the product (385 mg, 93%) as a light brown solid. M/z 276.2 (M+H)+.

g. tert-butyl 2-(2-(((6-((1r,3r)-3-((dimethylamino) methyl)cyclobutyl)benzo[d]thiazol-2-yl)methyl)carbamoyl)-2,3-dihydro-1H-inden-2-yl)acetate To a stirred suspension of 1-((1r,3r)-3-(2-(aminomethyl) benzo[d]thiazol-6-yl)cyclobutyl)-N,N-dimethylmethanamine hydrochloride (410 mg, 1.3 mmol) in DMF (8 mL) was added Et$_3$N (1 mL, 6.5 mmol) at RT and stirred for 10 min. Then 2-(2-(tert-butoxy)-2-oxoethyl)-2,3-dihydro-1H-indene-2-carboxylic acid (400 mg, 1.4 mmol), and T$_3$P (1.3 mL, 1.9 mmol, 50% in EtOAc) was added to the reaction mixture. The light brown colour solution was stirred at RT for 16 h. The reaction mixture was partitioned between EtOAc (80 mL) and cold water (70 mL). The organic layer was separated and washed with water (2×50 mL) and brine. The organic extracts were then dried with Na$_2$SO$_4$, filtered and the solvent removed. The crude compound was purified by column chromatography (24 g silica cartridge, gradient 6%-10% MeOH/DCM) to yield the product (350 mg, 56.4%) as a pale brown thick solid. M/z 534.3 (M+H)+.

h. 2-(2-(((6-((1 r,3r)-3-((dimethylamino)methyl) cyclobutyl)benzo[d]thiazol-2-yl)methyl)carbamoyl)-2,3-dihydro-1H-inden-2-yl)acetic acid To a solution of tert-butyl 2-(2-(((6-((1r,3r)-3-((dimethylamino)methyl)cyclobutyl)benzo[d]thiazol-2-yl)methyl)carbamoyl)-2,3-dihydro-1H-inden-2-yl)acetate (150 mg, 0.28 mmol) in DCM (10 mL) was added TFA (2.5 mL) at 0° C. The reaction mixture was stirred vigorously at RT for 4 h and the solvent was removed. The residue was triturated with n-pentane and Et$_2$O. The crude compound was purified by preparative HPLC [YMC-TRIART-C18 (150*25 mm), 10 u, Mobile phase: A: 0.1% FA in H$_2$O, B: ACN, Gradient: (T % B):-0/10, 8/50, 9/50, 9.1/98, 11/98, 11.1/10, 13/10; Flow rate: 25 mL/min] to obtain the title product (80 mg, 60%) as a white solid. M/z 478.2 (M+H)+. $^1$H NMR (500 MHz, DMSO-d$_6$): δ 9.21 (1H, bs), 7.90 (1H, s), 7.83 (1H, d, J=8 Hz), 7.36 (1H, dd, J=8 Hz, J=1 Hz), 7.21-7.19 (2H, m), 7.14-7.12 (2H, m), 4.63 (2H, d, J=5.5 Hz), 3.71-3.64 (1H, m), 3.45 (2H, d, J=16 Hz), 2.99 (2H, d, J=16 Hz), 2.69 (2H, s), 2.50-2.40 (3H, obs), 2.25-2.05 (4H, m), 2.14 (6H, s).

Example 92

2-[2-[[6-[(1r,3r)-3-[(trimethylammonio)methyl]cyclobutyl]-1,3-benzothiazol-2-yl]methylcarbamoyl] indan-2-yl]acetate

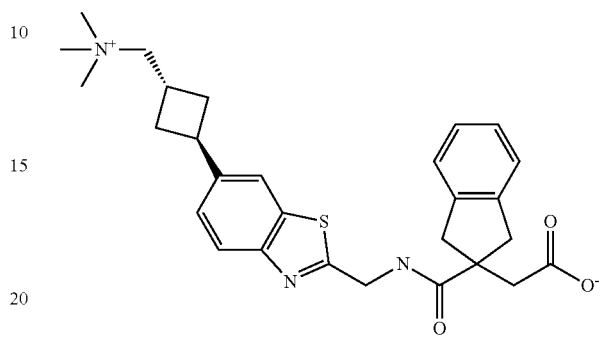

Prepared from tert-butyl 2-(2-(((6-((1r,3r)-3-((dimethylamino)methyl)cyclobutyl)benzo[d]thiazol-2-yl)methyl)carbamoyl)-2,3-dihydro-1H-inden-2-yl)acetate (example 91), using the conditions described in example 82. M/z 492.2 (M)+. $^1$H NMR (500 MHz, DMSO-d$_6$): δ 11.76 (1H, bs), 8.06 (1H, s), 7.86 (1H, d, J=8.5 Hz), 7.39 (1H, dd, J=8.5 Hz, J=1.5 Hz), 7.18-7.16 (2H, m), 7.12-7.10 (2H, m), 4.65 (2H, d, J=5 Hz), 3.65-3.61 (1H, m), 3.53 (2H, d, J=7 Hz), 3.42 (2H, d, J=16 Hz), 3.04 (9H, s), 3.02-2.96 (1H, m), 2.92 (2H, d, J=16 Hz), 2.50-2.42 (2H, obs), 2.38 (4H, t, J=7.5 Hz).

Example 93

2-(2-(((6-((1s,3s)-3-((dimethylamino)methyl)cyclobutyl)benzo[d]thiazol-2-yl)methyl)carbamoyl)-2,3-dihydro-1H-inden-2-yl)acetic acid

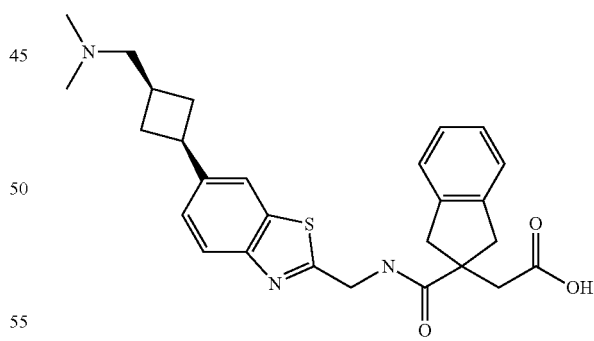

Prepared from tert-butyl ((6-((1 s,3s)-3-(hydroxymethyl) cyclobutyl)benzo[d]thiazol-2-yl)methyl)carbamate (example 91 step c), using the conditions described in example 91 above. M/z 478.2 (M)+. $^1$H NMR (500 MHz, DMSO-d$_6$): δ 9.43 (1H, bs), 7.84 (1H, s), 7.81 (1H, d, J=8.5 Hz), 7.31 (1H, dd, J=8.5 Hz, J=1.5 Hz), 7.21-7.19 (2H, m), 7.14-7.12 (2H, m), 4.63 (2H, d, J=5.5 Hz), 3.50-3.42 (1H, obs), 3.45 (2H, d, J=16.5 Hz), 2.99 (2H, d, J=16.5 Hz), 2.66 (2H, s), 2.51-2.48 (3H, obs), 2.31 (2H, d, J=7 Hz), 2.13 (6H, s), 1.80-1.70 (2H, m).

Example 94

2-[2-[[6-[(1s,3s)-3-[(trimethylammonio)methyl]cyclobutyl]-1,3-benzothiazol-2-yl]methylcarbamoyl]indan-2-yl]acetate

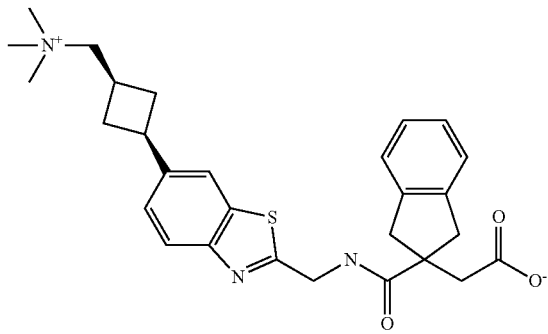 [SMILES: C[N+](C)(C)C[C@H]1C[C@@H](c2ccc3nc(CNC(=O)C4(CC(=O)[O-])Cc5ccccc5C4)sc3c2)C1]

Prepared from tert-butyl 2-(2-(((6-((1 s,3 s)-3-((dimethylamino)methyl)cyclobutyl)benzo[d]thiazol-2-yl)methyl)carbamoyl)-2,3-dihydro-1H-inden-2-yl)acetate (example 93), using the conditions described in example 82. M/z 492.2 (M)$^+$. $^1$H NMR (500 MHz, DMSO-d$_6$): δ 7.89 (1H, s), 7.85 (1H, d, J=8.5 Hz), 7.36 (1H, dd, J=8.5 Hz, J=1.5 Hz), 7.20-7.18 (2H, m), 7.14-7.11 (2H, m), 4.64 (2H, d, J=5.5 Hz), 3.55-3.48 (1H, m), 3.48-3.40 (4H, obs), 3.04 (9H, s), 2.95 (2H, d, J=16.5 Hz), 2.87-2.79 (1H, m), 2.64-2.60 (4H, m), 2.01-1.93 (2H, m).

Example 95

2-[2-[[6-[2-(dimethylamino)ethyl]-1,3-benzothiazol-2-yl]methylcarbamoyl]indan-2-yl]acetic acid

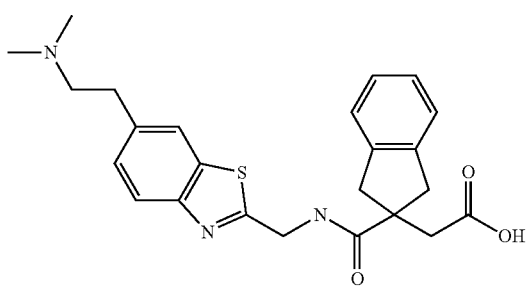 [SMILES: CN(C)CCc1ccc2nc(CNC(=O)C3(CC(=O)O)Cc4ccccc4C3)sc2c1]

a. tert-butyl ((6-vinylbenzo[d]thiazol-2-yl)methyl)carbamate

To a solution of tert-butyl ((6-bromobenzo[d]thiazol-2-yl)methyl)carbamate (1.5 g, 4.3 mmol) in dioxane:H$_2$O (5:1, 20 mL) was added K$_2$CO$_3$ (1.81 g, 13.1 mmol) and potassium trifluoro(vinyl)borate (1 g, 6.5 mmol) at RT and the reaction mixture was purged with argon for 15 min. Then PdCl$_2$(PPh$_3$)$_2$ (307 mg, 0.4 mmol) was added to the reaction mixture and purged with argon for a further 5 min. The reaction mixture was stirred in sealed tube at 90° C. for 8 h. The reaction mixture was diluted with EtOAc (50 mL), washed with water (2×50 mL) and brine. The organic extracts were then dried over sodium sulphate, filtered and the solvent removed. The crude compound was purified by column chromatography (24 g silica cartridge, gradient 15%-20% EtOAc/pet ether) to yield the product (1.0 g, 83%) as a yellow solid. M/z 291.1 (M+H)$^+$.

b. tert-butyl ((6-(2-hydroxyethyl)benzo[d]thiazol-2-yl)methyl)carbamate

To a solution of tert-butyl ((6-vinylbenzo[d]thiazol-2-yl)methyl)carbamate (1.0 g, 3.4 mmol) in THF (20 mL) was added RhCl$_3$.nH$_2$O (27 mg, 0.05 mmol). Then BH$_3$.DMS (2M in THF, 1.1 mL, 2.06 mmol) was added drop wise at RT and stirred at RT for 16 h. Then, the reaction mixture was cooled to 0° C. and added 3N sodium hydroxide solution (6 mL) drop wise, followed by hydrogen peroxide 30% (8 mL). The reaction mixture was stirred at 0° C. to RT for 1 h. The reaction mixture was quenched with saturated sodium chloride solution (30 mL) and extracted with EtOAc. The organic extracts were washed with brine, then dried over sodium sulphate, filtered and the solvent removed. The crude compound was purified by column chromatography (40 g silica cartridge, gradient 30%-35% EtOAc/pet ether) to yield the product (250 mg, 25%) as a yellow solid. M/z 309.1 (M+H)$^+$.

c. tert-butyl ((6-(2-bromoethyl)benzo[d]thiazol-2-yl)methyl)carbamate

To a solution of tert-butyl ((6-(2-hydroxyethyl)benzo[d]thiazol-2-yl)methyl)carbamate (250 mg, 0.8 mmol) in DCM (10 mL) was added triphenylphosphine (319 mg, 1.2 mmol), carbontetrabromide (403 mg, 1.2 mmol) at 0° C. The reaction mixture was stirred at 0° C. to RT for 2 h. The reaction mixture was diluted with water and DCM. The organic layer was separated, washed with brine and then dried over sodium sulphate. The organic layer was filtered and the solvent removed. The crude compound was purified by column chromatography (12 g silica cartridge, gradient 15%-20% EtOAc/pet ether) to yield the product (140 mg, 46%) as an off white solid. M/z 371 (M+H)$^+$.

d. tert-butyl ((6-(2-(dimethylamino)ethyl)benzo[d]thiazol-2-yl)methyl)carbamate To a solution of tert-butyl ((6-(2-bromoethyl)benzo[d]thiazol-2-yl)methyl)carbamate (140 mg, 0.37 mmol) in ACN (5 mL) was added dimethylamine (2M in THF, 0.56 mL, 1.2 mmol) at RT. The mixture was stirred at RT for 16 h. The reaction mixture was concentrated under reduced pressure. The resulting residue was triturated with n-pentane and Et$_2$O to yield the product (120 mg, crude) as a colourless semi solid. M/z 336.1 (M+H)$^+$.

e. 2-(2-(aminomethyl)benzo[d]thiazol-6-yl)-N,N-dimethylethanamine hydrochloride To a stirred solution of tert-butyl ((6-(2-(dimethylamino)ethyl)benzo[d]thiazol-2-yl)methyl)carbamate (120 mg, 0.358 mmol)) in 1,4-dioxane (2 mL) was added 4M HCl in dioxane (2 mL) at RT. The reaction mixture was stirred at RT for 4 h. The reaction mixture was concentrated under reduced pressure. The resulting residue was triturated with n-pentane and Et$_2$O to yield the product (86 mg, 89%) as a light brown solid. M/z 276.2 (M+H)$^+$.

f. tert-butyl 2-(2-(((6-(2-(dimethylamino)ethyl) benzo[d]thiazol-2-yl)methyl)carbamoyl)-2,3-dihydro-1H-inden-2-yl)acetate Prepared using the conditions described in example 91 step-g.

(70 mg, crude), colourless semi solid. M/z 494.2 (M+H)+.

g. 2-[2-[[6-[2-(dimethylamino)ethyl]-1,3-benzothiazol-2-yl]methylcarbamoyl]indan-2-yl]acetic acid Prepared using the conditions described in example 91 step-h. M/z 438.1 (M+H)+. $^1$H NMR (500 MHz, DMSO-d$_6$): δ 9.17 (1H, bs), 7.84 (1H, d, J=2.0 Hz), 7.80 (1H, d, J=8.5 Hz), 7.33 (1H, dd, J=8.5 Hz, J=2 Hz), 7.21-7.19 (2H, m), 7.15-7.12 (2H, m), 4.63 (2H, d, J=5.5 Hz), 3.45 (2H, d, J=16.5 Hz), 2.98 (2H, d, J=16.5 Hz), 2.82 (2H, t, J=7.5 Hz), 2.69 (2H, s), 2.52-2.48 (2H, obs), 2.19 (6H, s).

Example 96

2-[2-[[6-[2-(trimethylammonio)ethyl]-1,3-benzothiazol-2-yl]methylcarbamoyl]indan-2-yl]acetate

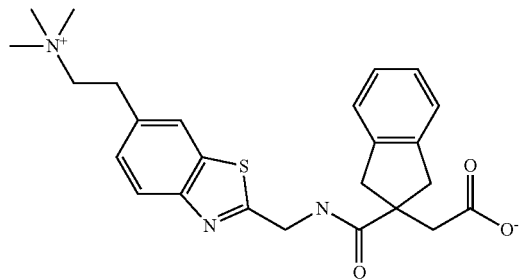 [SMILES: C[N+](C)(C)CCc1ccc2nc(CNC(=O)C3(CC(=O)[O-])Cc4ccccc4C3)sc2c1]

Prepared as described in example 37 using tert-butyl 2-(2-(((6-(2-(dimethylamino)ethyl)benzo[d]thiazol-2-yl) methyl)carbamoyl)-2,3-dihydro-1H-inden-2-yl)acetate obtained in the synthesis of example 95 (Method G—Suzuki coupling). M/z 452.2 (M)+. $^1$H NMR (500 MHz, DMSO-d$_6$): δ 12.65 (1H, bs), 7.98 (1H, s), 7.91 (1H, d, J=8.5 Hz), 7.43 (1H, dd, J=8.5 Hz, J=1.5 Hz), 7.17-7.15 (2H, m), 7.12-7.09 (2H, m), 4.66 (2H, d, J=5.5 Hz), 3.60-3.57 (2H, m), 3.40-3.30 (2H, obs), 3.20-3.16 (2H, m), 3.13 (9H, s), 2.89 (2H, d, J=16 Hz), 2.40 (2H, s).

Example 97

2-[2-[[5-[2-(dimethylamino)ethyl]-1,3-benzothiazol-2-yl]methylcarbamoyl]indan-2-yl]acetic acid

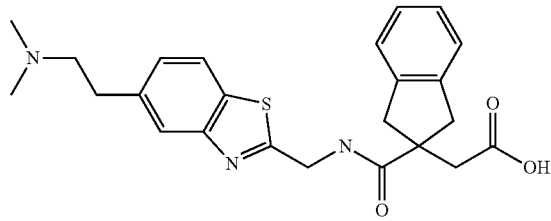 [SMILES: CN(C)CCc1ccc2sc(CNC(=O)C3(CC(=O)O)Cc4ccccc4C3)nc2c1]

a. Tert-butyl ((5-allylbenzo[d]thiazol-2-yl)methyl) carbamate

Synthesized from tert-butyl ((5-bromobenzo[d]thiazol-2-yl)methyl)carbamate following the same procedure described in example 95 step-a (56% yield, brown solid). M/z 305.1 (M+H)+.

b. tert-butyl ((5-(2-oxoethyl)benzo[d]thiazol-2-yl) methyl)carbamate

To a solution of tert-butyl ((5-allylbenzo[d]thiazol-2-yl) methyl)carbamate (1.2 g, 3.94 mmol) in acetone:H$_2$O (2:1, 15 mL) was added sodium periodate (2.53 g, 11.8 mmol) and OsO$_4$ (1M in water, 1.9 mL, 1.9 mmol) at RT and the reaction mixture was stirred at RT for 16 h. The reaction mixture was concentrated to remove the acetone solvent and residue was diluted with EtOAc (100 mL), washed with water (2×100 mL) and brine. The organic extracts were dried with Na$_2$SO$_4$, filtered and the solvent removed to give crude compound. M/z 307.1 (M+H)+.

c. tert-butyl ((5-(2-(dimethylamino)ethyl)benzo[d] thiazol-2-yl)methyl)carbamate To a solution of tert-butyl ((5-(2-oxoethyl)benzo[d]thiazol-2-yl)methyl)carbamate (1.2 g, 3.92 mmol) and Na(CN) BH$_3$ (246 mg, 3.92 mmol) in MeOH (1.9 mL) was cooled to 0° C. and added dimethylamine 2M solution in MeOH (1.96 mL, 3.92 mmol). The reaction mixture was stirred at RT for 16 h. Ice-water was added to the reaction mixture and extracted with EtOAc (100 mL), washed with water (2×100 mL) and brine. The organic extracts were dried with Na$_2$SO$_4$, filtered and the solvent removed. The crude was purified by column chromatography (100-200 silica gel, eluent 7% MeOH/DCM) to yield the product as a brown sticky material. M/z 336.0 (M+H)+.

d. 2-[2-[[5-[2-(dimethylamino)ethyl]-1,3-benzothiazol-2-yl]methylcarbamoyl]indan-2-yl]acetic acid Prepared from tert-butyl ((5-(2-(dimethylamino)ethyl) benzo[d]thiazol-2-yl)methyl)carbamate following the same procedure described in example 95 steps e, f and g. M/z 438.1 (M+H)+. $^1$H NMR (500 MHz, DMSO-d$_6$): δ 9.48 (1H, bs), 7.88 (1H, d, J=8 Hz), 7.76 (1H, d, J=1.5 Hz), 7.27 (1H, dd, J=8 Hz, J=1.5 Hz), 7.21-7.19 (2H, m), 7.13-7.12 (2H, m), 4.64 (2H, d, J=6 Hz), 3.45 (2H, d, J=16 Hz), 2.95 (2H, d, J=16.5 Hz), 2.83 (2H, t, J=7.5 Hz), 2.66 (2H, s), 2.52-2.50 (2H, obs), 2.19 (6H, s).

Example 98

2-[2-[[5-[2-(trimethylammonio)ethyl]-1,3-benzothiazol-2-yl]methylcarbamoyl]indan-2-yl]acetate

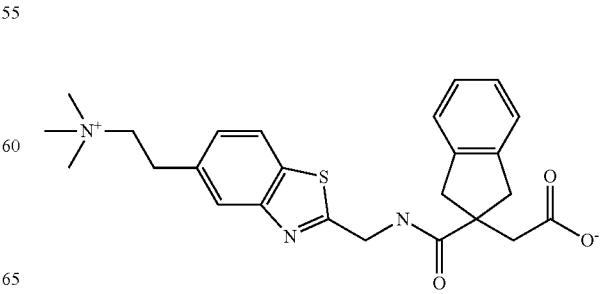

Prepared as described in example 37 using tert-butyl ((5-(2-(dimethylamino)ethyl)benzo[d]thiazol-2-yl)methyl) carbamate obtained in the synthesis of example 97 (Method G—Suzuki coupling). M/z 452.1 (M)+. 1H NMR (500 MHz, DMSO-d6): δ 8.02 (1H, d, J=8 Hz), 7.91 (1H, d, J=1.5 Hz), 7.34 (1H, dd, J=8 Hz, J=1.5 Hz), 7.20-7.18 (2H, m), 7.13-7.11 (2H, m), 4.65 (2H, d, J=5.5 Hz), 3.61-3.58 (2H, m), 3.43 (2H, d, J=16.5 Hz), 3.24-3.18 (2H, m), 3.14 (9H, s), 2.95 (2H, d, J=16.5 Hz), 2.56 (2H, s).

Example 99

2-[2-[[6-[3-(aminomethyl)azetidin-1-yl]-1,3-benzothiazol-2-yl]methylcarbamoyl]indan-2-yl]acetic acid

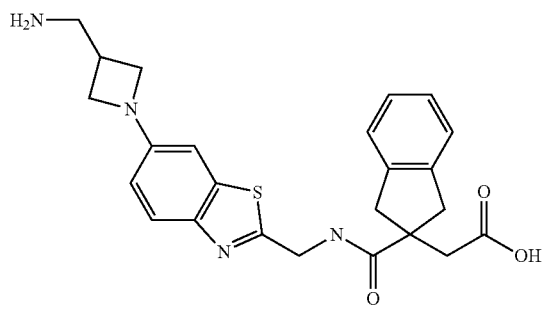 [SMILES: NCC1CN(c2ccc3nc(CNC(=O)C4(CC(=O)O)Cc5ccccc5C4)sc3c2)C1]

a. 2-(2-(((6-(3-(((tert-butoxycarbonyl)amino)methyl)azetidin-1-yl)benzo[d]thiazol-2-yl)methyl)carbamoyl)-2,3-dihydro-1H-inden-2-yl)acetic acid To a stirred solution of 2-(2-(((6-bromobenzo[d]thiazol-2-yl)methyl)carbamoyl)-2,3-dihydro-1H-inden-2-yl)acetic acid (200 mg, 0.44 mmol) in THF (10 mL) was added K3PO4 (286 mg, 1.34 mmol) and tert-butyl (azetidin-3-ylmethyl)carbamate (125 mg, 0.67 mmol) at RT and purged with argon for 15 min. Then, RuPhos-Pd-G1 (49 mg, 0.06 mmol) was added to the reaction mixture and purged with argon for further 5 min. The reaction mixture was stirred in sealed tube at 90° C. for 16 h. The reaction mixture cooled to RT, then filtered through celite pad and washed the pad with DCM. The filtrate was removed. The crude compound was purified by preparative HPLC [PRONTOSIL-C18 (20*250 mm), 10 u, Mobile phase: A: 0.05% FA in H2O, B: ACN, Gradient: (T % B):-0/55, 8/80, 8.1/98, 10/98, 10.1/55, 13/55; Flow rate: 20 mL/min] to yield the product (31 mg, 12.5%) as an off white solid. M/z 551.2 (M+H)+.

b. 2-[2-[[6-[3-(aminomethyl)azetidin-1-yl]-1,3-benzothiazol-2-yl]methylcarbamoyl]indan-2-yl]acetic acid To a solution of 2-(2-(((6-(3-(((tert-butoxycarbonyl)amino)methyl)azetidin-1-yl)benzo[d]thiazol-2-yl)methyl)carbamoyl)-2,3-dihydro-1H-inden-2-yl)acetic acid (60 mg, 0.10 mmol) in DCM (10 mL) was added TFA:TES (1.2 mL, 5:1) at RT. The reaction mixture was stirred vigorously at RT for 2 h. The reaction mixture was concentrated under reduced pressure. The crude compound was purified by preparative HPLC [X-BRIDGE AMIDA (250*30 mm), 5 u, Mobile phase: A: 0.05% FA in H2O, B: ACN, Gradient: (T % B):-0/90, 8/30, 12/30, 12.1/90, 16/90; Flow rate: 25 mL/min] to yield the title product (5.6 mg, 11.5%) as an off white solid. M/z 451 (M+H)+. 1H NMR (500 MHz, DMSO-d6): δ 7.68-7.58 (1H, d, J=8.5 Hz), 7.20-7.18 (2H, m), 7.13-7.11 (2H, m), 7.02/6.91 (1H, d, J=2 Hz), 6.79-6.56 (1H, dd, J=8.5 Hz, J=2 Hz), 4.60-4.50 (2H, m), 3.92-3.88 (2H, m), 3.65-3.30 (4H, obs), 3.00-2.91 (3H, m), 2.85-2.70 (2H, m), 2.62-2.57 (2H, m).

Example 100

2-[2-[[6-(3-aminoazetidin-1-yl)-1,3-benzothiazol-2-yl]methylcarbamoyl]indan-2-yl]acetic acid

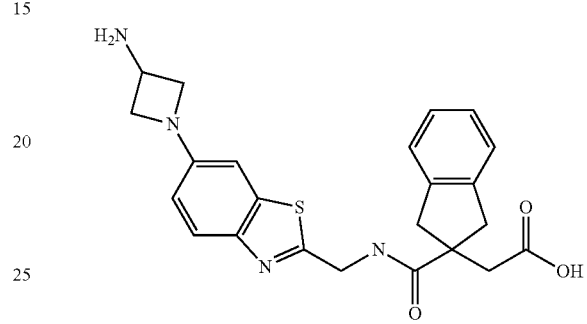

Prepared as described in example 99 using tert-butyl N-(azetidin-3-yl)carbamate as amine (Method H). M/z 437 (M+H)+. 1H NMR (500 MHz, DMSO-d6): δ 9.03 (1H, bs), 7.68-7.67 (1H, d, J=8.5 Hz), 7.21-7.18 (2H, m), 7.14-7.11 (2H, m), 6.92 (1H, d, J=2 Hz), 6.58 (1H, dd, J=8.5 Hz, J=2 Hz), 4.56 (2H, d, J=6 Hz), 4.07 (2H, t, J=7 Hz), 3.85-3.81 (1H, m), 3.54-3.43 (4H, obs), 2.97 (2H, d, J=16.5 Hz), 2.67 (2H, s).

Example 101

2-[2-[[6-[(3 S)-3-aminopyrrolidin-1-yl]-1,3-benzothiazol-2-yl]methylcarbamoyl]indan-2-yl]acetic acid

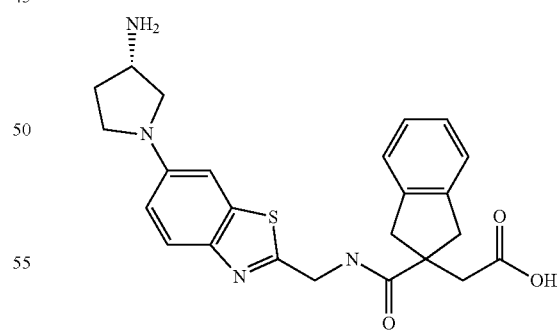

Prepared as described in example 99 using tert-butyl N-[(3S)-pyrrolidin-3-yl]carbamate as amine (Method H). M/z 451.2 (M+H)+. 1H NMR (500 MHz, DMSO-d6): δ 7.70-7.67 (1H, m), 7.20-7.17 (2H, m), 7.13-7.11 (2H, m), 7.03-7.0 (1H, d, J=2 Hz), 6.99-6.72 (1H, m), 4.57-4.52 (2H, d, J=5.5 Hz), 3.70-3.60 (1H, m), 3.55-3.30 (5H, obs), 3.02-2.90 (3H, m), 2.63-2.62 (2H, s), 2.28-2.11 (1H, m), 1.84-1.79 (1H, m).

Example 102

2-[2-[[6-[(3R)-3-aminopyrrolidin-1-yl]-1,3-benzothiazol-2-yl]methylcarbamoyl]indan-2-yl]acetic acid

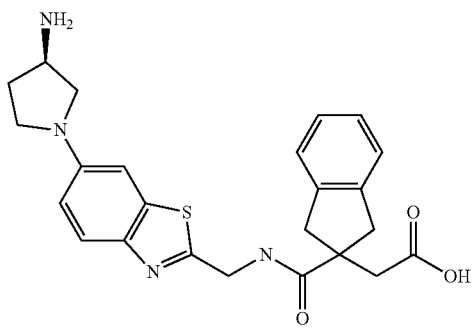 [SMILES: N[C@@H]1CCN(c2ccc3nc(CNC(=O)C4(CC(=O)O)Cc5ccccc5C4)sc3c2)C1]

Prepared as described in example 99 tert-butyl N-[(3R)-pyrrolidin-3-yl]carbamate using as amine (Method H). M/z 451.0 (M+H)+. $^1$H NMR (500 MHz, DMSO-$d_6$): δ 7.67 (1H, d, J=8.5 Hz), 7.20-7.18 (2H, m), 7.13-7.11 (2H, m), 6.99 (1H, d, J=2 Hz), 6.70 (1H, dd, J=8.5 Hz, J=2 Hz), 4.56 (2H, d, J=6 Hz), 3.70-3.60 (1H, m), 3.50-3.30 (5H, obs), 3.02-2.90 (3H, m), 2.63-2.62 (2H, s), 2.28-2.11 (1H, m), 1.84-1.79 (1H, m).

Example 103

2-[2-[[5-[(3 S)-3-aminopyrrolidin-1-yl]-1,3-benzothiazol-2-yl]methylcarbamoyl]indan-2-yl]acetic acid

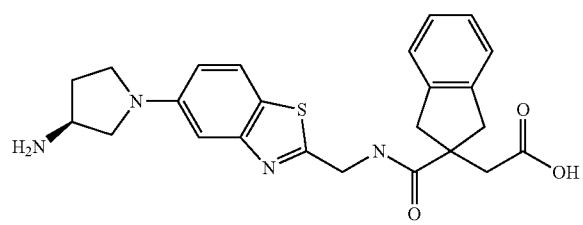 [SMILES: N[C@H]1CCN(c2ccc3sc(CNC(=O)C4(CC(=O)O)Cc5ccccc5C4)nc3c2)C1]

Prepared as described in example 99 from 2-(2-(((5-bromobenzo[d]thiazol-2-yl)methyl)carbamoyl)-2,3-dihydro-1H-inden-2-yl)acetic acid using tert-butyl N-[(3S)-pyrrolidin-3-yl]carbamate as amine (Method H). M/z 451.1 (M+H)+. $^1$H NMR (500 MHz, DMSO-$d_6$): δ 9.37 (1H, bs), 7.74 (1H, d, J=8.5 Hz), 7.21-7.19 (2H, m), 7.14-7.11 (2H, m), 6.96 (1H, d, J=2.5 Hz), 6.73 (1H, dd, J=8.5 Hz, J=2.5 Hz), 4.60 (2H, d, J=6.0 Hz), 3.75-3.70 (1H, m), 3.50-3.20 (5H, obs), 3.11-3.08 (1H, m), 2.97 (2H, d, J=16.5 Hz), 2.67 (2H, s), 2.22-2.18 (1H, m), 1.90-1.85 (1H, m).

Example 104

2-[2-[[5-[(3R)-3-aminopyrrolidin-1-yl]-1,3-benzothiazol-2-yl]methylcarbamoyl]indan-2-yl]acetic acid

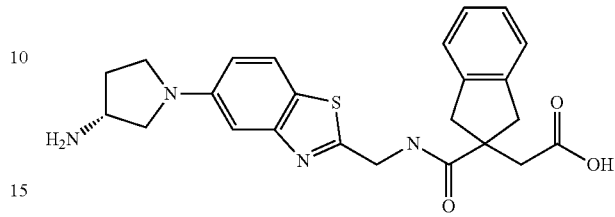

Prepared as described in example 99 from 2-(2-(((5-bromobenzo[d]thiazol-2-yl)methyl)carbamoyl)-2,3-dihydro-1H-inden-2-yl)acetic acid using tert-butyl N-[(3R)-pyrrolidin-3-yl]carbamate as amine (Method H). M/z 451.0 (M+H)+. $^1$H NMR (500 MHz, DMSO-$d_6$): δ 9.15 (1H, bs), 7.74 (1H, d, J=8.5 Hz), 7.21-7.20 (2H, m), 7.14-7.10 (2H, m), 6.98 (1H, d, J=2.5 Hz), 6.73 (1H, dd, J=8.5 Hz, J=2.5 Hz), 4.59 (2H, d, J=6.0 Hz), 3.85-3.75 (1H, m), 3.55-3.30 (5H, obs), 3.20-3.12 (1H, m), 2.99 (2H, d, J=16.5 Hz), 2.69 (2H, s), 2.26-2.24 (1H, m), 1.95-1.91 (1H, m).

Example 105

2-[2-[[6-[2-(dimethylamino)ethylamino]-1,3-benzothiazol-2-yl]methylcarbamoyl]indan-2-yl]acetic acid

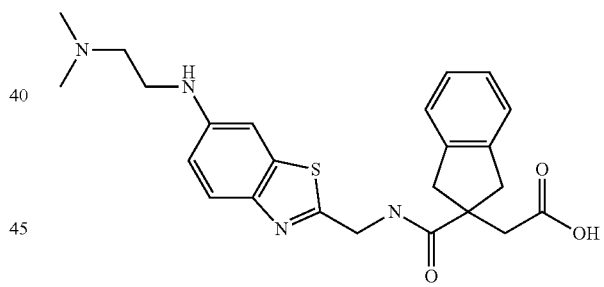

a. tert-butyl ((6-((2-(dimethylamino)ethyl)amino)benzo[d]thiazol-2-yl)methyl)carbamate To a solution of tert-butyl ((6-bromobenzo[d]thiazol-2-yl)methyl)carbamate (2 g, 5.84 mmol) in dioxane (30 mL) was added $Cs_2CO_3$ (3.8 g, 11.6 mmol) and N',N'-dimethylethane-1,2-diamine (772 mg, 8.7 mmol) at RT and the reaction mixture was purged with argon for 15 min. Then $Pd_2(dba)_3$ (802 mg, 0.87 mmol) and Xantphos (1 g, 1.75 mmol) was added to the reaction mixture and purged with argon for 5 min. The reaction mixture was stirred in sealed tube at 100° C. for 16 h. The reaction mixture was cooled to RT, then filtered through celite pad and washed the pad with EtOAc. The filtrate was evaporated. The crude compound was purified by column chromatography (40 g silica cartridge, gradient 5%-10% MeOH/DCM) to yield the product (250 mg, 12%) as a pale yellow solid. M/z 351.1 (M+H)+.

b. 2-[2-[[6-[2-(dimethylamino)ethylamino]-1,3-benzothiazol-2-yl]methylcarbamoyl]indan-2-yl]acetic acid Prepared from tert-butyl ((6-((2-(dimethylamino)ethyl)amino)benzo[d]thiazol-2-yl)methyl)carbamate following the procedure described in example 91 step-f, -g and -h. The crude compound was purified by preparative HPLC [INERTSIL ODS-C18 (250*19 mm), 5 u, Mobile phase: A: 0.1% FA in H$_2$O, B: ACN, Gradient: (T % B):-0/5, 2/5, 8/35, 11/35, 11.1/98, 13/98, 13.1/5, 15/5; Flow rate: 19 mL/min] to obtain 2-(2-(((6-((2-(dimethylamino)ethyl)amino)benzo[d]thiazol-2-yl)methyl)carbamoyl)-2,3-dihydro-1H-inden-2-yl)acetic acid (10 mg, 14%) as an off white solid. M/z 453.2 (M+H)$^+$. $^1$H NMR (500 MHz, DMSO-d$_6$): δ 9.03 (1H, bs), 7.57 (1H, d, J=9 Hz), 7.21-7.18 (2H, m), 7.14-7.12 (2H, m), 7.01 (1H, d, J=2 Hz), 6.79 (1H, dd, J=9 Hz, J=2 Hz), 4.54 (2H, d, J=6 Hz), 3.44 (2H, d, J=16.5 Hz), 3.13-3.11 (2H, m), 2.97 (2H, d, J=16.5 Hz), 2.68 (2H, s), 2.48 (2H, obs), 2.19 (6H, s).

Example 106

2-[2-[[5-(4-methylpiperazin-1-yl)-1,3-benzothiazol-2-yl]methylcarbamoyl]indan-2-yl]acetic acid

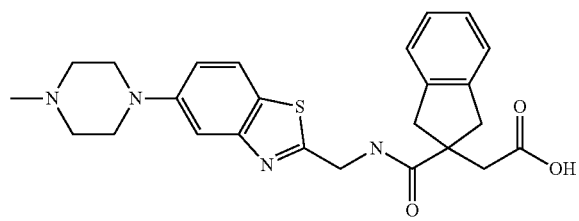 [SMILES: CN1CCN(c2ccc3sc(CNC(=O)C4(CC(=O)O)Cc5ccccc5C4)nc3c2)CC1]

a. tert-butyl ((5-(4-methylpiperazin-1-yl)benzo[d]thiazol-2-yl)methyl)carbamate A solution of tert-butyl (5-bromobenzo[d]thiazol-2-yl)methyl)carbamate (400 mg, 1.16 mmol) and K$_3$PO$_4$ (743 mg, 3.44 mmol) in THF (24 mL) was purged with argon for 10 min. Then, 1-methylpiperazine (350 mg, 3.44 mmol), RuPhos (108 mg, 0.16 mmol) and RuPhos-Pd-G1 (169 mg, 0.16 mmol) were added to the reaction mixture and purged with argon for further 5 min. The reaction mixture was stirred in sealed tube at 90° C. for 16 h. The reaction mixture was filtered through celite pad and washed the pad with EtOAc (50 mL). The filtrate was concentrated under reduced pressure. The crude compound was purified by column chromatography (24 g silica cartridge, gradient 0-4% MeOH/DCM) to yield the product (198 mg, 47%) as a brown gummy liquid. M/z 363.1 (M+H)$^+$.

b. 2-[2-[[6-[2-(dimethylamino)ethylamino]-1,3-benzothiazol-2-yl]methylcarbamoyl]indan-2-yl]acetic acid Prepared from tert-butyl ((5-(4-methylpiperazin-1-yl)benzo[d]thiazol-2-yl)methyl)carbamate following the procedure described in example 91 step-f, -g and -h. The crude compound was purified by preparative HPLC [SYMMETRY-C8 (300×19 mm), 7 u, Mobile phase: A: 0.1% FA in H$_2$O, B: ACN, Gradient: (T % B):-0/15, 7/50, 7.1/98, 9/98, 9.1/15, 12/15; Flow rate: 20 mL/min], 64% yield, off-white solid. M/z 465.2 (M+H)$^+$. $^1$H NMR (500 MHz, DMSO-d$_6$): δ 12.10 (1H, bs), 8.70 (1H, t, J=5.5 Hz), 7.83 (1H, d, J=8.5 Hz), 7.43 (1H, d, J=2.5 Hz), 7.22-7.20 (2H, m), 7.17-7.13 (3H, m), 4.61 (2H, d, J=6.0 Hz), 3.53 (2H, d, J=16.5 Hz), 3.34-3.30 (4H, obs), 3.12-2.90 (4H, bs), 2.99 (2H, d, J=16.5 Hz), 2.73 (2H, s), 2.65-2.54 (3H, bs).

Example 107

2-[2-[(6-hydroxy-1,3-benzothiazol-2-yl)methylcarbamoyl]indan-2-yl]acetic acid

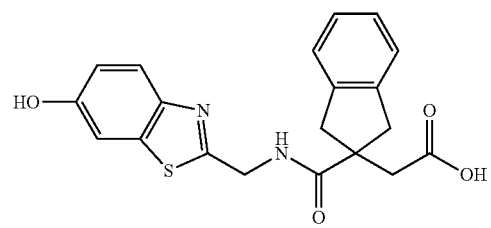 [SMILES: O=C(O)CC1(C(=O)NCc2nc3ccc(O)cc3s2)Cc2ccccc2C1]

a. tert-butyl ((6-bromobenzo(d)thiozol-2-yl)methyl)carbamate

To a stirred solution of 4-bromo-2-iodo aniline (1.5 g, 5.03 mmol) and tert-butyl (2-amino-2-thioethoxyethyl) carbamate (956 mg, 5.03 mmol) in DMF (15 mL) was added CuO (397 mg, 5.03 mmol) at RT and the reaction mixture was purged with argon for 15 min. Then dppf (278 mg, 0.503 mmol) and Pd$_2$(dba)$_3$ (230 mg, 0.251 mmol) were added to the reaction mixture and purged with argon for further 5 min. The reaction mixture was stirred in sealed tube at 80° C. for 3 h. The reaction mixture was filtered through celite pad and washed with EtOAc (50 mL). The filtrate was washed with water (2×30 mL) and concentrated under reduced pressure. The crude compound was purified by column chromatography (60-120 silica gel, gradient 15%-20% EtOAc/pet ether) to yield the product (1.4 g, 89%) as an off white solid. M/z 343.0 (M+H)$^+$.

b. tert-butyl ((6-(4,4,5,5-tetramethyl-1,3,2-dioxaborolan-2-yl) benzo[d]thiazol-2-yl) methyl) carbamate To a stirred solution of tert-butyl ((6-bromobenzo (d) thiozol-2-yl) methyl) carbamate (1.3 g, 3.80 mmol), and Bpin (1.44 g, 5.70 mmol) in 1,4-dioxane (15 mL) was added potassium acetate (745 mg, 7.60 mmol) at RT and the reaction mixture was purged with argon for 15 min. Then PdCl$_2$(dppf).DCM (155 mg, 0.190 mmol) was added to the reaction mixture and purged with argon for further 5 min. The reaction mixture was stirred to reflux in sealed tube for 12 h. The reaction mixture was filtered through celite pad and washed with EtOAc (50 mL). The filtrate was washed with water (2×30 mL), the organic layer was dried with sodium sulphate, filtered and concentrated under reduced pressure to get the product (1.5 g, crude) as a brown sticky solid. M/z 391.2 (M+H)$^+$.

c. tert-butyl ((6-hydroxybenzo[d]thiazol-2-yl) methyl)carbamate

To a stirred solution of tert-butyl((6-(4,4,5,5-tetramethyl-1,3,2-dioxaborolan-2-yl)benzo[d]thiazol-2-yl)methyl)carbamate (1.5 g, 3.84 mmol) in THF (15 mL) was added 1N NaOH (3.84 mL g, 3.84 mmol) at 0° C. and stirred for 10 min. Then $H_2O_2$(30% in $H_2O$, 0.21 mL, 8.84 mmol) was added to the reaction mixture at 0° C. and allowed to stir to RT for 1 h. The reaction mixture was partitioned between EtOAc (100 mL) and water (70 mL). The aqueous phase was extracted with EtOAc (2×100 mL) and the combined organic extracts were washed with brine, dried with $Na_2SO_4$, filtered and evaporated. The mixture was purified by column chromatography (60-120 silica gel, gradient 30%-40% EtOAc/pet ether) to get the product (1.0 g, 93.4%) as an off white solid. M/z 281.1 (M+H)$^+$.

d. 2-(amino methyl) benzo[d]thiazol-6-ol

To a stirred solution of tert-butyl ((6-hydroxybenzo[d]thiazol-2-yl) methyl) carbamate (250 mg, 0.89 mmol) in dioxane (10 mL) was added 4N HCl in dioxane (3 mL) at RT. Then the reaction mixture was stirred at RT for 2 h, then concentrated under reduced pressure. The crude compound was triturated with $Et_2O$ (20 mL) to obtain the product (220 mg) as an off white solid. M/z 181.1 (M+H)$^+$.

e. tert-butyl 2-(2-(((6-hydroxybenzo[d]thiazol-2-yl) methyl) carbamoyl)-2,3-dihydro-1H-inden-2-yl) acetate To a stirred solution of 2-(2-(tert-butoxy)-2-oxoethyl)-2,3-dihydro-1H-indene-2-carboxylic acid (150 mg, 0.543 mmol) in DMF (5 mL) was added $Et_3N$ (0.22 mL, 1.62 mmol) and $T_3P$ (0.23 mL, 0.814 mmol) at RT and stirred for 15 min. 2-(Amino methyl)benzo[d]thiazol-6-ol (128 mg, 0.597 mmol) was added and stirred at RT for 12 h. The reaction mixture was partitioned between EtOAc (50 mL) and cold water (20 mL). The aqueous phase was extracted with EtOAc (2×30 mL). The combined organic extracts were washed with brine, dried with $Na_2SO_4$, filtered and evaporated. The mixture was purified by preparative TLC (3% MeOH/DCM) to get the product (125 mg, 54.3%) as a pale yellow solid. M/z 439.1 (M+H)$^+$.

f. 2-[2-[(6-hydroxy-1,3-benzothiazol-2-yl)methylcarbamoyl]indan-2-yl]acetic acid To a stirred solution of tert-butyl 2-(2-(((6-hydroxybenzo[d]thiazol-2-yl) methyl) carbamoyl)-2,3-dihydro-1H-inden-2-yl) acetate (110 mg, 0.251 mmol) in DCM (5 mL) was added TFA (1 mL) at 0° C. The reaction mixture was allowed to stir to RT for 4 h. After completion of starting material based on LCMS, the reaction mixture was concentrated under reduced pressure. The crude compound was purified by preparative HPLC [SYMMETRY-C8 (300*19 mm), 7 u, Mobile phase: A: 0.1% FA in $H_2O$, B:ACN, Gradient:(% B): 0/20, 11/73, 11.1/98, 12/98, 12.1/20, 15/20, Flow Rate: 20 mL/min] to obtain the title product (41 mg, 43%) as an off white solid. M/z 381.0 (M−H)$^−$. $^1$H NMR (500 MHz, DMSO-$d_6$) δ 12.13 (1H, bs), 9.69 (1H, s), 8.70 (1H, bs), 7.69 (1H, d, J=8.5 Hz), 7.28 (1H, d, J=2 Hz), 7.22-7.19 (2H, m), 7.15-7.11 (2H, m), 6.91 (1H, dd, J=8.5 Hz, J=2.5 Hz), 4.58 (1H, d, J=6 Hz), 3.47 (2H, d, J=16.5 Hz), 3.00 (2H, d, J=16.5 Hz), 2.72 (2H, s).

Example 108

2-[2-[(6-ethoxy-1,3-benzothiazol-2-yl)methylcarbamoyl]indan-2-yl]acetic acid

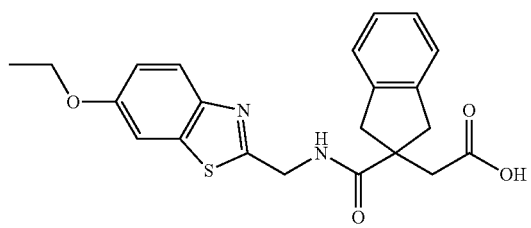 [SMILES: CCOc1ccc2nc(CNC(=O)C3(CC(=O)O)Cc4ccccc4C3)sc2c1]

a. tert-butyl ((6-ethoxybenzo[d]thiazol-2-yl)methyl) carbamate

To a stirred solution of tert-butyl ((6-hydroxybenzo[d]thiazol-2-yl)methyl)carbamate (300 mg, 1.07 mmol) in ACN (5 mL) was added $K_2CO_3$, (221 mg, 1.60 mmol) and ethyl iodide (200 mg, 1.28 mmol) at RT. The reaction mixture was stirred in sealed tube at 90° C. for 2 h, then partitioned between EtOAc (80 mL) and water (40 mL). The aqueous phase was extracted with EtOAc (2×30 mL) and the combined organic extracts were washed with brine, dried $Na_2SO_4$, filtered and evaporated. The mixture was purified by column chromatography (60-120 silica gel, gradient 40%-50% EtOAc/pet ether) to yield the product (250 mg, 91.6%) as a pale yellow solid. M/z (M+H)$^+$.

b. 2-[2-[(6-ethoxy-1,3-benzothiazol-2-yl)methylcarbamoyl]indan-2-yl]acetic acid

The title product is obtained following the procedure described in example 107 steps d, e and f. The crude compound was purified by preparative HPLC [SYMMETRY-C8 (300*19 mm), 7 u, Mobile phase: A: 0.1% FA in $H_2O$, B: ACN, Gradient:(% B): 0/50, 8/80, 8.1/98, 10/98, 10.1/50, 13/50 Flow Rate: 20 mL/min] 38.5% yield, off white solid. M/z 411.1 (M+H)$^+$. $^1$H NMR (500 MHz, DMSO-$d_6$): δ 12.14 (1H, s), 8.69 (1H, t, J=6 Hz), 7.78 (1H, d, J=9 Hz), 7.55 (1H, d, J=2.5 Hz), 7.22-7.19 (2H, m), 7.15-7.13 (2H, m), 7.05 (1H, dd, J=9 Hz, J=5 Hz), 4.60 (2H, d, J=5 Hz), 4.07 (2H, q, J=7 Hz), 3.45 (2H, d, J=16.5 Hz), 2.99 (2H, d, J=16.5 Hz), 2.73 (2H, s), 1.34 (3H, t, J=7 Hz).

Example 109

2-[2-[[6-(2-hydroxyethoxy)-1,3-benzothiazol-2-yl]methylcarbamoyl]indan-2-yl]acetic acid

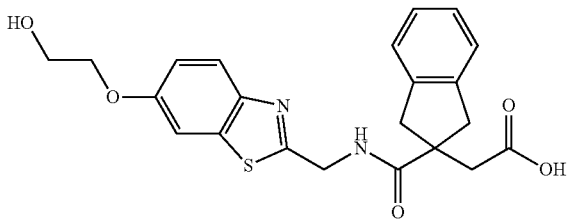 [SMILES: O=C(O)CC1(C(=O)NCc2nc3ccc(OCCO)cc3s2)Cc2ccccc2C1]

The title product was synthesised from tert-butyl ((6-hydroxybenzo[d]thiazol-2-yl)methyl)carbamate following the same procedure described for the synthesis of example 108, using 3-bromopropan-1-ol in step-a. The crude compound was purified by preparative HPLC [KROMASIL-C18 (25*150 mm), 10 u, Mobile phase: A: 0.1% FA in H$_2$O, B: ACN, Gradient: (% B): 0/20, 8/80, 9/85, 9.1/98, 10/98, 10.1/20, 12/20, Flow Rate: 25 mL/min] 25% yield, off white solid. M/Z 427.1 (M+H)$^+$. $^1$H NMR (500 MHz, DMSO-d$_6$): δ 12.20 (1H, bs), 8.96 (1H, bs), 7.79 (1H, d, J=8.5 Hz), 7.58 (1H, d, J=2.5 Hz), 7.22-7.20 (2H, m), 7.14-7.13 (2H, m), 7.08 (1H, dd, J=8.5 Hz, J=2.5 Hz), 4.90 (1H, t, J=5.5 Hz), 4.61 (1H, d, J=5.5 Hz), 4.03 (2H, t, J=5 Hz), 3.75-3.72 (2H, m), 3.47 (2H, d, J=16.5 Hz), 3.00 (2H, d, J=16.5 Hz), 2.70 (2H, s).

Example 110

2-[2-[[6-[2-(dimethylamino)ethoxy]-1,3-benzothiazol-2-yl]methylcarbamoyl]indan-2-yl]acetic acid

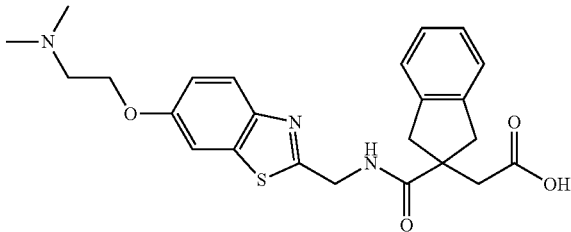 [SMILES: CN(C)CCOc1ccc2nc(CNC(=O)C3(CC(=O)O)Cc4ccccc4C3)sc2c1]

The title product was synthesised from tert-butyl ((6-hydroxybenzo[d]thiazol-2-yl)methyl)carbamate following the same procedure described for the synthesis of example 108, using 2-chloro-N,N-dimethyl-ethanamine hydrochloride in step-a. The crude compound was purified by preparative HPLC [YMC-TRIART-C18-(150*25 mm), 10 u, Mobile phase: A: 0.05% FA in H$_2$O, B: ACN, Gradient (% B): 0/5, 8/50, 8.1/98, 10/98, 10.1/5, 12/5, Flow rate: 25 mL/min], 56.3% yield, off white solid. M/z 454.1 (M+H)$^+$. $^1$H NMR (500 MHz, DMSO-d$_6$): δ 8.78 (1H, bs), 7.79 (1H, d, J=8.5 Hz), 7.59 (1H, d, J=2.5 Hz), 7.22-7.19 (2H, m), 7.15-7.12 (2H, m), 7.07 (1H, dd, J=8.5 Hz, J=2.5 Hz), 4.61 (2H, d, J=6 Hz), 4.10 (2H, t, J=6 Hz), 3.47 (2H, d, J=16.5 Hz), 3.00 (2H, d, J=16.5 Hz), 2.72 (2H, s), 2.66 (2H, t, J=5.5 Hz), 2.24 (6H, s).

Example 111

2-[2-[[6-[2-(trimethylammonio)ethoxy]-1,3-benzothiazol-2-yl]methylcarbamoyl]indan-2-yl]acetate

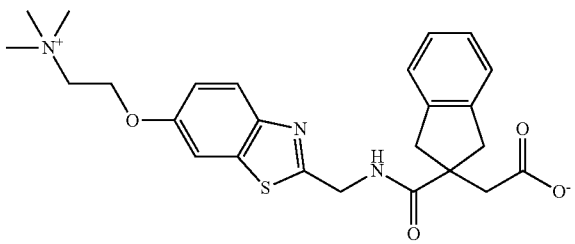 [SMILES: C[N+](C)(C)CCOc1ccc2nc(CNC(=O)C3(CC(=O)[O-])Cc4ccccc4C3)sc2c1]

The title product was synthesised from tert-butyl ((6-hydroxybenzo[d]thiazol-2-yl)methyl)carbamate following the same procedure described for the synthesis of example 37. The crude compound was purified by preparative HPLC [Column SUNFIRE-C18 (150*30 mm), 5 u, Mobile phase: A: 0.05% FA in H$_2$O, B: ACN, Gradient (% B): 0/10, 8/45, 8.1/98, 10/98, 10.1/10, 13/10, Flow rate: 25 mL/min], 20% yield, off white solid. M/z 468.1 (M)$^+$. $^1$H NMR (500 MHz, DMSO-d$_6$) δ 11.26 (1H, bs), 7.85 (1H, d, J=9 Hz), 7.70 (1H, d, J=2.5 Hz), 7.18-7.09 (5H, m), 4.62 (2H, d, J=5 Hz), 4.52 (2H, bs), 3.80 (2H, t, J=4.5 Hz), 3.43 (2H, d, J=16 Hz), 3.18 (9H, s), 2.94 (2H, d, J=16 Hz), 2.49 (2H, s).

Example 112

2-[2-[[5-[2-(dimethylamino)ethoxy]-1,3-benzothiazol-2-yl]methylcarbamoyl]indan-2-yl]acetic acid

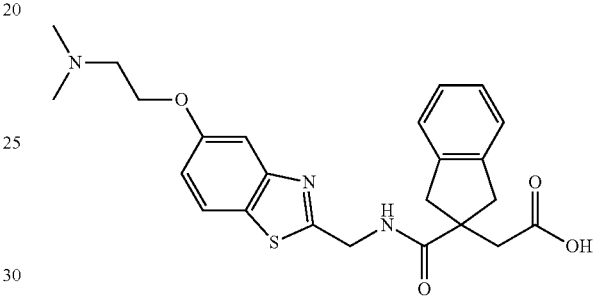

The title product was synthesised from tert-butyl ((5-hydroxybenzo[d]thiazol-2-yl)methyl)carbamate following the same procedure described for the synthesis of example 108, using 2-chloro-N,N-dimethyl-ethanamine hydrochloride in step-a. The crude compound was purified by preparative HPLC [YMC-TRIART-C18-(150*25 mm), 10 u, mobile phase: A: 0.05% FA in H$_2$O, B: ACN, Gradient (% B): 0/5, 8/50, 8.1/98, 10/98, 10.1/5, 12/5, Flow rate: 25 mL/min], 56.8% yield, off white solid. M/z 454.1 (M+H)$^+$. $^1$H NMR (500 MHz, DMSO-d$_6$); δ 12.2 (1H, bs), 8.80 (1H, bs), 7.87 (1H, d, J=8.5 Hz), 7.47 (1H, d, J=2.5 Hz), 7.22-7.20 (2H, m), 7.15-7.13 (2H, m), 7.03 (1H, dd, J=8.5 Hz, J=2.5 Hz), 4.63 (2H, d, J=6 Hz), 4.12 (2H, t, J=6 Hz), 3.48 (2H, d, J=16.5 Hz), 3.01 (2H, d, J=16.5 Hz), 2.73 (2H, s), 2.68 (2H, t, J=6 Hz), 2.26 (6H, s).

Example 113

2-[2-[[5-[2-(trimethylammonio)ethoxy]-1,3-benzothiazol-2-yl]methylcarbamoyl]indan-2-yl]acetate

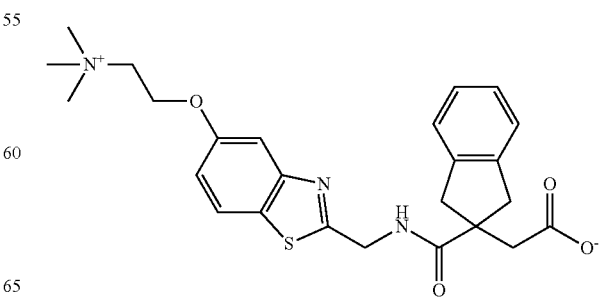

The title product was synthesised from tert-butyl ((5-hydroxybenzo[d]thiazol-2-yl)methyl)carbamate following the same procedure described for the synthesis of example 37. The crude compound was purified by preparative HPLC [SUNFIRE-C18 (150*30 mm), 5 u, mobile phase: A: 0.05% FA in H$_2$O, B: ACN, Gradient (% B): 0/10, 7/40, 8/40, 8.1/98, 9/98, 9.1/10, 12/10, Flow rate: 25 mL/min], 53.7% yield, off white solid. M/z 468.2 (M)$^+$. $^1$H NMR (500 MHz, DMSO-d$_6$): δ 11.72 (1H, bs), 7.95 (1H, d, J=9 Hz), 7.59 (1H, d, J=2.5 Hz), 7.17-7.15 (2H, m), 7.12-7.07 (3H, m), 4.66 (2H, d, J=5 Hz), 4.56 (2H, bs), 3.81 (2H, t, J=5 Hz), 3.40 (2H, d, J=16 Hz), 3.18 (9H, s), 2.91 (2H, d, J=16 Hz), 2.47 (2H, s).

Example 114

2-[2-[(5,6-dimethoxy-1,3-benzothiazol-2-yl)methylcarbamoyl]indan-2-yl]acetic acid

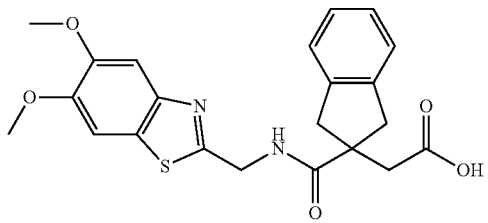 [SMILES: COc1cc2nc(CNC(=O)C3(CC(=O)O)Cc4ccccc4C3)sc2cc1OC]

a. N-(2-iodo-4,5-dimethoxyphenyl)acetamide

To a stirred solution of N-(3,4-dimethoxyphenyl)acetamide (12 g, 61.5 mmol) in DCM (600 mL) was added AcOH (12 mL) at RT and stirred for 10 min. Then iodine monochloride (12 g, 73.8 mmol) in DCM (100 mL) was added dropwise for 15 min. The dark brown solution was stirred for 4 h at RT. The reaction mixture was diluted with DCM (200 mL), washed with water (2×100 mL), sat. sodium thiosulfate (2×100 mL) and brine. The organic extracts were then dried with Na$_2$SO$_4$, filtered and the solvent removed. The crude compound was purified by column chromatography (120 g silica cartridge, gradient 40%-50% EtOAc/pet ether) to yield the product (5.2 g, 27%) as a pale yellow solid. M/z 321.9 (M+H)$^+$.

b. 2-iodo-4,5-dimethoxyaniline

To a solution of N-(2-iodo-4,5-dimethoxyphenyl)acetamide (5.2 g, 16.1 mmol) in EtOH:H$_2$O (2:1, 150 mL) was added sodium hydroxide (32.3 g, 810 mmol) at RT. The reaction mixture was stirred at 100° C. for 6 h. The reaction mixture was concentrated under reduced pressure to give the residue. The residue was partitioned between EtOAc and cold water and the phases were separated. The organic extracts were washed with brine, dried with Na$_2$SO$_4$, filtered and the solvent removed. The crude compound was triturated with n-pentane and Et$_2$O to yield the product (4.1 g, 91%) as a light brown sticky solid. M/z 280 (M+H)$^+$.

c. Tert-butyl ((5,6-dimethoxybenzo[d]thiazol-2-yl)methyl)carbamate

To a stirred solution of 2-iodo-4,5-dimethoxyaniline (1 g, 3.5 mmol) in DMF (10 mL) was added tert-butyl (2-amino-2-thioxoethyl)carbamate (1 g, 5.3 mmol), CuO (425 mg, 5.3 mmol) and purged with argon for 10 min. Then Pd$_2$(dba)$_3$ (164 mg, 0.17 mmol) and dppf (198 mg, 0.35 mmol) was added and then reaction mixture was purged with argon for 5 min. The mixture was stirred at 110° C. in sealed tube for 16 h. The reaction mixture was allowed to RT, diluted with EtOAc (50 mL) and water (50 mL). The reaction mixture was filtered through celite pad and the pad washed with EtOAc (100 mL). The organic layer was separated, washed with water, brine, dried with Na$_2$SO$_4$, filtered and the solvent removed. The crude compound was purified by column chromatography (24 g silica cartridge, gradient 50%-75% EtOAc/pet ether) to yield the product (400 mg, 21%) as a light brown sticky solid. M/z 325.1 (M+H)$^+$.

d. (5,6-dimethoxybenzo[d]thiazol-2-yl)methanamine hydrochloride

To a solution of tert-butyl ((5,6-dimethoxybenzo[d]thiazol-2-yl)methyl)carbamate (900 mg, 2.7 mmol) in 1,4-dioxane (5 mL) was added 4M HCl in dioxane (5 mL) at RT. The reaction mixture was stirred at RT for 4 h. The reaction mixture was concentrated under reduced pressure. The resulting residue was triturated with n-pentane and Et$_2$O to yield the product (700 mg) as a pale brown solid. M/z 225.1 (M+H)$^+$.

e. Tert-butyl 2-(2-(((5,6-dimethoxybenzo[d]thiazol-2-yl)methyl)carbamoyl)-2,3-dihydro-1H-inden-2-yl)acetate To a suspension of (5,6-dimethoxybenzo[d]thiazol-2-yl)methanamine hydrochloride (700 mg, 2.6 mmol) in DMF (10 mL) was added Et$_3$N (817 mg, 8.0 mmol) at RT and stirred for 10 min. Then 2-(2-(tert-butoxy)-2-oxoethyl)-2,3-dihydro-1H-indene-2-carboxylic acid (817 mg, 2.9 mmol), EDC.HCl (771 mg, 4.0 mmol) and HOBt (363 mg, 2.6 mmol) was added and the reaction mixture was stirred at RT for 16 h. The reaction mixture was diluted with cold water (50 mL) and stirred for 10 min. The resulting precipitate was filtered, washed with water and dried in vacuum. The crude compound was purified by column chromatography (24 g silica cartridge, gradient 40%-50% EtOAc/pet ether) to yield the product (510 mg, 39.5%) as a yellow solid. M/z 483.2 (M+H)$^+$.

f. 2-[2-[(5,6-dimethoxy-1,3-benzothiazol-2-yl)methylcarbamoyl]indan-2-yl]acetic acid To a solution of tert-butyl 2-(2-(((5,6-dimethoxybenzo[d]thiazol-2-yl)methyl)carbamoyl)-2,3-dihydro-1H-inden-2-yl)acetate (500 mg, 1.07 mmol) in DCM (10 mL) was added TFA (5 mL) at 0° C. The reaction mixture was stirred vigorously at RT for 8 h and the solvent was removed. The above residue was triturated with n-pentane and Et$_2$O. The crude compound was purified by preparative HPLC [SYMMETRY-C8 (300*19), 7 u, Mobile phase: A: 0.1% FA in H$_2$O, B: ACN, Gradient: (T % B):-0/35, 8/80, 8.1/98, 10/98, 10.1/35, 13/35; Flow rate: 20 mL/min] to obtain the title product (270 mg, 61.3%) as an off-white solid. M/z 427 (M+H)$^+$. $^1$H NMR (500 MHz, DMSO-d$_6$): δ 12.13 (1H, bs), 8.68 (1H, t, J=6.0 Hz), 7.55 (1H, s), 7.44 (1H, s), 7.22-7.20 (2H, m), 7.15-7.13 (2H, m), 4.60 (2H, d, J=6.0 Hz), 3.82 (3H, s), 3.80 (3H, s), 3.45 (2H, d, J=16.5 Hz), 2.98 (2H, d, J=16.5 Hz), 2.73 (2H, s).

Example 115

2-[2-([1,3]dioxolo[4,5-f][1,3]benzothiazol-6-ylmethylcarbamoyl)indan-2-yl]acetic acid

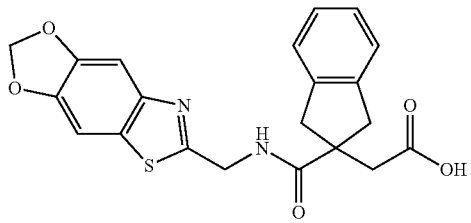 [SMILES: O=C(O)CC1(C(=O)NCc2nc3cc4c(cc3s2)OCO4)Cc2ccccc2C1]

a. N-(benzo[d][1,3]dioxol-5-yl)acetamide

To a stirred solution of benzo[d][1,3]dioxol-5-amine (4.5 g, 32.8 mmol) in AcOH (70 mL) was added acetic anhydride (35 mL) at RT and stirred at RT for 16 h. The reaction mixture was slowly poured into sat. NaHCO$_3$ solution and stirred for 10 min. The product was extracted with DCM (2×100 mL). The organic layer was washed with water (2×100 mL) and brine. The organic extracts were then dried with Na$_2$SO$_4$, filtered and the solvent removed. The crude compound was purified by column chromatography (40 g silica cartridge, gradient 50%-60% EtOAc/pet ether) to yield the product (4.6 g, 79%) as a pale brown solid. M/z 180 (M+H)$^+$.

b. 2-[2-([1,3]dioxolo[4,5-f][1,3]benzothiazol-6-ylmethylcarbamoyl)indan-2-yl]acetic acid The title product was synthesized following the same procedure described for the synthesis of example 114. Note: CaO was used in place of CuO in equal molar quantities for step-c. The title product was purified by preparative HPLC [SYMMETRY-C8 (300*19), 7 u, Mobile phase: A: 0.1% FA in H$_2$O: B: ACN, Gradient: (T % B):-0/35, 8/75, 8.1/98, 10/98, 10.1/35, 13/35; Flow rate: 20 mL/min], yield 68.7%, off-white solid. M/z 411.1 (M+H)$^+$. $^1$H NMR (500 MHz, DMSO-d$_6$): δ 12.13 (1H, bs), 8.71 (1H, bs), 7.54 (1H, s), 7.42 (1H, s), 7.22-7.19 (2H, m), 7.15-7.12 (2H, m), 6.10 (2H, s), 4.59 (2H, d, J=6 Hz), 3.44 (2H, d, J=16.5 Hz), 2.98 (2H, d, J=16.5 Hz), 2.72 (2H, s).

Example 116

(S)-2-(2-((1-((1,1-dimethylpiperidin-1-ium-4-yl)oxy)-3-(1H-indol-3-yl)-1-oxopropan-2-yl)carbamoyl)-2,3-dihydro-1H-inden-2-yl)acetate

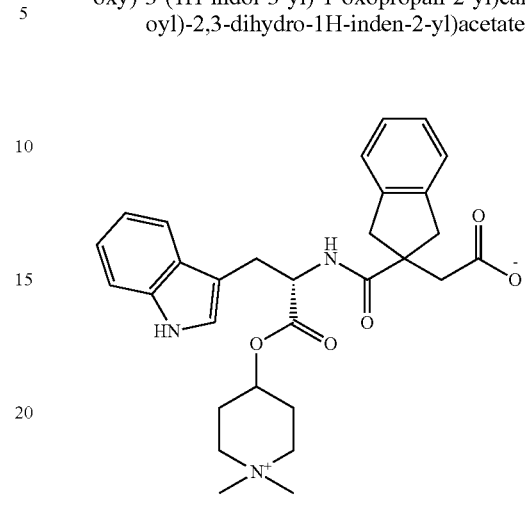

a. 1-methylpiperidin-4-yl ((benzyloxy)carbonyl)-L-tryptophanate

To a solution of L-N-carbobenzyloxytryptophan (1.0 g, 3.0 mmol) in DCM (20 mL) at RT were added sequentially DMAP (37 mg, 0.3 mmol), EDC.HCl (850 mg, 4.43 mmol) and 1-methyl-piperidin-4-ol (510 mg, 4.43 mmol) and the mixture stirred at RT for 2.5 h. The mixture was washed with saturated aq. NaHCO$_3$ solution (25 mL), dried (Na$_2$SO$_4$), filtered and concentrated in vacuo. FCC (0-50% IPA in DCM) gave the title compound as a beige foam (1.05 g, 82%). M/z 436 (M+H)$^+$.

b. 1-methylpiperidin-4-yl L-tryptophanate

A mixture of (S)-2-benzyloxycarbonylamino-3-(1H-indol-3-yl)-propionic acid 1-methyl-piperidin-4-yl ester (1.05 g, 2.41 mmol) and 10% Pd/C (350 mg) in IPA (25 mL) was stirred under H$_2$ (balloon) at RT for 1 h. The mixture was filtered through Celite, and the pad washed with IPA. The combined organics were concentrated in vacuo to leave the title compound as a cream foam (350 mg, 48%). M/z 302 (M+H)$^+$.

c. 1-methylpiperidin-4-yl (2-(2-(tert-butoxy)-2-oxoethyl)-2,3-dihydro-1H-indene-2-carbonyl)-L-tryptophanate To a solution of 2-[2-(tert-butoxy)-2-oxoethyl]-2,3-dihydro-1H-indene-2-carboxylic acid (320 mg, 1.16 mmol) in DMF (10 mL) were added sequentially DIPEA (0.50 mL, 2.95 mmol) and HATU (536 mg, 1.41 mmol). The mixture was stirred at RT for 30 min, then 1-methylpiperidin-4-yl L-tryptophanate (320 mg, 1.09 mmol) added and the mixture stirred at RT for 45 min. EtOAc (20 mL) was added, the mixture washed with aq. NaHCO$_3$ solution (25 mL), water (2×25 mL) and brine (20 mL), then dried (MgSO$_4$), filtered and concentrated in vacuo to leave a gum. FCC (0-80% IPA in DCM) gave the title compound as a cream foam (192 mg, 30%). M/z 560 (M+H)$^+$.

d. (S)-2-(2-((1-((1,1-dimethylpiperidin-1-ium-4-yl)oxy)-3-(1H-indol-3-yl)-1-oxopropan-2-yl)carbamoyl)-2,3-dihydro-1H-inden-2-yl)acetate A solution of 1-methylpiperidin-4-yl (2-(2-(tert-butoxy)-2-oxoethyl)-2,3-dihydro-1H-indene-2-carbonyl)-L-tryptophanate (100 mg, 0.179 mmol) and MeI (14 μL, 0.22 mmol) in ACN (2.5 mL) was stirred at RT for 3 h. The solvent was removed and the residue redissolved in DCM (3 mL). The solution was treated with triisopropylsilane (0.15 mL) and TFA (1 mL) and the mixture stirred at RT for 30 min. The mixture was azeotroped with toluene (×2) to leave a residue. Preparative HPLC (X-BRIDGE-C18; 0.05% FA in water:ACN) afforded the title product as a white solid (53 mg, 57%). M/z 518.2 (M+H)+. 1H NMR (d6-DMSO) δ 11.19 (1H, bs), 10.91 (1H, s), 7.52 (1H, d), 7.32 (1H, d), 7.20 (1H, s), 7.16-7.09 (4H, m), 7.06 (1H, t), 6.98 (1H, t), 4.78 (1H, bs), 4.62 (1H, q), 3.50-3.42 (4H, m), 3.33 (2H, d), 3.23-3.09 (6H, m), 2.98 (2H, s), 2.87 (2H, dd), 2.44 (2H, d), 2.07-1.94 (2H, m), 1.65 (1H, bd), 1.37 (1H, bd).

Example 117

(S)-2-(2-((2-(1H-indol-3-yl)-1-(5-methyl-1,3,4-oxadiazol-2-yl)ethyl)carbamoyl)-2,3-dihydro-1H-inden-2-yl)acetic acid

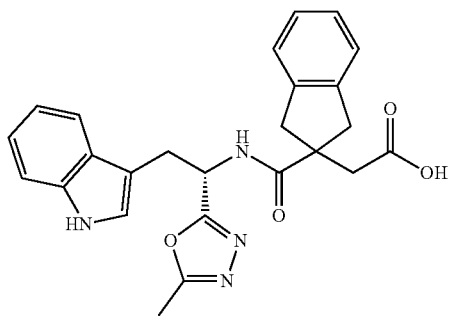 [SMILES: Cc1nnc([C@H](Cc2c[nH]c3ccccc23)NC(=O)C2(CC(=O)O)Cc3ccccc3C2)o1]

a. tert-butyl (S)-(1-(2-acetylhydrazineyl)-3-(1H-indol-3-yl)-1-oxopropan-2-yl)carbamate To a solution of (tert-butoxycarbonyl)-L-tryptophan 304 mg, 1 mmol) in DMF (3 mL) was added DIPEA (0.35 mL, 2.0 mmol) then HATU (456 mg, 1.2 mmol). The mixture was stirred at RT for 15 min, then acetylhydrazide (96 mg, 1.3 mmol) was added and the mixture stirred at RT for 18 h. The mixture was partitioned between EtOAc and water. The organic layer was washed with brine, then dried (Na2SO4), filtered and concentrated in vacuo. The residue was triturated with Et2O, filtered and the solid collected to afford the title compound (356 mg, 99%) as a beige solid. M/z 383.0 (M+Na)+.

b. tert-butyl (S)-(2-(1H-indol-3-yl)-1-(5-methyl-1,3,4-oxadiazol-2-yl)ethyl)carbamate To a solution of triphenylphosphine (517 mg, 1.97 mmol) in DCM (10 mL) under N2 was added iodine (500 mg, 1.97 mmol). The mixture was stirred at RT for 5 min, then Et3N (0.58 mL, 4.14 mmol) was added, followed by a suspension of (S)-(1-(2-acetylhydrazineyl)-3-(1H-indol-3-yl)-1-oxopropan-2-yl)carbamate (355 mg, 0.99 mmol) in DCM (5 mL). The mixture was stirred at RT for 2 h and then quenched with aq. sodium thiosulfate. The phases were separated and the organic layer was washed with brine, then dried (Na2SO4), filtered and concentrated in vacuo. FCC (50-100% EtOAc in isohexane) gave the title compound (337 mg, 100%) as a pale yellow oil. M/z 365.3 (M+Na)+.

c. (S)-2-(1H-indol-3-yl)-1-(5-methyl-1,3,4-oxadiazol-2-yl)ethan-1-amine

To a solution of tert-butyl (S)-(2-(1H-indol-3-yl)-1-(5-methyl-1,3,4-oxadiazol-2-yl)ethyl)carbamate (337 mg, 0.99 mmol) in DCM (4 mL) was added TFA (1 mL, 13 mmol). The solution was stirred at RT for 3 h then loaded directly onto an SCX-2 cartridge (5 g, pre-washed with MeOH). The cartridge was washed with MeOH and then eluted with 7M NH3 in MeOH. The eluent was concentrated in vacuo to yield the title compound (115 mg, 48%) as a pale yellow oil. M/z 243.1 (M+H)+.

d. tert-butyl (S)-2-(2-((2-(1H-indol-3-yl)-1-(5-methyl-1,3,4-oxadiazol-2-yl)ethyl)-carbamoyl)-2,3-dihydro-1H-inden-2-yl)acetate To a solution of 2-(2-(tert-butoxy)-2-oxoethyl)-2,3-dihydro-1H-indene-2-carboxylic acid (100 mg, 0.36 mmol) in DMF (2 mL) was added DIPEA (0.13 mL, 0.72 mmol) then HATU (165 mg, 0.43 mmol). The mixture was stirred at RT for 5 min, then (S)-2-(1H-indol-3-yl)-1-(5-methyl-1,3,4-oxadiazol-2-yl)ethan-1-amine (115 mg, 0.48 mmol) was added and the mixture stirred at RT for 2 h. The mixture was partitioned between EtOAc and water. The organic layer was washed with brine, then dried (Na2SO4), filtered and concentrated in vacuo. FCC (50-100% EtOAc in isohexane) gave the title compound (196 mg, 108%) as a white foam. M/z 501.4 (M+H)+.

e. (S)-2-(2-((2-(1H-indol-3-yl)-1-(5-methyl-1,3,4-oxadiazol-2-yl)ethyl)carbamoyl)-2,3-dihydro-1H-inden-2-yl)acetic acid tert-Butyl (S)-2-(2-((2-(1H-indol-3-yl)-1-(5-methyl-1,3,4-oxadiazol-2-yl)ethyl)carbamoyl)-2,3-dihydro-1H-inden-2-yl)acetate (196 mg, 0.36 mmol) was dissolved in DCM (3 mL) then water (0.1 mL) and TFA (1 mL) were added. The mixture was stirred vigorously at RT for 2 h and the solvent was removed, azeotroping with toluene. The residue was purified by mass directed HPLC (Waters XSelect C18 column, 5 m, 19×250 mm, gradient 10-98% ACN/water with 0.1% v/v FA) and the desired fractions freeze-dried to give the title compound (73 mg, 45%) as a white solid. M/z 445.1 (M+H)+. 1H NMR (d6-DMSO) δ 12.10 (1H, bs), 8.52 (1H, bs), 7.50 (1H, d), 7.31 (1H, d), 7.18-7.09 (4H, m), 7.09-7.03 (2H, m), 6.96 (1H, t), 5.29 (1H, q), 4.10 (1H, bs), 3.40-3.23 (2H, m, obscured by water signal), 3.17 (2H, s), 2.90 (2H, dd), 2.66 (2H, dd), 2.42 (3H, s).

Example 118

(S)-2-(2-((1-(5-(aminomethyl)-1,3,4-oxadiazol-2-yl)-2-(1H-indol-3-yl)ethyl)carbamoyl)-2,3-dihydro-1H-inden-2-yl)acetic acid

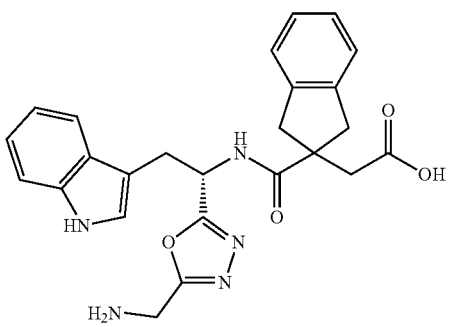 [SMILES: NCc1nnc([C@H](Cc2c[nH]c3ccccc23)NC(=O)C2(CC(=O)O)Cc3ccccc3C2)o1]

a. tert-butyl (2-hydrazineyl-2-oxoethyl)carbamate

To a solution of N-(tert-butoxycarbonyl)glycine methyl ester (1.89 g, 10 mmol) in EtOH (5 mL) was added hydrazine hydrate (1.2 mL, 40 mmol) and the mixture stirred at RT for 5 days. The solvent was removed and the residue triturated with pentane, filtered and the solid dried to yield the title compound (1.9 g, 100%) as a white solid. M/z 212.2 (M+Na)$^+$.

b. Benzyl (S)-(1-(2-((tert-butoxycarbonyl)glycyl)hydrazineyl)-3-(1H-indol-3-yl)-1-oxopropan-2-yl)carbamate To a solution of ((benzyloxy)carbonyl)-L-tryptophan (338 mg, 1 mmol) in DMF (3 mL) was added DIPEA (0.35 mL, 2 mmol) then HATU (456 mg, 1.2 mmol). The mixture was stirred at RT for 15 min, then tert-butyl (2-hydrazineyl-2-oxoethyl)carbamate (246 mg, 1.3 mmol) was added and the mixture stirred at RT for 3 h. The mixture was partitioned between EtOAc and water. The organic layer was washed with brine, then dried (Na$_2$SO$_4$), filtered and concentrated in vacuo. FCC (50-100% EtOAc in isohexane) gave the title compound (446 mg, 87%) as a pale yellow oil M/z 510.3 (M+H)$^+$.

c. tert-butyl (S)-((5-(1-(((benzyloxy)carbonyl)amino)-2-(1H-indol-3-yl)ethyl)-1,3,4-oxadiazol-2-yl)methyl)carbamate To a solution of triphenylphosphine (459 mg, 1.75 mmol) in DCM (10 mL) under N$_2$ was added iodine (444 mg, 1.75 mmol). The mixture was stirred at RT for 5 min, then Et$_3$N (0.51 mL, 3.68 mmol) was added, followed by a solution of benzyl (S)-(1-(2-((tert-butoxycarbonyl)glycyl)hydrazineyl)-3-(1H-indol-3-yl)-1-oxopropan-2-yl)carbamate (446 mg, 0.88 mmol) in DCM (5 mL). The mixture was stirred at RT for 18 h and then quenched with aq. sodium thiosulfate. The phases were separated and the organic layer was washed with brine, then dried (Na$_2$SO$_4$), filtered and concentrated in vacuo. FCC (30-100% EtOAc in isohexane) gave the title compound (354 mg, 82%) as a pale yellow oil M/z 492.4 (M+H)$^+$.

d. tert-butyl (S)-((5-(1-amino-2-(1H-indol-3-yl)ethyl)-1,3,4-oxadiazol-2-yl)methyl)-carbamate tert-butyl (S)-((5-(1-(((benzyloxy)carbonyl)amino)-2-(1H-indol-3-yl)ethyl)-1,3,4-oxadiazol-2-yl)methyl)carbamate (351 mg, 0.71 mmol) and 5% palladium on carbon (151 mg) was suspended in EtOH (5 mL) under N$_2$. The N$_2$ was evacuated and replaced with H$_2$ (balloon) and the mixture stirred at RT for 18 h. The H$_2$ was evacuated and replaced with N$_2$. The mixture was then filtered through a pad of celite, eluting with EtOAc. The eluent was concentrated in vacuo to yield the title compound (252 mg, 99%) as a white foam M/z 358.3 (M+H)$^+$.

e. tert-butyl (S)-2-(2-((1-(5-(((tert-butoxycarbonyl)amino)methyl)-1,3,4-oxadiazol-2-yl)-2-(1H-indol-3-yl)ethyl)carbamoyl)-2,3-dihydro-1H-inden-2-yl)acetate To a solution of 2-(2-(tert-butoxy)-2-oxoethyl)-2,3-dihydro-1H-indene-2-carboxylic acid (111 mg, 0.40 mmol) in DMF (4 mL) was added DIPEA (0.14 mL, 0.8 mmol) then HATU (165 mg, 0.43 mmol). The mixture was stirred at RT for 5 min, then tert-butyl (S)-((5-(1-amino-2-(1H-indol-3-yl)ethyl)-1,3,4-oxadiazol-2-yl)methyl)carbamate (252 mg, 0.71 mmol) was added and the mixture stirred at RT for 2 h. The mixture was partitioned between EtOAc and water. The organic layer was washed with brine, then dried (Mg$_2$SO$_4$), filtered and concentrated in vacuo. FCC (30-100% EtOAc in isohexane) gave the title compound (202 mg, 84%) as a white foam. M/z 616.5 (M+H)$^+$.

f. ((S)-2-(2-((1-(5-(aminomethyl)-1,3,4-oxadiazol-2-yl)-2-(1H-indol-3-yl)ethyl)carbamoyl)-2,3-dihydro-1H-inden-2-yl)acetic acid tert-Butyl (S)-2-(2-((1-(5-(((tert-butoxycarbonyl)amino)methyl)-1,3,4-oxadiazol-2-yl)-2-(1H-indol-3-yl)ethyl)carbamoyl)-2,3-dihydro-1H-inden-2-yl)acetate (199 mg, 0.32 mmol) was dissolved in DCM (3 mL) then water (0.1 mL) and TFA (1 mL) were added. The mixture was stirred vigorously at RT for 4 h and the solvent was removed, azeotroping with toluene. The residue was purified by mass directed HPLC (Waters XSelect C18 column, 5 µm, 19×250 mm, gradient 5-95% ACN/water with 0.1% v/v FA) and the desired fractions freeze dried to yield the title compound (15 mg, 10%) as a white solid. M/z 460.1 (M+H)$^+$. $^1$H NMR (d6-DMSO) δ 10.83 (1H, s), 8.51 (1H, d), 7.51 (1H, d), 7.32 (1H, d), 7.18-6.93 (7H, m), 5.31 (1H, dd), 3.83 (2H, s), 3.41-3.22 (4H, m), 2.91 (2H, d), 2.66 (2H, dd). 3H exchangeable proton signals not observed.

Example 119

(S)-2-(2-((1-(5-(2-aminopropan-2-yl)-1,3,4-oxadi-azol-2-yl)-2-(1H-indol-3-yl)ethyl)carbamoyl)-2,3-dihydro-1H-inden-2-yl)acetic acid

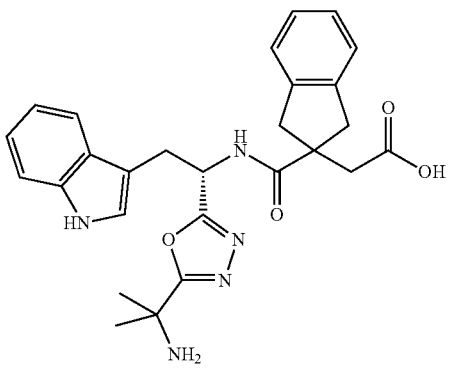 [SMILES: CC(C)(N)c1nnc([C@H](Cc2c[nH]c3ccccc23)NC(=O)C2(CC(=O)O)Cc3ccccc3C2)o1]

a. tert-butyl 2-(((benzyloxy)carbonyl)-L-tryptophyl)hydrazine-1-carboxylate

To a suspension of ((benzyloxy)carbonyl)-L-tryptophan (1.69 g, 5 mmol) and tert-butyl carbazate (859 mg, 6.5 mmol) in DCM (15 mL) was added Et$_3$N (1.4 mL, 10 mmol) then HATU (2.28 g, 6.0 mmol). The mixture was stirred at RT for 3 h. The mixture was partitioned between DCM and water. The organic layer was washed with brine, then dried (Na$_2$SO$_4$), filtered and concentrated in vacuo. FCC (60-100% EtOAc in isohexane) gave the title compound (2.26 g, 100%) as a white foam. M/z 453.3 (M+H)$^+$.

b. Benzyl (S)-(1-hydrazineyl-3-(1H-indol-3-yl)-1-oxopropan-2-yl)carbamate hydrochloride salt tert-butyl 2-(((benzyloxy)carbonyl)-L-tryptophyl)hydrazine-1-carboxylate (2.26 g, 5.0 mmol) was dissolved in 4M HCl in dioxane (20 mL, 80 mmol) and stirred at RT for 2 h. The solvent was removed to yield the title compound (2 g, 100%). M/z 353.2 (M+H)$^+$.

c. Benzyl (S)-(1-(2-(2-((tert-butoxycarbonyl)amino)-2-methylpropanoyl)hydrazineyl)-3-(1H-indol-3-yl)-1-oxopropan-2-yl)carbamate To a suspension of benzyl (S)-(1-hydrazineyl-3-(1H-indol-3-yl)-1-oxopropan-2-yl)carbamate hydrochloride salt (389 mg, 1.0 mmol) and 2-((tert-butoxycarbonyl)amino)-2-methyl-propanoic acid (264 mg, 1.3 mmol) in DCM (3 mL) was added Et$_3$N (0.42 mL, 3.0 mmol) then HATU (456 mg, 1.2 mmol). The mixture was stirred at RT for 5 h. The mixture was partitioned between DCM and brine, then the organic layer concentrated in vacuo. FCC (50-100% EtOAc in isohexane) gave the title compound (180 mg, 33%) as a white solid. M/z 538.3 (M+H)$^+$.

d. tert-butyl (S)-(2-(5-(1-(((benzyloxy)carbonyl)amino)-2-(1H-indol-3-yl)ethyl)-1,3,4-oxadiazol-2-yl)propan-2-yl)carbamate To a solution of triphenylphosphine (173 mg, 0.66 mmol) in DCM (4 mL) under N$_2$ was added iodine (167 mg, 0.66 mmol). The mixture was stirred at RT for 5 min, then Et$_3$N (0.19 mL, 1.38 mmol) was added, followed by a solution of benzyl (S)-(1-(2-(2-((tert-butoxycarbonyl)amino)-2-methyl-propanoyl)hydrazineyl)-3-(1H-indol-3-yl)-1-oxopropan-2-yl)carbamate (177 mg, 0.33 mmol) in DCM (2 mL). The mixture was stirred at RT for 18 h and then quenched with aq. sodium thiosulfate. The organic layer was washed with brine, then dried (Na$_2$SO$_4$), filtered and concentrated in vacuo. FCC (30-100% EtOAc in isohexane) gave the title compound (142 mg, 83%) as a colourless oil. M/z 520.3 (M+H)$^+$.

e. tert-butyl (S)-(2-(5-(1-amino-2-(1H-indol-3-yl)ethyl)-1,3,4-oxadiazol-2-yl)propan-2-yl)carbamate tert-butyl (S)-(2-(5-(1-(((benzyloxy)carbonyl)amino)-2-(1H-indol-3-yl)ethyl)-1,3,4-oxadiazol-2-yl)propan-2-yl)carbamate (141 mg, 0.27 mmol) and 5% palladium on carbon (58 mg) was suspended in EtOH (5 mL) under N$_2$. The N$_2$ was evacuated and replaced with H$_2$ (balloon) and the mixture stirred at RT for 18 h. The H$_2$ was evacuated and replaced with N$_2$. The mixture was then filtered through a pad of celite, eluting with EtOAc. The eluent was concentrated in vacuo to yield the title compound (105 mg, 100%) as an off-white solid. M/z 386.2 (M+H)$^+$.

f. tert-butyl (S)-2-(2-((1-(5-(2-((tert-butoxycarbonyl)amino)propan-2-yl)-1,3,4-oxadi-azol-2-yl)-2-(1H-indol-3-yl)ethyl)carbamoyl)-2,3-dihydro-1H-inden-2-yl)acetate To a suspension of 2-(2-(tert-butoxy)-2-oxoethyl)-2,3-dihydro-1H-indene-2-carboxylic acid (100 mg, 0.36 mmol) and tert-butyl (S)-((5-(1-amino-2-(1H-indol-3-yl)ethyl)-1,3,4-oxadiazol-2-yl)methyl)carbamate (106 mg, 0.28 mmol) in DCM (3 mL) was added Et$_3$N (0.15 mL, 1.1 mmol) then HATU (165 mg, 1.1 mmol). The mixture was stirred at RT for 3 h. The mixture was partitioned between DCM and brine and the organic layer was collected and concentrated in vacuo. FCC (30-100% EtOAc in isohexane) gave the title compound (116 mg, 66%) as a colourless oil. M/z 644.4 (M+H)$^+$.

g. (S)-2-(2-((1-(5-(2-aminopropan-2-yl)-1,3,4-oxadi-azol-2-yl)-2-(1H-indol-3-yl)ethyl)carbamoyl)-2,3-dihydro-1H-inden-2-yl)acetic acid tert-butyl (S)-2-(2-((1-(5-(2-((tert-butoxycarbonyl)amino)propan-2-yl)-1,3,4-oxadiazol-2-yl)-2-(1H-indol-3-yl)ethyl)carbamoyl)-2,3-dihydro-1H-inden-2-yl)acetate (113 mg, 0.18 mmol) was dissolved in DCM (3 mL) then water (0.16 mL) and TFA (1.6 mL) were added. The mixture was stirred vigorously at RT for 2 h and the solvent was removed, azeotroping with toluene. The residue was purified by mass directed HPLC (Waters XSelect C18 column, 5 μm, 19×250 mm, gradient 5-95% ACN/water with 0.1% v/v FA) and the desired fractions freeze dried to yield the title compound (25 mg, 29%) as a white solid. M/z=488.4 (M+H)$^+$. $^1$H NMR (d6-DMSO) δ 10.82 (1H, s), 8.48 (1H, bs), 7.46 (1H, d), 7.32 (1H, d), 7.18-7.03 (6H, m), 6.97-6.91 (1H, m), 5.28 (1H, q), 3.41-3.22 (4H, m), 2.92 (2H, d), 2.66 (2H, dd), 1.33 (6H, s). 3H exchangeable proton signals not observed.

Example 120

2-(2-((benzo[d]thiazol-2-ylmethyl)carbamoyl)-5,6-difluoro-2,3-dihydro-1H-inden-2-yl)acetic acid

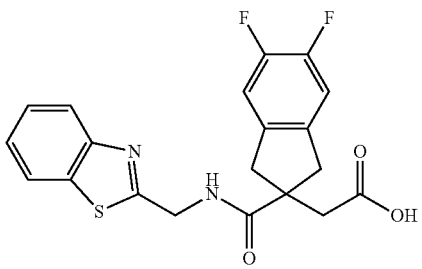 [SMILES: O=C(O)CC1(C(=O)NCc2nc3ccccc3s2)Cc2cc(F)c(F)cc2C1]

a. Dimethyl 4,5-difluorophthalate

To an ice-cooled solution of 4,5-difluorophthalic acid (11.9 g, 58.9 mmol) in MeOH (250 mL) was added concentrated $H_2SO_4$ (40 mL, 0.75 mol) keeping the temperature <20° C. The mixture was stirred at 65° C. for 4 h. The cooled reaction mixture was concentrated in vacuo, then the residue was cautiously added to EtOAc and aq. $NaHCO_3$. The aq. phase was extracted with EtOAc and the combined organic extracts were washed with aq. $NaHCO_3$, then brine, dried ($Na_2SO_4$), filtered and concentrated in vacuo to yield the title compound as a colourless oil (12.98 g, 96%). $^1$H NMR ($CDCl_3$) δ 7.56 (2H, t, J=8.7 Hz), 3.91 (6H, s).

b. (4,5-Difluoro-1,2-phenylene)dimethanol

To an ice-cooled solution of lithium aluminium hydride (1M in THF, 226 mL, 0.226 mol) was added a solution of dimethyl 4,5-difluorophthalate (12.98 g, 56.4 mmol) in THF (100 mL) over 30 min keeping the temperature below 12° C. The mixture was stirred in the ice bath for 30 min, then at RT for 1 h. The reaction mixture was cooled to 0° C. then, cautiously, water (8.5 mL), 15% aq. NaOH (8.5 mL) and water (26 mL) were added successively, keeping the temperature below 15° C. Celite was added and the mixture stirred at RT for 1 h, then filtered through a celite pad, washing through with more THF. The filtrate was concentrated in vacuo to yield the title compound as a white solid (9.52 g, 97%). $^1$H NMR (d6-DMSO) δ 7.36 (2H, t, J=10.1 Hz), 5.29 (2H, t, J=5.5 Hz), 4.47 (4H, d, J=5.4 Hz).

c. 1,2-Bis(bromomethyl)-4,5-difluorobenzene

A mixture of (4,5-difluoro-1,2-phenylene)dimethanol (9.52 g, 54.7 mmol) and 48% hydrobromic acid (68.5 mL) was stirred at 110° C. for 1 h. The cooled reaction mixture was diluted with water and then extracted with $Et_2O$. The aq. phase was extracted with $Et_2O$ and the combined organic extracts were washed with water, then brine, dried ($Na_2SO_4$), filtered and concentrated in vacuo to leave a residue. FCC (1-10% EtOAc in isohexane) to yield the title compound as a colourless oil (15.2 g, 93%). $^1$H NMR ($CDCl_3$) δ 7.20 (2H, t, J=9.1 Hz), 4.55 (4H, s).

d. Diethyl 5,6-difluoro-1,3-dihydro-2H-indene-2,2-dicarboxylate

Sodium hydride (60% in oil, 4.46 g, 112 mmol) was added over 15 min to a mixture of 1,2-bis(bromomethyl)-4,5-difluorobenzene (15.2 g, 50.7 mmol) and diethyl malonate (9.74 g, 60.8 mmol) in THF (200 mL) keeping the temperature below 20° C. The mixture was stirred at RT for 4 h, then saturated ammonium chloride was added. The mixture was concentrated in vacuo and then extracted twice with EtOAc. The combined organic extracts were washed with brine, dried ($Na_2SO_4$), filtered and concentrated in vacuo to leave a residue. FCC (5-25% EtOAc in isohexane) yielded the title compound as a colourless oil (9.95 g, 66%). $^1$H NMR ($CDCl_3$) δ 6.97 (2H, t, J=8.7 Hz), 4.21 (4H, q, J=7.1 Hz), 3.52 (4H, s), 1.26 (6H, t, J=7.1 Hz).

e. 5,6-Difluoro-2,3-dihydro-1H-indene-2-carboxylic acid

To a solution of diethyl 5,6-difluoro-1,3-dihydro-2H-indene-2,2-dicarboxylate (9.94 g, 33.3 mmol) in dioxane (130 mL) was added water (130 mL) and concentrated HCl (140 mL). The mixture was refluxed for 23 h. The cooled reaction mixture was diluted with water and extracted with $Et_2O$ (×3). The combined organic extracts were washed with water, then brine, dried ($Na_2SO_4$), filtered and concentrated in vacuo to yield the title compound as a colourless solid (6.6 g, quant.). M/z 197 (M-H)$^-$.

f. Methyl 5,6-difluoro-2,3-dihydro-1H-indene-2-carboxylate

To an ice-cooled solution of 5,6-difluoro-2,3-dihydro-1H-indene-2-carboxylic acid (6.6 g, 33.3 mmol) in MeOH (200 mL) was added concentrated $H_2SO_4$ (40 mL, 0.75 mol) keeping the temperature <20° C. The mixture was stirred at 65° C. for 1 h. The cooled reaction mixture was concentrated in vacuo, then the residue was cautiously added to EtOAc and aq. $NaHCO_3$. The aq. phase was extracted with more EtOAc and the combined organic extracts were washed with brine, dried ($Na_2SO_4$), filtered and concentrated in vacuo to leave a residue. FCC (5-25% EtOAc in isohexane) yielded the title compound as a pale yellow solid (5.97 g, 84%). $^1$H NMR ($CDCl_3$) δ 6.98 (2H, t, J=8.8 Hz), 3.73 (3H, s), 3.39 (1H, m), 3.24-3.12 (4H, m).

g. Methyl 2-(2-(tert-butoxy)-2-oxoethyl)-5,6-difluoro-2,3-dihydro-1H-indene-2-carboxylate To a solution of methyl 5,6-difluoro-2,3-dihydro-1H-indene-2-carboxylate (5.97 g, 28.2 mmol) in THF (120 mL), cooled to −78° C., was added sodium bis(trimethylsilyl)amide (1M in THF, 42.2 mL, 42.2 mol) over 15 min. The mixture was stirred at −78° C. for 45 min then a solution of tert-butyl bromoacetate (8.24 g, 42.2 mmol) in THF (15 mL) was added over 10 min. The reaction mixture was allowed to warm to −10 OC over 1 h. Saturated ammonium chloride was added, the mixture was concentrated under reduced pressure. The residue was extracted twice with EtOAc and the combined organic extracts were washed with brine, dried ($Na_2SO_4$), filtered and concentrated in vacuo to leave a residue. FCC (5-20% EtOAc in isohexane) yielded the title compound as a pale yellow gum (8.78 g, 96%). $^1$H NMR ($CDCl_3$) δ 6.96 (2H, t, J=8.9 Hz), 3.72 (3H, s), 3.47 (2H, d, J=16.2 Hz), 2.90 (2H, d, J=16.2 Hz), 2.71 (2H, s), 1.42 (9H, s).

h. 2-(2-(tert-butoxy)-2-oxoethyl)-5,6-difluoro-2,3-dihydro-1H-indene-2-carboxylic acid To a solution of methyl 2-(2-(tert-butoxy)-2-oxoethyl)-5,6-difluoro-2,3-dihydro-1H-indene-2-carboxylate (0.834 g, 2.56 mmol) in THF (25 mL) and MeOH (10 mL) was added lithium hydroxide (0.5M in water, 10.2 mL, 5.1 mmol). The mixture was stirred at RT for 2.5 h, then concentrated in vacuo. The residual solution was layered with EtOAc and acidified by addition of 6M HCl. The aq. phase was extracted with more EtOAc and the combined organic extracts were washed with brine, dried ($Na_2SO_4$), filtered and concentrated in vacuo to leave a residue. FCC (2-6% MeOH in DCM) yielded the title compound as a cream solid (0.59 g, 74%). $^1$H NMR (d6-DMSO) δ 12.47 (1H, bs), 7.26 (2H, t, J=9.2 Hz), 3.33 (2H, d, J=16.4 Hz), 2.91 (2H, d, J=16.4 Hz), 2.67 (2H, s), 1.37 (9H, s). M/z 311 (M−H)⁻.

i. 2-(2-((benzo[d]thiazol-2-ylmethyl)carbamoyl)-5,6-difluoro-2,3-dihydro-1H-inden-2-yl)acetic acid Using Method C, but using 1,3-benzothiazol-2-ylmethanamine and 2-(2-(tert-butoxy)-2-oxoethyl)-5,6-difluoro-2,3-dihydro-1H-indene-2-carboxylic acid, the title compound was made as a white solid. M/z 425 (M+Na)⁺. $^1$H NMR (d6-DMSO) δ 12.20 (1H, bs), 8.99 (1H, bs), 8.02 (1H, d, J=8.0 Hz), 7.92 (1H, d, J=8.0 Hz), 7.94 (1H, dt, J=7.7, 1.3 Hz), 7.40 (1H, dt, J=7.6, 1.1 Hz), 7.28 (2H, t, J=9.2 Hz), 4.65 (2H, d, J=5.7 Hz), 3.43 (2H, d, J=16.4 Hz), 2.99 (2H, d, J=16.4 Hz), 2.76 (2H, s).

Example 121

2-(2-((benzo[d]thiazol-2-ylmethyl)carbamoyl)-5,6-dichloro-2,3-dihydro-1H-inden-2-yl)acetic acid

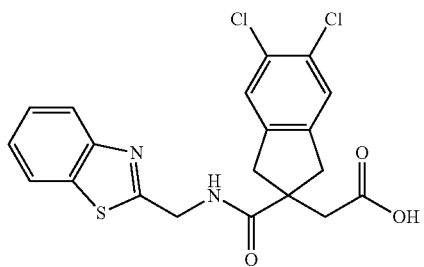 [SMILES: O=C(O)CC1(C(=O)NCc2nc3ccccc3s2)Cc2cc(Cl)c(Cl)cc2C1]

Using the procedures described for example 120, but using 4,5-dichlorophthalic acid the title compound was made. M/z 435.1 (M+H)⁺. $^1$H NMR (d6-DMSO) δ 12.66 (1H, br s), 8.04 (1H, d, J=8.0 Hz), 7.92 (1H, d, J=8.0 Hz), 7.50-7.46 (1H, m), 7.44 (2H, s), 7.42-7.38 (1H, m), 4.67 (2H, d, J=5.7 Hz), 3.39 (2H, d, J=16.4 Hz), 2.92 (2H, d, J=16.4 Hz), 2.39 (2H, s).

Example 122

2-(2-(((5-(3-(dimethylamino)azetidin-1-yl)-6-methoxybenzo[d]thiazol-2-yl)methyl)carbamoyl)-2,3-dihydro-1H-inden-2-yl)acetic acid

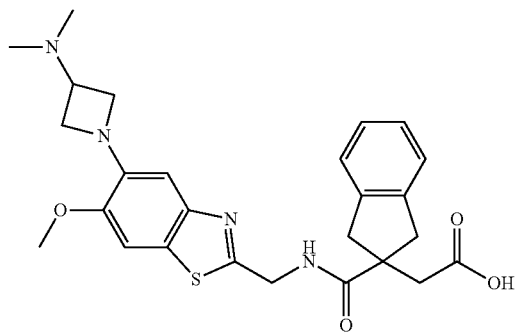 [SMILES: COc1cc2sc(CNC(=O)C3(CC(=O)O)Cc4ccccc4C3)nc2cc1N1CC(N(C)C)C1]

a. 1-bromo-4-iodo-2-methoxy-5-nitrobenzene

To a solution of 4-bromo-5-methoxy-2-nitroaniline (6.42 g, 26 mmol) in ACN (220 mL) at 0° C. was added 98% $H_2SO_4$ (3.5 mL, 66.2 mmol) followed by a solution of sodium nitrite (3.59 g, 52 mmol) in water (20 mL) dropwise at such a rate to keep the internal temperature below 2° C. The solution was stirred at 0° C. for a further 15 min, and then a solution of potassium iodide (17.3 g, 104 mmol) in water (20 mL) was added dropwise at such a rate to keep the internal temperature below 2° C. The solution was stirred for a further 1 h. The reaction was quenched at 0° C. by the addition of 1M aq. sodium metabisulfite and allowed to warm to RT with stirring. The mixture was extracted with EtOAc (×2), then the combined organic extracts washed with brine, dried ($Na_2SO_4$), filtered and concentrated in vacuo to give the title compound. The residue was used directly in the next step without further purification. $^1$H NMR (CDCl₃) δ 8.25 (1H, s), 7.47 (1H, s), 3.98 (3H, s).

b. 5-bromo-2-iodo-4-methoxyaniline

To a solution of 1-bromo-4-iodo-2-methoxy-5-nitrobenzene (16.55 g, 46.2 mmol) in EtOH (300 mL) was added iron powder (25.8 g, 462 mmol) and iron (II) chloride (5.86 g, 46.2 mmol) followed by 1M HCl (23.1 mL, 23.1 mmol). The mixture was stirred at 80° C. for 2 h, and then cooled to RT. The mixture was filtered through a celite pad, eluting with EtOAc (600 mL). The filtrate was washed successively with 1M aq. $Na_2CO_3$ and brine, then dried ($Na_2SO_4$), filtered and concentrated in vacuo. FCC (0-50% EtOAc in isohexane) gave the title compound (8.52 g, 56% over 2 steps) as a light pink solid. M/z 327.9 and 329.9 (M+H)⁺.

c. tert-butyl ((5-bromo-6-methoxybenzo[d]thiazol-2-yl)methyl)carbamate

5-Bromo-2-iodo-4-methoxyaniline (3.0 g, 9.16 mmol), tert-butyl(2-amino-2-thioxoethyl)-carbamate (2.1 g, 11.0 mmol), calcium oxide (1.03 g, 18.3 mmol), $Pd_2(dba)_3$ (0.84 g, 0.92 mmol) and dppf (2.03 g, 3.67 mmol) were suspended in ACN (40 mL) under $N_2$ and the mixture was stirred at 80° C. for 5 h and then cooled to RT. The mixture was partitioned between EtOAc and water. The organic layer was washed with brine, dried (Na$_2$SO$_4$), filtered and concentrated in vacuo. FCC (0-50% EtOAc in isohexane) gave the title compound (3.06 g, 89%) as an orange solid. M/z 316.9 and 318.9 (M+H)$^+$.

d. tert-butyl ((5-(3-(dimethylamino)azetidin-1-yl)-6-methoxybenzo[d]thiazol-2-yl)methyl)carbamate A suspension of tert-butyl ((5-bromo-6-methoxybenzo[d]thiazol-2-yl)methyl)carbamate (467 mg, 1.25 mmol), N,N-dimethylazetidine-3-amine hydrochloride (205 mg, 1.5 mmol), RuPhosPdG2 (97 mg, 0.125 mmol), RuPhos (58 mg, 0.125 mmol) and sodium tert-butoxide (360 mg, 3.75 mmol) in THF (3 mL) under N$_2$ was stirred at 80° C. for 16 h then allowed to warm to RT. The mixture was partitioned between DCM and brine, then the organic layer concentrated in vacuo. FCC (1-10% [7M NH$_3$ in MeOH] in DCM) gave the title compound (405 mg, 82%) as a yellow oil. M/z 393.2 (M+H)$^+$.

e. 1-(2-(aminomethyl)-6-methoxybenzo[d]thiazol-5-yl)-N,N-dimethylazetidin-3-amine To a mixture of tert-butyl ((5-(3-(dimethylamino)azetidin-1-yl)-6-methoxybenzo[d]thiazol-2-yl)methyl)carbamate (402 mg, 1.02 mmol) in DCM (5 mL) was added TFA (2.4 mL, 30.7 mmol). The solution was stirred at RT for 1 h then loaded directly onto an SCX-2 cartridge (10 g, pre-washed with DCM). The cartridge was washed with DCM then MeOH. The cartridge was then eluted with 7M NH$_3$ in MeOH; concentration in vacuo gave the title compound (283 mg, 95%) as a yellow oil. M/z 293.2 (M+H)$^+$.

f. tert-butyl 2-(2-(((5-(3-(dimethylamino)azetidin-1-yl)-6-methoxybenzo[d]thiazol-2-yl)methyl)carbamoyl)-2,3-dihydro-1H-inden-2-yl)acetate To a solution of 2-(2-(tert-butoxy)-2-oxoethyl)-2,3-dihydro-1H-indene-2-carboxylic acid (265 mg, 0.96 mmol) and 1-(2-(aminomethyl)-6-methoxybenzo[d]thiazol-5-yl)-N,N-dimethylazetidin-3-amine (280 mg, 0.96 mmol) in DCM (3 mL) was added Et$_3$N (0.4 mL, 2.87 mmol) followed by HATU (437 mg, 1.15 mmol). The mixture was stirred at RT for 2 h. The mixture was partitioned between DCM and brine, then the organic layer concentrated in vacuo. FCC (1-10% [7M NH$_3$ in MeOH] in DCM) gave the title compound (410 mg, 78%) as a pale yellow foam. M/z 551.3 (M+H)$^+$.

g. 2-(2-(((5-(3-(dimethylamino)azetidin-1-yl)-6-methoxybenzo[d]thiazol-2-yl)methyl)carbamoyl)-2,3-dihydro-1H-inden-2-yl)acetic acid To a solution of tert-butyl 2-(2-(((5-(3-(dimethylamino)azetidin-1-yl)-6-methoxybenzo[d]thiazol-2-yl)methyl)carbamoyl)-2,3-dihydro-1H-inden-2-yl)acetate (193 mg, 0.35 mmol) in DCM (3 mL) was added water (0.16 mL) then TFA (1.6 mL). The mixture was stirred vigorously at RT for 3 h and the solvent was removed, azeotroping with toluene. The residue was purified by mass directed HPLC (Sunfire column, gradient 5-60% ACN/water with 10 mM ammonium carbonate) and the desired fractions were freeze dried to yield the title compound (92 mg, 53%) as a white solid. M/z 495.2 (M+H)$^+$. $^1$H NMR (d6-DMSO) δ 12.11 (1H, bs), 8.70 (1H, bs), 7.41 (1H, s), 7.24-7.18 (2H, m), 7.16-7.10 (2H, m), 6.84 (1H, s), 4.58 (2H, d, J=5 Hz), 3.98 (2H, t, J=7 Hz), 3.78 (3H, s), 3.54 (2H, t, J=7 Hz), 3.45 (2H, d, J=16 Hz), 3.07 (1H, quint., J=6 Hz), 2.98 (2H, d, J=16 Hz), 2.72 (2H, s), 2.09 (6H, s).

Example 123

2-(2-(((6-methoxy-5-(3-(trimethylammonio)azetidin-1-yl)benzo[d]thiazol-2-yl)methyl)carbamoyl)-2,3-dihydro-1H-inden-2-yl)acetate

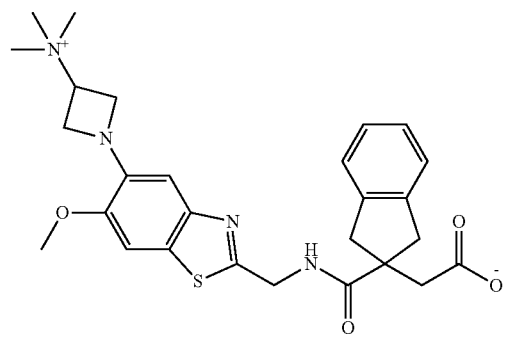 [SMILES: COc1cc2sc(CNC(=O)C3(CC(=O)O)Cc4ccccc4C3)nc2cc1N1CC([N+](C)(C)C)C1]

A solution of tert-butyl 2-(2-(((5-(3-(dimethylamino)azetidin-1-yl)-6-methoxybenzo[d]-thiazol-2-yl)methyl)carbamoyl)-2,3-dihydro-1H-inden-2-yl)acetate (149 mg, 0.27 mmol) and MeI (0.084 mL, 1.35 mmol) in THF (2 mL) was stirred at RT for 18 h, then the mixture concentrated in vacuo. The residue was dissolved in DCM (3 mL) then water (0.081 mL) and TFA (1.1 mL) were added. The mixture was stirred vigorously at RT for 2 h, then concentrated in vacuo, azeotroping with toluene. The residue was purified by mass directed HPLC (Xbridge Phenyl 19×150 mm, 10 um column, gradient 20-80% MeOH/water with 10 mM ammonium carbonate) and the desired fractions freeze dried to yield the title compound (52 mg, 38%) as an off-white solid. M/z 509.3 (M+H)$^+$. $^1$H NMR (d6-DMSO) δ 13.2 (1H, t, J=5 Hz), 7.55 (1H, s), 7.17-7.12 (2H, m), 7.12-7.07 (2H, m), 6.94 (1H, s), 4.60 (2H, d, J=5 Hz), 4.43-4.36 (1H, m), 4.31 (2H, dd, J=3.5 and 10 Hz), 4.12 (2H, dd, J=8 and 10 Hz), 3.82 (3H, s), 3.3 (2H, d, J=16 Hz), 3.15 (9H, s), 2.87 (2H, d, J=16 Hz), 2.32 (2H, s).

Example 124

2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetic acid

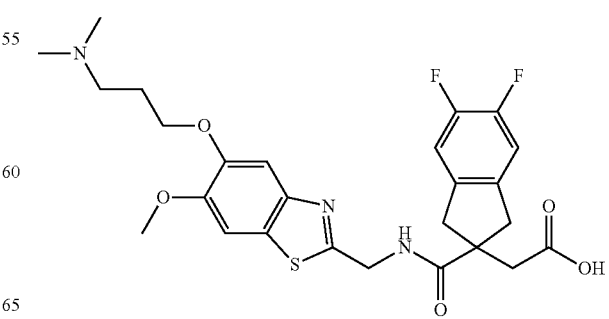

a. tert-butyl ((6-methoxy-5-(4,4,5,5-tetramethyl-1,3,2-dioxaborolan-2-yl)benzo[d]thiazol-2-yl)methyl)carbamate tert-Butyl ((5-bromo-6-methoxybenzo[d]thiazol-2-yl)methyl)carbamate (3.0 g, 8.0 mmol), Bpin (2.86 g, 11.3 mmol), $PdCl_2$(dppf).DCM (656 mg, 0.80 mmol) and potassium acetate (2.37 g, 24.11 mmol) were suspended in 1,4-dioxane (80 mL). The vessel was sealed, evacuated and flushed with $N_2$ twice, then stirred at 100° C. for 4 h and allowed to RT. The mixture was filtered through a celite pad, eluting with EtOAc. The filtrate was washed successively with water and brine, then dried ($Na_2SO_4$), filtered and concentrated in vacuo. FCC (0-60% EtOAc in isohexane) gave the title compound (4.5 g, >100%, contains excess pinacol) as a beige solid. M/z 421.2 $(M+H)^+$ b. tert-butyl ((5-hydroxy-6-methoxybenzo[d]thiazol-2-yl)methyl)carbamate

To a solution of tert-butyl ((6-methoxy-5-(4,4,5,5-tetramethyl-1,3,2-dioxaborolan-2-yl)benzo[d]thiazol-2-yl)methyl)carbamate (4.5 g, 8.04 mmol) in 1,4-dioxane (20 mL) and MeOH (60 mL) was added 30% aq. hydrogen peroxide solution (3.2 mL, 37 mmol) and the mixture stirred at RT for 18 h. The mixture was cooled to 0° C. and quenched with 2M aq. sodium metabisulfite solution and stirred vigorously for 5 min. The mixture was extracted with EtOAc (×2). The organic extracts were washed with brine, then dried ($Na_2SO_4$), filtered and concentrated in vacuo. FCC (30-100% EtOAc in isohexane) gave a residue that was triturated with $Et_2O$ to yield the title compound (1.79 g, 72% over 2 steps) as an off-white solid. M/z 311.1 $(M+H)^+$.

c. tert-Butyl ((5-(3-(dimethylamino)propoxy)-6-methoxybenzo[d]thiazol-2-yl)methyl)-carbamate tert-Butyl ((5-hydroxy-6-methoxybenzo[d]thiazol-2-yl)methyl)carbamate (310 mg, 1 mmol), 3-dimethylamino-1-propylchloride hydrochloride (174 mg, 1.1 mmol) and $Cs_2CO_3$ (977 mg, 3 mmol) were suspended in ACN and stirred at 60° C. for 18 h. The mixture was allowed to RT and then the mixture was partitioned between DCM and brine. The organic layer was concentrated in vacuo to give a residue. FCC (1-10% [7M $NH_3$ in MeOH] in DCM) gave the title compound (286 mg, 72%) as an orange oil. M/z 396.3 $(M+H)^+$.

d. 3-((2-(aminomethyl)-6-methoxybenzo[d]thiazol-5-yl)oxy)-N,N-dimethylpropan-1-amine To a solution of tert-butyl ((5-(3-(dimethylamino)propoxy)-6-methoxybenzo[d]thiazol-2-yl)methyl)carbamate (284 mg, 0.72 mmol) in DCM (3 mL) was added TFA (1.6 mL, 21.5 mmol). The solution was stirred at RT for 1 h then loaded directly onto an SCX-2 cartridge (5 g, prewashed with MeOH). The cartridge was washed with MeOH and then eluted with 7M $NH_3$ in MeOH; concentration in vacuo gave the title compound (196 mg, 92%) as an orange oil. M/z 296.1 $(M+H)^+$.

e. tert-Butyl 2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetate To a solution of 2-(2-(tert-butoxy)-2-oxoethyl)-5,6-difluoro-2,3-dihydro-1H-indene-2-carboxylic acid (205 mg, 0.66 mmol) and 3-((2-(aminomethyl)-6-methoxybenzo[d]thiazol-5-yl)oxy)-N,N-dimethylpropan-1-amine (194 mg, 0.66 mmol) in DCM (3 mL) was added $Et_3N$ (0.427 mL, 1.97 mmol) followed by HATU (300 mg, 0.79 mmol). The mixture was stirred at RT for 2 h, then partitioned between DCM and brine. The organic layer was concentrated in vacuo to give a residue. FCC (1-10% [7M $NH_3$ in MeOH] in DCM) gave the title compound (280 mg, 72%) as a yellow solid. M/z 590.3 $(M+H)^+$.

f. 2-(2-(((5-(3-(dimethylamino)propoxy)-6-methoxy-benzo[d]thiazol-2-yl)methyl)carbamoyl)-5,6-difluoro-2,3-dihydro-1H-inden-2-yl)acetic acid To a solution of tert-butyl 2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetate (125 mg, 0.21 mmol) in DCM (2 mL) was added water (0.1 mL) then TFA (1 mL). The mixture was stirred vigorously at RT for 4 h and the solvent was removed, azeotroping with toluene. The residue was purified by mass directed HPLC (Sunfire column, gradient 5-60% ACN/water with 10 mM ammonium carbonate) and the desired fractions freeze dried to yield the title compound (41 mg, 36%) as a white solid. M/z 534.3 $(M+H)^+$. $^1$H NMR (d6-DMSO) δ 9.04 (1H, bs), 7.55 (1H, s), 7.43 (1H, s), 7.31-7.24 (2H, m), 4.59 (2H, d, J=5 Hz), 4.05 (2H, t, J=6 Hz), 3.81 (3H, s), 3.42 (2H, d, J=16 Hz), 2.96 (2H, d, J=16 Hz), 2.74 (2H, s), 2.40 (2H, t, J=6 Hz), 2.18 (6H, s), 1.92-1.84 (2H, m). OH signal not observed.

Example 125

2-(5,6-difluoro-2-((((6-methoxy-5-(3-(trimethylammonio)propoxy)benzo[d]thiazol-2-yl)methyl)carbamoyl)-2,3-dihydro-1H-inden-2-yl)acetate

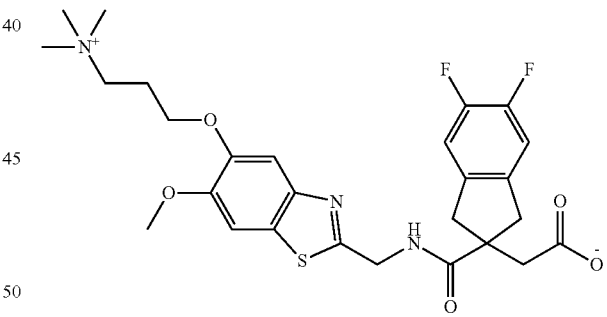

A solution of tert-butyl 2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetate (150 mg, 0.254 mmol) and MeI (0.079 mL, 1.27 mmol) in THF (2 mL) was stirred at RT for 18 h, then concentrated in vacuo. The residue was dissolved in DCM (2 mL) then water (0.12 mL, 6.5 mmol) and TFA (1.2 mL, 15.2 mmol) were added. The mixture was stirred vigorously at RT for 2 h, then concentrated in vacuo, azeotroping with toluene. The residue was purified by mass directed HPLC (Sunfire 19×150 mm, 10 um column, gradient 5-60% ACN/water with 10 mM ammonium carbonate) and the desired fractions freeze dried to yield the title compound (90 mg, 65%) as a white solid. M/z 548.4 $(M+H)^+$. $^1$H NMR (d6-DMSO) δ 13.09 (1H, bs), 7.64 (1H, s), 7.54 (1H, s), 7.24-7.18 (2H, m), 4.61

(2H, d, J=5 Hz), 4.13 (2H, d, J=5 Hz), 3.82 (3H, s), 3.53-3.47 (2H, m), 3.35 (2H, d, J=16 Hz), 3.10 (9H, s), 2.86 (2H, d, J=16 Hz), 2.34 (2H, s), 2.27-2.19 (2H, m).

Example 126

2-(2-(((5-(2-(dimethylamino)ethoxy)-6-methoxy-benzo[d]thiazol-2-yl)methyl)carbamoyl)-2,3-dihydro-1H-inden-2-yl)acetic acid

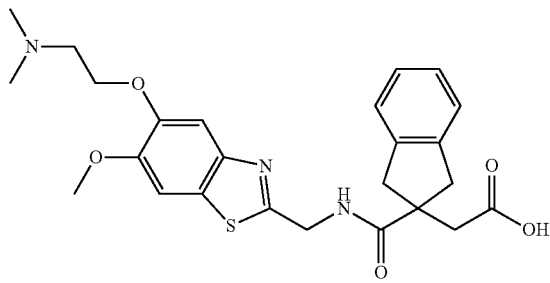 [SMILES: COc1cc2sc(CNC(=O)C3(CC(=O)O)Cc4ccccc4C3)nc2cc1OCCN(C)C]

Using the same procedure as for example 124, but using 2-dimethylaminoethyl chloride hydrochloride and 2-[2-(tert-butoxy)-2-oxoethyl]-2,3-dihydro-1H-indene-2-carboxylic acid. M/z 484.4 (M+H)+. $^1$H NMR (d6-DMSO) δ 8.73 (1H, t, J=5 Hz), 7.56 (1H, s), 7.49 (1H, s), 7.24-7.19 (2H, m), 7.17-7.12 (2H, m), 4.60 (2H, d, J=5 Hz), 4.12 (2H, t, J=5 Hz), 3.81 (3H, s), 3.46 (2H, d, J=16 Hz), 2.99 (2H, d, J=16 Hz), 2.74 (2H, t, J=5 Hz), 2.73 (2H, s), 2.29 (6H, s). OH signal not observed.

Example 127

2-[2-(thiazolo[4,5-c]pyridin-2-ylmethylcarbamoyl)indan-2-yl]acetic acid

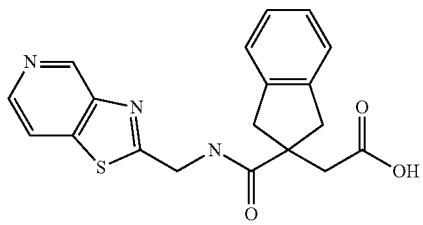 [SMILES: O=C(O)CC1(C(=O)NCc2nc3cnccc3s2)Cc2ccccc2C1]

a. tert-butyl (thiazolo[4,5-c]pyridin-2-ylmethyl) carbamate

To a stirred solution of 4-iodopyridin-3-amine (500 mg, 2.2 mmol) in acetonitrile (5 mL) was added tert-butyl (2-amino-2-thioethoxyethyl)carbamate (561 mg, 2.9 mmol) and CaO (255 mg, 4.5 mmol) at room temperature. The reaction mixture was purged with argon for 15 minutes, then dppf (151 mg, 0.27 mmol) and Pd$_2$(dba)$_3$ (64 mg, 0.06 mmol) was added to the reaction mixture. The reaction mixture was purged with argon for further 5 minutes and stirred in sealed tube at 60° C. for 16 h. The reaction mixture was filtered through celite pad and washed the pad with EtOAc (50 mL). The filtrate was washed with water (2×30 mL), dried with sodium sulfate, filtered and solvent removed. The crude compound was purified by column chromatography (60-120 silica gel, gradient 60%-70% ethyl acetate/pet ether) to the product (370 mg, 61.6% yield) as a pale brown sticky. M/z 266.1 (M+H)+.

b. 2-[2-(thiazolo[4,5-c]pyridin-2-ylmethylcarbamoyl)indan-2-yl]acetic acid

The title compound has been prepared from tert-butyl (thiazolo[4,5-c]pyridin-2-ylmethyl) carbamate following the procedure described in example 91 steps-f, -g and -h. The crude compound was purified by preparative HPLC [YMC-TRIART-C18 (150*25 mm), 10 u, Mobile phase: A: 0.1% FORMIC ACID in H$_2$O, B: MeCN, Gradient: (% B): 0/10, 1/10, 8/60, 9/60, 9.1/98, 11/98, 11.1/10, 13/10 0/10, 8/45, 9/45, 9.1/98, 11/98, 11.1/10, 13/10, Flow Rate: 25 mL/min], 25% yield, off white solid. M/z 368.1 (M+H)+. $^1$H NMR (500 MHz, DMSO-d$_6$): δ 12.17 (1H, s), 9.19 (1H, d, J=1 Hz), 8.80 (1H, t, J=5.5 Hz), 8.48 (1H, d, J=5.5 Hz), 8.11 (1H, dd, J=5.5 Hz, J=1 Hz), 7.22-7.21 (2H, m), 7.15-7.13 (2H, m), 4.70 (2H, d, J=6 Hz), 3.46 (2H, d, J=16.5 Hz), 2.99 (2H, d, J=16.5 Hz), 2.75 (2H, s).

Example 128

2-[2-[[6-(trifluoromethoxy)-1,3-benzothiazol-2-yl]methylcarbamoyl]indan-2-yl]acetic acid

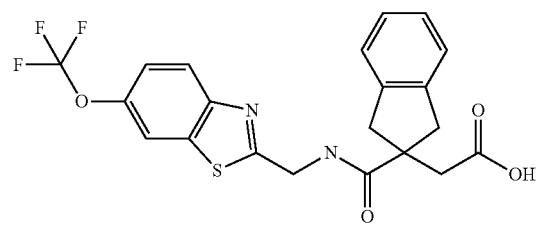 [SMILES: O=C(O)CC1(C(=O)NCc2nc3ccc(OC(F)(F)F)cc3s2)Cc2ccccc2C1]

a. tert-butyl ((6-(trifluoromethoxy) benzo[d]thiazol-2-yl) methyl) carbamate

To a stirred solution of 2-iodo-4-(trifluoromethoxy)aniline (300 mg, 0.9 mmol) in DMF (10 mL) was added tert-butyl (2-amino-2-thioethoxyethyl)carbamate (188 mg, 0.9 mmol) and CuO (79 mg, 0.9 mmol) at room temperature. The reaction mixture was purged with argon for 15 minutes. Then, dppf (55 mg, 0.09 mmol) and Pd$_2$(dba)$_3$ (46 mg, 0.04 mmol) was added to the reaction mixture. The reaction mixture was purged with argon for further 5 minutes and stirred in sealed tube at 90° C. for 6 h. The reaction mixture was filtered through celite pad and washed the pad with EtOAc (50 mL). The filtrate was washed with cold water (2×15 mL) dried with sodium sulfate, filtered and solvent removed. The crude compound was purified by column chromatography (60-120 silica gel, gradient 30%-40% ethyl acetate/pet ether) to yield the product (180 mg, 52% yield) as a pale yellow solid. M/z 349.0 (M+H)+.

b. 2-[2-[[6-(trifluoromethoxy)-1,3-benzothiazol-2-yl]methylcarbamoyl]indan-2-yl]acetic acid The title compound has been prepared from tert-butyl ((6-(trifluoromethoxy) benzo[d]thiazol-2-yl) methyl) carbamate following the procedure described in example 91 steps-f, -g and -h. The crude compound was purified by preparative HPLC [X-BRIDGE-C18 (150×30 mm) 5 u, Mobile phase: A: 0.1% FORMIC ACID in H₂O, B: MeCN, Gradient: (T % B): 0/40, 8/80, 8.2/98, 10/98, 10/40, 13/40, Flow Rate: 25 mL/min], 43% yield, off white solid. M/z 451.1 (M+H)⁺. ¹H NMR (500 MHz, DMSO-d₆): δ 12.25 (1H, bs), 9.16 (1H, bs), 8.17 (1H, d, J=1 Hz), 8.02 (1H, d, J=9 Hz), 7.49-7.47 (1H, m), 7.22-7.19 (2H, m), 7.15-7.13 (2H, m), 4.67 (2H, d, J=5.5 Hz), 3.46 (2H, d, J=16.5 Hz), 2.99 (2H, d, J=16.5 Hz), 2.70 (2H, s).

Example 129

2-[2-[(5-methyl-6,7-dihydro-4H-thiazolo[5,4-c]pyridin-2-yl)methylcarbamoyl]indan-2-yl]acetic acid

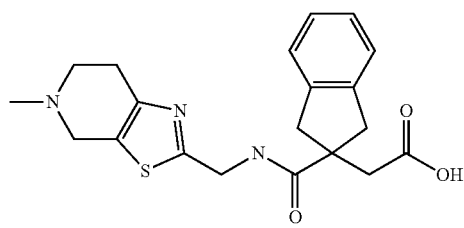 [SMILES: CN1CCc2nc(CNC(=O)C3(CC(=O)O)Cc4ccccc4C3)sc2C1]

a. benzyl 3-bromo-4-oxopiperidine-1-carboxylate

To a stirred solution of benzyl 4-oxopiperidine-1-carboxylate (5.0 g, 21.4 mmol) in DCM (50 mL) was added DIPEA (4.64 mL, 26.8 mmol) and TMSOTf (4.29 mL, 25.7 mmol) at 0° C. stirred for 30 minutes. Then, NBS (3.81 g, 21.4 mmol) was added to the reaction mixture at 0° C. and stirred at room temperature 16 h. The reaction mixture was partitioned between DCM (200 mL) and water (120 mL). The aqueous phase separated and was extracted with DCM (2×100 mL). The combined organic extracts was washed with brine, dried with Na₂SO₄, filtered and evaporated. The crude compound was purified by column chromatography (100-200 silica gel, gradient 10%-15% ethyl acetate/pet ether) to get the product (4.5 g, 67%) as a pale yellow liquid. M/z 312.2 (M+H)⁺.

b. benzyl 2-(aminomethyl)-6,7-dihydrothiazolo[5,4-c]pyridine-5(4H)-carboxylate

To a stirred solution of benzyl 3-bromo-4-oxopiperidine-1-carboxylate (4.5 g, 14.4 mmol) in isopropanol (55 mL) was added tert-butyl (2-amino-2-thioxoethyl) carbamate (2.75 g, 14.4 mmol) at room temperature. The reaction mixture was stirred in sealed tube at 90° C. for 16 h. The reaction mixture was evaporated and then treated with H₂O (100 mL), acidified with 1N HCl and extracted with diethyl ether (2×200 mL). The aqueous layer was basified with aq NaHCO₃. Then the reaction mixture was extracted with DCM (2×250 mL). The combined organic layer was washed with brine, dried with Na₂SO₄, filtered and evaporated to get the product (1.2 g, crude) as pale brown sticky material. M/z 304.0 (M+H)⁺.

c. benzyl 2-((2-(2-(tert-butoxy)-2-oxoethyl)-2,3-dihydro-1H-indene-2-carboxamido)methyl)-6,7-dihydrothiazolo[5,4-c]pyridine-5(4H)-carboxylate To a stirred solution of 2-(2-(tert-butoxy)-2-oxoethyl)-2,3-dihydro-1H-indene-2-carboxylic acid (1.5 g, 5.43 mmol) in DMF (15 mL) was added Et₃N (1.5 mL, 1.08 mmol), EDC.HCl (1.25 g, 6.51 mmol) and HOBt (1.02 g, 7.06 mmol) at room temperature and stirred for 15 minutes. Then benzyl 2-(aminomethyl)-6,7-dihydrothiazolo[5,4-c]pyridine-5(4H)-carboxylate (1.64 g, 5.43 mmol) was added to the reaction mixture and stirred at room temperature for 12 h. The reaction mixture was partitioned between ethyl acetate (150 mL) and cold water (60 mL). The aqueous phase was separated and extracted with ethyl acetate (2×150 mL). The combined organic extracts were washed with brine, dried with Na₂SO₄, filtered and evaporated. The crude compound was purified by column chromatography (100-200 silica gel, gradient 3%-5% MeOH/DCM) to get the product (1.9 g, 63%) as pale brown sticky material. M/z 562.2 (M+H)⁺.

d. tert-butyl 2-(2-(((5-methyl-4,5,6,7-tetrahydrothiazolo[5,4-c]pyridin-2-yl)methyl)carbamoyl)-2,3-dihydro-1H-inden-2-yl)acetate To a stirred solution of benzyl 2-((2-(2-(tert-butoxy)-2-oxoethyl)-2,3-dihydro-1H-indene-2-carboxamido)methyl)-6,7-dihydrothiazolo[5,4-c]pyridine-5(4H)-carboxylate (200 mg, 0.35 mmol) in MeOH (5 mL) was added Pd/C (200 mg, 100% wt/wt) to the reaction mixture under nitrogen atmosphere and stirred under hydrogen balloon pressure for 24 h. The reaction mixture was filtered through celite pad and washed with MeOH (100 mL). The filtrate was concentrated under vacuum. The crude compound was purified by column chromatography (100-200 silica gel, gradient 10%-20% MeOH/DCM) to get the product (50 mg, 19.1%) as pale yellow solid. M/z 442.2 (M+H)⁺.

e. 2-[2-[(5-methyl-6,7-dihydro-4H-thiazolo[5,4-c]pyridin-2-yl)methylcarbamoyl]indan-2-yl]acetic acid To a stirred solution of tert-butyl 2-(2-(((5-methyl-4,5,6,7-tetrahydrothiazolo[5,4-c]pyridin-2-yl)methyl)carbamoyl)-2,3-dihydro-1H-inden-2-yl)acetate (50 mg, 0.113 mmol) in DCM (3 mL) was added TFA (0.5 mL) and TES (0.2 mL) at 0° C. The reaction mixture was stirred at room temperature for 3 h. After completion of starting material based on LCMS, the reaction mixture was concentrated under reduced pressure. The crude compound was purified by preparative HPLC [X-BRIDGE-C18 (150*30 mm), 5 u, mobile phase: A: 0.05% Formic Acid in H₂O, B: MeCN, Flow rate: 25 mL/min] to obtain the title product (32 mg, 74%) as an off white solid. M/z 386.2 (M+H)⁺. ¹H NMR (500 MHz, DMSO-d₆): δ 9.86 (1H, bs), 7.18-7.15 (2H, m), 7.12-7.10 (2H, m), 4.45 (2H, d, J=5 Hz), 3.50 (2H, s), 3.38 (2H, d, J=16 Hz), 2.93 (2H, d, J=16 Hz), 2.69-2.66 (4H, m), 2.56 (2H, s), 2.34 (3H, s).

Example 130

2-[2-[(5-hydroxy-1,3-benzothiazol-2-yl)methylcarbamoyl]indan-2-yl]acetic acid

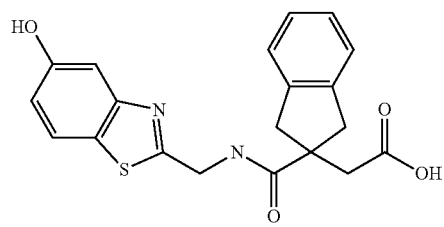 [SMILES: O=C(O)CC1(C(=O)NCc2nc3cc(O)ccc3s2)Cc2ccccc2C1]

The title product was prepared from tert-butyl N-[(5-hydroxy-1,3-benzothiazol-2-yl)methyl]carbamate using the procedure described for Example 107 step-d, -e and -f. The crude compound was purified by preparative HPLC [INERTSIL-ODS (250*20 mm), 5 u, Mobile phase: A: 0.05% Formic Acid in H$_2$O, B: MeCN, Gradient: (% B): 0/10, 8/60, 11/60, 11.1/98, 13/98, 13.1/10, 16/10, Rate: 25 mL/min], 15% yield, off white solid. M/z 383.0 (M+H)$^+$. $^1$H NMR (500 MHz, DMSO-d$_6$): δ 12.13 (1H, bs), 9.62 (1H, s), 8.85 (1H, bs), 7.75 (1H, d, J=8.5 Hz), 7.24-7.20 (3H, m), 7.14-7.12 (2H, m), 6.88 (1H, dd, J=8.5 Hz, J=2.5 Hz), 4.61 (2H, d, J=5.5 Hz), 3.47 (2H, d, J=16.5 Hz), 3.00 (2H, d, J=16.5 Hz), 2.71 (2H, s).

Example 131: LasB Inhibitory Activity Measurements

The relevance of LasB to PA infection is illustrated in FIG. 1, which shows lung burden in a rat model of chronic lung infection following infection with WT PA (which expresses LasB) and a mutant form of PA (ΔlasB PA) in which LasB is not expressed. It can be clearly seen in that following infection, whereas a wild type strain is able to persist at least for 14 days, a LasB deficient strain was not able to persist beyond day 5.

Figure 2:
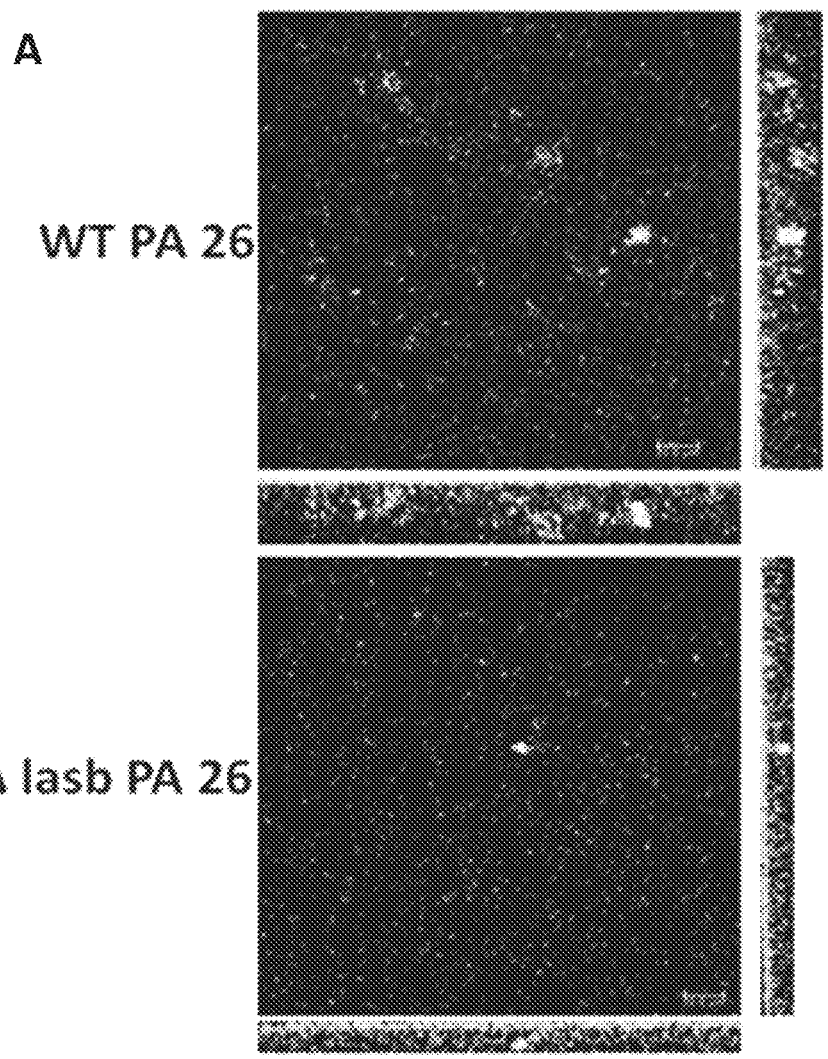
FIG. 2 shows further results of experiments described in Example 47: Confocal images and measurement of thickness and biomass of biofilm formed by *P. aeruginosa* PA26 WT and PA26 ΔlasB.
Figure 2:
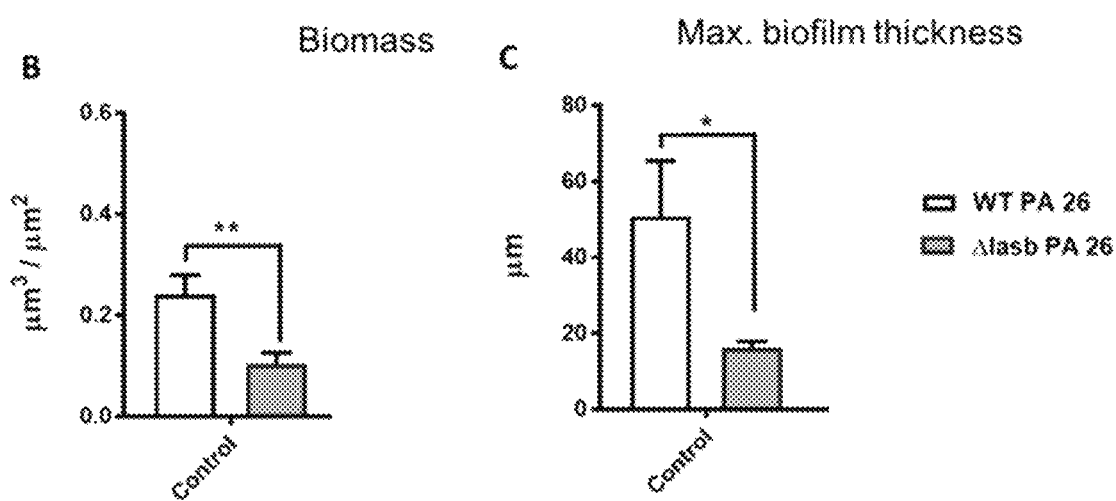

The relevance of LasB to PA biofilm development is shown in FIG. 2. Biofilms formed after 3 days by both PA26 wt and PA26 lasB deletion strains were investigated by confocal imaging and subsequent analysis (with Comstat software). This study demonstrated that biofilms formed by the PA26 lasB deletion strain were highly reduced in thickness and biomass compared to the wt strain, demonstrating the essential role of LasB in PA biofilm development (Asterisks  and * indicates statistical difference for P<0.05, P<0.01; respectively).

Experiments were therefore conducted (1) to measure the potency of inhibition of compounds of the invention against purified *Pseudomonas aeruginosa* LasB enzyme and also experiments were conducted (2) to measure the ability of compounds of the invention to inhibit LasB-catalysed elastin degradation. The first assay uses a commercial fluorescent synthetic peptide and purified LasB enzyme. The LasB hydrolysis kinetics are measured allowing the determination of the IC50 and Ki of the inhibitors; the second is a more physiological assay using dialysed *Pseudomonas aeruginosa* supernatant as source of enzyme, plus its natural substrate Elastin. It is an "end point assay" that determines the percentage of LasB inhibition by each compound for one particular time point and inhibitor concentration. Technical details are described below:

Fluorometric Assay to Determine Ki

This assay uses commercially available substrate (Abz-Ala-Gly-Leu-Ala-p-Nitro-Benzyl-Amide (Ex: 340 nm, Em: 415 nm) from Peptide International) and purified LasB protein from *P. aeruginosa* (provided by Merck or Charles River Laboratories). It is performed to determine LasB elastase activity and assess compound inhibition in 96-well plate format. Some compounds of Formula (I) were assessed using the method of Assay 1 (described below). Other compounds of Formula (I) were assessed using the alternative but equivalent method of Assay 2 (described below). For a given compound, results from Assay 1 and Assay 2 are comparable.

Method: 10 to 140 ng/ml purified LasB is incubated with 250 µM Abz-Ala-Gly-Leu-Ala-p-Nitro-Benzyl-Amide in 50 mM Tris-HCl pH 7.4, 2.5 mM CaCl$_2$), 0.01% of Triton X100 at 37° C. LasB activity (corresponding to fluorescence emission induced by substrate hydrolysis) is measured over 30 min at 37° C. with a fluorescence plate reader such as the Perkin Elmer Envision or similar. Different range of inhibitor concentrations are routinely assessed depending of inhibitor potency from 0.006 to 200 µM (Assay 1; 2-fold dilutions series) or from 0.0016 to 200 µM (Assay 2; 2-fold dilutions series) in order to determine IC50.

The equation used to calculate the Ki from IC50 is: Ki=IC50/(1+([S]/Km)) where [S]=250 µM and Km=214 µM.

Elastin Assay to Determine % Inhibition

The Elastin assay uses as source of enzyme dialysed supernatant from *P. aeruginosa* and the elastin congo red as substrate. The natural LasB substrate, elastin, is complexed with the congo red dye (Elastin Congo Red, ECR). The elastolysis activity from the culture supernatant will degrade elastin and release the congo red dye into the supernatant. This red dye release can be measured with a spectrophotometer. Some compounds of Formula (I) were assessed using the method of Assay 1 (described below). Other compounds of Formula (I) were assessed using the alternative but equivalent method of Assay 2 (described below). For a given compound, results from Assay 1 and Assay 2 are comparable.

Method (Assay 1): To determine LasB elastase activity and assess compound inhibition, an overnight culture of *P. aeruginosa* strain PA01 is diluted thousand-fold in LB medium. This diluted solution is incubated during 19 hours in a shaking incubator. Culture supernatants are recovered by centrifugation and filtrated through a 0.22 µM filter. These supernatants are dialysed (filtration molecules <20 kDa) into a 50 mM Tris pH 7.4, 2.5 mM CaCl$_2$ solution at 4° C. under agitation for 24 hours. Supernatant dialysed is then mixed volume/volume with the ECR suspension (20 mg/mL of ECR in 100 mM Tris buffer supplemented with 1 mM CaCl$_2$) supplemented with TritonX 100 (final concentration of 0.01%) in presence of different concentrations of compound (routinely 50 and 25 µM). The mixed reaction is then incubated for 24 hours in a 37° shaking incubator. As a negative control, the mixed supernatant is replaced by Tris solution (50 mM Tris pH 7.4, 2.5 mM CaCl$_2$). The reaction supernatant is recovered by centrifugation and the release of congo red is measured by its absorbance at OD520. Percentage inhibition is determined using the following equation:

(OD520 value of DMSO SN−OD520 value of LB)−
(OD520 value of Compound SN−OD520 value
of LB)/(OD520 value of DMSO SN−OD520
value of LB)×100.

Method (Assay 2): To determine LasB elastase activity and assess compound inhibition, an overnight culture of *P. aeruginosa* strain PA01 is diluted in LB medium. After reaching an OD$_{600}$ nm of 0.6, this culture is diluted and incubated for additional 18-24 h in a shaking incubator. Culture supernatants are recovered by centrifugation and filtrated through a 0.22 µM filter. These supernatants are dialysed (filtration molecules <20 kDa) into a 50 mM Tris-HCl pH 7.4, 2.5 mM CaCl$_2$ solution at 4° C. under agitation for 24 h. Supernatant dialysed is then mixed volume/volume with the ECR suspension (20 mg/mL of ECR in 100 mM Tris-HCl pH 7.4 buffer supplemented with 1 mM CaCl$_2$) supplemented with TritonX 100 (final concentration of 0.01%) in presence of DMSO (positive control) and/or different concentrations of compound (routinely 50 to 6.25 M). As a negative control, the dialysed supernatant is replaced by Tris-HCl solution (50 mM Tris-HCl pH 7.4, 2.5 mM CaCl$_2$). The mixed reaction is then incubated overnight in a 37° C. shaking incubator. The reaction supernatant is recovered by centrifugation and the release of congo-red is measured by its absorbance at 495 nm ($OD_{495}$ nm).

Percentage inhibition is determined using the following equation:

(($OD_{495\ nm}$ value of positive control–$OD_{495\ nm}$ value of negative control)–($OD_{495\ nm}$ value of treated supernatant–$OD_{495\ nm}$ value of negative control))/($OD_{495\ nm}$ value of positive control–$OD_{495\ nm}$ value of negative control)×100.

Results are shown in the Table below and categorised into A, B and C for both assays. The Ki values are grouped as A (Ki=0.00 to 0.30 μM), B (Ki=0.30 to 2.00 μM) and C (Ki=2.00 to 10.00 μM). Similarly, for the elastase hydrolysis assay, values are grouped into A (>60% inhibition), B (30 to 60% inhibition) and C (15 to 30% inhibition) all at 50 μM inhibitor concentration. (n.d. not determined).

For the avoidance of doubt, in the structures shown in the following Table, R is the moiety:

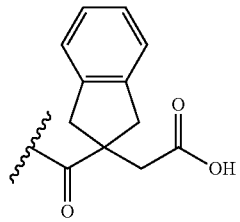 [SMILES: *C(=O)C1(CC(=O)O)Cc2ccccc2C1]

| Example | Structure | Ki (μM) Assay 1 | Ki (μM) Assay 2 | Elastin hydrolysis % inhibition @ 50/25 μM inhibitor concentration Assay 1 | Assay 2 |
|---|---|---|---|---|---|
| 1 | | B | | B | |
| 2 | | B | | B | |
| 3 | | C | | B | |
| 4 | | C | | C | |
| 5 | | B | | B | |
| 6 | | A | | A | |

-continued

| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 7 | 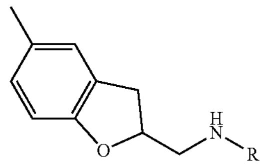 | A | | A | |
| 8 | 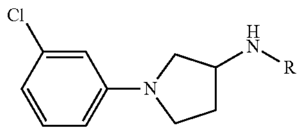 | A | | A | |
| 9 | 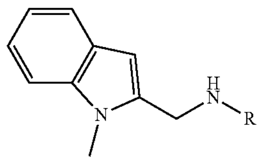 | A | | A | |
| 10 | 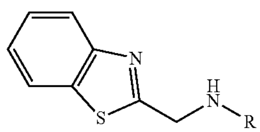 | A | | A | |
| 11 | 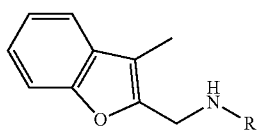 | B | | B | |
| 12 | 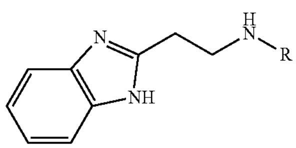 | C | | C | |
| 13 | 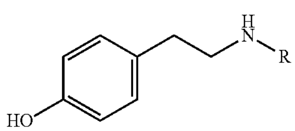 | C | | B | |
| 14 | 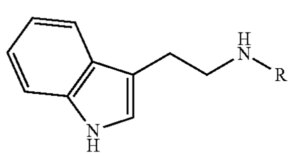 | A | | B | |
| 15 | 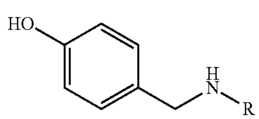 | B | | B | |
| 16 | 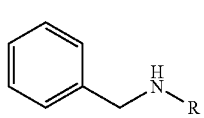 | C | | B | |

-continued
| Example | Structure | Ki (μM) | | Elastin hydrolysis % inhibition @ 50/25 μM inhibitor concentration | |
|---|---|---|---|---|---|
| | | Assay 1 | Assay 2 | Assay 1 | Assay 2 |
| 17 | 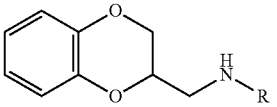 | B | | B | |
| 18 | 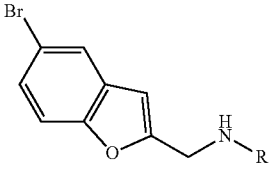 | A | | A | |
| 19 | 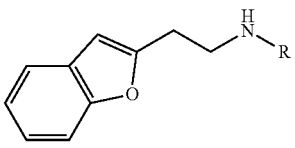 | C | | C | |
| 20 | 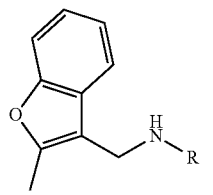 | C | | B | |
| 21 | 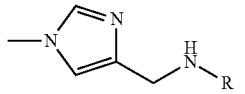 | C | | B | |
| 22 | 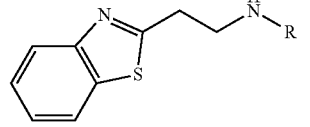 | C | | C | |
| 23 | 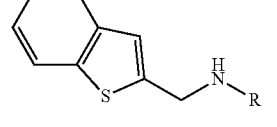 | A | | B | |
| 24 | 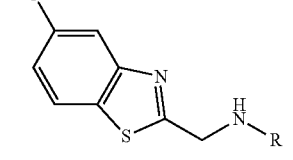 | A | | A | |
| 25 | 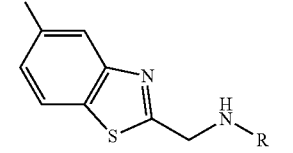 | A | | A | |

-continued

| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 26 | | C | | B | |
| 27 | | C | | C | |
| 28 | | B | | B | |
| 29 | | A | | B | |
| 30 | | C | | C | |
| 31 | | C | | n.d. | |
| 32 | | A | | A | |
| 33 | | B | | B | |
| 34 | | C | | B | |

-continued

| Example | Structure | Ki (μM) Assay 1 | Ki (μM) Assay 2 | Elastin hydrolysis % inhibition @ 50/25 μM inhibitor concentration Assay 1 | Assay 2 |
|---|---|---|---|---|---|
| 35 | 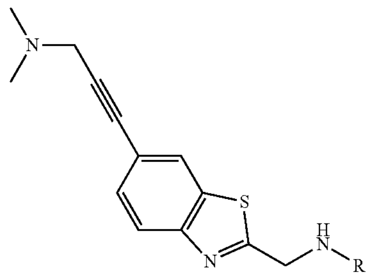 | A | | A | |
| 36 | 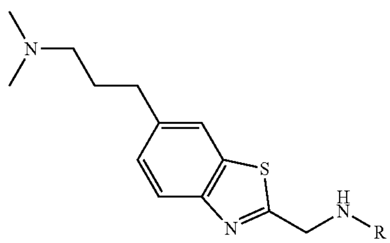 | A | | A | |
| 37 | 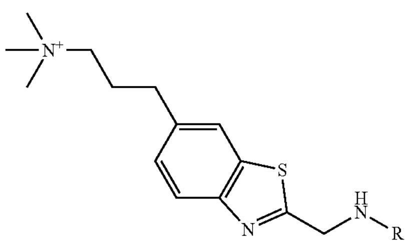 | B | | A | |
| 38 | 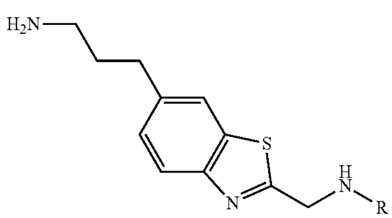 | B | | A | |
| 39 | 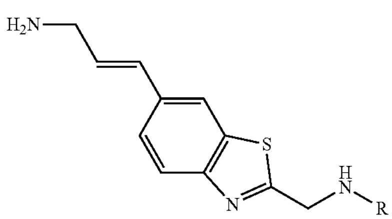 | A | | A | |
| 40 | 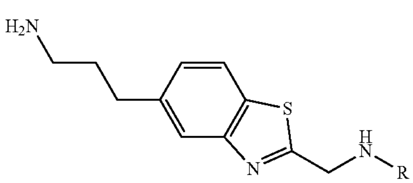 | A | | A | |

-continued

| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 41 | 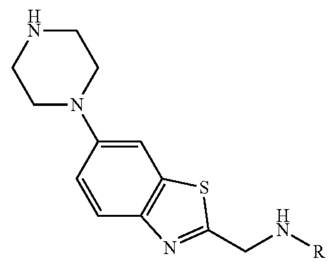 | B | | B | |
| 42 | 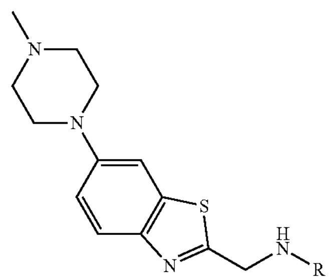 | B | | A | |
| 43 | 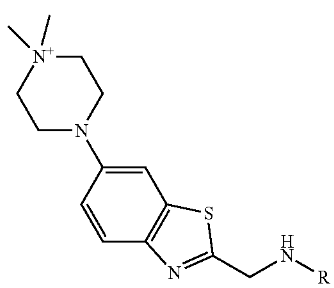 | B | | B | |
| 44 | 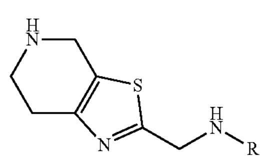 | C | | C | |
| 45 | 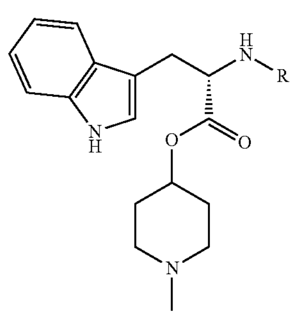 | A | | A | |

-continued

| Example | Structure | Ki (μM) | | Elastin hydrolysis % inhibition @ 50/25 μM inhibitor concentration | |
|---|---|---|---|---|---|
| | | Assay 1 | Assay 2 | Assay 1 | Assay 2 |
| 46 | 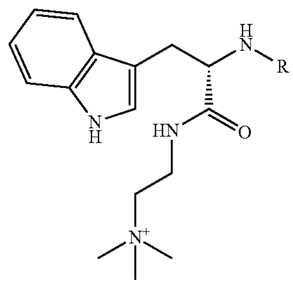 | C | | B | |
| 47 | 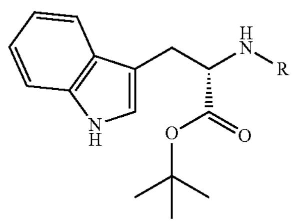 | A | | A | |
| 48 | 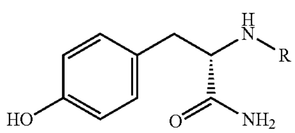 | C | | B | |
| 49 | 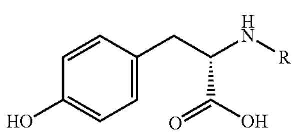 | B | | A | |
| 50 | 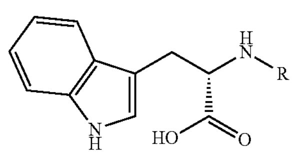 | A | | A | |
| 51 | 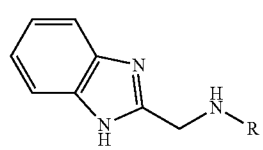 | C | | C | |
| 52 | 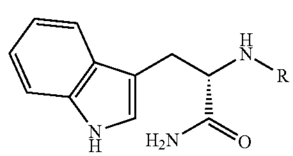 | A | | A | |
| 53 | 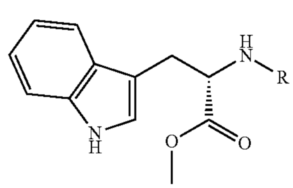 | B | | A | |

-continued

| Example | Structure | Ki (μM) Assay 1 | Ki (μM) Assay 2 | Elastin hydrolysis % inhibition @ 50/25 μM inhibitor concentration Assay 1 | Assay 2 |
|---|---|---|---|---|---|
| 54 | thiazol-2-ylmethyl-NH-R | B | | A | |
| 55 | quinolin-3-ylmethyl-NH-R | B | | A | |
| 56 | 1-methylbenzimidazol-2-ylmethyl-NH-R | B | | B | |
| 57 | benzofuran-3-ylmethyl-NH-R | B | | B | |
| 58 | 1-(benzofuran-2-yl)ethyl-NH-R | C | | B | |
| 59 | 1-(benzofuran-2-yl)ethyl-NH-R | B | | B | |
| 60 | 4-fluorobenzothiazol-2-ylmethyl-NH-R | A | | A | |
| 61 | 4-bromobenzothiazol-2-ylmethyl-NH-R | A | | A | |
| 62 | 4-methoxybenzothiazol-2-ylmethyl-NH-R | A | | A | |
| 63 | 4-iodobenzothiazol-2-ylmethyl-NH-R | A | | A | |

-continued
| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 64 | 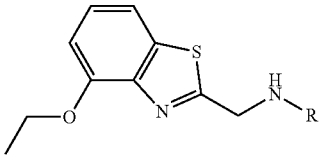 | B | | A | |
| 65 | 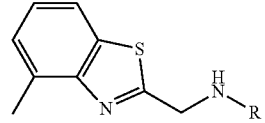 | A | | A | |
| 66 | 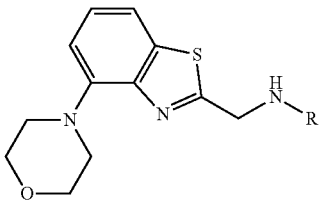 | B | | A | |
| 67 | 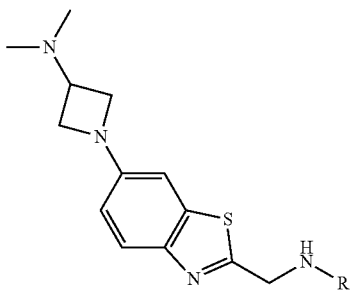 | B | | A | |
| 68 | 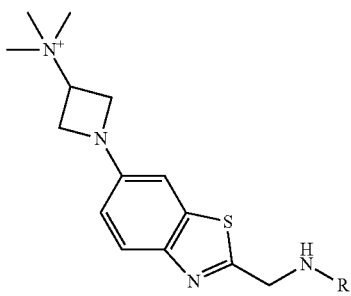 | B | | B | |
| 69 | 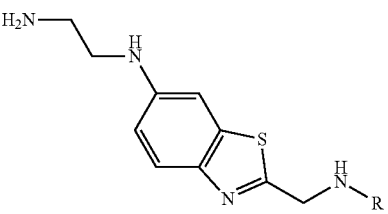 | B | | A | |

-continued

| Example | Structure | Ki (μM) Assay 1 | Ki (μM) Assay 2 | Elastin hydrolysis % inhibition @ 50/25 μM inhibitor concentration Assay 1 | Assay 2 |
|---|---|---|---|---|---|
| 70 | 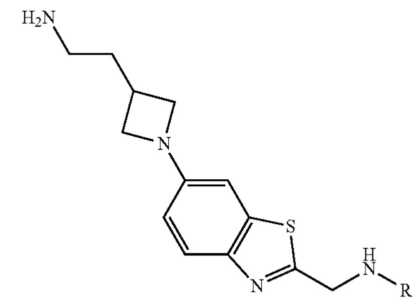 | A | | A | |
| 71 | 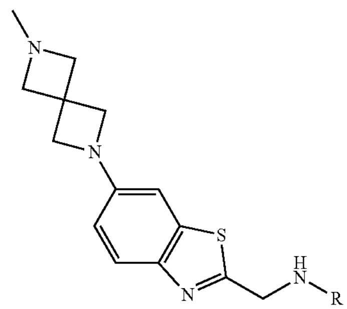 | A | | A | |
| 72 | 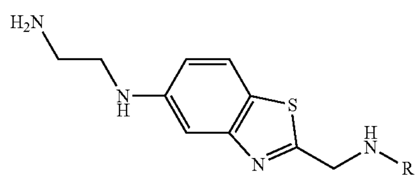 | B | | A | |
| 73 | 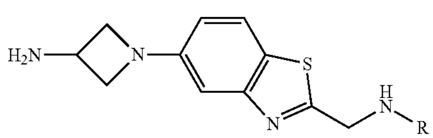 | A | | A | |
| 74 | 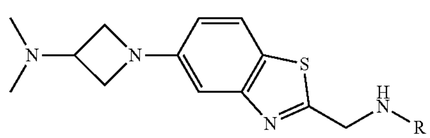 | A | | A | |
| 75 | 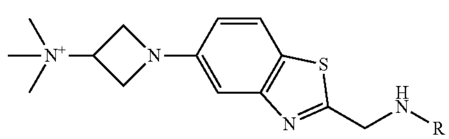 | B | | A | |
| 76 | 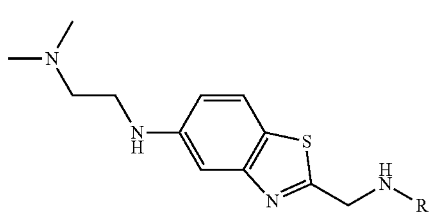 | B | | A | |

-continued
| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 77 | 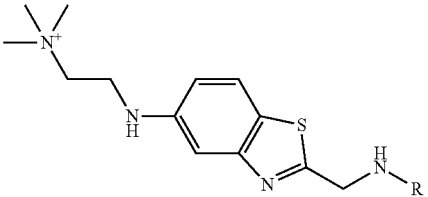 | B | | ND | |
| 78 | 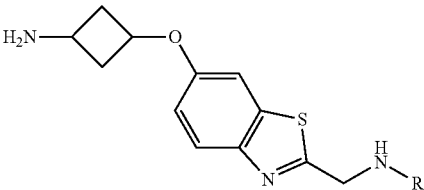 | B | | ND | |
| 79 | 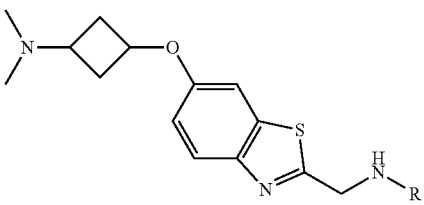 | B | | ND | |
| 80 | 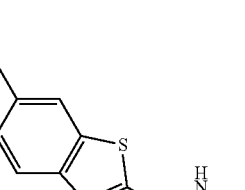 | B | | A | |
| 81 | 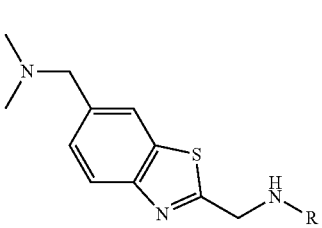 | C | | ND | |
| 82 | 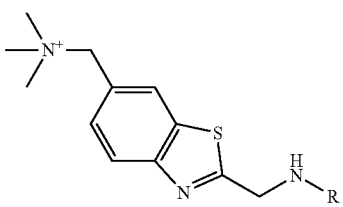 | C | | ND | |
| 83 | 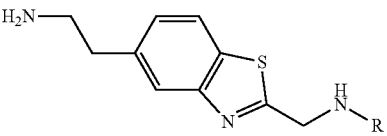 | B | | ND | |

-continued
| Example | Structure | Ki (μM) Assay 1 | Ki (μM) Assay 2 | Elastin hydrolysis % inhibition @ 50/25 μM inhibitor concentration Assay 1 | Assay 2 |
|---|---|---|---|---|---|
| 84 | 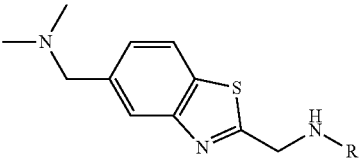 | B | | ND | |
| 85 | 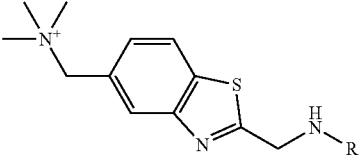 | B | | ND | |
| 86 | 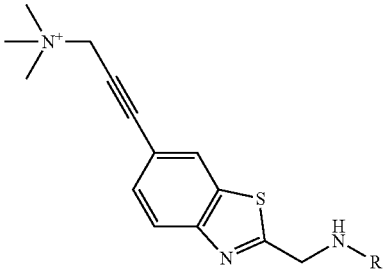 | A | | A | |
| 87 | 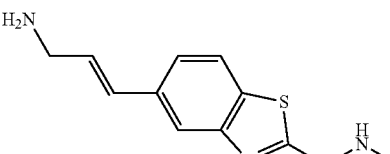 | B | | A | |
| 88 | 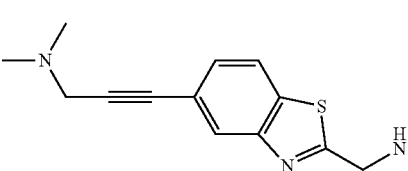 | A | | A | |
| 89 | 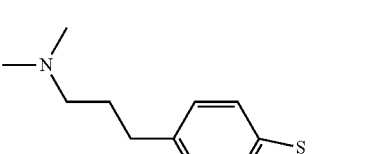 | B | | A | |
| 90 | 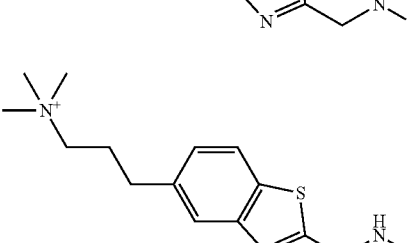 | B | | A | |

-continued
| Example | Structure | Ki (μM) Assay 1 | Ki (μM) Assay 2 | Elastin hydrolysis % inhibition @ 50/25 μM inhibitor concentration Assay 1 | Assay 2 |
|---|---|---|---|---|---|
| 91 | 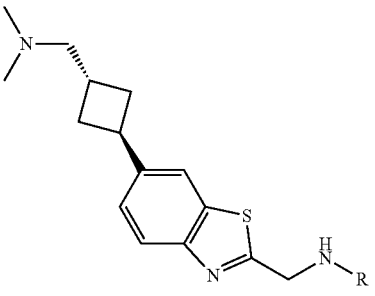 | A |  | A |  |
| 92 | 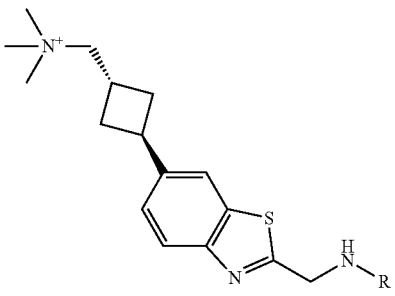 | B |  | A |  |
| 93 | 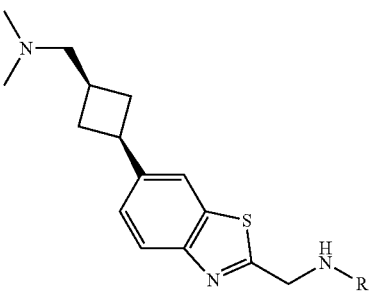 | A |  | A |  |
| 94 | 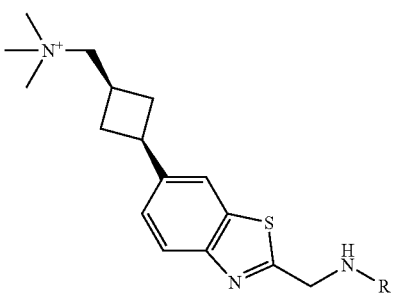 | A |  | A |  |
| 95 | 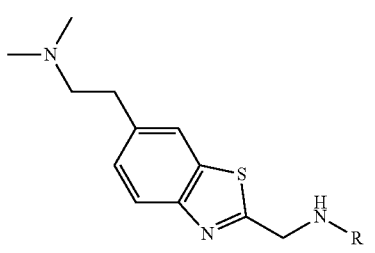 | B |  | B |  |

-continued

| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 96 | | B | | B | |
| 97 | | B | | ND | |
| 98 | | B | | ND | |
| 99 | | A | | A | |
| 100 | | A | | A | |
| 101 | | B | | A | |

-continued

| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 102 | 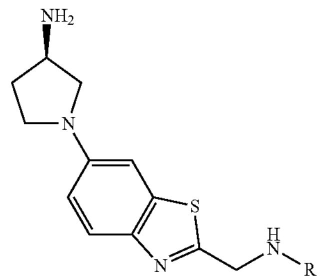 | A | | A | |
| 103 | 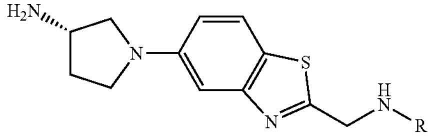 | B | | A | |
| 104 | 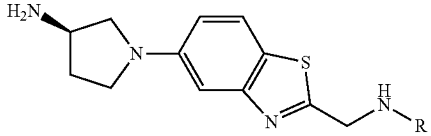 | B | | A | |
| 105 | 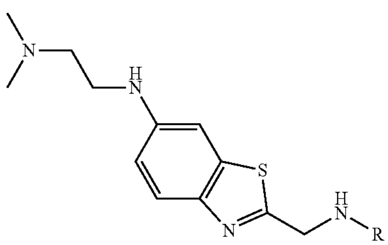 | B | | B | |
| 106 | 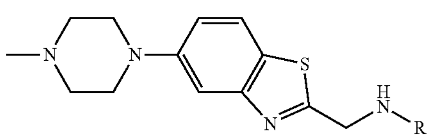 | A | | A | |
| 107 | 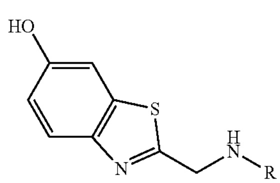 | | A | | A |
| 108 | 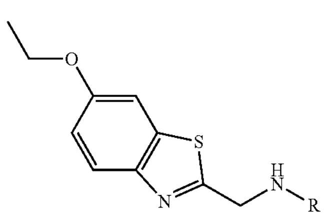 | | A | | A |

-continued
| | | Ki (μM) | | Elastin hydrolysis % inhibition @ 50/25 μM inhibitor concentration | |
|---|---|---|---|---|---|
| Example | Structure | Assay 1 | Assay 2 | Assay 1 | Assay 2 |
| 109 | 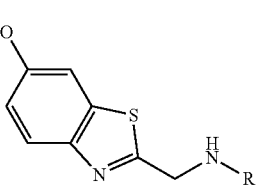 | | A | | A |
| 110 | 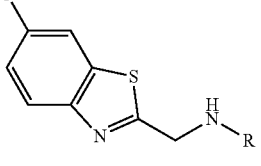 | B | | B | |
| 111 | 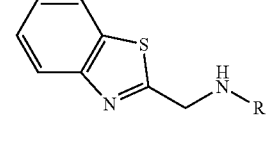 | B | | B | |
| 112 | 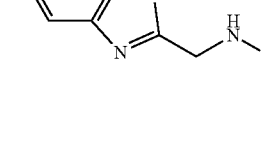 | A | | A | |
| 113 | 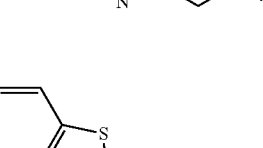 | B | | A | |
| 114 | 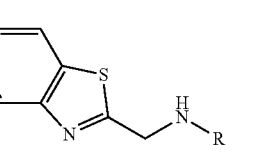 | | A | | A |
| 115 | 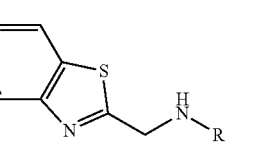 | | A | | A |

-continued

| Example | Structure | Ki (μM) | | Elastin hydrolysis % inhibition @ 50/25 μM inhibitor concentration | |
|---|---|---|---|---|---|
| | | Assay 1 | Assay 2 | Assay 1 | Assay 2 |
| 116 | 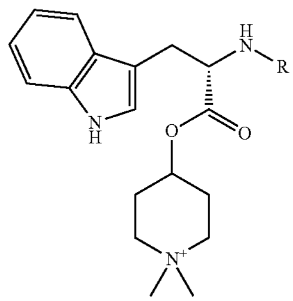 | B | | A | |
| 117 | 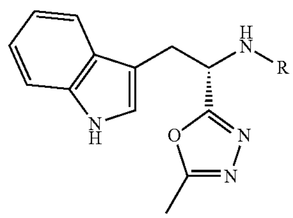 | B | | A | |
| 118 | 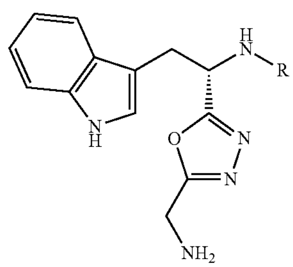 | A | | A | |
| 119 | 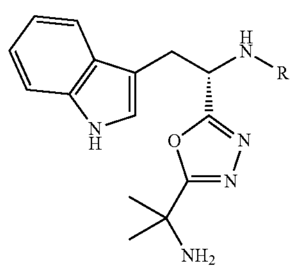 | B | | ND | |
| 122 | 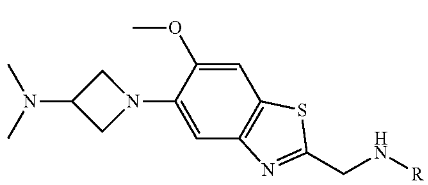 | | A | | A |
| 123 | 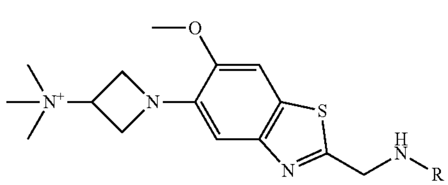 | | A | | A |

-continued

| Example | Structure | Ki (μM) Assay 1 | Ki (μM) Assay 2 | Elastin hydrolysis % inhibition @ 50/25 μM inhibitor concentration Assay 1 | Elastin hydrolysis % inhibition @ 50/25 μM inhibitor concentration Assay 2 |
|---|---|---|---|---|---|
| 126 | 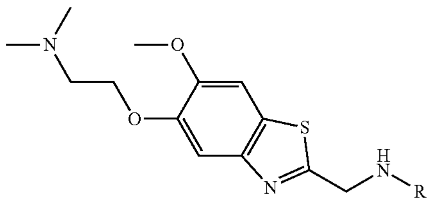 | | A | | A |
| 127 | 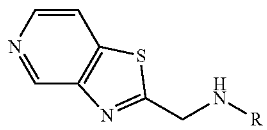 | B | | A | |
| 128 | 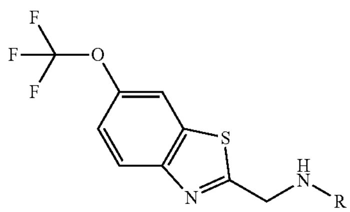 | | A | | A |
| 129 | 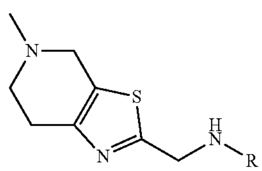 | B | | B | |
| 130 | 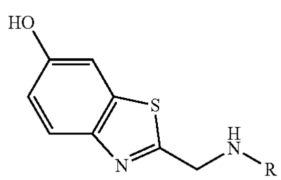 | A | | A | |

For the avoidance of doubt, the full structures of other compounds tested are shown in the table below:

| Example | Structure | Ki (μM) Assay 1 | Ki (μM) Assay 2 | Elastic hydrolysis % inhibition @ 50/25 μM inhibitor concentration Assay 1 | Elastic hydrolysis % inhibition @ 50/25 μM inhibitor concentration Assay 2 |
|---|---|---|---|---|---|
| 120 | 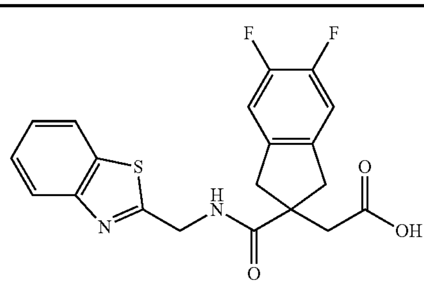 | | A | | A |

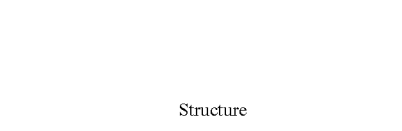

| Example | Structure | Ki (μM) | | Elastic hydrolysis % inhibition @ 50/25 μM inhibitor concentration | |
|---|---|---|---|---|---|
| | | Assay 1 | Assay 2 | Assay 1 | Assay 2 |
| 121 | 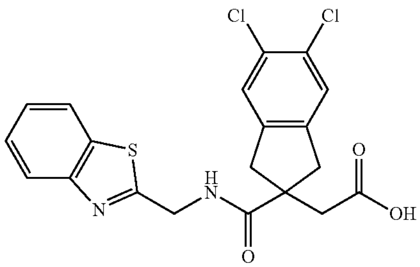 [SMILES: O=C(O)CC1(C(=O)NCc2nc3ccccc3s2)Cc2cc(Cl)c(Cl)cc2C1] | B | | ND | |
| 124 | 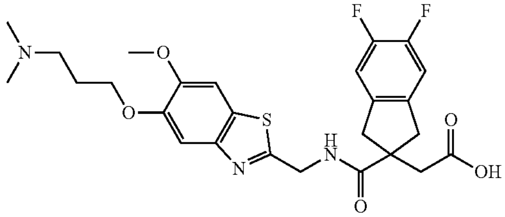 [SMILES: COc1cc2sc(CNC(=O)C3(CC(=O)O)Cc4cc(F)c(F)cc4C3)nc2cc1OCCCN(C)C] | A | | A | A |
| 125 | 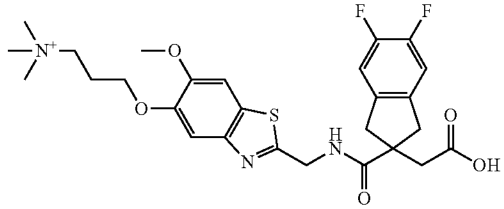 [SMILES: COc1cc2sc(CNC(=O)C3(CC(=O)O)Cc4cc(F)c(F)cc4C3)nc2cc1OCCC[N+](C)(C)C] | A | | A | A |

The invention claimed is:

1. A compound which is an indane derivative according to Formula (I), or a pharmaceutically acceptable salt thereof,

[FORMULA (I)]

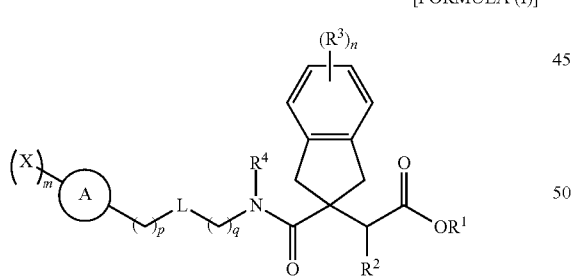

wherein
 $R^1$ is selected from H, $R^{1a}$ and —$CH_2OC(O)R^{1a}$, wherein Ria is selected from an unsubstituted $C_1$ to $C_4$ alkyl group and phenyl;
 $R^2$ is selected from H and unsubstituted $C_1$ to $C_3$ alkyl;
 each $R^3$ group is independently selected from halogen; —OH; —$NH_2$, methyl and —$CF_3$;
 n is an integer from 0 to 4;
 $R^4$ is selected from H and unsubstituted $C_1$ to $C_3$ alkyl;
 p is 0 or 1;
 q is 0 or 1;

L is selected from the moieties:

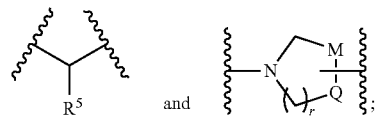

$R^5$ is selected from —$R^6$, —C(O)O$R^6$; —C(O)N$R^{10}R^6$; and —C(O)$R^6$;
 $R^6$ is selected from
  H;
  a $C_1$ to $C_4$ alkyl group which is unsubstituted or is substituted with one, two or three groups independently selected from —OH; —$NR^{10}R^{11}$; —$N^+R^{10}R^{11}R^{12}$; and halogen; and
  a cyclic group selected from 3- to 10-membered carbocyclic and heterocyclic groups, 5- to 10-membered heteroaromatic groups and 6- to 10-membered aromatic groups; which cyclic group is unsubstituted or is substituted by one or two substituents independently selected from —OH; —$NR^{10}R^{11}$; —$N^+R^{10}R^{11}R^{12}$; halogen; and $C_1$ to $C_4$ alkyl groups which are themselves each independently unsubstituted or substituted with one, two or three groups independently selected from —OH; —$NR^{10}R^{11}$; —$N^+R^{10}R^{11}R^{12}$; and halogen;
 wherein when said cyclic group is a heterocyclic group comprising at least one nitrogen atom, said nitrogen atom(s) are independently selected from secondary, tertiary and quaternary nitrogen atom(s);

the moiety -M-Q- is selected from —CH$_2$—CH$_2$—; —CH$_2$—NH—; and —CH$_2$—O—;

wherein a hydrogen atom from one of M and Q is replaced with the bond to the moiety

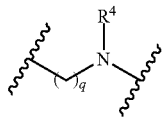

of Formula (I); with the proviso that when q is 0, the moiety -M-Q- is bonded to the —NR$^4$— moiety of Formula (I) via a ring carbon atom;

r is 1 or 2;

Ⓐ is a cyclic group selected from C$_6$ to C$_{10}$ aryl, 5- to 14-membered heteroaryl, and 4- to 14-membered carbocyclic and heterocyclic groups; wherein when Ⓐ is a heterocyclic or heteroaryl group comprising at least one nitrogen atom, said nitrogen atom(s) are independently selected from secondary, tertiary and quaternary nitrogen atom(s);

each X is independently selected from:
a 4- to 10-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; halogen, —OH; and C$_1$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; wherein each alkyl, alkenyl, alkoxy and alkynyl group is independently unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;

wherein the nitrogen atom(s) in said heterocyclic group are independently selected from secondary, tertiary and quaternary nitrogen atom(s);

C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl each of which is unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; and methoxy which is substituted by one, two or three halogen substituents;

halogen, —OH and unsubstituted methoxy; and

C$_3$ to C$_6$ carbocyclyl; —O—C$_3$ to C$_6$ carbocyclyl; and —NR$^X$—C$_3$ to C$_6$ carbocyclyl; wherein each carbocyclyl group is unsubstituted or is substituted with one or two groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; C$_1$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; wherein each alkyl, alkenyl, alkoxy and alkynyl group is independently unsubstituted or is substituted with one, two or three groups independently selected from —OH, halogen; methoxy; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;

m is an integer from 0 to 3;

each R$^{10}$, R$^{11}$, R$^{12}$, R$^{13}$ and R$^{14}$ is independently H or methyl; and R$^X$ is H or unsubstituted C$_1$ to C$_3$ alkyl.

2. A compound according to claim 1 wherein:
R$^1$ is selected from H and R$^{1a}$;
R$^2$ is selected from H and unsubstituted C$_1$ to C$_2$ alkyl; and
R$^4$ is H.

3. A compound according to claim 1, wherein n is an integer from 0 to 2 and each R$^3$ group is independently selected from halogen; —OH; and —NH$_2$.

4. A compound according to claim 1 wherein R$^1$ is H, R$^2$ is H, n is 0, and R$^4$ is H.

5. A compound according to claim 1 wherein q is 0.

6. A compound according to claim 1 wherein L is the moiety

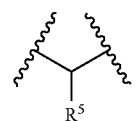

7. A compound according to claim 1 wherein:
L is selected from the moieties

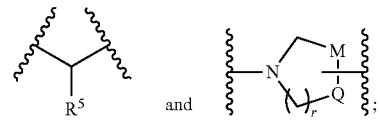

R$^5$ is selected from —R$^6$, —C(O)R$^6$; —C(O)NR$^{10}$R$^6$; and —C(O)R$^6$;

R$^6$ is selected from:
(i) H;
(ii) a C$_1$ to C$_4$ alkyl group which is unsubstituted or is substituted with one or two groups independently selected from —OH; —NR$^{10}$R$^{11}$; and —N$^+$R$^{10}$R$^{11}$R$^{12}$;
and
(iii) a 5- to 6-membered heterocyclic group which is unsubstituted or is substituted by one or two substituents independently selected from C$_1$ to C$_2$ alkyl groups which are each independently unsubstituted or substituted with one group selected from —OH; —NR$^{10}$R$^{11}$; —N$^+$R$^{10}$R$^{11}$R$^{12}$; and the moiety

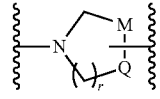

is selected from piperidinylene or pyrrolidinylene.

8. A compound according to claim 1 wherein:
q is 0;
p is 0;

L is the moiety

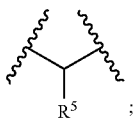;

R$^5$ is —R$^6$; and
R$^6$ is selected from:
(i) H;
(ii) a C$_1$ to C$_2$ alkyl group which is unsubstituted or is substituted with one group selected from —NR$^{10}$R$^{11}$ and —N$^+$R$^{10}$R$^{11}$R$^{12}$;
and
(iii) piperidine and piperazine, each of which is unsubstituted or is substituted by one or two methyl substituents.

9. A compound according to claim 1 wherein Ⓐ is a 5- to 10-membered heteroaryl group or a 4- to 10-membered heterocyclic group.

10. A compound according to claim 1 wherein Ⓐ is selected from pyrazole, benzene, benzothiazole, benzofuran, benzimidazole, benzothiophene, benzoxazole, indole, isoquinoline, 2,3-dihydrobenzofuran, 2,3-dihydrobenzo[b][1,4]dioxine, and 4,5,6,7-tetrahydrothiazolo[5,4-c]pyridine.

11. A compound according to claim 1 wherein each X is independently selected from:
(i) a 4- to 7-membered nitrogen-containing heterocyclic group which is unsubstituted or is substituted by one or two substituents independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; —C(NR$^{11}$)R$^{12}$; and unsubstituted or substituted C$_1$ to C$_2$ alkyl; wherein each substituted alkyl group is substituted with one, two or three groups independently selected from —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;
wherein the nitrogen atom(s) in said heterocyclic group are independently selected from secondary, tertiary and quaternary nitrogen atom(s);
(ii) C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl each of which is unsubstituted or is substituted with one, two or three groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; and methoxy which is substituted by one, two or three fluorine substituents;
(iii) halogen, —OH and unsubstituted methoxy; and
(iv) C$_3$ to C$_6$ carbocyclyl; and —O—C$_3$ to C$_6$ carbocyclyl; wherein each carbocyclyl group is unsubstituted or is substituted with one or two groups independently selected from —NR$^{10}$R$^{11}$; —N$^+$R$^{10}$R$^{11}$R$^{12}$; and C$_1$ to C$_4$ alkyl which is unsubstituted or is substituted with one or two groups independently selected from —NR$^{10}$R$^{11}$; and —N$^+$R$^{10}$R$^{10}$R$^{12}$.

12. A compound according to claim 1 wherein each X is independently selected from:
(i) a 4- to 6-membered nitrogen-containing heterocyclic group which is unsubstituted or is substituted by one or two substituents selected from unsubstituted C$_1$ to C$_2$ alkyl; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$;
wherein the nitrogen atom(s) in said heterocyclic group are independently selected from secondary, tertiary and quaternary nitrogen atom(s);
(ii) C$_2$ to C$_4$ alkoxy; C$_1$ to C$_4$ alkyl; C$_2$ to C$_4$ alkenyl; C$_2$ to C$_4$ alkynyl; and —NR$^X$—C$_1$ to C$_4$ alkyl; each of which is unsubstituted or is substituted with one or two groups independently selected from —OH, halogen; —NR$^{10}$R$^{11}$; —N$^+$R$^{10}$R$^{11}$R$^{12}$; —NR$^{10}$C(NR$^{11}$)NR$^{12}$R$^{13}$; —NR$^{10}$C(N$^+$R$^{11}$R$^{12}$)NR$^{13}$R$^{14}$; —NR$^{10}$C(NR$^{11}$)R$^{12}$; and —C(NR$^{11}$)R$^{12}$; and
(iii) halogen, —OH and methoxy.

13. A compound according to claim 1 wherein each X is independently selected from:
(i) a 4- to 6-membered nitrogen-containing heterocyclic group which is unsubstituted or is substituted by one or two substituents selected from C$_1$ to C$_2$ alkyl; —NR$^{10}$R$^{11}$; and —N$^+$R$^{10}$R$^{11}$R$^{12}$;
(ii) C$_2$ to C$_4$ alkoxy; C$_1$ to C$_4$ alkyl; C$_2$ to C$_4$ alkenyl; C$_2$ to C$_4$ alkynyl; and —NR$^X$C$_1$ to C$_4$ alkyl; each of which is unsubstituted or is substituted with one or two groups independently selected from —NR$^{10}$R$^{11}$ and —N$^+$R$^{10}$R$^{11}$R$^{12}$; and
(iii) chlorine, bromine, —OH and methoxy.

14. A compound according to claim 1 wherein m is 0 or 1.

15. A compound according to claim 1, which compound is an indane derivative according to Formula (I), or a pharmaceutically acceptable salt thereof, wherein:
R$^1$ is selected from H and methyl;
R$^2$ is selected from H and methyl;
each R$^3$ group is independently selected from halogen; —OH; and —NH$_2$;
n is 0 or 1;
R$^4$ is H;
q is 0;
p is 0 or 1;
L is selected from the moieties

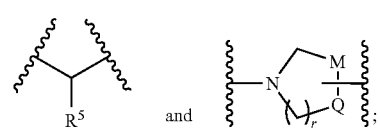;

R$^5$ is selected from —R$^6$, —C(O)OR$^6$; —C(O)NR$^{10}$R$^6$; and —C(O)R$^6$;
R$^6$ is selected from:
(i) H;
(ii) a C$_1$ to C$_4$ alkyl group which is unsubstituted or is substituted with one or two groups independently selected from —OH; —NR$^{10}$R$^{11}$; and —N$^+$R$^{10}$R$^{11}$R$^{12}$;
and
(iii) a 5- to 6-membered heterocyclic group which is unsubstituted or is substituted by one or two substituents independently selected from C$_1$ to C$_2$ alkyl groups which are each independently unsubstituted or substituted with one group selected from —OH; —NR$^{10}$R$^{11}$; —N$^+$R$^{10}$R$^{11}$R$^{12}$; and the moiety

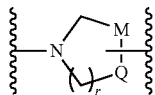

is selected from piperidinylene or pyrrolidinylene.

16. A compound according to claim 15, wherein:

Ⓐ is selected from pyrazole, benzene, benzothiazole, benzofuran, benzimidazole, benzothiophene, benzoxazole, indole, isoquinoline, 2,3-dihydrobenzofuran, 2,3-dihydrobenzo[b][1,4]dioxine, and 4,5,6,7-tetrahydrothiazolo[5,4-c]pyridine;

m is 0, 1 or 2; and each X is independently selected from:
  (i) a 4- to 6-membered nitrogen-containing heterocyclic group which is unsubstituted or is substituted by one or two substituents selected from $C_1$ to $C_2$ alkyl; —$NR^{10}R^{11}$ and —$N^+R^{10}R^{11}R^{12}$;
  (ii) $C_2$ to $C_4$ alkoxy; $C_1$ to $C_4$ alkyl; $C_2$ to $C_4$ alkenyl; $C_2$ to $C_4$ alkynyl; and —$NR^X$—$C_1$ to $C_4$ alkyl; each of which is unsubstituted or is substituted with one or two groups independently selected from —$NR^{10}R^{11}$ and —$N^+R^{10}R^{11}R^{12}$; and
  (iii) chlorine, bromine, —OH and methoxy.

17. A compound according to claim 1, which compound is an indane derivative according to Formula (I), or a pharmaceutically acceptable salt thereof, wherein:

$R^1$ is H;
$R^2$ is H;
n is 0;
$R^4$ is H;
q is 0;
p is 0;
L is the moiety

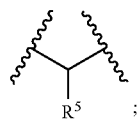

$R^5$ is —$R^6$;
$R^6$ is selected from:
  (i) H;
  (ii) a $C_1$ to $C_2$ alkyl group which is unsubstituted or is substituted with one group selected from —$NR^{10}R^{11}$ and —$N^+R^{10}R^{11}R^{12}$; and
  (iii) piperidine and piperazine, each of which is unsubstituted or is substituted by one or two methyl substituents;

Ⓐ is selected from benzene, benzothiazole, benzofuran, and indole;

m is 1; and

X is independently selected from:
  (i) piperazine, piperidine, pyrrolidine and azetidine each of which is unsubstituted or is substituted by one substituent selected from methyl, —$NH_2$ and —$N^+Me_3$; and
  (ii) $C_1$ to $C_3$ alkyl, $C_2$ to $C_2$ alkenyl and $C_2$ to $C_3$ alkynyl, each of which is substituted with one group selected from —$NR^{10}R^{11}$ and —$N^+R^{10}R^{11}R^{12}$.

18. A compound according to claim 1, wherein p=q=0 and L represents —$CH_2$—.

19. A compound according to claim 1, which compound is selected from 2-(2-{[(5-chloro-1H-1,3-benzodiazol-2-yl)methyl]carbamoyl}-2,3-dihydro-1H-inden-2-yl)acetic acid;
2-[2-(3-isoquinolylmethylcarbamoyl)indan-2-yl]acetic acid;
2-[2-[(1-methylpyrazol-4-yl)methylcarbamoyl]indan-2-yl]acetic acid;
2-[2-[(5-methoxy-1H-benzimidazol-2-yl)methylcarbamoyl]indan-2-yl]acetic acid;
2-(2-{[(1-benzofuran-2-yl)methyl]carbamoyl}-2,3-dihydro-1H-inden-2-yl)acetic acid;
2-(2-{[(5-methyl-1-benzofuran-2-yl)methyl]carbamoyl}-2,3-dihydro-1H-inden-2-yl)acetic acid;
2-[2-[(5-methyl-2,3-dihydrobenzofuran-2-yl)methylcarbamoyl]indan-2-yl]acetic acid;
2-[2-[[1-(3-chlorophenyl)pyrrolidin-3-yl]carbamoyl]indan-2-yl]acetic acid;
2-[2-[(1-methylindol-2-yl)methylcarbamoyl]indan-2-yl]acetic acid;
2-(2-{[(1,3-benzothiazol-2-yl)methyl]carbamoyl}-2,3-dihydro-1H-inden-2-yl)acetic acid;
2-(2-{[2-(3-methyl-1-benzofuran-2-yl)methyl]carbamoyl}-2,3-dihydro-1H-inden-2-yl)acetic acid;
2-[2-[2-(1H-benzimidazol-2-yl)ethylcarbamoyl]indan-2-yl]acetic acid;
2-[2-[2-(4-hydroxyphenyl)ethylcarbamoyl]indan-2-yl]acetic acid;
2-[2-[2-(1H-indol-3-yl)ethylcarbamoyl]indan-2-yl]acetic acid;
2-[2-[(4-hydroxyphenyl)methylcarbamoyl]indan-2-yl]acetic acid;
2-[2-(benzylcarbamoyl)indan-2-yl]acetic acid;
2-[2-(2,3-dihydro-1,4-benzodioxin-3-ylmethylcarbamoyl)indan-2-yl]acetic acid;
2-[2-[(5-bromobenzofuran-2-yl)methylcarbamoyl]indan-2-yl]acetic acid;
2-[2-[2-(benzofuran-2-yl)ethylcarbamoyl]indan-2-yl]acetic acid;
2-[2-[(2-methylbenzofuran-3-yl)methylcarbamoyl]indan-2-yl]acetic acid;
2-[2-[(1-methylimidazol-4-yl)methylcarbamoyl]indan-2-yl]acetic acid;
2-[2-[2-(1,3-benzothiazol-2-yl)ethylcarbamoyl]indan-2-yl]acetic acid;
2-[2-(benzothiophen-2-ylmethylcarbamoyl)indan-2-yl]acetic acid;
2-[2-[(5-methoxy-1,3-benzothiazol-2-yl)methylcarbamoyl]indan-2-yl]acetic acid;
2-[2-[(5-chloro-1,3-benzothiazol-2-yl)methylcarbamoyl]indan-2-yl]acetic acid;
2-[2-(1H-indol-3-ylmethylcarbamoyl)indan-2-yl]acetic acid;
2-[2-[2-(1H-indol-2-yl)ethylcarbamoyl]indan-2-yl]acetic acid;
2-[2-(benzofuran-3-ylmethylcarbamoyl)indan-2-yl]acetic acid;
2-[2-(1H-indol-2-ylmethylcarbamoyl)indan-2-yl]acetic acid;
2-[2-[2-(benzothiophen-2-yl)ethylcarbamoyl]indan-2-yl]acetic acid;
2-[2-[2-(1,3-benzoxazol-2-yl)ethylcarbamoyl]indan-2-yl]acetic acid;
2-[2-[[6-(3-aminopropyl)-1,3-benzothiazol-2-yl]methylcarbamoyl]indan-2-yl]acetic acid;

2-[2-[(6-methoxy-1,3-benzothiazol-2-yl)methylcarbamoyl]indan-2-yl]acetic acid;
2-[2-(4,5,6,7-tetrahydrothiazolo[5,4-c]pyridin-2-ylmethylcarbamoyl)indan-2-yl]acetic acid;
(2-{[(2S)-1-hydroxy-3-(1H-indol-3-yl)propan-2-yl]carbamoyl}-1,3-dihydroinden-2-yl)acetic acid;
(2-{[(1S)-1-{[2-(dimethylamino)ethyl]carbamoyl}-2-(1H-indol-3-yl)ethyl]carbamoyl}-1,3-dihydroinden-2-yl)acetic acid;
2-(2-{[(2S)-3-(1H-indol-3-yl)-1-[(1-methylpiperidin-4-yl)oxy]-1-oxopropan-2-yl]carbamoyl}-2,3-dihydro-1H-inden-2-yl)acetic acid;
(2-{[(1S)-2-(1H-indol-3-yl)-1-{[2-(trimethylammonio)ethyl]carbamoyl}ethyl]carbamoyl}-1,3-dihydroinden-2-yl)acetate
2-[2-[[6-[3-(dimethylamino)prop-1-ynyl]-1,3-benzothiazol-2-yl]methylcarbamoyl]indan-2-yl]acetic acid;
2-[2-[[6-[3-(dimethylamino)propyl]-1,3-benzothiazol-2-yl]methylcarbamoyl]indan-2-yl]acetic acid;
3-[2-[[[2-(carboxymethyl)indane-2-carbonyl]amino]methyl]-1,3-benzothiazol-6-yl]propyl-trimethyl-ammonium;
2-[2-[[6-[(E)-3-aminoprop-1-enyl]-1,3-benzothiazol-2-yl]methylcarbamoyl]indan-2-yl]acetic acid;
2-[2-[[5-(3-aminopropyl)-1,3-benzothiazol-2-yl]methylcarbamoyl]indan-2-yl]acetic acid;
2-[2-[(6-piperazin-1-yl-1,3-benzothiazol-2-yl)methylcarbamoyl]indan-2-yl]acetic acid;
2-[2-[[6-(4-methylpiperazin-1-yl)-1,3-benzothiazol-2-yl]methylcarbamoyl]indan-2-yl]acetic acid;
2-[2-[[6-(4,4-dimethylpiperazin-4-ium-1-yl)-1,3-benzothiazol-2-yl]methylcarbamoyl]indan-2-yl]acetic acid;
(S)-2-(2-((1-(tert-butoxy)-3-(1H-indol-3-yl)-1-oxopropan-2-yl)carbamoyl)-2,3-dihydro-1H-inden-2-yl)acetic acid;
(S)-2-(2-((1-amino-3-(4-hydroxyphenyl)-1-oxopropan-2-yl)carbamoyl)-2,3-dihydro-1H-inden-2-yl)acetic acid;
(2-(carboxymethyl)-2,3-dihydro-1H-indene-2-carbonyl)-L-tyrosine;
(2-(carboxymethyl)-2,3-dihydro-1H-indene-2-carbonyl)-L-tryptophan;
2-(2-(((1H-benzo[d]imidazol-2-yl)methyl)carbamoyl)-2,3-dihydro-1H-inden-2-yl)acetic acid;
(S)-2-(2-((1-amino-3-(1H-indol-3-yl)-1-oxopropan-2-yl)carbamoyl)-2,3-dihydro-1H-inden-2-yl)acetic acid;
(S)-2-(2-((3-(1H-indol-3-yl)-1-methoxy-1-oxopropan-2-yl)carbamoyl)-2,3-dihydro-1H-inden-2-yl)acetic acid;
2-(2-((thiazol-2-ylmethyl)carbamoyl)-2,3-dihydro-1H-inden-2-yl)acetic acid;
2-(2-((quinolin-2-ylmethyl)carbamoyl)-2,3-dihydro-1H-inden-2-yl)acetic acid;
2-(2-(((1-methyl-1H-benzo[d]imidazol-2-yl)methyl)carbamoyl)-2,3-dihydro-1H-inden-2-yl)acetic acid;
2-[2-(benzofuran-3-ylmethylcarbamoyl)indan-2-yl]acetic acid;
2-[2-[[(1R*)-1-(benzofuran-2-yl)ethyl]carbamoyl]indan-2-yl]acetic acid;
2-[2-[[(1S*)-1-(benzofuran-2-yl)ethyl]carbamoyl]indan-2-yl]acetic acid;
2-(2-(((4-fluorobenzo[d]thiazol-2-yl)methyl)carbamoyl)-2,3-dihydro-1H-inden-2-yl)acetic acid;
2-(2-(((4-bromobenzo[d]thiazol-2-yl)methyl)carbamoyl)-2,3-dihydro-1H-inden-2-yl)acetic acid;
2-(2-(((4-methoxybenzo[d]thiazol-2-yl)methyl)carbamoyl)-2,3-dihydro-1H-inden-2-yl)acetic acid;
2-(2-(((4-iodobenzo[d]thiazol-2-yl)methyl)carbamoyl)-2,3-dihydro-1H-inden-2-yl)acetic acid;
2-(2-(((4-ethoxybenzo[d]thiazol-2-yl)methyl)carbamoyl)-2,3-dihydro-1H-inden-2-yl)acetic acid;
2-(2-(((4-methylbenzo[d]thiazol-2-yl)methyl)carbamoyl)-2,3-dihydro-1H-inden-2-yl)acetic acid;
2-(2-(((4-morpholinobenzo[d]thiazol-2-yl)methyl)carbamoyl)-2,3-dihydro-1H-inden-2-yl)acetic acid;
2-(2-(((6-(3-(dimethylamino)azetidin-1-yl)benzo[d]thiazol-2-yl)methyl)carbamoyl)-2,3-dihydro-1H-inden-2-yl)acetic acid;
2-[2-[[6-(3-(trimethylammonio)azetidin-1-yl]-1,3-benzothiazol-2-yl]methylcarbamoyl]indan-2-yl]acetate;
2-[2-[[6-(2-aminoethylamino)-1,3-benzothiazol-2-yl]methylcarbamoyl]indan-2-yl]acetic acid;
2-[2-[[6-[3-(2-aminoethyl)azetidin-1-yl]-1,3-benzothiazol-2-yl]methylcarbamoyl]indan-2-yl]acetic acid;
2-[2-[[6-(6-methyl-2,6-diazaspiro[3.3]heptan-2-yl)-1,3-benzothiazol-2-yl]methylcarbamoyl]indan-2-yl]acetic acid;
2-[2-[[5-(2-aminoethylamino)-1,3-benzothiazol-2-yl]methylcarbamoyl]indan-2-yl]acetic acid;
2-[2-[[5-(3-aminoazetidin-1-yl)-1,3-benzothiazol-2-yl]methylcarbamoyl]indan-2-yl]acetic acid;
2-[2-[[5-[3-(dimethylamino)azetidin-1-yl]-1,3-benzothiazol-2-yl]methylcarbamoyl]indan-2-yl]acetic acid;
2-[2-[[5-[3-(trimethylammonio)azetidin-1-yl]-1,3-benzothiazol-2-yl]methylcarbamoyl]indan-2-yl]acetate;
2-[2-[[5-[2-(dimethylamino)ethylamino]-1,3-benzothiazol-2-yl]methylcarbamoyl]indan-2-yl]acetic acid;
2-[2-[[5-[2-(trimethylammonio)ethylamino]-1,3-benzothiazol-2-yl]methylcarbamoyl]indan-2-yl]acetate;
2-[2-[[6-(3-aminocyclobutoxy)-1,3-benzothiazol-2-yl]methylcarbamoyl]indan-2-yl]acetic acid;
2-[2-[[6-[3-(dimethylamino)cyclobutoxy]-1,3-benzothiazol-2-yl]methylcarbamoyl]indan-2-yl]acetic acid;
2-[2-[[6-(2-aminoethyl)-1,3-benzothiazol-2-yl]methylcarbamoyl]indan-2-yl]acetic acid;
2-[2-[[6-[(dimethylamino)methyl]-1,3-benzothiazol-2-yl]methylcarbamoyl]indan-2-yl]acetic acid;
2-[2-[[6-[(trimethylammonio)methyl]-1,3-benzothiazol-2-yl]methylcarbamoyl]indan-2-yl]acetate;
2-[2-[[5-(2-aminoethyl)-1,3-benzothiazol-2-yl]methylcarbamoyl]indan-2-yl]acetic acid;
2-[2-[[5-[(dimethylamino)methyl]-1,3-benzothiazol-2-yl]methylcarbamoyl]indan-2-yl]acetic acid;
2-[2-[[5-[(trimethylammonio)methyl]-1,3-benzothiazol-2-yl]methylcarbamoyl]indan-2-yl]acetate;
2-[2-[[6-[3-(trimethylammonio)prop-1-ynyl]-1,3-benzothiazol-2-yl]methylcarbamoyl]indan-2-yl]acetate;
2-[2-[[5-[(E)-3-aminoprop-1-enyl]-1,3-benzothiazol-2-yl]methylcarbamoyl]indan-2-yl]acetic acid;
2-[2-[[5-[3-(dimethylamino)prop-1-ynyl]-1,3-benzothiazol-2-yl]methylcarbamoyl]indan-2-yl]acetic acid;
2-[2-[[5-[3-(dimethylamino)propyl]-1,3-benzothiazol-2-yl]methylcarbamoyl]indan-2-yl]acetic acid;
2-[2-[[5-[3-(trimethylammonio)propyl]-1,3-benzothiazol-2-yl]methylcarbamoyl]indan-2-yl]acetate;
2-(2-(((6-((1r,3r)-3-((dimethylamino)methyl)cyclobutyl)benzo[d]thiazol-2-yl)methyl)carbamoyl)-2,3-dihydro-1H-inden-2-yl)acetic acid;
2-[2-[[6-[(1r,3r)-3-[(trimethylammonio)methyl]cyclobutyl]-1,3-benzothiazol-2-yl]methylcarbamoyl]indan-2-yl]acetate;
2-(2-(((6-((1s,3s)-3-((dimethylamino)methyl)cyclobutyl)benzo[d]thiazol-2-yl)methyl)carbamoyl)-2,3-dihydro-1H-inden-2-yl)acetic acid;

2-[2-[[6-[(1s,3s)-3-[(trimethylammonio)methyl]cyclobutyl]-1,3-benzothiazol-2-yl]methylcarbamoyl]indan-2-yl]acetate;
2-[2-[[6-[2-(dimethylamino)ethyl]-1,3-benzothiazol-2-yl]methylcarbamoyl]indan-2-yl]acetic acid;
2-[2-[[6-[2-(trimethylammonio)ethyl]-1,3-benzothiazol-2-yl]methylcarbamoyl]indan-2-yl]acetate;
2-[2-[[5-[2-(dimethylamino)ethyl]-1,3-benzothiazol-2-yl]methylcarbamoyl]indan-2-yl]acetic acid;
2-[2-[[5-[2-(trimethylammonio)ethyl]-1,3-benzothiazol-2-yl]methylcarbamoyl]indan-2-yl]acetate;
2-[2-[[6-[3-(aminomethyl)azetidin-1-yl]-1,3-benzothiazol-2-yl]methylcarbamoyl]indan-2-yl]acetic acid;
2-[2-[[6-(3-aminoazetidin-1-yl)-1,3-benzothiazol-2-yl]methylcarbamoyl]indan-2-yl]acetic acid;
2-[2-[[6-[(3S)-3-aminopyrrolidin-1-yl]-1,3-benzothiazol-2-yl]methylcarbamoyl]indan-2-yl]acetic acid;
2-[2-[[6-[(3R)-3-aminopyrrolidin-1-yl]-1,3-benzothiazol-2-yl]methylcarbamoyl]indan-2-yl]acetic acid;
2-[2-[[5-[(3S)-3-aminopyrrolidin-1-yl]-1,3-benzothiazol-2-yl]methylcarbamoyl]indan-2-yl]acetic acid;
2-[2-[[5-[(3R)-3-aminopyrrolidin-1-yl]-1,3-benzothiazol-2-yl]methylcarbamoyl]indan-2-yl]acetic acid;
2-[2-[[6-[2-(dimethylamino)ethylamino]-1,3-benzothiazol-2-yl]methylcarbamoyl]indan-2-yl]acetic acid;
2-[2-[[5-(4-methylpiperazin-1-yl)-1,3-benzothiazol-2-yl]methylcarbamoyl]indan-2-yl]acetic acid;
2-[2-[(6-hydroxy-1,3-benzothiazol-2-yl)methylcarbamoyl]indan-2-yl]acetic acid;
2-[2-[(6-ethoxy-1,3-benzothiazol-2-yl)methylcarbamoyl]indan-2-yl]acetic acid;
2-[2-[[6-(2-hydroxyethoxy)-1,3-benzothiazol-2-yl]methylcarbamoyl]indan-2-yl]acetic acid;
2-[2-[[6-[2-(dimethylamino)ethoxy]-1,3-benzothiazol-2-yl]methylcarbamoyl]indan-2-yl]acetic acid;
2-[2-[[6-[2-(trimethylammonio)ethoxy]-1,3-benzothiazol-2-yl]methylcarbamoyl]indan-2-yl]acetate;
2-[2-[[5-[2-(dimethylamino)ethoxy]-1,3-benzothiazol-2-yl]methylcarbamoyl]indan-2-yl]acetic acid;
2-[2-[[5-[2-(trimethylammonio)ethoxy]-1,3-benzothiazol-2-yl]methylcarbamoyl]indan-2-yl]acetate;
2-[2-[(5,6-dimethoxy-1,3-benzothiazol-2-yl)methylcarbamoyl]indan-2-yl]acetic acid;
2-[2-([1,3]dioxolo[4,5-f][1,3]benzothiazol-6-ylmethylcarbamoyl)indan-2-yl]acetic acid;
(S)-2-(2-((1-(((1,1-dimethylpiperidin-1-ium-4-yl)oxy)-3-(1H-indol-3-yl)-1-oxopropan-2-yl)carbamoyl)-2,3-dihydro-1H-inden-2-yl)acetate;
(S)-2-(2-((2-(1H-indol-3-yl)-1-(5-methyl-1,3,4-oxadiazol-2-yl)ethyl)carbamoyl)-2,3-dihydro-1H-inden-2-yl)acetic acid;
(S)-2-(2-((1-(5-(aminomethyl)-1,3,4-oxadiazol-2-yl)-2-(1H-indol-3-yl)ethyl)carbamoyl)-2,3-dihydro-1H-inden-2-yl)acetic acid;
(S)-2-(2-((1-(5-(2-aminopropan-2-yl)-1,3,4-oxadiazol-2-yl)-2-(1H-indol-3-yl)ethyl)carbamoyl)-2,3-dihydro-1H-inden-2-yl)acetic acid;
2-(2-((benzo[d]thiazol-2-ylmethyl)carbamoyl)-5,6-difluoro-2,3-dihydro-1H-inden-2-yl)acetic acid;
2-(2-((benzo[d]thiazol-2-ylmethyl)carbamoyl)-5,6-dichloro-2,3-dihydro-1H-inden-2-yl)acetic acid;
2-(2-(((5-(3-(dimethylamino)azetidin-1-yl)-6-methoxybenzo[d]thiazol-2-yl)methyl)carbamoyl)-2,3-dihydro-1H-inden-2-yl)acetic acid;
2-(2-(((6-methoxy-5-(3-(trimethylammonio)azetidin-1-yl)benzo[d]thiazol-2-yl)methyl)carbamoyl)-2,3-dihydro-1H-inden-2-yl)acetate;
2-(2-(((5-(3-(dimethylamino)propoxy)-6-methoxybenzo[d]thiazol-2-yl)methyl)carbamoyl)-5,6-difluoro-2,3-dihydro-1H-inden-2-yl)acetic acid;
2-(5,6-difluoro-2-(((6-methoxy-5-(3-(trimethylammonio)propoxy)benzo[d]thiazol-2-yl)methyl)carbamoyl)-2,3-dihydro-1H-inden-2-yl)acetate;
2-(2-(((5-(2-(dimethylamino)ethoxy)-6-methoxybenzo[d]thiazol-2-yl)methyl)carbamoyl)-2,3-dihydro-1H-inden-2-yl)acetic acid;
2-[2-(thiazolo[4,5-c]pyridin-2-ylmethylcarbamoyl)indan-2-yl]acetic acid;
2-[2-[[6-(trifluoromethoxy)-1,3-benzothiazol-2-yl]methylcarbamoyl]indan-2-yl]acetic acid;
2-[2-[(5-methyl-6,7-dihydro-4H-thiazolo[5,4-c]pyridin-2-yl)methylcarbamoyl]indan-2-yl]acetic acid;
2-[2-[(5-hydroxy-1,3-benzothiazol-2-yl)methylcarbamoyl]indan-2-yl]acetic acid;
2-[2-[2-(1-methyl-4-piperidyl)ethylcarbamoyl]indan-2-yl]acetic acid;
2-[2-[2-(1,1-dimethylpiperidin-1-ium-4-yl)ethylcarbamoyl]indan-2-yl]acetate;
2-[2-[(1-benzylpyrrolidin-3-yl)carbamoyl]indan-2-yl]acetic acid;
2-[2-[(1,3-dimethylbenzimidazol-3-ium-2-yl)methylcarbamoyl]indan-2-yl]acetate;
2-[2-[(2-methylisoquinolin-2-ium-3-yl)methylcarbamoyl]indan-2-yl]acetate;
2-[2-[(1-methyl-4-piperidyl)methylcarbamoyl]indan-2-yl]acetic acid;
2-[2-[(1,1-dimethylpiperidin-1-ium-4-yl)methylcarbamoyl]indan-2-yl]acetate;
2-[2-[2-(1-methylimidazol-4-yl)ethylcarbamoyl]indan-2-yl]acetic acid;
2-[2-[(5,5-dimethyl-6,7-dihydro-4H-thiazolo[5,4-c]pyridin-5-ium-2-yl)methylcarbamoyl]indan-2-yl]acetate;
2-[2-[[(3R)-1-phenylpyrrolidin-3-yl]carbamoyl]indan-2-yl]acetic acid;
2-[2-[[(3S)-1-phenylpyrrolidin-3-yl]carbamoyl]indan-2-yl]acetic acid;
2-[2-(imidazo[1,2-a]pyridin-2-ylmethylcarbamoyl)indan-2-yl]acetic acid;
2-[2-(1,3-benzoxazol-2-ylmethylcarbamoyl)indan-2-yl]acetic acid;
2-[2-[(3-hydroxyphenyl)methylcarbamoyl]indan-2-yl]acetic acid;
2-[2-[(5-methylthiazolo[4,5-c]pyridin-5-ium-2-yl)methylcarbamoyl]indan-2-yl]acetate;
2-[2-[(5-hydroxy-2-pyridyl)methylcarbamoyl]indan-2-yl]acetic acid; and
2-[2-[1,3-benzothiazol-2-ylmethyl(methyl)carbamoyl]indan-2-yl]acetic acid;
or a pharmaceutically acceptable salt thereof.

20. A pharmaceutical composition comprising a compound according to claim 1 together with at least one pharmaceutically acceptable carrier or diluent.

21. A combination comprising (i) a compound according to claim 1 and (ii) an antibiotic agent; and optionally (iii) at least one pharmaceutically acceptable carrier or diluent.

22. A combination according to claim 21, wherein the antibiotic agent is selected from tobramycin, neomycin, streptomycin, gentamycin, ceftazidime, ticarcillin, piperacillin, tazobactam, imipenem, meropenem, rifampicin, ciprofloxacin, amikacin, colistin, aztreonam and levofloxacin.

23. A cleaning composition comprising (i) a compound according to claim 1 and (ii) a detergent, a surfactant, a diluent, a bleach, an alcohol or a disinfectant.

24. A method of treating or preventing bacterial infection in a subject, comprising administering an effective amount of (i) a compound according to claim or (ii) a pharmaceutical composition comprising a compound according to claim 1 together with at least one pharmaceutically acceptable carrier or diluent to the subject.

25. A method according to claim 24, wherein wherein the bacterial infection is caused by *Bacillus, Pseudomonas, Staphylococcus, Streptococcus, Listeria, Burkholderia* or *Escherichia*.

26. A method according to claim 25 wherein the bacterial infection is caused by *Pseudomonas aeruginosa*.

27. A method according to claim 24 wherein the subject suffers from cystic fibrosis.

28. A method of treating or preventing pneumonia in a subject, comprising administering administering an effective amount of (i) a compound according to claim 1 or (ii) a pharmaceutical composition comprising a compound according to claim 1 together with at least one pharmaceutically acceptable carrier or diluent to the subject.

29. A method according to claim 28 wherein the subject suffers from cystic fibrosis.

30. A method of treating or preventing bacterial infection in a subject, comprising administering an effective amount of a combination according to claim 21 the subject.

31. A method according to claim 30, wherein the bacterial infection is caused by *Bacillus, Pseudomonas, Staphylococcus, Streptococcus, Listeria, Burkholderia* or *Escherichia*.

32. A method according to claim 31 wherein the bacterial infection is caused by *Pseudomonas aeruginosa*.

33. A method according to claim 30 wherein the subject suffers from cystic fibrosis.

34. A method of treating or preventing pneumonia in a subject, comprising administering an effective amount of a combination according to claim 21 the subject.

35. A method according to claim 34, wherein the subject suffers from cystic fibrosis.

36. An in vitro method of treating or preventing bacterial contamination on a surface comprising contacting the surface with an effective amount of a cleaning composition according to claim 23.

37. A compound according to claim 1 wherein:
L is selected from the moieties

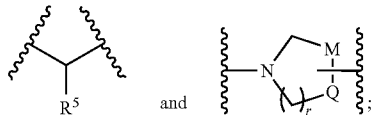
and $R^5$ is selected from —$R^6$ and —C(O)O$R^6$;
$R^6$ is selected from:
(i) H;
(ii) a $C_1$ to $C_4$ alkyl group which is unsubstituted or is substituted with one group selected from —OH; —NR$^{10}$R$^{11}$; and —N$^+$R$^{10}$R$^{11}$R$^{12}$;

and
(iii) a 5- to 6-membered heterocyclic group which is unsubstituted or is substituted by one or two substituents independently selected from $C_1$ to $C_2$ alkyl groups which are each independently unsubstituted or substituted with one group selected from —OH; —NR$^{10}$R$^{11}$; —N$^+$R$^{10}$R$^{11}$R$^{12}$; and
the moiety

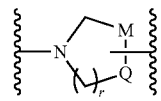

is selected from piperidinylene or pyrrolidinylene.

38. A compound according to claim 3, which compound is an indane derivative according to Formula (I), or a pharmaceutically acceptable salt thereof, wherein:
$R^1$ is selected from H and methyl;
$R^2$ is selected from H and methyl;
each $R^3$ group is independently selected from halogen; —OH; and —NH$_2$;
n is 0 or 1;
$R^4$ is H;
q is 0;
p is 0 or 1;
L is selected from the moieties

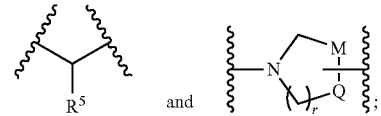

$R^5$ is selected from —$R^6$ and —C(O)O$R^6$;
$R^6$ is selected from:
(i) H;
(ii) a $C_1$ to $C_4$ alkyl group which is unsubstituted or is substituted with one group selected from —OH; —NR$^{10}$R$^{11}$; and —N$^+$R$^{10}$R$^{11}$R$^{12}$; and
(iii) a 5- to 6-membered heterocyclic group which is unsubstituted or is substituted by one or two substituents independently selected from $C_1$ to $C_2$ alkyl groups which are each independently unsubstituted or substituted with one group selected from —OH; —NR$^{10}$R$^{11}$; —N$^+$R$^{10}$R$^{11}$R$^{12}$; and
the moiety

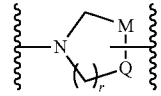

is selected from piperidinylene or pyrrolidinylene.

* * * * *